United States Patent
Maldonado

(10) Patent No.: US 9,993,548 B2
(45) Date of Patent: *Jun. 12, 2018

(54) TOLEROGENIC SYNTHETIC NANOCARRIERS FOR INDUCING REGULATORY B CELLS

(71) Applicant: Selecta Biosciences, Inc., Watertown, MA (US)

(72) Inventor: Roberto A. Maldonado, Jamaica Plain, MA (US)

(73) Assignee: Selecta Biosciences, Inc., Watertown, MA (US)

( * ) Notice: Subject to any disclaimer, the term of this patent is extended or adjusted under 35 U.S.C. 154(b) by 13 days.

This patent is subject to a terminal disclaimer.

(21) Appl. No.: 14/161,660

(22) Filed: Jan. 22, 2014

(65) Prior Publication Data

US 2014/0199340 A1 Jul. 17, 2014

Related U.S. Application Data

(63) Continuation of application No. 13/458,179, filed on Apr. 27, 2012, now Pat. No. 8,652,487.

(Continued)

(51) Int. Cl.

| | | |
|---|---|---|
| *A61K 47/48* | (2006.01) | |
| *A61K 39/00* | (2006.01) | |
| *C07K 16/18* | (2006.01) | |
| *A61K 9/51* | (2006.01) | |
| *A61K 9/58* | (2006.01) | |
| *A61K 47/00* | (2006.01) | |
| *A61K 9/14* | (2006.01) | |
| *A61K 39/385* | (2006.01) | |
| *A61K 39/35* | (2006.01) | |
| *G01N 33/50* | (2006.01) | |
| *G01N 33/569* | (2006.01) | |
| *B82Y 5/00* | (2011.01) | |
| *A61K 39/36* | (2006.01) | |
| *A61K 9/127* | (2006.01) | |
| *A61K 38/38* | (2006.01) | |
| *A61K 31/192* | (2006.01) | |

(Continued)

(52) U.S. Cl.

CPC ............ *A61K 39/385* (2013.01); *A61K 9/127* (2013.01); *A61K 9/14* (2013.01); *A61K 9/51* (2013.01); *A61K 9/5115* (2013.01); *A61K 9/5146* (2013.01); *A61K 9/5153* (2013.01); *A61K 31/192* (2013.01); *A61K 38/13* (2013.01); *A61K 38/1816* (2013.01); *A61K 38/38* (2013.01); *A61K 39/00* (2013.01); *A61K 39/001* (2013.01); *A61K 39/0008* (2013.01); *A61K 39/35* (2013.01); *A61K 39/36* (2013.01); *A61K 47/50* (2017.08); *A61K 47/52* (2017.08); *A61K 47/544* (2017.08); *A61K 47/593* (2017.08); *A61K 47/643* (2017.08); *A61K 47/69* (2017.08); *A61K 47/6923* (2017.08); *A61K 47/6929* (2017.08); *A61K 47/6937* (2017.08); *B82Y 5/00* (2013.01); *G01N 33/505* (2013.01); *G01N 33/56972* (2013.01); *A61K 2039/5154* (2013.01); *A61K 2039/55511* (2013.01); *A61K 2039/55555* (2013.01); *A61K 2039/577* (2013.01); *B82Y 40/00* (2013.01); *G01N 2333/7051* (2013.01); *G01N 2333/70514* (2013.01); *G01N 2333/70517* (2013.01)

(58) Field of Classification Search

CPC ...... A61K 39/00; A61K 39/005; A61K 9/127; A61K 47/482; A61K 47/47192; A61K 47/48215; A61K 47/48861; A61K 47/47915; A61K 9/5115; A61K 9/5146; A61K 47/48; A61K 39/36; A61K 47/48769; A61K 39/008; A61K 38/38; A61K 39/385; A61K 39/25; A61K 31/436; A61K 39/001; A61K 2039/55555; A61K 2039/577; A61K 2039/6093; A61K 2039/55511; A61K 2039/5154; A61K 2333/70517; A61K 2033/7051; A61K 2300/00; A61K 39/35; A61K 47/50; A61K 47/593; A61K 47/6923; A61K 47/544; A61K 47/52; A61K 9/515; A61K 47/643; A61K 47/69; A61K 47/6937; A61K 9/14; A61K 9/51; A61K 9/115; A61K 47/6929; A61K 39/0008; B82Y 5/00; G01N 33/50972; G01N 33/5052

See application file for complete search history.

(56) References Cited

U.S. PATENT DOCUMENTS 5,543,158 A 8/1996 Gref et al.
5,578,325 A 11/1996 Domb et al.

(Continued)

FOREIGN PATENT DOCUMENTS

CN 101437491 A 5/2009
CN 101646418 A 2/2010

(Continued)

OTHER PUBLICATIONS

Mason et al., Molecular Endocrinology 8(3): 325-332, 1994.*
Skolnick et al., Trends in Biotechnology, 18: 34-39, 2000.*
Jones et al., Pharmacogenomics Journal, 1:126-134, 2001.*
Tosatto et al., Current Pharmaceutical Design, 12:2067-2086, 2006.*
Dobrovoskaia et al., Nature nanotechnology 2: 469-478, 2007.*
Fifis et al., J Immunology 173: 3148-3154, 2004.*
Miyara et al., J allergy Clin Immunol 123(4): 749-755, Apr. 2009.*
Bawarski et al., Nanomedicine 4: 273-282, 2008.*
Gray et al., Eur J Immunology 40: 2677-2679; 2010.*
International Search Report and Written Opinion for PCT/US2012/035431 dated Nov. 28, 2012.

(Continued)

*Primary Examiner* — Phuong Huynh

(74) *Attorney, Agent, or Firm* — Wolf, Greenfield & Sacks, P.C.

(57) ABSTRACT

Disclosed are synthetic nanocarrier methods, and related compositions, comprising B cell and/or MHC Class II-restricted epitopes and immunosuppressants in order to generate tolerogenic immune responses, such as the generation of antigen-specific regulatory B cells.

17 Claims, 2 Drawing Sheets

Related U.S. Application Data

(60) Provisional application No. 61/531,147, filed on Sep. 6, 2011, provisional application No. 61/531,153, filed on Sep. 6, 2011, provisional application No. 61/531,164, filed on Sep. 6, 2011, provisional application No. 61/531,168, filed on Sep. 6, 2011, provisional application No. 61/531,175, filed on Sep. 6, 2011, provisional application No. 61/531,180, filed on Sep. 6, 2011, provisional application No. 61/531,194, filed on Sep. 6, 2011, provisional application No. 61/531,204, filed on Sep. 6, 2011, provisional application No. 61/531,209, filed on Sep. 6, 2011, provisional application No. 61/531,215, filed on Sep. 6, 2011, provisional application No. 61/513,514, filed on Jul. 29, 2011, provisional application No. 61/480,946, filed on Apr. 29, 2011.

(51) Int. Cl.
A61K 38/13 (2006.01)
A61K 38/18 (2006.01)
A61K 47/50 (2017.01)
A61K 47/52 (2017.01)
A61K 47/54 (2017.01)
A61K 47/59 (2017.01)
A61K 47/64 (2017.01)
A61K 47/69 (2017.01)
B82Y 40/00 (2011.01)

(56) References Cited

U.S. PATENT DOCUMENTS

| | | |
|---|---|---|
| 5,679,347 A | 10/1997 | Porcelli et al. |
| 5,762,904 A | 6/1998 | Okada et al. |
| 5,912,017 A | 6/1999 | Mathiowitz et al. |
| 5,928,647 A | 7/1999 | Rock |
| 6,007,845 A | 12/1999 | Domb et al. |
| 6,060,082 A | 5/2000 | Chen et al. |
| 6,197,229 B1 | 3/2001 | Ando et al. |
| 6,254,890 B1 | 7/2001 | Hirosue et al. |
| 6,306,640 B1 | 10/2001 | Nicolette |
| 6,387,397 B1 | 5/2002 | Chen et al. |
| 6,800,296 B1 | 10/2004 | Langer et al. |
| 6,881,421 B1 | 4/2005 | da Silveira et al. |
| 7,045,508 B2 | 5/2006 | Scaria |
| 7,550,441 B2 | 6/2009 | Farokhzad et al. |
| 7,727,969 B2 | 6/2010 | Farokhzad |
| 8,367,113 B2 | 2/2013 | Gu et al. |
| 8,629,151 B2 | 1/2014 | Zepp et al. |
| 8,652,487 B2 | 2/2014 | Maldonado et al. |
| 9,005,665 B2 | 4/2015 | Gourapura |
| 9,006,254 B2 | 4/2015 | Zepp et al. |
| 9,017,697 B2 | 4/2015 | Thomas |
| 9,066,978 B2 | 6/2015 | Ilyinskii et al. |
| 9,265,815 B2 | 2/2016 | Fraser et al. |
| 9,289,476 B2 | 3/2016 | Fraser et al. |
| 9,289,477 B2 | 3/2016 | Fraser et al. |
| 9,295,718 B2 | 3/2016 | Fraser et al. |
| 9,764,031 B2 | 9/2017 | Ilyinskii et al. |
| 2002/0019361 A1 | 2/2002 | Scaria |
| 2002/0086049 A1 | 7/2002 | Bolton et al. |
| 2002/0095135 A1 | 7/2002 | Meeker |
| 2004/0038406 A1 | 2/2004 | Unger et al. |
| 2004/0043483 A1 | 3/2004 | Qian et al. |
| 2004/0141958 A1 | 7/2004 | Steinaa et al. |
| 2006/0002852 A1 | 1/2006 | Saltzman et al. |
| 2006/0002971 A1 | 1/2006 | Saltzman et al. |
| 2006/0147432 A1 | 7/2006 | Moore et al. |
| 2006/0159766 A1 | 7/2006 | Jenkins et al. |
| 2006/0210638 A1 | 9/2006 | Liversidge et al. |
| 2006/0222652 A1 | 10/2006 | Sebbel et al. |
| 2006/0251677 A1 | 11/2006 | Bachmann et al. |
| 2006/0251710 A1 | 11/2006 | Kwon et al. |
| 2006/0251711 A1 | 11/2006 | Konduri et al. |
| 2006/0269540 A1 | 11/2006 | Robert et al. |
| 2007/0110685 A1 | 5/2007 | Auspitz et al. |
| 2007/0254897 A1 | 11/2007 | Gjorstrup |
| 2008/0031899 A1 | 2/2008 | Reddy et al. |
| 2008/0044484 A1 | 2/2008 | Minev |
| 2008/0064859 A1 | 3/2008 | Vandenbark et al. |
| 2008/0145441 A1 | 6/2008 | Penades et al. |
| 2008/0160089 A1 | 7/2008 | Vitiello et al. |
| 2008/0254045 A1 | 10/2008 | Donda et al. |
| 2008/0311140 A1 | 12/2008 | Lee et al. |
| 2009/0004259 A1 | 1/2009 | Rabinovich et al. |
| 2009/0028910 A1 | 1/2009 | DeSimone et al. |
| 2009/0074828 A1 | 3/2009 | Alexis et al. |
| 2009/0082260 A1 | 3/2009 | Lamb et al. |
| 2009/0155292 A1 | 6/2009 | Santamaria et al. |
| 2009/0226525 A1 | 9/2009 | de los Rios et al. |
| 2010/0008932 A1 | 1/2010 | Bensussan et al. |
| 2010/0055076 A1 | 3/2010 | Lim et al. |
| 2010/0055189 A1 | 3/2010 | Hubbell et al. |
| 2010/0062968 A1 | 3/2010 | Pulendran et al. |
| 2010/0068261 A1 | 3/2010 | Tamarkin et al. |
| 2010/0068286 A1 | 3/2010 | Troiano et al. |
| 2010/0080816 A1 | 4/2010 | Hadeiba et al. |
| 2010/0099613 A1 | 4/2010 | Buyse et al. |
| 2010/0111993 A1 | 5/2010 | Tureci et al. |
| 2010/0112077 A1 | 5/2010 | Desai et al. |
| 2010/0129392 A1 | 5/2010 | Shi et al. |
| 2010/0129439 A1 | 5/2010 | Alexis et al. |
| 2010/0151000 A1 | 6/2010 | Thomas et al. |
| 2010/0172994 A1 | 7/2010 | Sigmund et al. |
| 2010/0183602 A1 | 7/2010 | Carballido Herrera et al. |
| 2010/0183727 A1 | 7/2010 | Iannacone et al. |
| 2010/0189742 A1 | 7/2010 | Van Der Burg et al. |
| 2010/0196401 A1 | 8/2010 | Scaria |
| 2010/0233197 A1 | 9/2010 | Wakatsuki Pedersen et al. |
| 2010/0233251 A1 | 9/2010 | Von Andrian et al. |
| 2010/0303850 A1 | 12/2010 | Lipford et al. |
| 2010/0323199 A1 | 12/2010 | Gu et al. |
| 2011/0020388 A1 | 1/2011 | Zepp et al. |
| 2011/0027217 A1 | 2/2011 | Zepp et al. |
| 2011/0052697 A1 | 3/2011 | Farokhzad et al. |
| 2011/0070153 A1 | 3/2011 | Hyde et al. |
| 2011/0070154 A1 | 3/2011 | Hyde et al. |
| 2011/0076273 A1 | 3/2011 | Adler et al. |
| 2011/0110965 A1 | 5/2011 | Fraser et al. |
| 2011/0171248 A1 | 7/2011 | Pittet et al. |
| 2011/0223201 A1 | 9/2011 | Lipford et al. |
| 2011/0262491 A1 | 10/2011 | Keegan et al. |
| 2011/0272836 A1 | 11/2011 | Keegan et al. |
| 2011/0293700 A1 | 12/2011 | Bratzler et al. |
| 2011/0293701 A1 | 12/2011 | Bratzler et al. |
| 2011/0293723 A1 | 12/2011 | Bratzler et al. |
| 2012/0014966 A1 | 1/2012 | Solinger et al. |
| 2012/0027806 A1 | 2/2012 | Ilyinskii et al. |
| 2012/0027808 A1 | 2/2012 | Iannacone et al. |
| 2012/0058153 A1 | 3/2012 | Ilyinskii et al. |
| 2012/0058154 A1 | 3/2012 | Ilyinskii et al. |
| 2012/0064110 A1 | 3/2012 | Ilyinskii et al. |
| 2012/0070493 A1 | 3/2012 | Fraser et al. |
| 2012/0077860 A1 | 3/2012 | Garcia |
| 2012/0114677 A1 | 5/2012 | Zepp et al. |
| 2012/0171229 A1 | 7/2012 | Zepp et al. |
| 2012/0244222 A1 | 9/2012 | Altreuter et al. |
| 2012/0276109 A1 | 11/2012 | Fraser et al. |
| 2012/0276133 A1 | 11/2012 | Maldonado et al. |
| 2012/0276134 A1 | 11/2012 | Fraser et al. |
| 2012/0276155 A1 | 11/2012 | Kishimoto et al. |
| 2012/0276156 A1 | 11/2012 | Fraser et al. |
| 2012/0276157 A1 | 11/2012 | Fraser et al. |
| 2012/0276158 A1 | 11/2012 | Fraser et al. |
| 2012/0276159 A1 | 11/2012 | Fraser et al. |
| 2012/0276160 A1 | 11/2012 | Maldonado et al. |
| 2012/0294888 A1 | 11/2012 | Kishimoto et al. |
| 2012/0301498 A1 | 11/2012 | Altreuter et al. |
| 2012/0301510 A1 | 11/2012 | Kishimoto et al. |
| 2012/0308563 A1 | 12/2012 | Arya et al. |
| 2013/0028857 A1 | 1/2013 | Gao et al. |
| 2013/0028941 A1 | 1/2013 | Altreuter et al. |

(56) References Cited

U.S. PATENT DOCUMENTS

| | | |
|---|---|---|
| 2013/0039954 A1 | 2/2013 | Pittet et al. |
| 2013/0058894 A1 | 3/2013 | Maldonado et al. |
| 2013/0058901 A1 | 3/2013 | Maldonado et al. |
| 2013/0058902 A1 | 3/2013 | Kishimoto et al. |
| 2013/0058963 A1 | 3/2013 | Maldonado et al. |
| 2013/0058970 A1 | 3/2013 | Kishimoto et al. |
| 2013/0058974 A1 | 3/2013 | Maldonado et al. |
| 2013/0058975 A1 | 3/2013 | Maldonado et al. |
| 2013/0058976 A1 | 3/2013 | Kishimoto et al. |
| 2013/0058977 A1 | 3/2013 | Maldonado et al. |
| 2013/0058978 A1 | 3/2013 | Maldonado et al. |
| 2013/0059009 A1 | 3/2013 | Kishimoto et al. |
| 2014/0030344 A1 | 1/2014 | Zepp et al. |
| 2014/0199340 A1 | 7/2014 | Maldonado |
| 2014/0212462 A1 | 7/2014 | Kang et al. |
| 2014/0242173 A1 | 8/2014 | Zepp et al. |
| 2014/0294982 A1 | 10/2014 | Freund et al. |
| 2014/0328854 A1 | 11/2014 | Maldonado et al. |
| 2014/0328921 A1 | 11/2014 | Maldonado |
| 2014/0328922 A1 | 11/2014 | Maldonado |
| 2014/0328923 A1 | 11/2014 | Maldonado et al. |
| 2014/0328924 A1 | 11/2014 | Kishimoto |
| 2014/0335186 A1 | 11/2014 | Kishimoto et al. |
| 2014/0356361 A1 | 12/2014 | Maldonado et al. |
| 2015/0320728 A1 | 11/2015 | Fraser et al. |
| 2015/0320856 A1 | 11/2015 | Altreuter et al. |
| 2015/0320870 A1 | 11/2015 | Maldonado |
| 2015/0320884 A1 | 11/2015 | Fraser et al. |
| 2015/0328300 A1 | 11/2015 | Zepp et al. |
| 2015/0328309 A1 | 11/2015 | Ilyinskii et al. |
| 2015/0328333 A1 | 11/2015 | Fraser et al. |
| 2015/0335762 A1 | 11/2015 | Fraser et al. |
| 2015/0359865 A1 | 12/2015 | Kishimoto |
| 2015/0374815 A1 | 12/2015 | Kishimoto et al. |
| 2016/0022650 A1 | 1/2016 | Fraser et al. |
| 2016/0030554 A1 | 2/2016 | Kishimoto et al. |
| 2016/0030555 A1 | 2/2016 | Kishimoto et al. |
| 2016/0067228 A1 | 3/2016 | Kishimoto |
| 2016/0074372 A1 | 3/2016 | Kishimoto |
| 2016/0074427 A1 | 3/2016 | Kishimoto |
| 2016/0074531 A1 | 3/2016 | Kishimoto |
| 2016/0074532 A1 | 3/2016 | Kishimoto |
| 2016/0128986 A1 | 5/2016 | O'Neil et al. |
| 2016/0128987 A1 | 5/2016 | O'Neil et al. |
| 2016/0220501 A1 | 8/2016 | Fraser et al. |
| 2016/0243253 A1 | 8/2016 | Fraser et al. |
| 2016/0256401 A1 | 9/2016 | Fraser et al. |
| 2016/0279234 A1 | 9/2016 | Kishimoto et al. |
| 2017/0258927 A1 | 9/2017 | Johnston |

FOREIGN PATENT DOCUMENTS

| | | |
|---|---|---|
| CN | 101703781 A | 5/2010 |
| CN | 101861165 A | 10/2010 |
| EP | 1 153 122 A2 | 11/2001 |
| EP | 1 932 538 A1 | 6/2008 |
| EP | 2073848 A2 | 7/2009 |
| EP | 2345412 A1 | 7/2011 |
| EP | 2522338 A2 | 11/2012 |
| JP | 2006-257095 | 9/2006 |
| JP | 2009-531068 | 9/2009 |
| JP | 2010-514805 | 5/2010 |
| JP | 2010100578 A | 5/2010 |
| JP | 2010533160 A | 10/2010 |
| KR | 10-2010-0099849 A | 9/2010 |
| WO | WO 95/11696 A1 | 5/1995 |
| WO | WO 95/22963 A1 | 8/1995 |
| WO | WO 1996/012406 A1 | 2/1996 |
| WO | WO 96/20698 A2 | 7/1996 |
| WO | WO 1998/010056 A1 | 12/1998 |
| WO | WO 99/22762 A1 | 5/1999 |
| WO | WO 99/34826 A1 | 7/1999 |
| WO | WO 00/32626 A1 | 6/2000 |
| WO | WO 2002/009770 A1 | 2/2002 |
| WO | WO 02/088304 A2 | 11/2002 |
| WO | WO 2004/098509 A2 | 11/2004 |
| WO | WO 2006/041890 A2 | 4/2006 |
| WO | WO 2007/001448 A2 | 1/2007 |
| WO | WO 2007/067683 A2 | 6/2007 |
| WO | WO 2007/068747 A1 | 6/2007 |
| WO | WO 2007/070682 A2 | 6/2007 |
| WO | WO 2007/087341 A2 | 8/2007 |
| WO | WO 2007/098254 A2 | 8/2007 |
| WO | WO 2007/133807 A2 | 11/2007 |
| WO | WO 2007/137117 A2 | 11/2007 |
| WO | WO 2007/144150 A1 | 12/2007 |
| WO | WO 2007/150030 A2 | 12/2007 |
| WO | WO 2008/019142 A2 | 2/2008 |
| WO | WO 2008/036374 A2 | 3/2008 |
| WO | WO 2008/043157 A1 | 4/2008 |
| WO | WO 2008/071774 A1 | 6/2008 |
| WO | WO 2008/105773 A2 | 9/2008 |
| WO | WO 2008/109163 A1 | 9/2008 |
| WO | WO 2008/124632 A1 | 10/2008 |
| WO | WO 2008/124634 A1 | 10/2008 |
| WO | WO 2008/124639 A2 | 10/2008 |
| WO | WO 2008/129020 A1 | 10/2008 |
| WO | WO 2008/147456 A2 | 12/2008 |
| WO | WO 2008/150868 A1 | 12/2008 |
| WO | WO 2009/007750 A1 | 1/2009 |
| WO | WO 2009/022154 A2 | 2/2009 |
| WO | WO 2009/039502 A1 | 3/2009 |
| WO | WO 2009/051837 A2 | 4/2009 |
| WO | WO 2009/106999 A2 | 9/2009 |
| WO | WO 2009/131712 A2 | 10/2009 |
| WO | WO 2009/145238 A1 | 12/2009 |
| WO | WO 2010/018384 A1 | 2/2010 |
| WO | WO 2010/027471 A2 | 3/2010 |
| WO | WO 2010/037402 A2 | 4/2010 |
| WO | WO 2010/042863 A1 | 4/2010 |
| WO | WO 2010/042866 | 4/2010 |
| WO | WO 2010/042870 A1 | 4/2010 |
| WO | WO 2010/042876 | 4/2010 |
| WO | WO 2010/047839 A1 | 4/2010 |
| WO | WO 2010/075072 A2 | 7/2010 |
| WO | WO 2010/085509 A1 | 7/2010 |
| WO | WO 2010/116141 A2 | 10/2010 |
| WO | WO 2010/123569 A2 | 10/2010 |
| WO | WO 2010/138192 A2 | 12/2010 |
| WO | WO 2010/138193 A2 | 12/2010 |
| WO | WO 2010/138194 A2 | 12/2010 |
| WO | WO 2011/005850 A1 | 1/2011 |
| WO | WO 2011/033090 A1 | 3/2011 |
| WO | WO 2011/109833 A2 | 9/2011 |
| WO | WO 2011/156119 A1 | 12/2011 |
| WO | WO 2012/019041 A2 | 2/2012 |
| WO | WO 2012/054920 A2 | 4/2012 |
| WO | WO 2012/149247 A2 | 11/2012 |
| WO | WO 2012/149255 A2 | 11/2012 |
| WO | WO 2012/149259 A1 | 11/2012 |
| WO | WO 2012/149265 A2 | 11/2012 |
| WO | WO 2012/149268 A1 | 11/2012 |
| WO | WO 2012/149393 A2 | 11/2012 |
| WO | WO 2012/149405 A2 | 11/2012 |
| WO | WO 2013/058812 A1 | 4/2013 |
| WO | WO 2014/179771 A1 | 11/2014 |

OTHER PUBLICATIONS

[No Author Listed] Autologous Dendritic Cell Therapy for Type 1 Diabetes Suppression: A Safety Study. Clinical Trials. Mar. 2007. Last accessed Jan. 5, 2012 available at http://www.clinicaltrials.gov/ct2/show/NCT00445913?term=dendritic&cond=%22Autoimmune+Diseases%22&rank=4. 5 pages.

[No Author Listed] Autologous Tolerogenic Dendritic Cells for Rheumatoid Arthritis (AutoDECRA). Clinical Trials. May 2011. Last accessed Jan. 5, 2012 available at http://www.clinicaltrials.gov/ct2/show/NCT01352858?term=tolerogenic&rank=1. 4 pages.

[No Author Listed] Innovative rheumatoid arthritis therapy receives backing from Janssen. Available at http://www.di.uq.edu.au/innovative-rheumatoid-arthritis-therapy-backed. Jan. 18, 2012. 3 pages.

[No Author Listed] New Research Shows Transplanting Stem Cells from the Brain to the Pancreas Could Cure Diabetes, as Reported by

(56) References Cited

OTHER PUBLICATIONS

DiabeticLive.com. Oct. 18, 2011. Last accessed Jan. 5, 2012 at http://www.fiercebiotech.com/press-releases/new-research-shows-transplanting-stem-cells-brain-pancreas-could-cure-diabe. 2 pages.
[No Author Listed] Novel nanoparticle vaccine cures type 1 diabetes in mice. Apr. 8, 2010. Last accessed Dec. 6, 2011 at http://www.sciencedaily.com/releases/2010/04/100408121054.htm. 2 pages.
[No Author Listed] Scientists Use Rat's Own Stem Cells to Cure Their Diabetes. Oct. 16, 2011. Last accessed Jan. 5, 2012 at http://www.diabeteshealth.com/read/2011/10/16/7321/scientists-use-rats-own-stem-cells-to-cure-their-diabetes. 4 pages.
Ackerman et al., Cellular mechanisms governing cross-presentation of exogenous antigens. Nat Immunol. 2004;5(7):678-84.
Adorini et al., Tolerogenic dendritic cells induced by vitamin D receptor ligands enhance regulatory T cells inhibiting allograft rejection and autoimmune diseases. J Cell Biochem. Feb. 1, 2003;88(2):227-33.
Alexander et al., Universal influenza DNA vaccine encoding conserved CD4+ T cell epitopes protects against lethal viral challenge in HLA-DR transgenic mice. Vaccine. Jan. 8, 2010;28(3):664-72. Epub Nov. 4, 2009.
Anikeeva et al., Quantum dot/peptide-MHC biosensors reveal strong CD8-dependent cooperation between self and viral antigens that augment the T cell response. Proc Natl Acad Sci U S A. Nov. 7, 2006;103(45):16846-51. Epub Oct. 31, 2006.
Asano et al., Targeting activated lymphocytes with lipid microsphere containing a cytotoxic agent; efficacy of immunosuppression with a new drug delivery system. J Urology. 2001;165(5)384.
Ashe et al., Inhibition of glycogen biosynthesis via mTORC1 suppression as an adjunct therapy for Pompe disease. Mol Genet Metab. Aug. 2010;100(4):309-15. doi: 10.1016/j.ymgme.2010.05.001. Epub May 5, 2010.
Bachem et al., Superior antigen cross-presentation and XCR1 expression define human CD11c+CD141+ cells as homologues of mouse CD8+ dendritic cells. J Exp Med. Jun. 7, 2010;207(6):1273-81. Epub May 17, 2010.
Bachmann et al., T helper cell-independent neutralizing B cell response against vesicular stomatitis virus: role of antigen patterns in B cell induction?. Eur J Immunol. 1995;25(12):3445-51.
Bae et al., Mixed polymeric micelles for combination cancer chemotherapy through the concurrent delivery of multiple chemotherapeutic agents. J Control Release. Oct. 8, 2007;122(3):324-30. Epub Jun. 13, 2007.
Barchet et al., Virus-induced interferon alpha production by a dendritic cell subset in the absence of feedback signaling in vivo. J Exp Med. 2002;195(4):507-16.
Batista et al., The who, how and where of antigen presentation to B cells. Nat Rev Immunol. Jan. 2009;9(1):15-27.
Bayard et al., Hepatitis B virus (HBV)-derived DRB1*0101-restricted CD4 T-cell epitopes help in the development of HBV-specific CD8+ T cells in vivo. Vaccine. May 14, 2010;28(22):3818-26. Epub Mar. 31, 2010.
Blander, Phagocytosis and antigen presentation: a partnership initiated by Toll-like receptors. Ann Rheum Dis. Dec. 2008;67 Suppl 3:iii44-9.
Boden et al., Regulatory T cells in inflammatory bowel disease. Curr Opin Gastroenterol. Nov. 2008;24(6):733-41.
Boes et al., T-cell engagement of dendritic cells rapidly rearranges MHC class II transport. Nature. 418(6901):983-988 (2002).
Bonifaz et al., Efficient targeting of protein antigen to the dendritic cell receptor DEC-205 in the steady state leads to antigen presentation on major histocompatibility complex class I products and peripheral CD8+ T cell tolerance. J Exp Med. 2002;196(12):1627-38.
Bozzacco et al., DEC-205 receptor on dendritic cells mediates presentation of HIV gag protein to CD8+ T cells in a spectrum of human MHC I haplotypes. Proc Natl Acad Sci USA. 2007;104(4):1289-94.

Brennan et al., Invariant natural killer T cells recognize lipid self antigen induced by microbial danger signals. Nat Immunol. Oct. 30, 2011;12(12):1202-11. doi: 10.1038/ni.2143.
Busson et al., Prediction of CD4(+) T cell epitopes restricted to HLA-DP4 molecules. J Immunol Methods. Dec. 20, 2006;317(1-2):144-51. Epub Oct. 26, 2006.
Capini et al., Antigen-specific suppression of inflammatory arthritis using liposomes. J Immunol. Mar. 15, 2009;182(6):3556-65.
Carrasco et al., B cells acquire particulate antigen in a macrophage-rich area at the boundary between the follicle and the subcapsular sinus of the lymph node.Immunity. Jul. 2007;27(1):160-71. Epub Jul. 19, 2007.
Carroll, Stem cell therapy used to cure types 1&2 diabetes in rat models. Oct. 18, 2011. Last accessed Jan. 5, 2012 available at http://www.fiercebiotechresearch.com/story/stem-cell-therapy-used-cure-type-12-diabetes-rat-models/Oct. 18, 2011. 2 pages.
Casola et al., B cell receptor signal strength determines B cell fate. Nat Immunol. 2004;5(3):317-27.
Castelli et al., HLA-DP4, the most frequent HLA II molecule, defines a new supertype of peptide-binding specificity. J Immunol. Dec. 15, 2002;169(12):6928-34.
Chao et al., Induction of tolerance to human factor VIII in mice. Blood. May 15, 2001;97(10):3311-2.
Chapoval et al., HLA-DQ6 and HLA-DQ8 transgenic mice respond to ragweed allergens and recognize a distinct set of epitopes on short and giant ragweed group 5 antigens. J Immunol. Aug. 15, 1998;161(4):2032-7.
Chayen et al., Lysosomal enzymes and inflammation with particular reference to rheumatoid diseases. Ann Rheum Dis. Sep. 1971;30(5):522-36.
Chengalvala et al., Enhanced immunogenicity of hepatitis B surface antigen by insertion of a helper T cell epitope from tetanus toxoid. Vaccine. Mar. 5, 1999;17(9-10):1035-41.
Chinen et al., Basic and clinical immunology. J Allergy Clin Immunol. Aug. 2005;116(2):411-8.
Chinnery et al., The chemokine receptor CX3CR1 mediates homing of MHC class II-positive cells to the normal mouse corneal epithelium. Invest Ophthalmol Vis Sci. Apr. 2007;48(4):1568-74.
Clark, The reticulum of lymph nodes in mice studied with the electron microscope. Am J Anat. 1962;110:217-57.
Colman, Effects of amino acid sequence changes on antibody-antigen interactions. Res Immunol. Jan. 1994;145(1):33-6.
Coombes et al., A functionally specialized population of mucosal CD103+ DCs induces Foxp3+ regulatory T cells via a TGF-beta and retinoic acid-dependent mechanism. J Exp Med. Aug. 6, 2007;204(8):1757-64. Epub Jul. 9, 2007.
Crozat et al. The XC chemokine receptor 1 is a conserved selective marker of mammalian cells homologous to mouse CD8alpha+ dendritic cells. J Exp Med. Jun. 7, 2010;207(6):1283-92. Epub May 17, 2010.
Cruz et al., The influence of PEG chain length and targeting moiety on antibody-mediated delivery of nanoparticle vaccines to human dendritic cells. Biomaterials. Oct. 2011;32(28):6791-803. Epub Jul. 2, 2011. E-pub version.
Cvetanovich et al., Human regulatory T cells in autoimmune diseases. Curr Opin Immunol. Dec. 2010;22(6):753-60. Epub Sep. 24, 2010.
Dane et al., Nano-sized drug-loaded micelles deliver payload to lymph node immune cells and prolong allograft survival. J Control Release. Dec. 10, 2011;156(2):154-60. Epub Aug. 12, 2011.
Dang et al., Stimulation of B lymphocytes through surface Ig receptors induces LFA-1 and ICAM-1-dependent adhesion. J Immunol. 1991;146(10):3273-9.
Del Rio et al., Development and functional specialization of CD103+ dendritic cells. Immunol Rev. Mar. 2010;234(1):268-81.
Delemarre et al., Repopulation of macrophages in popliteal lymph nodes of mice after liposome-mediated depletion. J Leukoc Biol. 1990;47(3):251-7.
Demangel et al., Single chain antibody fragments for the selective targeting of antigens to dendritic cells. Mol Immunol. May 2005;42(8):979-85. Epub Dec. 10, 2004.

(56) References Cited

OTHER PUBLICATIONS

Diethelm-Okita et al., Universal epitopes for human CD4+ cells on tetanus and diphtheria toxins. J Infect Dis. Mar. 2000;181(3):1001-9.

DiLillo et al., B10 cells and regulatory B cells balance immune responses during inflammation, autoimmunity, and cancer. Ann N Y Acad Sci. Jan. 2010;1183:38-57.

Dorner et al., Selective expression of the chemokine receptor XCR1 on cross-presenting dendritic cells determines cooperation with CD8+ T cells. Immunity. Nov. 20, 2009;31(5):823-33. Epub Nov. 12, 2009.

Farokhzad et al., Drug delivery systems in urology—getting "smarter". Urology. Sep. 2006;68(3):463-9.

Farr et al., The structure of the sinus wall of the lymph node relative to its endocytic properties and transmural cell passage. Am J Anat. 1980;157(3):265-84.

Fasier et al., Antagonistic peptides specifically inhibit proliferation, cytokine production, CD40L expression, and help for IgE synthesis by Der p 1-specific human T-cell clones. J Allergy Clin Immunol. Apr. 1998;101(4 Pt 1):521-30.

Faunce et al., Cutting edge: in vitro-generated tolerogenic APC induce CD8+ T regulatory cells that can suppress ongoing experimental autoimmune encephalomyelitis. J Immunol. Feb. 15, 2004;172(4):1991-5.

Fischer et al., Rapamycin-conditioned, alloantigen-pulsed myeloid dendritic cells present donor MHC class I/peptide via the semi-direct pathway and inhibit survival of antigen-specific CD8(+) T cells in vitro and in vivo. Transpl Immunol. Jul. 2011;25(1):20-6. Epub May 10, 2011.

Gaitonde et al., Downregulation of CD40 signal and induction of TGF-β by phosphatidylinositol mediates reduction in immunogenicity against recombinant human Factor VIII. J Pharm Sci. Jan. 2012;101(1):48-55. doi: 10.1002/jps.22746. Epub Sep. 23, 2011.

Garcia et al., CCR9+ and CD103+ tolerogenic dendritic cell populations in food allergy patients undergoing oral immunotherapy. Clin Transl Allergy. 2011; 1(Suppl 1): O51.

Getts et al., Microparticles bearing encephalitogenic peptides induce T-cell tolerance and ameliorate experimental autoimmune encephalomyelitis. Nat Biotechnol. Nov. 18, 2012. doi: 10.1038/nbt.2434. [Epub ahead of print].

Giannoukakis et al., Phase I (safety) study of autologous tolerogenic dendritic cells in type 1 diabetic patients. Diabetes Care. Sep. 2011;34(9):2026-32. Epub Jun. 16, 2011.

Gray et al., Apoptotic cells protect mice from autoimmune inflammation by the induction of regulatory B cells. Proc Natl Acad Sci U S A. Aug. 28, 2007;104(35):14080-5. Epub Aug. 21, 2007.

Gray et al., What are regulatory B cells? Eur J Immunol. Oct. 2010;40(10):2677-9.

Gross et al., Fulfilling the dream: tolerogenic dendritic cells to treat multiple sclerosis. Eur J Immunol. Mar. 2012;42(3):569-72. doi: 10.1002/eji.201242402.

Hamdy et al., Co-delivery of cancer-associated antigen and Toll-like receptor 4 ligand in PLGA nanoparticles induces potent CD8+ T cell-mediated anti-tumor immunity. Vaccine. Sep. 15, 2008;26(39):5046-57. Epub Aug. 3, 2008.

Hangartner et al., Antiviral immune responses in gene-targeted mice expressing the immunoglobulin heavy chain of virus-neutralizing antibodies. Proc Natl Acad Sci USA. 2003;100:12883-88.

Harry et al., Generation and characterisation of therapeutic tolerogenic dendritic cells for rheumatoid arthritis. Ann Rheum Dis. Nov. 2010;69(11):2042-50. Epub Jun. 15, 2010.

Hawiger et al., Dendritic cells induce peripheral T cell unresponsiveness under steady state conditions in vivo. J Exp Med. 2001;194(6):769-79.

Jordan et al., Promotion of B cell immune responses via an alum-induced myeloid cell population. Science. Jun. 18, 2004;304(5678):1808-10.

Junt et al., Subcapsular sinus macrophages in lymph nodes clear lymph-borne viruses and present them to antiviral B cells. Nature. 2007;450:110-4. Supplemental material.

Kang et al., Cutting edge: Immunosuppressant as adjuvant for tolerogenic immunization. J Immunol. Apr. 15, 2008;180(8):5172-6.

Karrer et al., On the key role of secondary lymphoid organs in antiviral immune responses studied in alymphoplastic (aly/aly) and spleenless (Hox11(−)/−) mutant mice. J Exp Med. 1997;185(12):2157-70.

Katsnelson, Next-generation proteasome inhibitor approved in multiple myeloma. Next-generation proteasome inhibitor approved in multiple myeloma. Nat Biotechnol. Nov. 2012;30(11):1011-2. doi: 10.1038/nbt1112-1011.

Kim et al., Inhibition of follicular T-helper cells by CD8(+) regulatory T cells is essential for self tolerance. Nature. Sep. 16, 2010;467(7313):328-32.

Kingsley et al., Transplantation tolerance: lessons from experimental rodent models. Transpl Int. Oct. 2007;20(10):828-41. Epub Aug. 17, 2007.

Krieg et al., CpG motifs in bacterial DNA trigger direct B-cell activation. Nature. 1995;374(6522):546-9.

Kuwabara et al., Insulin biosynthesis in neuronal progenitors derived from adult hippocampus and the olfactory bulb. EMBO Mol Med. Dec. 2011;3(12):742-54. doi: 10.1002/emmm.201100177. Epub Oct. 10, 2011. E-pub verion.

Lanza et al., Transplantation of encapsulated cells and tissues. Surgery. Jan. 1997;121(1):1-9.

Liu et al., Origin and development of dendritic cells. Immunol Rev. Mar. 2010;234(1):45-54.

Livingston et al., A rational strategy to design multiepitope immunogens based on multiple Thlymphocyte epitopes. J Immunol. Jun. 1, 2002;168(11):5499-506.

Lloyd, Disulphide reduction in lysosomes. The role of cysteine. Biochem J. Jul. 1, 1986;237(1):271-2.

Ludewig et al., Induction of optimal anti-viral neutralizing B cell responses by dendritic cells requires transport and release of virus particles in secondary lymphoid organs. Eur J Immunol. 2000;30(1):185-96.

Lund et al., Effector and regulatory B cells: modulators of CD4(+) T cell immunity. Nat Rev Immunol. Apr. 2010;10(4):236-47. Epub Mar. 12, 2010.

Lutsiak et al., Analysis of poly(D,L-lactic-co-glycolic acid) nanosphere uptake by human dendritic cells and macrophages in vitro. Pharm Res. Oct. 2002;19(10):1480-7.

Martin et al., A vector-based minigene vaccine approach results in strong induction of T-cell responses specific of hepatitis C virus. Vaccine. May 12, 2008;26(20):2471-81. Epub Apr. 1, 2008.

Martinez-Pomares et al., Antigen presentation the macrophage way. Cell. Nov. 16, 2007;131(4):641-3.

Martín-Gayo et al., Plasmacytoid dendritic cells resident in human thymus drive natural Treg cell development. Blood. Jul. 1, 2010;115(26):5366-75. Epub Mar. 31, 2010.

Matta et al., Tolerogenic plasmacytoid DC. Eur J Immunol. Oct. 2010;40(10):2667-76.

Matteoli et al., Gut CD103+ dendritic cells express indoleamine 2,3-dioxygenase which influences T regulatory/T effector cell balance and oral tolerance induction. Gut. May 2010;59(5):595-604.

Maye et al., Comparison of the phagocytosis of two types of cyclosporin (SDZ OXL 400 and SDZ IMM 125) by alveolar macrophages from hamsters. Cell Biol Toxicol. Dec. 1998;14(6):411-8.

Mempel et al., T-cell priming by dendritic cells in lymph nodes occurs in three distinct phases. Nature. 2004;427(6970):154-9.

Meng et al., Statins induce the accumulation of regulatory T cells in atherosclerotic plaque. Mol Med. May 9, 2012;18:598-605. doi: 10.2119/molmed.2011.00471.

Metelitsa et al., Antidisialoganglioside/granulocyte macrophage-colonystimulating factor fusion protein facilitates neutrophil antibody-dependent cellular cytotoxicity and depends on FcγRII (CD32) and Mac-1 (CD11b/CD18) for enhanced effector cell adhesion and azurophil granule exocytosis. Blood. 2002;99(11):4166-73.

(56) References Cited

OTHER PUBLICATIONS

Miyara et al., Therapeutic approaches to allergy and autoimmunity based on FoxP3+ regulatory T-cell activation and expansion. J Allergy Clin Immunol. Apr. 2009;123(4):749-55.
Moghimi et al., Induction of tolerance to factor VIII by transient co-administration with rapamycin. J Thromb Haemost. Aug. 2011;9(8):1524-33. doi: 10.1111/j.1538-7836.2011.04351.x.
Nepom et al., Challenges in the pursuit of immune tolerance. Challenges in the pursuit of immune tolerance. Immunol Rev. May 2011;241(1):49-62. doi: 10.1111/j.1600-065X.2011.01003.x.
Nikolic et al., Plasmacytoid dendritic cells in autoimmune diabetes—potential tools for immunotherapy. Immunobiology. 2009;214(9-10):791-9. Epub Jul. 22, 2009.
Notter et al., Targeting of a B7-1 (CD80) immunoglobulin G fusion protein to acute myeloid leukemia blasts increases their costimulatory activity for autologous remission T cells. Blood. 2001;97(10):3138-45.
Ochsenbein et al., Control of early viral and bacterial distribution and disease by natural antibodies. Science. 1999;286(5447):2156-9.
Ochsenbein et al., Protective T cell-independent antiviral antibody responses are dependent on complement. J Exp Med. 1999;190(8):1165-74.
Oh et al., CD4+CD25+ regulatory T cells in autoimmune arthritis. Immunol Rev. Jan. 2010;233(1):97-111.
Okada et al., Antigen-engaged B cells undergo chemotaxis toward the T zone and form motile conjugates with helper T cells. PLoS Biol. 2005;3(6):e150. 1047-61.
O'Neil et al., Extracellular matrix binding mixed micelles for drug delivery applications. J Control Release. Jul. 20, 2009;137(2):146-51. Epub Mar. 27, 2009.
Orban et al., Prevention of Type 1 Diabetes Mellitus using a Novel Vaccine. Ther Adv Endocrinol Metab. Feb. 2011;2(1):9-16.
O'Sullivan et al., Truncation analysis of several DR binding epitopes. J Immunol. Feb. 15, 1991;146(4):1240-6.
Paolicelli et al., Surface-modified PLGA-based nanoparticles that can efficiently associate and deliver virus-like particles. Nanomedicine (Lond). Aug. 2010;5(6):843-53. doi: 10.2217/nnm.10.69.
Pape et al., The humoral immune response is initiated in lymph nodes by B cells that acquire soluble antigen directly in the follicles. Immunity. 2007;26(4):491-502.
Phillips et al., Enhanced antibody response to liposome-associated protein antigens: preferential stimulation of IgG2a/b production. Vaccine. 1992;10(3):151-8.
Qadura et al., Reduction of the immune response to factor VIII mediated through tolerogenic factor VIII presentation by immature dendritic cells. J Thromb Haemost. Dec. 2008;6(12):2095-104. Epub Sep. 27, 2008.
Qi et al., Extrafollicular activation of lymph node B cells by antigen-bearing dendritic cells. Science. 2006;312(5780):1672-6.
Ragni et al., Factor VIII-pulsed dendritic cells reduce anti-factor VIII antibody formation in the hemophilia A mouse model. Exp Hematol. Jun. 2009;37(6):744-54.
Reddy et al., Exploiting lymphatic transport and complement activation in nanoparticle vaccines. Nat Biotech. 2007;25(10):1159-64.
Reif et al., Balanced responsiveness to chemoattractants from adjacent zones determines B-cell position. Nature. 2002;416(6876):94-9.
Robbins et al., Stable expression of shRNAs in human CD34+ progenitor cells can avoid induction of interferon responses to siRNAs in vitro. Nature Biotechnology. 2006;24(5):566-71.
Rossbacher et al, The B cell receptor itself can activate complement to provide the complement receptor 1/2 ligand required to enhance B cell immune responses in vivo. J Exp Med. 2003;198(4):591-602.
Scardino et al., A polyepitope DNA vaccine targeted to Her-2/ErbB-2 elicits a broad range of human and murine CTL effectors to protect against tumor challenge. Cancer Res. Jul. 15, 2007;67(14):7028-36.
Seffernick et al., Melamine deaminase and atrazine chlorohydrolase: 98 percent identical but functionally different. J Bacteriol. Apr. 2001;183(8):2405-10.
Sharabi et al., The suppression of murine lupus by a tolerogenic peptide involves foxp3-expressing CD8 cells that are required for the optimal induction and function of foxp3-expressing CD4 cells. J Immunol. Sep. 1, 2008;181(5):3243-51.
Shen et al., Enhanced and prolonged cross-presentation following endosomal escape of exogenous antigens encapsulated in biodegradable nanoparticles. Immunol. 2006;117:78-88.
Shiow et al., CD69 acts downstream of interferon-alpha/beta to inhibit S1P1 and lymphocyte egress from lymphoid organs. Nature. Mar. 23, 2006;440(7083):540-4. Epub Mar. 8, 2006.
Shortman et al., Steady-state and inflammatory dendritic-cell development. Nat Rev Immunol. Jan. 2007;7(1):19-30. Epub Dec. 15, 2006.
Sondel et al., Preclinical and clinical development of immunocytokines. Curr Opin Investig Drugs. 2003;4(6):696-700.
Soroosh et al., Th9 and allergic disease. Immunology. Aug. 2009;127(4):450-8. doi: 10.1111/j.1365-2567.2009.03114.x.
Srinivasan et al., Prediction of class I T-cell epitopes: evidence of presence of immunological hot spots inside antigens. Bioinformatics. Aug. 4, 2004;20 Suppl 1:i297-302.
Storm et al., Surface Modification of Nanoparticles to Oppose Uptake by the Mononuclear Phagocyte System. Adv Drug Deliv Rev. 1995;17:31-48.
Tang et al., Adenovirus hexon T-cell epitope is recognized by most adults and is restricted by HLA DP4, the most common class II allele. Gene Ther. Sep. 2004;11(18):1408-15.
Tarlinton et al., Antigen to the node: B cells go native. Immunity. Apr. 2007;26(4):388-90.
Taylor et al., Macrophage receptors and immune recognition. Annu Rev Immunol. 2005;23:901-44.
Turnquist et al., Rapamycin-conditioned dendritic cells are poor stimulators of allogeneic CD4+ T cells, but enrich for antigen-specific Foxp3+ T regulatory cells and promote organ transplant tolerance. J Immunol. Jun. 1, 2007;178(11):7018-31.
Unkeless et al., Structure and function of human and murine receptors for IgG. Annu Rev Immunol. 1998;6:251-81.
Vascotto et al., Antigen presentation by B lymphocytes: how receptor signaling directs membrane trafficking. Curr Opin Immunol. 2007;19(1):93-8.
Velluto et al., PEG-b-PPS diblock copolymer aggregates for hydrophobic drug solubilization and release: cyclosporin A as an example. Mol Pharm. Jul.-Aug. 2008;5(4):632-42. Epub Jun. 12, 2008.
Vila et al., Regulatory T cells and autoimmunity. Curr Opin Hematol. Jul. 2009;16(4):274-9.
Villadangos et al., Found in translation: the human equivalent of mouse CD8+ dendritic cells. J Exp Med. Jun. 7, 2010;207(6):1131-4. Epub May 31, 2010.
Von Andrian et al., Homing and cellular traffic in lymph nodes. Nat Rev Immunol. 2003;3(11):867-78.
Wang et al., A systematic assessment of MHC class II peptide binding predictions and evaluation of a consensus approach. PLoS Comput Biol. Apr. 4, 2008;4(4):e1000048. doi: 10.1371/journal.pcbi.1000048.
Wang et al., Blood mononuclear cells induce regulatory NK T thymocytes in anterior chamber-associated immune deviation. J Leukoc Biol. May 2001;69(5):741-6.
Weber et al., T cell epitope: friend or foe? Immunogenicity of biologics in context. Adv Drug Deliv Rev. Sep. 30, 2009;61(11):965-76. Epub Jul. 18, 2009.
Wessels et al., Studies of group B streptococcal infection in mice deficient in complement component C3 or C4 demonstrate an essential role for complement in both innate and acquired immunity. Proc Natl Acad Sci USA. 1995;92(25):11490-4.
Witkowski et al., Conversion of a beta-ketoacyl synthase to a malonyl decarboxylase by replacement of the active-site cysteine with glutamine Biochemistry. Sep. 7, 1999;38(36):11643-50.
Wu et al., Humanization of a murine monoclonal antibody by simultaneous optimization of framework and CDR residues. J Mol Biol. Nov. 19, 1999;294(1):151-62.

(56) References Cited

OTHER PUBLICATIONS

Yeste et al., Nanoparticle-mediated codelivery of myelin antigen and a tolerogenic small molecule suppresses experimental autoimmune encephalomyelitis. Proc Natl Acad Sci U S A. Jul. 10, 2012;109(28):11270-5. Epub Jun. 27, 2012.
Zhang-Hoover et al., Tolerogenic APC generate CD8+ T regulatory cells that modulate pulmonary interstitial fibrosis. J Immunol. Jan. 1, 2004;172(1):178-85.
Zheng et al., How antigen quantity and quality determine T-cell decisions in lymphoid tissue. Mol Cell Biol. Jun. 2008;28(12):4040-51. Epub Apr. 21, 2008.
Zhu et al., T cell epitope mapping of ragweed pollen allergen Ambrosia artemisiifolia (Amb a 5) and Ambrosia trifida (Amb t 5) and the role of free sulfhydryl groups in T cell recognition. J Immunol. Nov. 15, 1995;155(10):5064-73.
U.S. Appl. No. 13/611,488, filed May 26, 2011, Bratzler et al.
U.S. Appl. No. 13/116,542, filed May 26, 2011, Ilyinskii et al.
U.S. Appl. No. 13/458,021, filed Apr. 27, 2012, Fraser et al.
U.S. Appl. No. 13/458,980, filed Apr. 27, 2012, Altreuter et al.
U.S. Appl. No. 13/458,067, filed Apr. 27, 2012, Fraser et al.
U.S. Appl. No. 13/457,999, filed Apr. 27, 2012, Fraser et al.
U.S. Appl. No. 13/457,977, filed Apr. 27, 2012, Kishimoto et al.
U.S. Appl. No. 13/458,179, filed Apr. 27, 2012, Maldonado et al.
U.S. Appl. No. 14/138,601, filed Dec. 23, 2013, Zepp et al.
PCT/US2012/035431, dated Nov. 28, 2012, International Search Report and Written Opinion.
Extended European Search Report for Application No. EP 12777475.0 dated Feb. 2, 2015.
International Preliminary Report on Patentability for PCT/US2012/035431 dated Nov. 7, 2013.
Bouaziz et al., Regulatory B cells as inhibitors of immune responses and inflammation. Immunol Rev. Aug. 2008;224:201-14. doi: 10.1111/j.1600-065X.2008.00661.x. Review.
Bryant et al., Nanoparticle delivery of donor antigens for transplant tolerance in allogeneic islet transplantation. Biomaterials. Oct. 2014;35(31):8887-94. doi: 10.1016/j.biomaterials.2014.06.044.
Cappellano et al., Subcutaneous inverse vaccination with PLGA particles loaded with a MOG peptide and IL-10 decreases the severity of experimental autoimmune encephalomyelitis. Vaccine. Aug. 20, 2014. pii: S0264-410X(14)01129-3. doi: 10.1016/j.vaccine.2014.08.016. 9 pages.
Davila et al., Cell-based immunotherapy with suppressor CD8+ T cells in rheumatoid arthritis. J Immunol. Jun. 1, 2005;174(11):7292-301.
Dinesh et al., CD8+ Tregs in lupus, autoimmunity, and beyond. Autoimmun Rev. Jun. 2010;9(8):560-8. doi: 10.1016/j.autrev.2010.03.006. Epub Jun. 1, 2011. 21 pages.
Düchs, Dissertation entitled: Effects of Toll-like receptor agonists on the pathogenesis of atopic asthma in mice, University of Würzburg, Sep. 2011. 147 pages.
Eghtesad et al., Effect of rapamycin on immunity induced by vector-mediated dystrophin expression in mdx skeletal muscle. Sci Rep. 2012;2:399. doi: 10.1038/srep00399. Epub May 8, 2012. 6 pages.
Endharti et al., Cutting edge: CD8+CD122+ regulatory T cells produce IL-10 to suppress IFN-gamma production and proliferation of CD8+ T cells. J Immunol. Dec. 1, 2005;175(11):7093-7.
Gao et al., Contrasting effects of cyclosporine and rapamycin in de novo generation of alloantigen-specific regulatory T cells. Am J Transplant. Jul. 2007;7(7):1722-32. Epub May 19, 2007.
Getts et al., Harnessing nanoparticles for immune modulation. Trends Immunol. Jul. 2015;36(7):419-27.
Haddadi, Delivery of rapamycin by PLGA nanoparticles enhances its suppressive activity on dendritic cells. J Biomed Mat Res A. 2007;84A(4):885-98.
Hahn et al., Cellular and molecular mechanisms of regulation of autoantibody production in lupus. Ann N Y Acad Sci. Jun. 2005;1051:433-41. Review. Epub Apr. 10, 2008. 9 pages.

Hahn et al., Tolerogenic treatment of lupus mice with consensus peptide induces Foxp3-expressing, apoptosis-resistant, TGFbeta-secreting CD8+ T cell suppressors. J Immunol. Dec. 1, 2005;175(11):7728-37.
Hamdy et al., Targeting dendritic cells with nano-particulate PLGA cancer vaccine formulations. Adv Drug Deliv Rev. Sep. 10, 2011;63(10-11):943-55. doi: 10.1016/j.addr.2011.05.021. Epub Jun. 6, 2011. Review.
Imamura et al., Pravastatin attenuates allergic airway inflammation by suppressing antigen sensitisation, interleukin 17 production and antigen presentation in the lung. Thorax. Jan. 2009;64(1):44-9. doi: 10.1136/thx.2007.094540. Epub Oct. 3, 2008.
Kang et al., Very low-dose tolerance with nucleosomal peptides controls lupus and induces potent regulatory T cell subsets. J Immunol. Mar. 15, 2005;174(6):3247-55.
Karamloo et al., Prevention of allergy by a recombinant multi-allergen vaccine with reduced IgE binding and preserved T cell epitopes. Eur J Immunol. Nov. 2005;35(11):3268-76.
Keselowsky et al., Multifunctional dendritic cell-targeting polymeric microparticles: engineering new vaccines for type 1 diabetes. Hum Vaccin. Jan. 1, 2011;7(1):37-44. Epub Jan. 1, 2011. Review.
Kim et al., Simvastatin induces Foxp3+ T regulatory cells by modulation of transforming growth factor-beta signal transduction. Immunology. Aug. 2010;130(4):484-93. doi: 10.1111/j.1365-2567.2010.03269.x. Epub Apr. 12, 2010.
Konya et al., Treating autoimmune disease by targeting CD8(+) T suppressor cells. Expert Opin Biol Ther. Aug. 2009;9(8):951-65. doi: 10.1517/14712590903020759. Review. Epub Aug. 1, 2010. 22 pages.
Menzies et al., Simvastatin does not exhibit therapeutic anti-inflammatory effects in asthma. J Allergy Clin Immunol. Feb. 2007;119(2):328-35. Epub Dec. 4, 2006.
Mottram et al., Type 1 and 2 immunity following vaccination is influenced by nanoparticle size: formulation of a model vaccine for respiratory syncytial virus. Mol Pharm. Jan.-Feb. 2007;4(1):73-84.
Nixon et al., Synthetic peptides entrapped in microparticles can elicit cytotoxic T cell activity. Vaccine. Nov. 1996;14(16):1523-30.
Reichardt et al., Impact of Mammalian Target of Rapamycin Inhibition on Lymphoid Homing and Tolerogenic Function of Nanoparticle-Labeled Dendritic Cells following Allogeneic Hematopoietic Cell Transplantation. J Immunol. 2008;181:4770-9.
Shimizu et al., Direct anti-inflammatory mechanisms contribute to attenuation of experimental allograft arteriosclerosis by statins. Circulation. Oct. 28, 2003;108(17):2113-20. Epub Sep. 29, 2003.
Suzuki et al., Inhibitory CD8+ T cells in Autoimmune Disease. Hum Immunol. Nov. 2008;69(11):781-9. doi:10.1016/j.humimm.2008.08.283. Epub Nov. 1, 2009.
Tai et al., A novel rapamycin-polymer conjugate based on a new poly(ethylene glycol) multiblock copolymer. Pharm Res. Mar. 2014;31(3):706-19. doi: 10.1007/s11095-013-1192-3. Epub Sep. 26, 2013.
Tarzi et al., Peptide immunotherapy for allergic disease. Expert Opin Biol Ther. Jul. 2003;3(4):617-26. Review.
Yeste et al., Nanoparticle-mediated codelivery of myelin antigen and a tolerogenic small molecule suppresses experimental autoimmune encephalomyelitis. Proc Natl Acad Sci U S A. Jul. 10, 2012;109(28):11270-5. doi: 10.1073/pnas.1120611109. Epub Jun. 27, 2012.
Zhang et al., The mechanism of B lymphocytes in inducing immune tolerance. Immunol J. Jul. 2010;26(7):643-6.
Aalbers et al., Preclinical Potency and Biodistribution Studies of an AAV 5 Vector Expressing Human Interferon-β (ART-I02) for Local Treatment of Patients with Rheumatoid Arthritis. PLoS One. Jun. 24, 2015;10(6):e0130612. doi:10.1371/journal.pone.0130612. 17 pages.
Amu et al., Regulatory B cells prevent and reverse allergic airway inflammation via FoxP3-positive T regulatory cells in a murine model. J Allergy Clin Immunol. 2010;125:1114-24.
Anguela et al., Robust ZFN-mediated genome editing in adult hemophilic mice. Blood. Nov. 7, 2013;122(19):3283-7. doi: 10.1182/blood-2013-04-497354. Epub Oct. 1, 2013.

(56) References Cited

OTHER PUBLICATIONS

Arruda et al., Strategies to modulate immune responses: a new frontier for gene therapy. Mol Ther. Sep. 2009;17(9):1492-503. doi: 10.1038/mt.2009.150. Epub Jul. 7, 2009. Review.

Barzel et al., Promoterless gene targeting without nucleases ameliorates haemophilia B in mice. Nature. Jan. 15, 2015;517(7534):360-4. doi: 10.1038/nature13864. Epub Jul. 15, 2015. 21 pages.

Battaglia et al., Rapamycin promotes expansion of functional CD4+CD25+FOXP3+ regulatory T cells of both healthy subjects and type 1 diabetic patients. J Immunol. Dec. 15, 2006;177(12):8338-47.

Beevers et al., Curcumin inhibits the mammalian target of rapamycin-mediated signaling pathways in cancer cells. Int J Cancer. Aug. 15, 2006;119(4):757-64.

Binder et al., Tumor necrosis factor-inhibiting therapy preferentially targets bone destruction but not synovial inflammation in a tumor necrosis factor-driven model of rheumatoid arthritis. Arthritis Rheum. Mar. 2013;65(3):608-17. doi: 10.1002/art.37797.

Bisset et al., Therapeutic impact of systemic AAV-mediated RNA interference in a mouse model of myotonic dystrophy. Hum Mol Genet. Sep. 1, 2015;24(17):4971-83. doi: 10.1093/hmg/ddv219. Epub Jun. 16, 2015.

Bocian et al., Rapamycin, unlike cyclosporine A, enhances suppressive functions of in vitro-induced CD4+CD25+ Tregs. Nephrol Dial Transplant. Mar. 2010;25(3):710-7. doi: 10.1093/ndt/gfp586. Epub Nov. 9, 2009.

Brown et al., Endogenous microRNA regulation suppresses transgene expression in hematopoietic lineages and enables stable gene transfer. Nat Med. May 2006;12(5):585-91. Epub Apr. 23, 2006.

Caccamo et al., Rapamycin rescues TDP-43 mislocalization and the associated low molecular mass neurofilament instability. J Biol Chem. Oct. 2, 2009;284(40):27416-24. doi: 10.1074/jbc.M109.031278. Epub Aug. 3, 2009.

Carpentier et al., Effect of alipogene tiparvovec (AAV1-LPL(S447X)) on postprandial chylomicron metabolism in lipoprotein lipase-deficient patients. J Clin Endocrinol Metab. May 2012;97(5):1635-44. doi: 10.1210/jc.2011-3002. Epub Mar. 21, 2012.

Chen et al., Targeting transgene to the heart and liver with AAV9 by different promoters. Clin Exp Pharmacol Physiol. Oct. 2015;42(10):1108-17. doi: 10.1111/1440-1681.12453. Original Article. 24 pages.

Cheng et al., Efficient gene editing in adult mouse livers via adenoviral delivery of CRISPR/Cas9. FEBS Lett. Nov. 3, 2014;588(21):3954-8. doi: 10.1016/j.febslet.2014.09.008. Epub Sep. 19, 2014.

Corti et al., B-Cell Depletion is Protective Against Anti-AAV Capsid Immune Response: A Human Subject Case Study. Mol Ther Methods Clin Dev. 2014;1. pii: 14033. 7 pages.

Dao et al., Pharmacokinetics and pharmacodynamics evaluation of therapeutic protein drugs. China Pharm. Dec. 31, 2007;18(32):2546-7.

Das et al., Delivery of rapamycin-loaded nanoparticle down regulates ICAM-1 expression and maintains an immunosuppressive profile in human CD34+ progenitor-derived dendritic cells. J Biomed Mater Res A. Jun. 15, 2008;85(4):983-92.

Delgoffe et al., The mTOR kinase differentially regulates effector and regulatory T cell lineage commitment. Immunity. Jun. 19, 2009;30(6):832-44. doi: 10.1016/j.immuni.2009.04.014.

Denti et al., Body-wide gene therapy of Duchenne muscular dystrophy in the mdx mouse model. Proc Natl Acad Sci U S A. Mar. 7, 2006;103(10):3758-63. Epub Feb. 24, 2006.

Dinarvand et al., Polylactide-co-glycolide nanoparticles for controlled delivery of anticancer agents. Int J Nanomedicine. 2011;6:877-95. doi: 10.2147/IJN.S18905. Epub May 27, 2011.

Falk et al., Induction and suppression of an autoimmune disease by oligomerized T cell epitopes: enhanced in vivo potency of encephalitogenic peptides. J Exp Med. Feb. 21, 2000;191(4):717-30.

Fourtounas et al., Different immunosuppressive combinations on T-cell regulation in renal transplant recipients. Am J Nephrol. 2010;32(1):1-9. doi: 10.1159/000313940. Epub May 20, 2010.

Fraser et al., Nanoparticle therapy for allergic and inflammatory disease. Anti-Inflammatory & Anti-Allergy Agents Med Chem. Mar. 2010;9(1):54-70.

Gajofatto et al., Treatment strategies for multiple sclerosis: When to start, when to change, when to stop? World J Clin Cases. Jul. 16, 2015;3(7):545-55. doi: 10.12998/wjcc.v3.i7.545.

Goyenvalle et al., Engineering multiple U7snRNA constructs to induce single and multiexon-skipping for Duchenne muscular dystrophy. Mol Ther. Jun. 2012;20(6):1212-21. doi: 10.1038/mt.2012.26. Epub Feb. 21, 2012.

Hamdy et al., Part I: targeted particles for cancer immunotherapy. Curr Drug Deliv. May 2011;8(3):261-73.

Hamdy et al., The immunosuppressive activity of polymeric micellar formulation of cyclosporine A: in vitro and in vivo studies. AAPS J. Jun. 2011;13(2):159-68. doi: 10.1208/s12248-011-9259-8. Epub Feb. 19, 2011.

Händel et al., Versatile and efficient genome editing in human cells by combining zinc-finger nucleases with adeno-associated viral vectors. HumGene Ther. Mar. 2012;23(3):321-9. doi: 10.1089/hum.2011.140. Epub Dec. 14, 2011.

Hui et al., Modulation of CD8+ T cell responses to AAV vectors with IgG-derived MHC class II epitopes. Mol Ther. Sep. 2013;21(9):1727-37. doi: 10.1038/mt.2013.166. Epub Jul. 16, 2013.

Ito et al., A convenient enzyme-linked immunosorbent assay for rapid screening of anti-adeno-associated virus neutralizing antibodies. Ann Clin Biochem. Nov. 2009;46(Pt 6):508-10. doi: 10.1258/acb.2009.009077. Epub Sep. 3, 2009.

Jhunjhunwala et al., Delivery of rapamycin to dendritic cells using degradable microparticles. J Control Release. Feb. 10, 2009;133(3):191-7. doi: 10.1016/j.jconrel.2008.10.011. Epub Oct. 26, 2008.

Jiang et al., Effects of transient immunosuppression on adenoassociated, virus-mediated, liver-directed gene transfer in rhesus macaques and implications for human gene therapy. Blood. Nov. 15, 2006;108(10):3321-8. Epub Jul. 25, 2006.

Kim et al., Effects of cyclosporine and rapamycin on immunoglobulin production by preactivated human B cells. Clin Exp Immunol. Jun. 1994;96(3):508-12.

Lassmann et al., The molecular basis of neurodegeneration in multiple sclerosis. FEBS Lett. Dec. 1, 2011;585(23):3715-23. doi: 10.1016/j.febslet.2011.08.004. Epub Aug. 16, 2011.

Le Hir et al., AAV genome loss from dystrophic mouse muscles during AAV-U7 snRNA-mediated exon-skipping therapy. Mol Ther. Aug. 2013;21(8):1551-8. doi: 10.1038/mt.2013.121. Epub Jun. 11, 2013.

Louis Jeune et al., Pre-existing anti-adeno-associated virus antibodies as a challenge in AAV gene therapy. Hum Gene Ther Methods. Apr. 2013;24(2):59-67. doi: 10.1089/hgtb.2012.243. Epub Apr. 3, 2013. Review.

Lu et al., Rapamycin promotes the expansion of CD4(+) Foxp3(+) regulatory T cells after liver transplantation. Transplant Proc. Jun. 2010;42(5):1755-7. doi: 10.1016/j.transproceed.2009.10.008.

Maldonado et al., Polymeric synthetic nanoparticles for the induction of antigen-specific immunological tolerance. Proc Natl Acad Sci U S A. Jan. 13, 2015;112(2):E156-65. doi: 10.1073/pnas.1408686111. Epub Dec. 29, 2014.

Manno et al., Successful transduction of liver in hemophilia by AAV-Factor IX and limitations imposed by the host immune response. Nat Med. Mar. 2006;12(3):342-7. Epub Feb. 12, 2006. Erratum in: Nat Med. May 2006;12(5):592.

Martino et al., Engineered AAV vector minimizes in vivo targeting of transduced hepatocytes by capsid-specific CD8+ T cells. Blood. Mar. 21, 2013;121(12):2224-33. doi: 10.1182/blood-2012-10-460733. Epub Jan. 16, 2013.

(56) References Cited

OTHER PUBLICATIONS

McMahon et al., Epitope spreading initiates in the CNS in two mouse models of multiple sclerosis. Nat Med. Mar. 2005;11(3):335-9. Epub Feb. 27, 2005.
Meliani et al., Determination of anti-adeno-associated virus vector neutralizing antibody titer with an in vitro reporter system. Hum Gene Ther Methods. Apr. 2015;26(2):45-53. doi: 10.1089/hgtb.2015.037.
Mingozzi et al., Modulation of tolerance to the transgene product in a nonhuman primate model of AAV-mediated gene transfer to liver. Blood. Oct. 1, 2007;110(7):2334-41. Epub Jul. 3, 2007.
Moraes-Fontes et al., Steroid treatments in mice do not alter the number and function of regulatory T cells, but amplify cyclophosphamide-induced autoimmune disease. J Autoimmun. Sep. 2009;33(2):109-20. doi: 10.1016/j.jaut.2009.03.008. Epub Apr. 11, 2009.
Nathwani et al., Adenovirus-associated virus vector-mediated gene transfer in hemophilia B. N Engl J Med. Dec. 22, 2011;365(25):2357-65. doi: 10.1056/NEJMoa1108046. Epub Dec. 10, 2011.
Nathwani et al., Long-term safety and efficacy of factor IX gene therapy in hemophilia B. N Engl J Med. Nov. 20, 2014;371(21):1994-2004. doi: 10.1056/NEJMoa1407309. Epub May 20, 2015. 17 pages.
Nathwani et al., Self-complementary adeno-associated virus vectors containing a novel liverspecific human factor IX expression cassette enable highly efficient transduction of murine and nonhuman primate liver. Blood. Apr. 1, 2006;107(7):2653-61. doi: 10.1182/blood2005104035. Epub Dec. 1, 2005.
Nayak et al., Prevention and Reversal of Antibody Responses Against Factor IX in Gene Therapy for Hemophilia B. Front Microbiol. Dec. 7, 2011;2:244. doi: 10.3389/fmicb.2011.00244. eCollection 2011.
Ngo et al., In the Protein Folding Problem and Tertiary Structure Prediction, 1994. Eds Mertz et al. Birkhauser. Boston, MA. 1994:433,491-5.
Omata et al., Ovalbumin-specific IgE modulates ovalbumin-specific T-cell response after repetitive oral antigen administration. J Allergy Clin Immunol. Apr. 2005;115(4):822-7.
Papisov, Acyclic polyacetals from polysaccharides: biomimetic biomedical "stealth" polymers. Chapter 19. ACS Symposium Series. Feb. 15, 2001:786:301-14.
Platt et al., CRISPR-Cas9 knockin mice for genome editing and cancer modeling. Cell. Oct. 9, 2014;159(2):440-55. doi: 10.1016/j.cell.2014.09.014. Epub Sep. 25, 2014.
Post et al., Adenoviral PR39 improves blood flow and myocardial function in a pig model of chronic myocardial ischemia by enhancing collateral formation. Am J Physiol Regul Integr Comp Physiol. Mar. 2006;290(3):R494-500. Epub Oct. 27, 2005.
Ran et al., In vivo genome editing using *Staphylococcus aureus* Cas9. Nature. Apr. 9, 2015;520(7546):186-91. doi: 10.1038/nature14299. Epub Apr. 1, 2015.
Samuel et al., Polymeric nanoparticles for targeted delivery of Therapeutic Vaccines to dendritic cells. Proceedings of the International Conference on MEMS, NANO and Smart Systems. (ICMENS'03). IEEE 2003. 5 pages.
Sbiera et al., Influence of short-term glucocorticoid therapy on regulatory T cells in vivo. PLoS One. 2011;6(9):e24345. doi: 10.1371/journal.pone.0024345. Epub Sep. 2, 2011.
Schmidt et al., CRISPR genome engineering and viral gene delivery: a case of mutual attraction. Biotechnol J. Feb. 2015;10(2):258-72. doi: 10.1002/biot.201400529. Epub Feb. 6, 2015.
Senís et al., CRISPR/Cas9-mediated genome engineering: an adeno-associated viral (AAV) vector toolbox. Biotechnol J. Nov. 2014;9(11):1402-12. doi: 10.1002/biot.201400046. Epub Oct. 6, 2014. Supporting Information. 26 pages.
Shen et al., Combined effect of cyclosporine and sirolimus on improving the longevity of recombinant adenovirus-mediated transgene expression in the retina. Arch Ophthalmol. Jul. 2001;119(7):1033-43.
Stanek et al., Silencing mutant huntingtin by adeno-associated virus-mediated RNA interference ameliorates disease manifestations in the YAC128 mouse model of Huntington's disease. Hum Gene Ther. May 2014;25(5):461-74. doi: 10.1089/hum.2013.200. Epub Mar. 21, 2014.
Stepkowski et al., Inhibition of host-versus-graft and graft-versus-host responses after small bowel transplantation in rats by rapamycin. Transplantation. Feb. 1992;53(2):258-64.
Tuohy, Peptide determinants of myelin proteolipid protein (PLP) in autoimmune demyelinating disease: a review. Neurochem Res. Aug. 1994;19(8):935-44.
Weber et al., AAV-mediated delivery of zinc finger nucleases targeting hepatitis B virus inhibits active replication. PLoS One. May 14, 2014;9(5):e97579. doi: 10.1371/journal.pone.0097579. eCollection 2014. 14 pages.
Yamaki et al., Preventive and therapeutic effects of rapamycin, a mammalian target of rapamycin inhibitor, on food allergy in mice. Allergy. Oct. 2012;67(10):1259-70. doi: 10.1111/all.12000. Epub Aug. 23, 2012.
Yuan et al., Preparation of rapamycin-loaded chitosan/PLA nanoparticles for immunosuppression in corneal transplantation. Int J Pharm. Feb. 12, 2008;349(1-2):241-8. Epub Aug. 11, 2007.
Zweers, Biodegradable nanoparticles of intravascular drug delivery. Unversiteit Twente, 2003.
"Pluronic." Oxford Dictionary entry accessed via www.oxforddictionary.com on May 6, 2016. 8 pages.
Bae et al., Vinyl sulfone-terminated PEG-PLLA diblock coploymer for thiol-reactive polymeric micelle. Apr. 9, 2009;42(10):3437-42.
Fiorino et al., A single cohort, dose escalation phase 1 study of intravenous infusion of pegsiticase (formerly Uricase-PEG 20), a drug for managing hyperuricemia in refractory gout [Abstract]. Abstracts of the American College of Rheumatology/Association of Rheumatology Health Professionals Annual Scientific Meeting. Atlanta, Georgia. Nov. 6-11, 2010. Arthritis Rheum. Nov. 2010;62 Suppl 10: 144. DOI: 10.1002/art.27913. 2 pages.
Hashimoto et al., Stimulation of host NKT cells by synthetic glycolipid regulates acute graft-versus-host disease by inducing Th2 polarization of donor T cells. J Immunol. Jan. 2005;174(1):551-6.
Neuhaus et al., mTOR inhibitors: an overview. Liver Transpl. Jun. 2001;7(6):473-84.
Samuel et al., Nanoparticle delivery systems for control of immunity. Proceedings of the 2004 Intl. Conference on MEMS, NANO and Smart Systems (CMENS '04). IEEE 2004. 3 pages.
Thomson et al., Immunoregulatory functions of mTOR inhibition. Nat Rev Immunol. May 2009;9(5):324-37. doi: 10.1038/nri2546.
Yamaguchi et al., Around hematological malignancies. Trends in Hematological Malignancies. 2010;2(2):96-98.
Zhou et al., Updates of mTOR inhibitors. Anticancer Agents Med Chem. Sep. 2010;10(7):571-81.
U.S. Appl. No. 12/788,260, filed May 26, 2010, Zepp et al.
U.S. Appl. No. 13/948,129, filed Jul. 22,2013, Zepp et al.
U.S. Appl. No. 13/116,448, filed May 26, 2011, Bratzler et al.
U.S. Appl. No. 14/717,451, filed May 20, 2015, Ilyinskii et al.
[No Author Listed], Clinical Trial of Sel-212, Designed to be the First Non-Immunogenic Biologic Treatment for Gout. Selecta Biosciences. Dec. 23, 2015; 1-5.
Berhanu et al., Pegloticase failure and a possible solution:Immunosuppression to prevent intolerance and inefficacy in patients with gout. Sem in Arth and Rheum. 2016;1-4.
Hershfield et al., Induced and pre-existing anti-polyethylene glycol antibody in a trial of every 3-week dosing of pegloticase for refractory gout, including in organ transplant recipients. Arthritis Research and Therapy. 2014;1-11.
Ishii, Allergen-specific immunotherapy utilizing mechanisms for immune regulation. Jpn J Clin Imunol. 2008;31(5):392-8.
Kishimoto et al., Improving the efficacy and safety of biologic drugs with tolerogenic nanoparticles. Nature Nanotechnology. Aug. 1, 2016; vol. 11:890-901.
Kunisawa et al., Fusogenic liposome functions as an efficient immune-adjuvant in inducing humoral immune-responses to soluble antigen. Drug Delivery System. Jan. 1998;vol. 13(1):216.

(56) References Cited

OTHER PUBLICATIONS

Lipsky et al., Pegloticase immunogenicity: the relationship between efficacy and antibody development in patients treated for refractory chronic gout. Arthritis Research and Therapy. 2014; 1-8.
Macary et al., Ovalbumin-Specific, MHC Class I-restricted, αβ—Postive, Tc1 and Tc0 CD8+T Cell Clones Mediate the In Vivo Inhibition of Rat IgE. J Immunol. 1998;580-7.
McKay et al., A Novel Anti-Inflammatory Role of Simvastatin in a Murine Model of Allergic Asthma. J Immunol. 2004; 2903-8.
Mine et al., Epitope characterization of ovalbumin in BALB/C mice using different entry routes. Biochimica et Biophysica Acta 1774. 2007; 200-12.
Quarcoo et al., Resiquimod, a new immune response modifier from the family of imidazoquinolinamines, inhibits allergen-induced Th2 responses, airway inflammation and airway hyper-reactivity in mice. Clin Exp Allergy. 2004;34:1314-20.
Renz et al., Comparison of the Allergenicity of Ovalbumin and Ovalbumin Peptide 323-339. J Immunol. Dec. 15, 1993; vol. 151: 7206-7213.
U.S. Appl. No. 13/948,129, filed Jul. 22, 2013, Zepp et al.
U.S. Appl. No. 14/273,099, filed May 8, 2014, Zepp et al.
U.S. Appl. No. 12/788,261, filed May 26, 2010, Lipford et al.
U.S. Appl. No. 14/658,040, filed Mar. 13, 2015, Zepp et al.
U.S. Appl. No. 12/862,076, filed Aug. 24, 2010, Fraser et al.
U.S. Appl. No. 13/116,453, filed May 26, 2011, Bratzler et al.
U.S. Appl. No. 12/764,569, filed Apr. 21, 2010, Lipford et al.
U.S. Appl. No. 15/629,973, filed Jun. 22, 2017, Lipford et al.
U.S. Appl. No. 13/116,488, filed May 26, 2011, Bratzler et al.
U.S. Appl. No. 15/684,896, filed Aug. 23, 2017, Ilyinskii et al.
U.S. Appl. No. 13/116,556, filed May 26, 2011, Bratzler et al.
U.S. Appl. No. 13/289,211, filed Nov. 4, 2011, Zepp et al.
U.S. Appl. No. 13/428,340, filed Mar. 23, 2012, Altreuter et al.
U.S. Appl. No. 15/050,397, filed Feb. 22, 2016, Fraser et al.
U.S. Appl. No. 14/810,418, filed Jul. 27, 2015, Fraser et al.
U.S. Appl. No. 14/802,260, filed Jul. 17, 2015, Altreuter et al.
U.S. Appl. No. 13/560,955, filed Jul. 27, 2012, Altreuter et al.
U.S. Appl. No. 14/810,427, filed Jul. 27, 2015, Fraser et al.
U.S. Appl. No. 15/061,096, filed Mar. 4, 2016, Fraser et al.
U.S. Appl. No. 13/457,994, filed Apr. 27, 2012, Fraser et al.
U.S. Appl. No. 14/810,442, filed Jul. 27, 2015, Fraser et al.
U.S. Appl. No. 14/810,450, filed Jul. 27, 2015, Fraser et al.
U.S. Appl. No. 14/810,457, filed Jul. 27, 2015, Kishimoto et al.
U.S. Appl. No. 15/061,204, filed Mar. 4, 2016, Kishimoto et al.
U.S. Appl. No. 13/457,936, filed Apr. 27, 2012, Kishimoto et al.
U.S. Appl. No. 14/810,466, filed Jul. 27, 2015, Kishimoto et al.
U.S. Appl. No. 13/458,220, filed Apr. 27, 2012, Fraser et al.
U.S. Appl. No. 14/810,472, filed Jul. 27, 2015, Fraser et al.
U.S. Appl. No. 14/810,476, filed Jul. 27, 2015, Maldonado.
U.S. Appl. No. 14/269,047, filed May 2, 2014, Maldonado et al.
U.S. Appl. No. 14/296,204, filed Jun. 4, 2014, Maldonado et al.
U.S. Appl. No. 14/269,048, filed May 2, 2014, Maldonado.
U.S. Appl. No. 14/269,054, filed May 2, 2014, Maldonado.
U.S. Appl. No. 14/269,058, filed May 2, 2014, Kishimoto.
U.S. Appl. No. 14/269,056, filed May 2, 2014, Maldonado et al.
U.S. Appl. No. 14/269,042, filed May 2, 2014, Kishimoto et al.
U.S. Appl. No. 14/742,583, filed Jun. 17, 2015, Kishimoto.
U.S. Appl. No. 14/751,106, filed Jun. 25, 2015, Kishimoto et al.
U.S. Appl. No. 14/846,949, filed Sep. 7, 2015, Kishimoto.
U.S. Appl. No. 14/846,952, filed Sep. 7, 2015, Kishimoto.
U.S. Appl. No. 14/846,958, filed Sep. 7, 2015, Kishimoto.
U.S. Appl. No. 14/846,964, filed Sep. 7, 2015, Kishimoto.
U.S. Appl. No. 14/934,132, filed Nov. 5, 2015, Griset et al.
U.S. Appl. No. 14/934,135, filed Nov. 5, 2015, Griset et al.
U.S. Appl. No. 14/846,967, filed Sep. 7, 2015, Kishimoto.
U.S. Appl. No. 15/456,520, filed Mar. 11, 2017, Johnston.
U.S. Appl. No. 15/685,648, filed Aug. 24, 2017, O'Neil.

\* cited by examiner

```
                        SEQUENCE LISTING

<160> NUMBER OF SEQ ID NOS: 943

<210> SEQ ID NO 1
    <211> LENGTH: 18
    <212> TYPE: PRT
    <213> ORGANISM: Artificial Sequence
    <220> FEATURE:
    <223> OTHER INFORMATION: Homo sapiens Aggrecan core protein precursor
          epitope

<400> SEQUENCE: 1

Ala Gly Met Asp Met Cys Ser Ala Gly Trp Leu Ala Asp Arg Ser Val
    1               5                   10                  15

Arg Tyr

<210> SEQ ID NO 2
    <211> LENGTH: 18
    <212> TYPE: PRT
    <213> ORGANISM: Artificial Sequence
    <220> FEATURE:
    <223> OTHER INFORMATION: Homo sapiens Aggrecan core protein precursor
          epitope

<400> SEQUENCE: 2

Glu Asp Ser Glu Ala Thr Leu Glu Val Val Val Lys Gly Ile Val Phe
    1               5                   10                  15

His Tyr

<210> SEQ ID NO 3
    <211> LENGTH: 18
    <212> TYPE: PRT
    <213> ORGANISM: Artificial Sequence
    <220> FEATURE:
    <223> OTHER INFORMATION: Homo sapiens Aggrecan core protein precursor
          epitope

<400> SEQUENCE: 3

Ser Arg Val Ser Lys Glu Lys Glu Val Val Leu Leu Val Ala Thr Glu
    1               5                   10                  15

Gly Arg

<210> SEQ ID NO 4
    <211> LENGTH: 18
    <212> TYPE: PRT
    <213> ORGANISM: Artificial Sequence
    <220> FEATURE:
    <223> OTHER INFORMATION: Homo sapiens Aggrecan core protein precursor
          epitope

<400> SEQUENCE: 4

Val Val Leu Leu Val Ala Thr Glu Gly Arg Val Arg Val Asn Ser Ala
    1               5                   10                  15

Tyr Gln

<210> SEQ ID NO 5
```

-continued

```
<211> LENGTH: 18
<212> TYPE: PRT
<213> ORGANISM: Artificial Sequence
<220> FEATURE:
<223> OTHER INFORMATION: Homo sapiens Aggrecan core protein precursor
      epitope

<400> SEQUENCE: 5

Val Val Val Lys Gly Ile Val Phe His Tyr Arg Ala Ile Ser Thr Arg
1               5                   10                  15

Tyr Thr

<210> SEQ ID NO 6
<211> LENGTH: 9
<212> TYPE: PRT
<213> ORGANISM: Artificial Sequence
<220> FEATURE:
<223> OTHER INFORMATION: Homo sapiens alpha 2 type VI collagen isoform
      2C2 precursor epitope

<400> SEQUENCE: 6

Asp Arg Ala Ser Phe Ile Lys Asn Leu
1               5

<210> SEQ ID NO 7
<211> LENGTH: 20
<212> TYPE: PRT
<213> ORGANISM: Artificial Sequence
<220> FEATURE:
<223> OTHER INFORMATION: Homo sapiens arrestin epitope

<400> SEQUENCE: 7

Ala Ser Ser Thr Ile Ile Lys Glu Gly Ile Asp Arg Thr Val Leu Gly
1               5                   10                  15

Ile Leu Val Ser
            20

<210> SEQ ID NO 8
<211> LENGTH: 20
<212> TYPE: PRT
<213> ORGANISM: Artificial Sequence
<220> FEATURE:
<223> OTHER INFORMATION: Homo sapiens arrestin epitope

<400> SEQUENCE: 8

Ala Ser Thr Pro Thr Lys Leu Gln Glu Ser Leu Leu Lys Lys Leu Gly
1               5                   10                  15

Ser Asn Thr Tyr
            20

<210> SEQ ID NO 9
<211> LENGTH: 20
<212> TYPE: PRT
<213> ORGANISM: Artificial Sequence
<220> FEATURE:
<223> OTHER INFORMATION: Homo sapiens arrestin epitope

<400> SEQUENCE: 9

Asp Arg Thr Val Leu Gly Ile Leu Val Ser Tyr Gln Ile Lys Val Lys
1               5                   10                  15

Leu Thr Val Ser
            20

<210> SEQ ID NO 10
<211> LENGTH: 20
```

```
<212> TYPE: PRT
<213> ORGANISM: Artificial Sequence
<220> FEATURE:
<223> OTHER INFORMATION: Homo sapiens arrestin epitope

<400> SEQUENCE: 10

Glu Phe Ala Arg His Asn Leu Lys Asp Ala Gly Glu Ala Glu Glu Gly
1               5                   10                  15

Lys Arg Asp Lys
            20

<210> SEQ ID NO 11
<211> LENGTH: 20
<212> TYPE: PRT
<213> ORGANISM: Artificial Sequence
<220> FEATURE:
<223> OTHER INFORMATION: Homo sapiens arrestin epitope

<400> SEQUENCE: 11

Glu Pro Asn His Val Ile Phe Lys Lys Ile Ser Arg Asp Lys Ser Val
1               5                   10                  15

Thr Ile Tyr Leu
            20

<210> SEQ ID NO 12
<211> LENGTH: 20
<212> TYPE: PRT
<213> ORGANISM: Artificial Sequence
<220> FEATURE:
<223> OTHER INFORMATION: Homo sapiens arrestin epitope

<400> SEQUENCE: 12

Phe Glu Val Lys Ala Phe Ala Thr Asp Ser Thr Asp Ala Glu Glu Asp
1               5                   10                  15

Lys Ile Pro Lys
            20

<210> SEQ ID NO 13
<211> LENGTH: 20
<212> TYPE: PRT
<213> ORGANISM: Artificial Sequence
<220> FEATURE:
<223> OTHER INFORMATION: Homo sapiens arrestin epitope

<400> SEQUENCE: 13

Gly Phe Leu Gly Glu Leu Thr Ser Ser Glu Val Ala Thr Glu Val Pro
1               5                   10                  15

Phe Arg Leu Met
            20

<210> SEQ ID NO 14
<211> LENGTH: 20
<212> TYPE: PRT
<213> ORGANISM: Artificial Sequence
<220> FEATURE:
<223> OTHER INFORMATION: Homo sapiens arrestin epitope

<400> SEQUENCE: 14

Gly Lys Ile Lys His Glu Asp Thr Asn Leu Ala Ser Ser Thr Ile Ile
1               5                   10                  15

Lys Glu Gly Ile
            20

<210> SEQ ID NO 15
```

```
<211> LENGTH: 20
<212> TYPE: PRT
<213> ORGANISM: Artificial Sequence
<220> FEATURE:
<223> OTHER INFORMATION: Homo sapiens arrestin epitope

<400> SEQUENCE: 15

Gly Asn Arg Asp Tyr Ile Asp His Val Ser Gln Val Gln Pro Val Asp
1               5                   10                  15

Gly Val Val Leu
            20

<210> SEQ ID NO 16
<211> LENGTH: 20
<212> TYPE: PRT
<213> ORGANISM: Artificial Sequence
<220> FEATURE:
<223> OTHER INFORMATION: Homo sapiens arrestin epitope

<400> SEQUENCE: 16

Lys Pro Val Ala Met Glu Glu Ala Gln Glu Lys Val Pro Pro Asn Ser
1               5                   10                  15

Thr Leu Thr Lys
            20

<210> SEQ ID NO 17
<211> LENGTH: 20
<212> TYPE: PRT
<213> ORGANISM: Artificial Sequence
<220> FEATURE:
<223> OTHER INFORMATION: Homo sapiens arrestin epitope

<400> SEQUENCE: 17

Lys Val Pro Pro Asn Ser Thr Leu Thr Lys Thr Leu Thr Leu Leu Pro
1               5                   10                  15

Leu Leu Ala Asn
            20

<210> SEQ ID NO 18
<211> LENGTH: 20
<212> TYPE: PRT
<213> ORGANISM: Artificial Sequence
<220> FEATURE:
<223> OTHER INFORMATION: Homo sapiens arrestin epitope

<400> SEQUENCE: 18

Leu Leu Lys Lys Leu Gly Ser Asn Thr Tyr Pro Phe Leu Leu Thr Phe
1               5                   10                  15

Pro Asp Tyr Leu
            20

<210> SEQ ID NO 19
<211> LENGTH: 20
<212> TYPE: PRT
<213> ORGANISM: Artificial Sequence
<220> FEATURE:
<223> OTHER INFORMATION: Homo sapiens arrestin epitope

<400> SEQUENCE: 19

Leu Thr Phe Arg Arg Asp Leu Tyr Phe Ser Arg Val Gln Val Tyr Pro
1               5                   10                  15

Pro Val Gly Ala
            20
```

```
<210> SEQ ID NO 20
<211> LENGTH: 20
<212> TYPE: PRT
<213> ORGANISM: Artificial Sequence
<220> FEATURE:
<223> OTHER INFORMATION: Homo sapiens arrestin epitope

<400> SEQUENCE: 20

Met Ala Ala Ser Gly Lys Thr Ser Lys Ser Glu Pro Asn His Val Ile
1               5                   10                  15

Phe Lys Lys Ile
            20

<210> SEQ ID NO 21
<211> LENGTH: 20
<212> TYPE: PRT
<213> ORGANISM: Artificial Sequence
<220> FEATURE:
<223> OTHER INFORMATION: Homo sapiens arrestin epitope

<400> SEQUENCE: 21

Asn Arg Glu Arg Arg Gly Ile Ala Leu Asp Gly Lys Ile Lys His Glu
1               5                   10                  15

Asp Thr Asn Leu
            20

<210> SEQ ID NO 22
<211> LENGTH: 20
<212> TYPE: PRT
<213> ORGANISM: Artificial Sequence
<220> FEATURE:
<223> OTHER INFORMATION: Homo sapiens arrestin epitope

<400> SEQUENCE: 22

Pro Cys Ser Val Met Leu Gln Pro Ala Pro Gln Asp Ser Gly Lys Ser
1               5                   10                  15

Cys Gly Val Asp
            20

<210> SEQ ID NO 23
<211> LENGTH: 20
<212> TYPE: PRT
<213> ORGANISM: Artificial Sequence
<220> FEATURE:
<223> OTHER INFORMATION: Homo sapiens arrestin epitope

<400> SEQUENCE: 23

Pro Phe Leu Leu Thr Phe Pro Asp Tyr Leu Pro Cys Ser Val Met Leu
1               5                   10                  15

Gln Pro Ala Pro
            20

<210> SEQ ID NO 24
<211> LENGTH: 20
<212> TYPE: PRT
<213> ORGANISM: Artificial Sequence
<220> FEATURE:
<223> OTHER INFORMATION: Homo sapiens arrestin epitope

<400> SEQUENCE: 24

Gln Asp Ser Gly Lys Ser Cys Gly Val Asp Phe Glu Val Lys Ala Phe
1               5                   10                  15

Ala Thr Asp Ser
            20
```

```
<210> SEQ ID NO 25
<211> LENGTH: 20
<212> TYPE: PRT
<213> ORGANISM: Artificial Sequence
<220> FEATURE:
<223> OTHER INFORMATION: Homo sapiens arrestin epitope

<400> SEQUENCE: 25

Gln Val Gln Pro Val Asp Gly Val Val Leu Val Asp Pro Asp Leu Val
1               5                   10                  15

Lys Gly Lys Lys
            20

<210> SEQ ID NO 26
<211> LENGTH: 20
<212> TYPE: PRT
<213> ORGANISM: Artificial Sequence
<220> FEATURE:
<223> OTHER INFORMATION: Homo sapiens arrestin epitope

<400> SEQUENCE: 26

Arg Val Gln Val Tyr Pro Pro Val Gly Ala Ala Ser Thr Pro Thr Lys
1               5                   10                  15

Leu Gln Glu Ser
            20

<210> SEQ ID NO 27
<211> LENGTH: 20
<212> TYPE: PRT
<213> ORGANISM: Artificial Sequence
<220> FEATURE:
<223> OTHER INFORMATION: Homo sapiens arrestin epitope

<400> SEQUENCE: 27

Ser Arg Asp Lys Ser Val Thr Ile Tyr Leu Gly Asn Arg Asp Tyr Ile
1               5                   10                  15

Asp His Val Ser
            20

<210> SEQ ID NO 28
<211> LENGTH: 20
<212> TYPE: PRT
<213> ORGANISM: Artificial Sequence
<220> FEATURE:
<223> OTHER INFORMATION: Homo sapiens arrestin epitope

<400> SEQUENCE: 28

Thr Leu Thr Leu Leu Pro Leu Leu Ala Asn Asn Arg Glu Arg Arg Gly
1               5                   10                  15

Ile Ala Leu Asp
            20

<210> SEQ ID NO 29
<211> LENGTH: 20
<212> TYPE: PRT
<213> ORGANISM: Artificial Sequence
<220> FEATURE:
<223> OTHER INFORMATION: Homo sapiens arrestin epitope

<400> SEQUENCE: 29

Val Ala Thr Glu Val Pro Phe Arg Leu Met His Pro Gln Pro Glu Asp
1               5                   10                  15

Pro Ala Lys Glu
            20
```

```
<210> SEQ ID NO 30
<211> LENGTH: 20
<212> TYPE: PRT
<213> ORGANISM: Artificial Sequence
<220> FEATURE:
<223> OTHER INFORMATION: Homo sapiens arrestin epitope

<400> SEQUENCE: 30

Val Asp Pro Asp Leu Val Lys Gly Lys Lys Val Tyr Val Thr Leu Thr
1               5                   10                  15

Cys Ala Phe Arg
            20

<210> SEQ ID NO 31
<211> LENGTH: 20
<212> TYPE: PRT
<213> ORGANISM: Artificial Sequence
<220> FEATURE:
<223> OTHER INFORMATION: Homo sapiens arrestin epitope

<400> SEQUENCE: 31

Val Val Leu Tyr Ser Ser Asp Tyr Tyr Val Lys Pro Val Ala Met Glu
1               5                   10                  15

Glu Ala Gln Glu
            20

<210> SEQ ID NO 32
<211> LENGTH: 20
<212> TYPE: PRT
<213> ORGANISM: Artificial Sequence
<220> FEATURE:
<223> OTHER INFORMATION: Homo sapiens arrestin epitope

<400> SEQUENCE: 32

Tyr Gln Ile Lys Val Lys Leu Thr Val Ser Gly Phe Leu Gly Glu Leu
1               5                   10                  15

Thr Ser Ser Glu
            20

<210> SEQ ID NO 33
<211> LENGTH: 9
<212> TYPE: PRT
<213> ORGANISM: Artificial Sequence
<220> FEATURE:
<223> OTHER INFORMATION: Homo sapiens Chain B, Structure Of Insulin
      epitope

<400> SEQUENCE: 33

Ala Leu Tyr Leu Val Cys Gly Glu Arg
1               5

<210> SEQ ID NO 34
<211> LENGTH: 10
<212> TYPE: PRT
<213> ORGANISM: Artificial Sequence
<220> FEATURE:
<223> OTHER INFORMATION: Homo sapiens Chain B, Structure Of Insulin
      epitope

<400> SEQUENCE: 34

Ser His Leu Val Glu Ala Leu Tyr Leu Val
1               5                   10

<210> SEQ ID NO 35
```

```
<211> LENGTH: 9
<212> TYPE: PRT
<213> ORGANISM: Artificial Sequence
<220> FEATURE:
<223> OTHER INFORMATION: Homo sapiens chaperonin (HSP60) epitope

<400> SEQUENCE: 35

Gln Met Arg Pro Val Ser Arg Val Leu
1               5

<210> SEQ ID NO 36
<211> LENGTH: 9
<212> TYPE: PRT
<213> ORGANISM: Artificial Sequence
<220> FEATURE:
<223> OTHER INFORMATION: Homo sapiens Collagen alpha-3(IV) chain epitope

<400> SEQUENCE: 36

Gly Ser Pro Ala Thr Trp Thr Thr Arg
1               5

<210> SEQ ID NO 37
<211> LENGTH: 9
<212> TYPE: PRT
<213> ORGANISM: Artificial Sequence
<220> FEATURE:
<223> OTHER INFORMATION: Homo sapiens collagen, type II, alpha 1 isoform
      1 precursor epitope

<400> SEQUENCE: 37

Ala Arg Gly Gln Pro Gly Val Met Gly
1               5

<210> SEQ ID NO 38
<211> LENGTH: 9
<212> TYPE: PRT
<213> ORGANISM: Artificial Sequence
<220> FEATURE:
<223> OTHER INFORMATION: Homo sapiens DNA topoisomerase 1 epitope

<400> SEQUENCE: 38

Lys Met Leu Asp His Glu Tyr Thr Thr
1               5

<210> SEQ ID NO 39
<211> LENGTH: 9
<212> TYPE: PRT
<213> ORGANISM: Artificial Sequence
<220> FEATURE:
<223> OTHER INFORMATION: Homo sapiens ezrin epitope

<400> SEQUENCE: 39

Glu Tyr Thr Ala Lys Ile Ala Leu Leu
1               5

<210> SEQ ID NO 40
<211> LENGTH: 10
<212> TYPE: PRT
<213> ORGANISM: Artificial Sequence
<220> FEATURE:
<223> OTHER INFORMATION: Homo sapiens ezrin epitope

<400> SEQUENCE: 40

Leu Asn Ile Tyr Glu Lys Asp Asp Lys Leu
1               5                   10

<210> SEQ ID NO 41
```

-continued

```
<211> LENGTH: 9
<212> TYPE: PRT
<213> ORGANISM: Artificial Sequence
<220> FEATURE:
<223> OTHER INFORMATION: Homo sapiens glial fibrillary acidic protein
      isoform 2 epitope

<400> SEQUENCE: 41

Asn Leu Ala Gln Asp Leu Ala Thr Val
1               5

<210> SEQ ID NO 42
<211> LENGTH: 9
<212> TYPE: PRT
<213> ORGANISM: Artificial Sequence
<220> FEATURE:
<223> OTHER INFORMATION: Homo sapiens glial fibrillary acidic protein
      isoform 2 epitope

<400> SEQUENCE: 42

Gln Leu Ala Arg Gln Gln Val His Val
1               5

<210> SEQ ID NO 43
<211> LENGTH: 9
<212> TYPE: PRT
<213> ORGANISM: Artificial Sequence
<220> FEATURE:
<223> OTHER INFORMATION: Homo sapiens glucagon receptor epitope

<400> SEQUENCE: 43

Arg Arg Arg Trp His Arg Trp Arg Leu
1               5

<210> SEQ ID NO 44
<211> LENGTH: 9
<212> TYPE: PRT
<213> ORGANISM: Artificial Sequence
<220> FEATURE:
<223> OTHER INFORMATION: Homo sapiens glucose-6-phosphatase, catalytic,
      related epitope

<400> SEQUENCE: 44

Phe Leu Trp Ser Val Phe Trp Leu Ile
1               5

<210> SEQ ID NO 45
<211> LENGTH: 15
<212> TYPE: PRT
<213> ORGANISM: Artificial Sequence
<220> FEATURE:
<223> OTHER INFORMATION: Homo sapiens Glutamate decarboxylase 1 epitope

<400> SEQUENCE: 45

Asn Met Phe Thr Tyr Glu Ile Ala Pro Val Phe Val Leu Met Glu
1               5                   10                  15

<210> SEQ ID NO 46
<211> LENGTH: 13
<212> TYPE: PRT
<213> ORGANISM: Artificial Sequence
<220> FEATURE:
<223> OTHER INFORMATION: Homo sapiens Glutamate decarboxylase 2 epitope

<400> SEQUENCE: 46

Ile Ala Phe Thr Ser Glu His Ser His Phe Ser Leu Lys
1               5                   10
```

<210> SEQ ID NO 47
<211> LENGTH: 13
<212> TYPE: PRT
<213> ORGANISM: Artificial Sequence
<220> FEATURE:
<223> OTHER INFORMATION: Homo sapiens Glutamate decarboxylase 2 epitope

<400> SEQUENCE: 47

Asn Phe Phe Arg Met Val Ile Ser Asn Pro Ala Ala Thr
1               5                   10

<210> SEQ ID NO 48
<211> LENGTH: 9
<212> TYPE: PRT
<213> ORGANISM: Artificial Sequence
<220> FEATURE:
<223> OTHER INFORMATION: Homo sapiens Glutamate decarboxylase 2 epitope

<400> SEQUENCE: 48

Phe Leu Gln Asp Val Met Asn Ile Leu
1               5

<210> SEQ ID NO 49
<211> LENGTH: 9
<212> TYPE: PRT
<213> ORGANISM: Artificial Sequence
<220> FEATURE:
<223> OTHER INFORMATION: Homo sapiens Glutamate decarboxylase 2 epitope

<400> SEQUENCE: 49

Leu Leu Gln Glu Tyr Asn Trp Glu Leu
1               5

<210> SEQ ID NO 50
<211> LENGTH: 10
<212> TYPE: PRT
<213> ORGANISM: Artificial Sequence
<220> FEATURE:
<223> OTHER INFORMATION: Homo sapiens Glutamate decarboxylase 2 epitope

<400> SEQUENCE: 50

Arg Met Met Glu Tyr Gly Thr Thr Met Val
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Homo sapiens Glutamate decarboxylase 2 epitope

<400> SEQUENCE: 51

Val Met Asn Ile Leu Leu Gln Tyr Val Val
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Homo sapiens Glutamate decarboxylase 2 epitope

<400> SEQUENCE: 52

Ala Phe Thr Ser Glu His Ser His Phe Ser Leu
1               5                   10

```
<210> SEQ ID NO 53
<211> LENGTH: 12
<212> TYPE: PRT
<213> ORGANISM: Artificial Sequence
<220> FEATURE:
<223> OTHER INFORMATION: Homo sapiens Glutamate decarboxylase 2 epitope

<400> SEQUENCE: 53

Ala Phe Thr Ser Glu His Ser His Phe Ser Leu Lys
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Homo sapiens Glutamate decarboxylase 2 epitope

<400> SEQUENCE: 54

Phe Lys Met Phe Pro Glu Val Lys Glu Lys Gly
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Homo sapiens Glutamate decarboxylase 2 epitope

<400> SEQUENCE: 55

Phe Thr Ser Glu His Ser His Phe Ser Leu
1               5                   10

<210> SEQ ID NO 56
<211> LENGTH: 15
<212> TYPE: PRT
<213> ORGANISM: Artificial Sequence
<220> FEATURE:
<223> OTHER INFORMATION: Homo sapiens Glutamate decarboxylase 2 epitope

<400> SEQUENCE: 56

Met Ile Ala Arg Phe Lys Met Phe Pro Glu Val Lys Glu Lys Gly
1               5                   10                  15

<210> SEQ ID NO 57
<211> LENGTH: 9
<212> TYPE: PRT
<213> ORGANISM: Artificial Sequence
<220> FEATURE:
<223> OTHER INFORMATION: Homo sapiens Glutamate decarboxylase 2 epitope

<400> SEQUENCE: 57

Arg Phe Lys Met Phe Pro Glu Val Lys
1               5

<210> SEQ ID NO 58
<211> LENGTH: 10
<212> TYPE: PRT
<213> ORGANISM: Artificial Sequence
<220> FEATURE:
<223> OTHER INFORMATION: Homo sapiens Glutamate decarboxylase 2 epitope

<400> SEQUENCE: 58

Arg Phe Lys Met Phe Pro Glu Val Lys Glu
1               5                   10

<210> SEQ ID NO 59
```

```
<211> LENGTH: 11
<212> TYPE: PRT
<213> ORGANISM: Artificial Sequence
<220> FEATURE:
<223> OTHER INFORMATION: Homo sapiens Glutamate decarboxylase 2 epitope

<400> SEQUENCE: 59

Arg Phe Lys Met Phe Pro Glu Val Lys Glu Lys
1               5                   10

<210> SEQ ID NO 60
<211> LENGTH: 9
<212> TYPE: PRT
<213> ORGANISM: Artificial Sequence
<220> FEATURE:
<223> OTHER INFORMATION: Homo sapiens Glutamate decarboxylase 2 epitope

<400> SEQUENCE: 60

Thr Ser Glu His Ser His Phe Ser Leu
1               5

<210> SEQ ID NO 61
<211> LENGTH: 9
<212> TYPE: PRT
<213> ORGANISM: Artificial Sequence
<220> FEATURE:
<223> OTHER INFORMATION: Homo sapiens Glutamate decarboxylase 2 epitope

<400> SEQUENCE: 61

Val Met Asn Ile Leu Leu Gln Tyr Val
1               5

<210> SEQ ID NO 62
<211> LENGTH: 9
<212> TYPE: PRT
<213> ORGANISM: Artificial Sequence
<220> FEATURE:
<223> OTHER INFORMATION: Homo sapiens Glutamate decarboxylase 2 epitope

<400> SEQUENCE: 62

Glu Leu Ala Glu Tyr Leu Tyr Asn Ile
1               5

<210> SEQ ID NO 63
<211> LENGTH: 9
<212> TYPE: PRT
<213> ORGANISM: Artificial Sequence
<220> FEATURE:
<223> OTHER INFORMATION: Homo sapiens Glutamate decarboxylase 2 epitope

<400> SEQUENCE: 63

Ile Leu Met His Cys Gln Thr Thr Leu
1               5

<210> SEQ ID NO 64
<211> LENGTH: 11
<212> TYPE: PRT
<213> ORGANISM: Artificial Sequence
<220> FEATURE:
<223> OTHER INFORMATION: Homo sapiens heat shock 27kDa protein 1 epitope

<400> SEQUENCE: 64

Gln Leu Ser Ser Gly Val Ser Glu Ile Arg His
1               5                   10

<210> SEQ ID NO 65
<211> LENGTH: 9
```

```
<212> TYPE: PRT
<213> ORGANISM: Artificial Sequence
<220> FEATURE:
<223> OTHER INFORMATION: Homo sapiens HLA class I histocompatibility
      antigen, B-27 alpha chain precursor epitope

<400> SEQUENCE: 65

Leu Arg Arg Tyr Leu Glu Asn Gly Lys
1               5

<210> SEQ ID NO 66
<211> LENGTH: 9
<212> TYPE: PRT
<213> ORGANISM: Artificial Sequence
<220> FEATURE:
<223> OTHER INFORMATION: Homo sapiens HLA class I histocompatibility
      antigen, B-7 alpha chain precursor epitope

<400> SEQUENCE: 66

Val Met Ala Pro Arg Thr Val Leu Leu
1               5

<210> SEQ ID NO 67
<211> LENGTH: 14
<212> TYPE: PRT
<213> ORGANISM: Artificial Sequence
<220> FEATURE:
<223> OTHER INFORMATION: Homo sapiens HLA class I histocompatibility
      antigen, B-7 alpha chain precursor epitope

<400> SEQUENCE: 67

Ala Leu Asn Glu Asp Leu Arg Ser Trp Thr Ala Ala Asp Thr
1               5                   10

<210> SEQ ID NO 68
<211> LENGTH: 14
<212> TYPE: PRT
<213> ORGANISM: Artificial Sequence
<220> FEATURE:
<223> OTHER INFORMATION: Homo sapiens HLA-B27 epitope

<400> SEQUENCE: 68

Ala Leu Asn Glu Asp Leu Ser Ser Trp Thr Ala Ala Asp Thr
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Homo sapiens HLA-B27 epitope

<400> SEQUENCE: 69

Leu Leu Arg Gly Tyr His Gln Asp Ala Tyr
1               5                   10

<210> SEQ ID NO 70
<211> LENGTH: 15
<212> TYPE: PRT
<213> ORGANISM: Artificial Sequence
<220> FEATURE:
<223> OTHER INFORMATION: Homo sapiens HLA-B27 epitope

<400> SEQUENCE: 70

Arg Val Ala Glu Gln Leu Arg Ala Tyr Leu Glu Gly Glu Cys Val
1               5                   10                  15
```

```
<210> SEQ ID NO 71
<211> LENGTH: 13
<212> TYPE: PRT
<213> ORGANISM: Artificial Sequence
<220> FEATURE:
<223> OTHER INFORMATION: Homo sapiens HLA-B27 epitope

<400> SEQUENCE: 71

Trp Asp Arg Glu Thr Gln Ile Cys Lys Ala Lys Ala Gln
1               5                   10

<210> SEQ ID NO 72
<211> LENGTH: 11
<212> TYPE: PRT
<213> ORGANISM: Artificial Sequence
<220> FEATURE:
<223> OTHER INFORMATION: Homo sapiens insulin epitope

<400> SEQUENCE: 72

Ala Leu Trp Gly Pro Asp Pro Ala Ala Ala Phe
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Homo sapiens insulin epitope

<400> SEQUENCE: 73

Leu Ala Leu Trp Gly Pro Asp Pro Ala Ala
1               5                   10

<210> SEQ ID NO 74
<211> LENGTH: 11
<212> TYPE: PRT
<213> ORGANISM: Artificial Sequence
<220> FEATURE:
<223> OTHER INFORMATION: Homo sapiens insulin epitope

<400> SEQUENCE: 74

Arg Leu Leu Pro Leu Leu Ala Leu Leu Ala Leu
1               5                   10

<210> SEQ ID NO 75
<211> LENGTH: 9
<212> TYPE: PRT
<213> ORGANISM: Artificial Sequence
<220> FEATURE:
<223> OTHER INFORMATION: Homo sapiens Insulin precursor epitope

<400> SEQUENCE: 75

Ala Leu Trp Met Arg Leu Leu Pro Leu
1               5

<210> SEQ ID NO 76
<211> LENGTH: 9
<212> TYPE: PRT
<213> ORGANISM: Artificial Sequence
<220> FEATURE:
<223> OTHER INFORMATION: Homo sapiens Insulin precursor epitope

<400> SEQUENCE: 76

His Leu Val Glu Ala Leu Tyr Leu Val
1               5

<210> SEQ ID NO 77
```

```
<211> LENGTH: 10
<212> TYPE: PRT
<213> ORGANISM: Artificial Sequence
<220> FEATURE:
<223> OTHER INFORMATION: Homo sapiens Insulin precursor epitope

<400> SEQUENCE: 77

Ser Leu Gln Lys Arg Gly Ile Val Glu Gln
1               5                   10

<210> SEQ ID NO 78
<211> LENGTH: 9
<212> TYPE: PRT
<213> ORGANISM: Artificial Sequence
<220> FEATURE:
<223> OTHER INFORMATION: Homo sapiens Insulin precursor epitope

<400> SEQUENCE: 78

Ser Leu Gln Pro Leu Ala Leu Glu Gly
1               5

<210> SEQ ID NO 79
<211> LENGTH: 9
<212> TYPE: PRT
<213> ORGANISM: Artificial Sequence
<220> FEATURE:
<223> OTHER INFORMATION: Homo sapiens Insulin precursor epitope

<400> SEQUENCE: 79

Ser Leu Tyr Gln Leu Glu Asn Tyr Cys
1               5

<210> SEQ ID NO 80
<211> LENGTH: 10
<212> TYPE: PRT
<213> ORGANISM: Artificial Sequence
<220> FEATURE:
<223> OTHER INFORMATION: Homo sapiens Insulin precursor epitope

<400> SEQUENCE: 80

Val Cys Gly Glu Arg Gly Phe Phe Tyr Thr
1               5                   10

<210> SEQ ID NO 81
<211> LENGTH: 8
<212> TYPE: PRT
<213> ORGANISM: Artificial Sequence
<220> FEATURE:
<223> OTHER INFORMATION: Homo sapiens Insulin precursor epitope

<400> SEQUENCE: 81

Trp Gly Pro Asp Pro Ala Ala Ala
1               5

<210> SEQ ID NO 82
<211> LENGTH: 9
<212> TYPE: PRT
<213> ORGANISM: Artificial Sequence
<220> FEATURE:
<223> OTHER INFORMATION: Homo sapiens Insulin precursor epitope

<400> SEQUENCE: 82

Phe Tyr Thr Pro Lys Thr Arg Arg Glu
1               5

<210> SEQ ID NO 83
<211> LENGTH: 8
```

```
<212> TYPE: PRT
<213> ORGANISM: Artificial Sequence
<220> FEATURE:
<223> OTHER INFORMATION: Homo sapiens Insulin precursor epitope

<400> SEQUENCE: 83

Gly Glu Arg Gly Phe Phe Tyr Thr
1               5

<210> SEQ ID NO 84
<211> LENGTH: 9
<212> TYPE: PRT
<213> ORGANISM: Artificial Sequence
<220> FEATURE:
<223> OTHER INFORMATION: Homo sapiens Insulin precursor epitope

<400> SEQUENCE: 84

Glu Arg Gly Phe Phe Tyr Thr Pro Lys
1               5

<210> SEQ ID NO 85
<211> LENGTH: 10
<212> TYPE: PRT
<213> ORGANISM: Artificial Sequence
<220> FEATURE:
<223> OTHER INFORMATION: Homo sapiens Insulin precursor epitope

<400> SEQUENCE: 85

Leu Cys Gly Ser His Leu Val Glu Ala Leu
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Homo sapiens Insulin precursor epitope

<400> SEQUENCE: 86

Leu Val Cys Gly Glu Arg Gly Phe Phe Tyr
1               5                   10

<210> SEQ ID NO 87
<211> LENGTH: 10
<212> TYPE: PRT
<213> ORGANISM: Artificial Sequence
<220> FEATURE:
<223> OTHER INFORMATION: Homo sapiens Insulin precursor epitope

<400> SEQUENCE: 87

Leu Tyr Leu Val Cys Gly Glu Arg Gly Phe
1               5                   10

<210> SEQ ID NO 88
<211> LENGTH: 9
<212> TYPE: PRT
<213> ORGANISM: Artificial Sequence
<220> FEATURE:
<223> OTHER INFORMATION: Homo sapiens Islet amyloid polypeptide
      precursor epitope

<400> SEQUENCE: 88

Phe Leu Ile Val Leu Ser Val Ala Leu
1               5

<210> SEQ ID NO 89
<211> LENGTH: 9
```

```
<212> TYPE: PRT
<213> ORGANISM: Artificial Sequence
<220> FEATURE:
<223> OTHER INFORMATION: Homo sapiens Islet amyloid polypeptide
      precursor epitope

<400> SEQUENCE: 89

Lys Leu Gln Val Phe Leu Ile Val Leu
1               5

<210> SEQ ID NO 90
<211> LENGTH: 9
<212> TYPE: PRT
<213> ORGANISM: Artificial Sequence
<220> FEATURE:
<223> OTHER INFORMATION: Homo sapiens islet-specific glucose-6-
      phosphatase-related protein epitope

<400> SEQUENCE: 90

Phe Leu Trp Ser Val Phe Met Leu Ile
1               5

<210> SEQ ID NO 91
<211> LENGTH: 9
<212> TYPE: PRT
<213> ORGANISM: Artificial Sequence
<220> FEATURE:
<223> OTHER INFORMATION: Homo sapiens islet-specific glucose-6-
      phosphatase-related protein isoform 1 epitope

<400> SEQUENCE: 91

Phe Leu Phe Ala Val Gly Phe Tyr Leu
1               5

<210> SEQ ID NO 92
<211> LENGTH: 9
<212> TYPE: PRT
<213> ORGANISM: Artificial Sequence
<220> FEATURE:
<223> OTHER INFORMATION: Homo sapiens islet-specific glucose-6-
      phosphatase-related protein isoform 1 epitope

<400> SEQUENCE: 92

Leu Asn Ile Asp Leu Leu Trp Ser Val
1               5

<210> SEQ ID NO 93
<211> LENGTH: 9
<212> TYPE: PRT
<213> ORGANISM: Artificial Sequence
<220> FEATURE:
<223> OTHER INFORMATION: Homo sapiens islet-specific glucose-6-
      phosphatase-related protein isoform 1 epitope

<400> SEQUENCE: 93

Val Leu Phe Gly Leu Gly Phe Ala Ile
1               5

<210> SEQ ID NO 94
<211> LENGTH: 9
<212> TYPE: PRT
<213> ORGANISM: Artificial Sequence
<220> FEATURE:
<223> OTHER INFORMATION: Homo sapiens islet-specific glucose-6-
      phosphatase-related protein isoform 1 epitope

<400> SEQUENCE: 94

Asn Leu Phe Leu Phe Leu Phe Ala Val
```

```
<210> SEQ ID NO 95
<211> LENGTH: 9
<212> TYPE: PRT
<213> ORGANISM: Artificial Sequence
<220> FEATURE:
<223> OTHER INFORMATION: Homo sapiens islet-specific glucose-6-
      phosphatase-related protein isoform 1 epitope

<400> SEQUENCE: 95

Tyr Leu Leu Leu Arg Val Leu Asn Ile
1               5

<210> SEQ ID NO 96
<211> LENGTH: 9
<212> TYPE: PRT
<213> ORGANISM: Artificial Sequence
<220> FEATURE:
<223> OTHER INFORMATION: Homo sapiens keratin 6C epitope

<400> SEQUENCE: 96

Ala Leu Gln Lys Ala Lys Gln Asp Leu
1               5

<210> SEQ ID NO 97
<211> LENGTH: 9
<212> TYPE: PRT
<213> ORGANISM: Artificial Sequence
<220> FEATURE:
<223> OTHER INFORMATION: Homo sapiens keratin 6C epitope

<400> SEQUENCE: 97

Asp Ala Lys Asn Lys Leu Glu Gly Leu
1               5

<210> SEQ ID NO 98
<211> LENGTH: 9
<212> TYPE: PRT
<213> ORGANISM: Artificial Sequence
<220> FEATURE:
<223> OTHER INFORMATION: Homo sapiens keratin 6C epitope

<400> SEQUENCE: 98

Gly Ala Ser Gly Val Gly Ser Gly Leu
1               5

<210> SEQ ID NO 99
<211> LENGTH: 9
<212> TYPE: PRT
<213> ORGANISM: Artificial Sequence
<220> FEATURE:
<223> OTHER INFORMATION: Homo sapiens keratin 6C epitope

<400> SEQUENCE: 99

Lys Ala Lys Gln Asp Leu Ala Arg Leu
1               5

<210> SEQ ID NO 100
<211> LENGTH: 9
<212> TYPE: PRT
<213> ORGANISM: Artificial Sequence
<220> FEATURE:
<223> OTHER INFORMATION: Homo sapiens keratin 6C epitope

<400> SEQUENCE: 100

Lys Leu Glu Gly Leu Glu Asp Ala Leu
```

```
1               5

<210> SEQ ID NO 101
<211> LENGTH: 9
<212> TYPE: PRT
<213> ORGANISM: Artificial Sequence
<220> FEATURE:
<223> OTHER INFORMATION: Homo sapiens keratin 6C epitope

<400> SEQUENCE: 101

Asn Met Gln Asp Leu Val Glu Asp Leu
1               5

<210> SEQ ID NO 102
<211> LENGTH: 9
<212> TYPE: PRT
<213> ORGANISM: Artificial Sequence
<220> FEATURE:
<223> OTHER INFORMATION: Homo sapiens keratin 6C epitope

<400> SEQUENCE: 102

Arg Leu Leu Lys Glu Tyr Gln Glu Leu
1               5

<210> SEQ ID NO 103
<211> LENGTH: 9
<212> TYPE: PRT
<213> ORGANISM: Artificial Sequence
<220> FEATURE:
<223> OTHER INFORMATION: Homo sapiens keratin 6C epitope

<400> SEQUENCE: 103

Trp Tyr Gln Thr Lys Tyr Glu Glu Leu
1               5

<210> SEQ ID NO 104
<211> LENGTH: 20
<212> TYPE: PRT
<213> ORGANISM: Artificial Sequence
<220> FEATURE:
<223> OTHER INFORMATION: Homo sapiens Keratin, type I cytoskeletal 17
      (Cytokeratin 17) (K17) (CK 17) (Version 2) epitope

<400> SEQUENCE: 104

Leu Arg Arg Val Leu Asp Glu Leu Thr Leu Ala Arg Thr Asp Leu Glu
1               5                   10                  15

Met Gln Ile Glu
            20

<210> SEQ ID NO 105
<211> LENGTH: 9
<212> TYPE: PRT
<213> ORGANISM: Artificial Sequence
<220> FEATURE:
<223> OTHER INFORMATION: Homo sapiens Keratin, type I cytoskeletal 17
      (Cytokeratin 17) (K17) (CK 17) (Version 2) epitope

<400> SEQUENCE: 105

Ala Leu Glu Glu Ala Asn Ala Asp Leu
1               5

<210> SEQ ID NO 106
<211> LENGTH: 9
<212> TYPE: PRT
<213> ORGANISM: Artificial Sequence
<220> FEATURE:
<223> OTHER INFORMATION: Homo sapiens Keratin, type I cytoskeletal 17
```

(Cytokeratin 17) (K17) (CK 17) (Version 2) epitope

<400> SEQUENCE: 106

Ala Asn Ala Asp Leu Glu Val Lys Ile
1               5

<210> SEQ ID NO 107
<211> LENGTH: 9
<212> TYPE: PRT
<213> ORGANISM: Artificial Sequence
<220> FEATURE:
<223> OTHER INFORMATION: Homo sapiens Keratin, type I cytoskeletal 17
      (Cytokeratin 17) (K17) (CK 17) (Version 2) epitope

<400> SEQUENCE: 107

Ala Arg Thr Asp Leu Glu Met Gln Ile
1               5

<210> SEQ ID NO 108
<211> LENGTH: 9
<212> TYPE: PRT
<213> ORGANISM: Artificial Sequence
<220> FEATURE:
<223> OTHER INFORMATION: Homo sapiens Keratin, type I cytoskeletal 17
      (Cytokeratin 17) (K17) (CK 17) (Version 2) epitope

<400> SEQUENCE: 108

Ala Ser Tyr Leu Asp Lys Val Arg Ala
1               5

<210> SEQ ID NO 109
<211> LENGTH: 9
<212> TYPE: PRT
<213> ORGANISM: Artificial Sequence
<220> FEATURE:
<223> OTHER INFORMATION: Homo sapiens Keratin, type I cytoskeletal 17
      (Cytokeratin 17) (K17) (CK 17) (Version 2) epitope

<400> SEQUENCE: 109

Asp Val Asn Gly Leu Arg Arg Val Leu
1               5

<210> SEQ ID NO 110
<211> LENGTH: 9
<212> TYPE: PRT
<213> ORGANISM: Artificial Sequence
<220> FEATURE:
<223> OTHER INFORMATION: Homo sapiens Keratin, type I cytoskeletal 17
      (Cytokeratin 17) (K17) (CK 17) (Version 2) epitope

<400> SEQUENCE: 110

Gly Leu Arg Arg Val Leu Asp Glu Leu
1               5

<210> SEQ ID NO 111
<211> LENGTH: 12
<212> TYPE: PRT
<213> ORGANISM: Artificial Sequence
<220> FEATURE:
<223> OTHER INFORMATION: Homo sapiens Keratin, type I cytoskeletal 17
      (Cytokeratin 17) (K17) (CK 17) (Version 2) epitope

<400> SEQUENCE: 111

Ile Ser Ser Val Leu Ala Gly Ala Ser Cys Pro Ala
1               5                   10

<210> SEQ ID NO 112

```
<211> LENGTH: 9
<212> TYPE: PRT
<213> ORGANISM: Artificial Sequence
<220> FEATURE:
<223> OTHER INFORMATION: Homo sapiens Keratin, type I cytoskeletal 17
      (Cytokeratin 17) (K17) (CK 17) (Version 2) epitope

<400> SEQUENCE: 112

Leu Asp Lys Val Arg Ala Leu Glu Glu
1               5

<210> SEQ ID NO 113
<211> LENGTH: 9
<212> TYPE: PRT
<213> ORGANISM: Artificial Sequence
<220> FEATURE:
<223> OTHER INFORMATION: Homo sapiens Keratin, type I cytoskeletal 17
      (Cytokeratin 17) (K17) (CK 17) (Version 2) epitope

<400> SEQUENCE: 113

Gln Ile Glu Gly Leu Lys Glu Glu Leu
1               5

<210> SEQ ID NO 114
<211> LENGTH: 12
<212> TYPE: PRT
<213> ORGANISM: Artificial Sequence
<220> FEATURE:
<223> OTHER INFORMATION: Homo sapiens Keratin, type I cytoskeletal 17
      (Cytokeratin 17) (K17) (CK 17) (Version 2) epitope

<400> SEQUENCE: 114

Arg Ala Leu Glu Glu Ala Asn Ala Asp Leu Glu Val
1               5                   10

<210> SEQ ID NO 115
<211> LENGTH: 9
<212> TYPE: PRT
<213> ORGANISM: Artificial Sequence
<220> FEATURE:
<223> OTHER INFORMATION: Homo sapiens Keratin, type I cytoskeletal 17
      (Cytokeratin 17) (K17) (CK 17) (Version 2) epitope

<400> SEQUENCE: 115

Arg Leu Ala Ser Tyr Leu Asp Lys Val
1               5

<210> SEQ ID NO 116
<211> LENGTH: 8
<212> TYPE: PRT
<213> ORGANISM: Artificial Sequence
<220> FEATURE:
<223> OTHER INFORMATION: Homo sapiens Keratin, type I cytoskeletal 17
      (Cytokeratin 17) (K17) (CK 17) (Version 2) epitope

<400> SEQUENCE: 116

Ser Tyr Leu Asp Lys Val Arg Ala
1               5

<210> SEQ ID NO 117
<211> LENGTH: 20
<212> TYPE: PRT
<213> ORGANISM: Artificial Sequence
<220> FEATURE:
<223> OTHER INFORMATION: Homo sapiens Keratin, type I cytoskeletal 17
      (Cytokeratin 17) (K17) (CK 17) (Version 2) epitope

<400> SEQUENCE: 117
```

```
Ser Tyr Leu Asp Lys Val Arg Ala Leu Glu Glu Ala Asn Ala Asp Leu
1               5                   10                  15

Glu Val Lys Ile
            20

<210> SEQ ID NO 118
<211> LENGTH: 9
<212> TYPE: PRT
<213> ORGANISM: Artificial Sequence
<220> FEATURE:
<223> OTHER INFORMATION: Homo sapiens maspin epitope

<400> SEQUENCE: 118

Gly Leu Glu Lys Ile Glu Lys Gln Leu
1               5

<210> SEQ ID NO 119
<211> LENGTH: 10
<212> TYPE: PRT
<213> ORGANISM: Artificial Sequence
<220> FEATURE:
<223> OTHER INFORMATION: Homo sapiens maspin epitope

<400> SEQUENCE: 119

Met Gly Asn Ile Asp Ser Ile Asn Cys Lys
1               5                   10

<210> SEQ ID NO 120
<211> LENGTH: 9
<212> TYPE: PRT
<213> ORGANISM: Artificial Sequence
<220> FEATURE:
<223> OTHER INFORMATION: Homo sapiens maspin epitope

<400> SEQUENCE: 120

Tyr Ser Leu Lys Leu Ile Lys Arg Leu
1               5

<210> SEQ ID NO 121
<211> LENGTH: 20
<212> TYPE: PRT
<213> ORGANISM: Artificial Sequence
<220> FEATURE:
<223> OTHER INFORMATION: Homo sapiens MBP protein epitope

<400> SEQUENCE: 121

Ala Ser Gln Lys Arg Pro Ser Gln Arg His Gly Ser Lys Tyr Leu Ala
1               5                   10                  15

Thr Ala Ser Thr
            20

<210> SEQ ID NO 122
<211> LENGTH: 15
<212> TYPE: PRT
<213> ORGANISM: Artificial Sequence
<220> FEATURE:
<223> OTHER INFORMATION: Homo sapiens MBP protein epitope

<400> SEQUENCE: 122

Glu Asn Pro Val Val His Phe Phe Lys Asn Ile Val Thr Pro Arg
1               5                   10                  15

<210> SEQ ID NO 123
<211> LENGTH: 9
<212> TYPE: PRT
<213> ORGANISM: Artificial Sequence
```

```
<220> FEATURE:
<223> OTHER INFORMATION: Homo sapiens MBP protein epitope

<400> SEQUENCE: 123

Val Val His Phe Phe Lys Asn Ile Val
1               5

<210> SEQ ID NO 124
<211> LENGTH: 19
<212> TYPE: PRT
<213> ORGANISM: Artificial Sequence
<220> FEATURE:
<223> OTHER INFORMATION: Homo sapiens MBP protein epitope

<400> SEQUENCE: 124

Asp Glu Asn Pro Val Val His Phe Phe Lys Asn Ile Val Thr Pro Arg
1               5                   10                  15

Thr Pro Pro

<210> SEQ ID NO 125
<211> LENGTH: 20
<212> TYPE: PRT
<213> ORGANISM: Artificial Sequence
<220> FEATURE:
<223> OTHER INFORMATION: Homo sapiens MBP protein epitope

<400> SEQUENCE: 125

His His Pro Ala Arg Thr Ala His Tyr Gly Ser Leu Pro Gln Lys Ser
1               5                   10                  15

His Gly Arg Thr
            20

<210> SEQ ID NO 126
<211> LENGTH: 20
<212> TYPE: PRT
<213> ORGANISM: Artificial Sequence
<220> FEATURE:
<223> OTHER INFORMATION: Homo sapiens MBP protein epitope

<400> SEQUENCE: 126

Val Val His Phe Phe Lys Asn Ile Val Thr Pro Arg Thr Pro Pro
1               5                   10                  15

Ser Gln Gly Lys
            20

<210> SEQ ID NO 127
<211> LENGTH: 21
<212> TYPE: PRT
<213> ORGANISM: Artificial Sequence
<220> FEATURE:
<223> OTHER INFORMATION: Homo sapiens MBP protein epitope

<400> SEQUENCE: 127

Ala Ser Gln Lys Arg Pro Ser Gln Arg His Gly Ser Lys Tyr Leu Ala
1               5                   10                  15

Thr Ala Ser Thr Met
            20

<210> SEQ ID NO 128
<211> LENGTH: 20
<212> TYPE: PRT
<213> ORGANISM: Artificial Sequence
<220> FEATURE:
<223> OTHER INFORMATION: Homo sapiens MBP protein epitope
```

-continued

<400> SEQUENCE: 128

Phe Lys Gly Val Asp Ala Gln Gly Thr Leu Ser Lys Ile Phe Lys Leu
1               5                   10                  15

Gly Gly Arg Asp
            20

<210> SEQ ID NO 129
<211> LENGTH: 19
<212> TYPE: PRT
<213> ORGANISM: Artificial Sequence
<220> FEATURE:
<223> OTHER INFORMATION: Homo sapiens MBP protein epitope

<400> SEQUENCE: 129

Arg Pro Gly Phe Gly Tyr Gly Gly Arg Ala Ser Asp Tyr Lys Ser Ala
1               5                   10                  15

His Lys Gly

<210> SEQ ID NO 130
<211> LENGTH: 38
<212> TYPE: PRT
<213> ORGANISM: Artificial Sequence
<220> FEATURE:
<223> OTHER INFORMATION: Homo sapiens MBP protein epitope

<400> SEQUENCE: 130

Ala Ser Gln Lys Arg Pro Ser Gln Arg His Gly Ser Lys Tyr Leu Ala
1               5                   10                  15

Thr Ala Ser Thr Met Asp His Ala Arg His Gly Phe Leu Pro Arg His
            20                  25                  30

Arg Asp Thr Gly Ile Leu
        35

<210> SEQ ID NO 131
<211> LENGTH: 9
<212> TYPE: PRT
<213> ORGANISM: Artificial Sequence
<220> FEATURE:
<223> OTHER INFORMATION: Homo sapiens MBP protein epitope

<400> SEQUENCE: 131

Lys Tyr Leu Ala Thr Ala Ser Thr Met
1               5

<210> SEQ ID NO 132
<211> LENGTH: 20
<212> TYPE: PRT
<213> ORGANISM: Artificial Sequence
<220> FEATURE:
<223> OTHER INFORMATION: Homo sapiens MBP protein epitope

<400> SEQUENCE: 132

Gly Leu Ser Leu Ser Arg Phe Ser Trp Gly Ala Glu Gly Gln Arg Pro
1               5                   10                  15

Gly Phe Gly Tyr
            20

<210> SEQ ID NO 133
<211> LENGTH: 43
<212> TYPE: PRT
<213> ORGANISM: Artificial Sequence
<220> FEATURE:
<223> OTHER INFORMATION: Homo sapiens MBP protein epitope

<400> SEQUENCE: 133

Phe Gly Gly Asp Arg Gly Ala Pro Lys Arg Gly Ser Gly Lys Asp Ser
1               5                   10                  15

His His Pro Ala Arg Thr Ala His Tyr Gly Ser Leu Pro Gln Lys Ser
            20                  25                  30

His Gly Arg Thr Gln Asp Glu Asn Pro Val Val
        35                  40

<210> SEQ ID NO 134
<211> LENGTH: 40
<212> TYPE: PRT
<213> ORGANISM: Artificial Sequence
<220> FEATURE:
<223> OTHER INFORMATION: Homo sapiens MBP protein epitope

<400> SEQUENCE: 134

Gly Leu Ser Leu Ser Arg Phe Ser Trp Gly Ala Glu Gly Gln Arg Pro
1               5                   10                  15

Gly Phe Gly Tyr Gly Arg Ala Ser Asp Tyr Lys Ser Ala His Lys
            20                  25                  30

Gly Phe Lys Gly Val Asp Ala Gln
        35                  40

<210> SEQ ID NO 135
<211> LENGTH: 9
<212> TYPE: PRT
<213> ORGANISM: Artificial Sequence
<220> FEATURE:
<223> OTHER INFORMATION: Homo sapiens MHC class I related protein A
      epitope

<400> SEQUENCE: 135

Ala Ala Ala Ala Ala Ile Phe Val Ile
1               5

<210> SEQ ID NO 136
<211> LENGTH: 9
<212> TYPE: PRT
<213> ORGANISM: Artificial Sequence
<220> FEATURE:
<223> OTHER INFORMATION: Homo sapiens Myelin basic protein epitope

<400> SEQUENCE: 136

Ser Leu Ser Arg Phe Ser Trp Gly Ala
1               5

<210> SEQ ID NO 137
<211> LENGTH: 9
<212> TYPE: PRT
<213> ORGANISM: Artificial Sequence
<220> FEATURE:
<223> OTHER INFORMATION: Homo sapiens Myelin basic protein epitope

<400> SEQUENCE: 137

Asp Tyr Lys Ser Ala His Lys Gly Phe
1               5

<210> SEQ ID NO 138
<211> LENGTH: 19
<212> TYPE: PRT
<213> ORGANISM: Artificial Sequence
<220> FEATURE:
<223> OTHER INFORMATION: Homo sapiens myelin basic protein epitope

<400> SEQUENCE: 138

```
Ser Lys Ile Phe Lys Leu Gly Gly Arg Asp Ser Arg Ser Gly Ser Pro
1               5                   10                  15

Met Ala Arg

<210> SEQ ID NO 139
<211> LENGTH: 8
<212> TYPE: PRT
<213> ORGANISM: Artificial Sequence
<220> FEATURE:
<223> OTHER INFORMATION: Homo sapiens myelin basic protein epitope

<400> SEQUENCE: 139

Thr Pro Arg Thr Pro Pro Pro Gln
1               5

<210> SEQ ID NO 140
<211> LENGTH: 9
<212> TYPE: PRT
<213> ORGANISM: Artificial Sequence
<220> FEATURE:
<223> OTHER INFORMATION: Homo sapiens myelin proteolipid protein epitope

<400> SEQUENCE: 140

Phe Leu Tyr Gly Ala Leu Leu Leu Ala
1               5

<210> SEQ ID NO 141
<211> LENGTH: 9
<212> TYPE: PRT
<213> ORGANISM: Artificial Sequence
<220> FEATURE:
<223> OTHER INFORMATION: Homo sapiens myelin proteolipid protein epitope

<400> SEQUENCE: 141

Lys Leu Ile Glu Thr Tyr Phe Ser Lys
1               5

<210> SEQ ID NO 142
<211> LENGTH: 9
<212> TYPE: PRT
<213> ORGANISM: Artificial Sequence
<220> FEATURE:
<223> OTHER INFORMATION: Homo sapiens Myelin-associated glycoprotein
      precursor epitope

<400> SEQUENCE: 142

Leu Met Trp Ala Lys Ile Gly Pro Val
1               5

<210> SEQ ID NO 143
<211> LENGTH: 9
<212> TYPE: PRT
<213> ORGANISM: Artificial Sequence
<220> FEATURE:
<223> OTHER INFORMATION: Homo sapiens Myelin-associated glycoprotein
      precursor epitope

<400> SEQUENCE: 143

Ser Leu Leu Leu Glu Leu Glu Glu Val
1               5

<210> SEQ ID NO 144
<211> LENGTH: 9
<212> TYPE: PRT
<213> ORGANISM: Artificial Sequence
<220> FEATURE:
```

```
<223> OTHER INFORMATION: Homo sapiens Myelin-associated glycoprotein
      precursor epitope

<400> SEQUENCE: 144

Val Leu Phe Ser Ser Asp Phe Arg Ile
1               5

<210> SEQ ID NO 145
<211> LENGTH: 9
<212> TYPE: PRT
<213> ORGANISM: Artificial Sequence
<220> FEATURE:
<223> OTHER INFORMATION: Homo sapiens Myosin heavy chain, skeletal
      muscle, adult 2 (Myosin heavy chain IIa) (MyHC-IIa) epitope

<400> SEQUENCE: 145

Glu Phe Gln Lys Met Arg Arg Asp Leu
1               5

<210> SEQ ID NO 146
<211> LENGTH: 9
<212> TYPE: PRT
<213> ORGANISM: Artificial Sequence
<220> FEATURE:
<223> OTHER INFORMATION: Homo sapiens Myosin heavy chain, skeletal
      muscle, adult 2 (Myosin heavy chain IIa) (MyHC-IIa) epitope

<400> SEQUENCE: 146

Lys Met Arg Arg Asp Leu Glu Glu Ala
1               5

<210> SEQ ID NO 147
<211> LENGTH: 12
<212> TYPE: PRT
<213> ORGANISM: Artificial Sequence
<220> FEATURE:
<223> OTHER INFORMATION: Homo sapiens peroxiredoxin-2 isoform a epitope

<400> SEQUENCE: 147

Glu Val Lys Leu Ser Asp Tyr Lys Gly Lys Tyr Val
1               5                   10

<210> SEQ ID NO 148
<211> LENGTH: 10
<212> TYPE: PRT
<213> ORGANISM: Artificial Sequence
<220> FEATURE:
<223> OTHER INFORMATION: Homo sapiens proinsulin precursor epitope

<400> SEQUENCE: 148

His Leu Cys Gly Ser His Leu Val Glu Ala
1               5                   10

<210> SEQ ID NO 149
<211> LENGTH: 10
<212> TYPE: PRT
<213> ORGANISM: Artificial Sequence
<220> FEATURE:
<223> OTHER INFORMATION: Homo sapiens proinsulin precursor epitope

<400> SEQUENCE: 149

Ala Leu Trp Gly Pro Asp Pro Ala Ala Ala
1               5                   10

<210> SEQ ID NO 150
<211> LENGTH: 9
<212> TYPE: PRT
```

```
<213> ORGANISM: Artificial Sequence
<220> FEATURE:
<223> OTHER INFORMATION: Homo sapiens proinsulin precursor epitope

<400> SEQUENCE: 150

Arg Leu Leu Pro Leu Leu Ala Leu Leu
1               5

<210> SEQ ID NO 151
<211> LENGTH: 10
<212> TYPE: PRT
<213> ORGANISM: Artificial Sequence
<220> FEATURE:
<223> OTHER INFORMATION: Homo sapiens proinsulin precursor epitope

<400> SEQUENCE: 151

Ala Leu Trp Met Arg Leu Leu Pro Leu Leu
1               5                   10

<210> SEQ ID NO 152
<211> LENGTH: 10
<212> TYPE: PRT
<213> ORGANISM: Artificial Sequence
<220> FEATURE:
<223> OTHER INFORMATION: Homo sapiens proinsulin precursor epitope

<400> SEQUENCE: 152

Trp Met Arg Leu Leu Pro Leu Leu Ala Leu
1               5                   10

<210> SEQ ID NO 153
<211> LENGTH: 10
<212> TYPE: PRT
<213> ORGANISM: Artificial Sequence
<220> FEATURE:
<223> OTHER INFORMATION: Homo sapiens proinsulin precursor epitope

<400> SEQUENCE: 153

Pro Leu Ala Leu Glu Gly Ser Leu Gln Lys
1               5                   10

<210> SEQ ID NO 154
<211> LENGTH: 10
<212> TYPE: PRT
<213> ORGANISM: Artificial Sequence
<220> FEATURE:
<223> OTHER INFORMATION: Homo sapiens proinsulin precursor epitope

<400> SEQUENCE: 154

Pro Leu Leu Ala Leu Leu Ala Leu Trp Gly
1               5                   10

<210> SEQ ID NO 155
<211> LENGTH: 9
<212> TYPE: PRT
<213> ORGANISM: Artificial Sequence
<220> FEATURE:
<223> OTHER INFORMATION: Homo sapiens Receptor-type tyrosine-protein
      phosphatase-like N precursor epitope

<400> SEQUENCE: 155

Leu Leu Pro Pro Leu Leu Glu His Leu
1               5

<210> SEQ ID NO 156
<211> LENGTH: 9
<212> TYPE: PRT
```

```
<213> ORGANISM: Artificial Sequence
<220> FEATURE:
<223> OTHER INFORMATION: Homo sapiens Receptor-type tyrosine-protein
      phosphatase-like N precursor epitope

<400> SEQUENCE: 156

Ser Leu Ala Ala Gly Val Lys Leu Leu
1               5

<210> SEQ ID NO 157
<211> LENGTH: 9
<212> TYPE: PRT
<213> ORGANISM: Artificial Sequence
<220> FEATURE:
<223> OTHER INFORMATION: Homo sapiens Receptor-type tyrosine-protein
      phosphatase-like N precursor epitope

<400> SEQUENCE: 157

Ser Leu Ser Pro Leu Gln Ala Glu Leu
1               5

<210> SEQ ID NO 158
<211> LENGTH: 9
<212> TYPE: PRT
<213> ORGANISM: Artificial Sequence
<220> FEATURE:
<223> OTHER INFORMATION: Homo sapiens Receptor-type tyrosine-protein
      phosphatase-like N precursor epitope

<400> SEQUENCE: 158

Ala Leu Thr Ala Val Ala Glu Glu Val
1               5

<210> SEQ ID NO 159
<211> LENGTH: 10
<212> TYPE: PRT
<213> ORGANISM: Artificial Sequence
<220> FEATURE:
<223> OTHER INFORMATION: Homo sapiens Receptor-type tyrosine-protein
      phosphatase-like N precursor epitope

<400> SEQUENCE: 159

Ser Leu Tyr His Val Tyr Glu Val Asn Leu
1               5                   10

<210> SEQ ID NO 160
<211> LENGTH: 9
<212> TYPE: PRT
<213> ORGANISM: Artificial Sequence
<220> FEATURE:
<223> OTHER INFORMATION: Homo sapiens Receptor-type tyrosine-protein
      phosphatase-like N precursor epitope

<400> SEQUENCE: 160

Thr Ile Ala Asp Phe Trp Gln Met Val
1               5

<210> SEQ ID NO 161
<211> LENGTH: 9
<212> TYPE: PRT
<213> ORGANISM: Artificial Sequence
<220> FEATURE:
<223> OTHER INFORMATION: Homo sapiens Receptor-type tyrosine-protein
      phosphatase-like N precursor epitope

<400> SEQUENCE: 161

Val Ile Val Met Leu Thr Pro Leu Val
1               5
```

<210> SEQ ID NO 162
<211> LENGTH: 9
<212> TYPE: PRT
<213> ORGANISM: Artificial Sequence
<220> FEATURE:
<223> OTHER INFORMATION: Homo sapiens Receptor-type tyrosine-protein
      phosphatase-like N precursor epitope

<400> SEQUENCE: 162

Met Val Trp Glu Ser Gly Cys Thr Val
1               5

<210> SEQ ID NO 163
<211> LENGTH: 14
<212> TYPE: PRT
<213> ORGANISM: Artificial Sequence
<220> FEATURE:
<223> OTHER INFORMATION: Homo sapiens S-arrestin epitope

<400> SEQUENCE: 163

Phe Leu Gly Glu Leu Thr Ser Ser Glu Val Ala Thr Glu Val
1               5                   10

<210> SEQ ID NO 164
<211> LENGTH: 20
<212> TYPE: PRT
<213> ORGANISM: Artificial Sequence
<220> FEATURE:
<223> OTHER INFORMATION: Homo sapiens S-arrestin epitope

<400> SEQUENCE: 164

Phe Met Ser Asp Lys Pro Leu His Leu Ala Val Ser Leu Asn Lys Glu
1               5                   10                  15

Ile Tyr Phe His
            20

<210> SEQ ID NO 165
<211> LENGTH: 15
<212> TYPE: PRT
<213> ORGANISM: Artificial Sequence
<220> FEATURE:
<223> OTHER INFORMATION: Homo sapiens S-arrestin epitope

<400> SEQUENCE: 165

Gly Glu Ala Glu Glu Gly Lys Arg Asp Lys Asn Asp Val Asp Glu
1               5                   10                  15

<210> SEQ ID NO 166
<211> LENGTH: 20
<212> TYPE: PRT
<213> ORGANISM: Artificial Sequence
<220> FEATURE:
<223> OTHER INFORMATION: Homo sapiens S-arrestin epitope

<400> SEQUENCE: 166

Gly Glu Pro Ile Pro Val Thr Val Thr Val Thr Asn Asn Thr Glu Lys
1               5                   10                  15

Thr Val Lys Lys
            20

<210> SEQ ID NO 167
<211> LENGTH: 20
<212> TYPE: PRT
<213> ORGANISM: Artificial Sequence
<220> FEATURE:

<223> OTHER INFORMATION: Homo sapiens S-arrestin epitope

<400> SEQUENCE: 167

His Pro Gln Pro Glu Asp Pro Ala Lys Glu Ser Tyr Gln Asp Ala Asn
1               5                   10                  15

Leu Val Phe Glu
            20

<210> SEQ ID NO 168
<211> LENGTH: 20
<212> TYPE: PRT
<213> ORGANISM: Artificial Sequence
<220> FEATURE:
<223> OTHER INFORMATION: Homo sapiens S-arrestin epitope

<400> SEQUENCE: 168

Ile Lys Ala Phe Val Glu Gln Val Ala Asn Val Val Leu Tyr Ser Ser
1               5                   10                  15

Asp Tyr Tyr Val
            20

<210> SEQ ID NO 169
<211> LENGTH: 20
<212> TYPE: PRT
<213> ORGANISM: Artificial Sequence
<220> FEATURE:
<223> OTHER INFORMATION: Homo sapiens S-arrestin epitope

<400> SEQUENCE: 169

Lys Ser Ser Val Arg Leu Leu Ile Arg Lys Val Gln His Ala Pro Leu
1               5                   10                  15

Glu Met Gly Pro
            20

<210> SEQ ID NO 170
<211> LENGTH: 20
<212> TYPE: PRT
<213> ORGANISM: Artificial Sequence
<220> FEATURE:
<223> OTHER INFORMATION: Homo sapiens S-arrestin epitope

<400> SEQUENCE: 170

Gln Pro Arg Ala Glu Ala Ala Trp Gln Phe Phe Met Ser Asp Lys Pro
1               5                   10                  15

Leu His Leu Ala
            20

<210> SEQ ID NO 171
<211> LENGTH: 20
<212> TYPE: PRT
<213> ORGANISM: Artificial Sequence
<220> FEATURE:
<223> OTHER INFORMATION: Homo sapiens S-arrestin epitope

<400> SEQUENCE: 171

Ser Tyr Gln Asp Ala Asn Leu Val Phe Glu Glu Phe Ala Arg His Asn
1               5                   10                  15

Leu Lys Asp Ala
            20

<210> SEQ ID NO 172
<211> LENGTH: 20
<212> TYPE: PRT
<213> ORGANISM: Artificial Sequence

```
<220> FEATURE:
<223> OTHER INFORMATION: Homo sapiens S-arrestin epitope

<400> SEQUENCE: 172

Thr Asp Ala Glu Glu Asp Lys Ile Pro Lys Lys Ser Ser Val Arg Leu
1               5                   10                  15

Leu Ile Arg Lys
            20

<210> SEQ ID NO 173
<211> LENGTH: 20
<212> TYPE: PRT
<213> ORGANISM: Artificial Sequence
<220> FEATURE:
<223> OTHER INFORMATION: Homo sapiens S-arrestin epitope

<400> SEQUENCE: 173

Thr Asn Asn Thr Glu Lys Thr Val Lys Lys Ile Lys Ala Phe Val Glu
1               5                   10                  15

Gln Val Ala Asn
            20

<210> SEQ ID NO 174
<211> LENGTH: 20
<212> TYPE: PRT
<213> ORGANISM: Artificial Sequence
<220> FEATURE:
<223> OTHER INFORMATION: Homo sapiens S-arrestin epitope

<400> SEQUENCE: 174

Val Gln His Ala Pro Leu Glu Met Gly Pro Gln Pro Arg Ala Glu Ala
1               5                   10                  15

Ala Trp Gln Phe
            20

<210> SEQ ID NO 175
<211> LENGTH: 20
<212> TYPE: PRT
<213> ORGANISM: Artificial Sequence
<220> FEATURE:
<223> OTHER INFORMATION: Homo sapiens S-arrestin epitope

<400> SEQUENCE: 175

Val Ser Leu Asn Lys Glu Ile Tyr Phe His Gly Glu Pro Ile Pro Val
1               5                   10                  15

Thr Val Thr Val
            20

<210> SEQ ID NO 176
<211> LENGTH: 20
<212> TYPE: PRT
<213> ORGANISM: Artificial Sequence
<220> FEATURE:
<223> OTHER INFORMATION: Homo sapiens S-arrestin epitope

<400> SEQUENCE: 176

Val Tyr Val Thr Leu Thr Cys Ala Phe Arg Tyr Gly Gln Glu Asp Ile
1               5                   10                  15

Asp Val Ile Gly
            20

<210> SEQ ID NO 177
<211> LENGTH: 20
<212> TYPE: PRT
```

-continued

```
<213> ORGANISM: Artificial Sequence
<220> FEATURE:
<223> OTHER INFORMATION: Homo sapiens S-arrestin epitope

<400> SEQUENCE: 177

Tyr Gly Gln Glu Asp Ile Asp Val Ile Gly Leu Thr Phe Arg Arg Asp
1               5                   10                  15

Leu Tyr Phe Ser
            20

<210> SEQ ID NO 178
<211> LENGTH: 10
<212> TYPE: PRT
<213> ORGANISM: Artificial Sequence
<220> FEATURE:
<223> OTHER INFORMATION: Homo sapiens SSA protein SS-56 epitope

<400> SEQUENCE: 178

Tyr Thr Cys Pro Leu Cys Arg Ala Pro Val
1               5                   10

<210> SEQ ID NO 179
<211> LENGTH: 8
<212> TYPE: PRT
<213> ORGANISM: Artificial Sequence
<220> FEATURE:
<223> OTHER INFORMATION: Homo sapiens Steroid 21-hydroxylase epitope

<400> SEQUENCE: 179

Glu Pro Leu Ala Arg Leu Glu Leu
1               5

<210> SEQ ID NO 180
<211> LENGTH: 20
<212> TYPE: PRT
<213> ORGANISM: Artificial Sequence
<220> FEATURE:
<223> OTHER INFORMATION: Homo sapiens Steroid 21-hydroxylase epitope

<400> SEQUENCE: 180

Glu Pro Leu Ala Arg Leu Glu Leu Phe Val Val Leu Thr Arg Leu Leu
1               5                   10                  15

Gln Ala Phe Thr
            20

<210> SEQ ID NO 181
<211> LENGTH: 20
<212> TYPE: PRT
<213> ORGANISM: Artificial Sequence
<220> FEATURE:
<223> OTHER INFORMATION: Homo sapiens Steroid 21-hydroxylase epitope

<400> SEQUENCE: 181

Ile Lys Asp Asp Asn Leu Met Pro Ala Tyr Tyr Lys Cys Ile Gln Glu
1               5                   10                  15

Val Leu Lys Thr
            20

<210> SEQ ID NO 182
<211> LENGTH: 20
<212> TYPE: PRT
<213> ORGANISM: Artificial Sequence
<220> FEATURE:
<223> OTHER INFORMATION: Homo sapiens Steroid 21-hydroxylase epitope

<400> SEQUENCE: 182
```

```
Ile Arg Asp Ser Met Glu Pro Val Val Glu Gln Leu Thr Gln Glu Phe
1               5                   10                  15

Cys Glu Arg Met
            20

<210> SEQ ID NO 183
<211> LENGTH: 8
<212> TYPE: PRT
<213> ORGANISM: Artificial Sequence
<220> FEATURE:
<223> OTHER INFORMATION: Homo sapiens T-cell receptor V beta chain 13.1
      epitope

<400> SEQUENCE: 183

Leu Gly Arg Ala Gly Leu Thr Tyr
1               5

<210> SEQ ID NO 184
<211> LENGTH: 9
<212> TYPE: PRT
<213> ORGANISM: Artificial Sequence
<220> FEATURE:
<223> OTHER INFORMATION: Homo sapiens transaldolase 1 epitope

<400> SEQUENCE: 184

Leu Leu Phe Ser Phe Ala Gln Ala Val
1               5

<210> SEQ ID NO 185
<211> LENGTH: 9
<212> TYPE: PRT
<213> ORGANISM: Artificial Sequence
<220> FEATURE:
<223> OTHER INFORMATION: Homo sapiens Vasoactive intestinal polypeptide
      receptor 1 precursor epitope

<400> SEQUENCE: 185

Arg Arg Lys Trp Arg Arg Trp His Leu
1               5

<210> SEQ ID NO 186
<211> LENGTH: 9
<212> TYPE: PRT
<213> ORGANISM: Artificial Sequence
<220> FEATURE:
<223> OTHER INFORMATION: Homo sapiens Vasoactive intestinal polypeptide
      receptor 1 precursor epitope

<400> SEQUENCE: 186

Arg Arg Lys Trp Arg Arg Trp His Leu
1               5

<210> SEQ ID NO 187
<211> LENGTH: 20
<212> TYPE: PRT
<213> ORGANISM: Artificial Sequence
<220> FEATURE:
<223> OTHER INFORMATION: Arachis hypogaea 2S protein 1 epitope

<400> SEQUENCE: 187

Ala His Ala Ser Ala Arg Gln Gln Trp Glu Leu Gln Gly Asp Arg Arg
1               5                   10                  15

Cys Gln Ser Gln
            20
```

```
<210> SEQ ID NO 188
<211> LENGTH: 20
<212> TYPE: PRT
<213> ORGANISM: Artificial Sequence
<220> FEATURE:
<223> OTHER INFORMATION: Arachis hypogaea 2S protein 1 epitope

<400> SEQUENCE: 188

Ala Lys Leu Thr Ile Leu Val Ala Leu Ala Leu Phe Leu Leu Ala Ala
1               5                   10                  15

His Ala Ser Ala
            20

<210> SEQ ID NO 189
<211> LENGTH: 19
<212> TYPE: PRT
<213> ORGANISM: Artificial Sequence
<220> FEATURE:
<223> OTHER INFORMATION: Arachis hypogaea 2S protein 1 epitope

<400> SEQUENCE: 189

Ala Leu Gln Gln Ile Met Glu Asn Gln Ser Asp Arg Leu Gln Gly Arg
1               5                   10                  15

Gln Gln Glu

<210> SEQ ID NO 190
<211> LENGTH: 20
<212> TYPE: PRT
<213> ORGANISM: Artificial Sequence
<220> FEATURE:
<223> OTHER INFORMATION: Arachis hypogaea 2S protein 1 epitope

<400> SEQUENCE: 190

Ala Asn Leu Arg Pro Cys Glu Gln His Leu Met Gln Lys Ile Gln Arg
1               5                   10                  15

Asp Glu Asp Ser
            20

<210> SEQ ID NO 191
<211> LENGTH: 20
<212> TYPE: PRT
<213> ORGANISM: Artificial Sequence
<220> FEATURE:
<223> OTHER INFORMATION: Arachis hypogaea 2S protein 1 epitope

<400> SEQUENCE: 191

Cys Asn Glu Leu Asn Glu Phe Glu Asn Asn Gln Arg Cys Met Cys Glu
1               5                   10                  15

Ala Leu Gln Gln
            20

<210> SEQ ID NO 192
<211> LENGTH: 16
<212> TYPE: PRT
<213> ORGANISM: Artificial Sequence
<220> FEATURE:
<223> OTHER INFORMATION: Homo sapiens 5-hydroxytryptamine receptor 2C
      (5-HT-2C) (Serotonin receptor 2C) (5-HT2C) (5-HTR2C) (5HT-1C)
      epitope

<400> SEQUENCE: 192

Pro Arg Gly Thr Met Gln Ala Ile Asn Asn Glu Arg Lys Ala Ser Lys
1               5                   10                  15

<210> SEQ ID NO 193
```

```
<211> LENGTH: 12
<212> TYPE: PRT
<213> ORGANISM: Artificial Sequence
<220> FEATURE:
<223> OTHER INFORMATION: Bos taurus Allergen Bos d 2 precursor epitope

<400> SEQUENCE: 193

Asp Gln Gly Thr Cys Leu Leu Leu Thr Glu Val Ala
1               5                   10

<210> SEQ ID NO 194
<211> LENGTH: 14
<212> TYPE: PRT
<213> ORGANISM: Artificial Sequence
<220> FEATURE:
<223> OTHER INFORMATION: Bos taurus Allergen Bos d 2 precursor epitope

<400> SEQUENCE: 194

Glu Leu Glu Lys Tyr Gln Gln Leu Asn Ser Glu Arg Gly Val
1               5                   10

<210> SEQ ID NO 195
<211> LENGTH: 13
<212> TYPE: PRT
<213> ORGANISM: Artificial Sequence
<220> FEATURE:
<223> OTHER INFORMATION: Bos taurus Allergen Bos d 2 precursor epitope

<400> SEQUENCE: 195

Gly Glu Arg Ile Thr Lys Met Thr Glu Gly Leu Ala Lys
1               5                   10

<210> SEQ ID NO 196
<211> LENGTH: 14
<212> TYPE: PRT
<213> ORGANISM: Artificial Sequence
<220> FEATURE:
<223> OTHER INFORMATION: Bos taurus Allergen Bos d 2 precursor epitope

<400> SEQUENCE: 196

Pro Gly Glu Trp Arg Ile Ile Tyr Ala Ala Ala Asp Asn Lys
1               5                   10

<210> SEQ ID NO 197
<211> LENGTH: 8
<212> TYPE: PRT
<213> ORGANISM: Artificial Sequence
<220> FEATURE:
<223> OTHER INFORMATION: Bos taurus Allergen Bos d 2 precursor epitope

<400> SEQUENCE: 197

Arg Ile Glu Cys Ile Asn Asp Cys
1               5

<210> SEQ ID NO 198
<211> LENGTH: 12
<212> TYPE: PRT
<213> ORGANISM: Artificial Sequence
<220> FEATURE:
<223> OTHER INFORMATION: Bos taurus Allergen Bos d 2 precursor epitope

<400> SEQUENCE: 198

Val Ala Lys Arg Gln Glu Gly Tyr Val Tyr Val Leu
1               5                   10

<210> SEQ ID NO 199
<211> LENGTH: 10
```

```
<212> TYPE: PRT
<213> ORGANISM: Artificial Sequence
<220> FEATURE:
<223> OTHER INFORMATION: Bos taurus Allergen Bos d 2 precursor epitope

<400> SEQUENCE: 199

Val Ser Glu Asn Met Leu Val Thr Tyr Val
1               5                   10

<210> SEQ ID NO 200
<211> LENGTH: 12
<212> TYPE: PRT
<213> ORGANISM: Artificial Sequence
<220> FEATURE:
<223> OTHER INFORMATION: Bos taurus Allergen Bos d 2 precursor epitope

<400> SEQUENCE: 200

Asp Gln Gly Thr Cys Leu Leu Leu Thr Glu Val Ala
1               5                   10

<210> SEQ ID NO 201
<211> LENGTH: 14
<212> TYPE: PRT
<213> ORGANISM: Artificial Sequence
<220> FEATURE:
<223> OTHER INFORMATION: Bos taurus Allergen Bos d 2 precursor epitope

<400> SEQUENCE: 201

Glu Leu Glu Lys Tyr Gln Gln Leu Asn Ser Glu Arg Gly Val
1               5                   10

<210> SEQ ID NO 202
<211> LENGTH: 16
<212> TYPE: PRT
<213> ORGANISM: Artificial Sequence
<220> FEATURE:
<223> OTHER INFORMATION: Bos taurus Allergen Bos d 2 precursor epitope

<400> SEQUENCE: 202

Glu Leu Glu Lys Tyr Gln Gln Leu Asn Ser Glu Arg Gly Val Pro Asn
1               5                   10                  15

<210> SEQ ID NO 203
<211> LENGTH: 13
<212> TYPE: PRT
<213> ORGANISM: Artificial Sequence
<220> FEATURE:
<223> OTHER INFORMATION: Bos taurus Allergen Bos d 2 precursor epitope

<400> SEQUENCE: 203

Gly Glu Arg Ile Thr Lys Met Thr Glu Gly Leu Ala Lys
1               5                   10

<210> SEQ ID NO 204
<211> LENGTH: 14
<212> TYPE: PRT
<213> ORGANISM: Artificial Sequence
<220> FEATURE:
<223> OTHER INFORMATION: Bos taurus Allergen Bos d 2 precursor epitope

<400> SEQUENCE: 204

Pro Gly Glu Trp Arg Ile Ile Tyr Ala Ala Ala Asp Asn Lys
1               5                   10

<210> SEQ ID NO 205
<211> LENGTH: 8
<212> TYPE: PRT
```

```
<213> ORGANISM: Artificial Sequence
<220> FEATURE:
<223> OTHER INFORMATION: Bos taurus Allergen Bos d 2 precursor epitope

<400> SEQUENCE: 205

Arg Ile Glu Cys Ile Asn Asp Cys
1               5

<210> SEQ ID NO 206
<211> LENGTH: 12
<212> TYPE: PRT
<213> ORGANISM: Artificial Sequence
<220> FEATURE:
<223> OTHER INFORMATION: Bos taurus Allergen Bos d 2 precursor epitope

<400> SEQUENCE: 206

Val Ala Lys Arg Gln Glu Gly Tyr Val Tyr Val Leu
1               5                   10

<210> SEQ ID NO 207
<211> LENGTH: 10
<212> TYPE: PRT
<213> ORGANISM: Artificial Sequence
<220> FEATURE:
<223> OTHER INFORMATION: Bos taurus Allergen Bos d 2 precursor epitope

<400> SEQUENCE: 207

Val Ser Glu Asn Met Leu Val Thr Tyr Val
1               5                   10

<210> SEQ ID NO 208
<211> LENGTH: 13
<212> TYPE: PRT
<213> ORGANISM: Artificial Sequence
<220> FEATURE:
<223> OTHER INFORMATION: Cryptomeria japonica Allergen Cry j 2 epitope

<400> SEQUENCE: 208

Asp Ile Phe Ala Ser Lys Asn Phe His Leu Gln Lys Asn
1               5                   10

<210> SEQ ID NO 209
<211> LENGTH: 13
<212> TYPE: PRT
<213> ORGANISM: Artificial Sequence
<220> FEATURE:
<223> OTHER INFORMATION: Cryptomeria japonica Allergen Cry j 2 epitope

<400> SEQUENCE: 209

Gly Ile Ile Ala Ala Tyr Gln Asn Pro Ala Ser Trp Lys
1               5                   10

<210> SEQ ID NO 210
<211> LENGTH: 12
<212> TYPE: PRT
<213> ORGANISM: Artificial Sequence
<220> FEATURE:
<223> OTHER INFORMATION: Cryptomeria japonica Allergen Cry j 2 epitope

<400> SEQUENCE: 210

Lys Leu Thr Ser Gly Lys Ile Ala Ser Cys Leu Asn
1               5                   10

<210> SEQ ID NO 211
<211> LENGTH: 12
<212> TYPE: PRT
<213> ORGANISM: Artificial Sequence
```

```
<220> FEATURE:
<223> OTHER INFORMATION: Cryptomeria japonica Allergen Cry j 2 epitope

<400> SEQUENCE: 211

Gln Phe Ala Lys Leu Thr Gly Phe Thr Leu Met Gly
1               5                   10

<210> SEQ ID NO 212
<211> LENGTH: 8
<212> TYPE: PRT
<213> ORGANISM: Artificial Sequence
<220> FEATURE:
<223> OTHER INFORMATION: Aspergillus fumigatus allergen I/a; Asp f I/a
      epitope

<400> SEQUENCE: 212

Ile Asn Gln Gln Leu Asn Pro Lys
1               5

<210> SEQ ID NO 213
<211> LENGTH: 15
<212> TYPE: PRT
<213> ORGANISM: Artificial Sequence
<220> FEATURE:
<223> OTHER INFORMATION: Aspergillus fumigatus allergen I/a; Asp f I/a
      epitope

<400> SEQUENCE: 213

Ile Asn Gln Gln Leu Asn Pro Lys Thr Asn Lys Trp Glu Asp Lys
1               5                   10                  15

<210> SEQ ID NO 214
<211> LENGTH: 11
<212> TYPE: PRT
<213> ORGANISM: Artificial Sequence
<220> FEATURE:
<223> OTHER INFORMATION: Aspergillus fumigatus allergen I/a; Asp f I/a
      epitope

<400> SEQUENCE: 214

Leu Asn Pro Lys Thr Asn Lys Trp Glu Asp Lys
1               5                   10

<210> SEQ ID NO 215
<211> LENGTH: 8
<212> TYPE: PRT
<213> ORGANISM: Artificial Sequence
<220> FEATURE:
<223> OTHER INFORMATION: Aspergillus fumigatus allergen I/a; Asp f I/a
      epitope

<400> SEQUENCE: 215

Ile Asn Gln Gln Leu Asn Pro Lys
1               5

<210> SEQ ID NO 216
<211> LENGTH: 15
<212> TYPE: PRT
<213> ORGANISM: Artificial Sequence
<220> FEATURE:
<223> OTHER INFORMATION: Aspergillus fumigatus allergen I/a; Asp f I/a
      epitope

<400> SEQUENCE: 216

Ile Asn Gln Gln Leu Asn Pro Lys Thr Asn Lys Trp Glu Asp Lys
1               5                   10                  15
```

-continued

```
<210> SEQ ID NO 217
<211> LENGTH: 11
<212> TYPE: PRT
<213> ORGANISM: Artificial Sequence
<220> FEATURE:
<223> OTHER INFORMATION: Aspergillus fumigatus allergen I/a; Asp f I/a
      epitope

<400> SEQUENCE: 217

Leu Asn Pro Lys Thr Asn Lys Trp Glu Asp Lys
1               5                   10

<210> SEQ ID NO 218
<211> LENGTH: 7
<212> TYPE: PRT
<213> ORGANISM: Artificial Sequence
<220> FEATURE:
<223> OTHER INFORMATION: Aspergillus fumigatus allergen I/a; Asp f I/a
      epitope

<400> SEQUENCE: 218

Thr Asn Lys Trp Glu Asp Lys
1               5

<210> SEQ ID NO 219
<211> LENGTH: 12
<212> TYPE: PRT
<213> ORGANISM: Artificial Sequence
<220> FEATURE:
<223> OTHER INFORMATION: Aspergillus fumigatus allergen I/a; Asp f I/a
      epitope

<400> SEQUENCE: 219

Leu Asn Pro Lys Thr Asn Lys Trp Glu Asp Lys Arg
1               5                   10

<210> SEQ ID NO 220
<211> LENGTH: 15
<212> TYPE: PRT
<213> ORGANISM: Artificial Sequence
<220> FEATURE:
<223> OTHER INFORMATION: Dermatophagoides farinae Allergen Mag epitope

<400> SEQUENCE: 220

Pro Arg Leu Ser Trp His Gln Tyr Thr Lys Arg Asp Ser Arg Glu
1               5                   10                  15

<210> SEQ ID NO 221
<211> LENGTH: 15
<212> TYPE: PRT
<213> ORGANISM: Artificial Sequence
<220> FEATURE:
<223> OTHER INFORMATION: Dermatophagoides farinae Allergen Mag epitope

<400> SEQUENCE: 221

Thr Val Asp Leu Ile Ser Pro Val Thr Lys Arg Ala Ser Leu Lys
1               5                   10                  15

<210> SEQ ID NO 222
<211> LENGTH: 18
<212> TYPE: PRT
<213> ORGANISM: Artificial Sequence
<220> FEATURE:
<223> OTHER INFORMATION: Bos taurus Alpha-S1-casein precursor epitope

<400> SEQUENCE: 222

Ala Trp Tyr Tyr Val Pro Leu Gly Thr Gln Tyr Thr Asp Ala Pro Ser
1               5                   10                  15
```

Phe Ser

<210> SEQ ID NO 223
<211> LENGTH: 18
<212> TYPE: PRT
<213> ORGANISM: Artificial Sequence
<220> FEATURE:
<223> OTHER INFORMATION: Bos taurus Alpha-S1-casein precursor epitope

<400> SEQUENCE: 223

Asp Ala Tyr Pro Ser Gly Ala Trp Tyr Tyr Val Pro Leu Gly Thr Gln
1               5                   10                  15

Tyr Thr

<210> SEQ ID NO 224
<211> LENGTH: 18
<212> TYPE: PRT
<213> ORGANISM: Artificial Sequence
<220> FEATURE:
<223> OTHER INFORMATION: Bos taurus Alpha-S1-casein precursor epitope

<400> SEQUENCE: 224

Asp Ile Gly Ser Glu Ser Thr Glu Asp Gln Ala Met Glu Asp Ile Lys
1               5                   10                  15

Gln Met

<210> SEQ ID NO 225
<211> LENGTH: 6
<212> TYPE: PRT
<213> ORGANISM: Artificial Sequence
<220> FEATURE:
<223> OTHER INFORMATION: Bos taurus Alpha-S1-casein precursor epitope

<400> SEQUENCE: 225

Glu Asp Ile Lys Gln Met
1               5

<210> SEQ ID NO 226
<211> LENGTH: 12
<212> TYPE: PRT
<213> ORGANISM: Artificial Sequence
<220> FEATURE:
<223> OTHER INFORMATION: Bos taurus Alpha-S1-casein precursor epitope

<400> SEQUENCE: 226

Glu Pro Met Ile Gly Val Asn Gln Glu Leu Ala Tyr
1               5                   10

<210> SEQ ID NO 227
<211> LENGTH: 18
<212> TYPE: PRT
<213> ORGANISM: Artificial Sequence
<220> FEATURE:
<223> OTHER INFORMATION: Bos taurus Alpha-S1-casein precursor epitope

<400> SEQUENCE: 227

Glu Pro Met Ile Gly Val Asn Gln Glu Leu Ala Tyr Phe Tyr Pro Glu
1               5                   10                  15

Leu Phe

<210> SEQ ID NO 228
<211> LENGTH: 17
<212> TYPE: PRT
<213> ORGANISM: Artificial Sequence

```
<220> FEATURE:
<223> OTHER INFORMATION: Arachis hypogaea Ara h 2.01 allergen epitope

<400> SEQUENCE: 228

Glu Leu Asn Glu Phe Glu Asn Asn Gln Arg Cys Met Cys Glu Ala Leu
1               5                   10                  15

Gln

<210> SEQ ID NO 229
<211> LENGTH: 16
<212> TYPE: PRT
<213> ORGANISM: Artificial Sequence
<220> FEATURE:
<223> OTHER INFORMATION: Arachis hypogaea Ara h 2.01 allergen epitope

<400> SEQUENCE: 229

Ser Gln Leu Glu Arg Ala Asn Leu Arg Pro Cys Glu Gln His Leu Met
1               5                   10                  15

<210> SEQ ID NO 230
<211> LENGTH: 15
<212> TYPE: PRT
<213> ORGANISM: Artificial Sequence
<220> FEATURE:
<223> OTHER INFORMATION: Cryptomeria japonica Cry j 1 precursor epitope

<400> SEQUENCE: 230

Gly Ala Thr Arg Asp Arg Pro Leu Trp Ile Ile Phe Ser Gly Asn
1               5                   10                  15

<210> SEQ ID NO 231
<211> LENGTH: 20
<212> TYPE: PRT
<213> ORGANISM: Artificial Sequence
<220> FEATURE:
<223> OTHER INFORMATION: Cryptomeria japonica Cry j 1 precursor epitope

<400> SEQUENCE: 231

Ile Phe Ser Gly Asn Met Asn Ile Lys Leu Lys Met Pro Met Tyr Ile
1               5                   10                  15

Ala Gly Tyr Lys
            20

<210> SEQ ID NO 232
<211> LENGTH: 20
<212> TYPE: PRT
<213> ORGANISM: Artificial Sequence
<220> FEATURE:
<223> OTHER INFORMATION: Cryptomeria japonica Cry j 1 precursor epitope

<400> SEQUENCE: 232

Lys Met Pro Met Tyr Ile Ala Gly Tyr Lys Thr Phe Asp Gly Arg Gly
1               5                   10                  15

Ala Gln Val Tyr
            20

<210> SEQ ID NO 233
<211> LENGTH: 20
<212> TYPE: PRT
<213> ORGANISM: Artificial Sequence
<220> FEATURE:
<223> OTHER INFORMATION: Cryptomeria japonica Cry j 1 precursor epitope

<400> SEQUENCE: 233

Leu Gly His Asp Asp Ala Tyr Ser Asp Asp Lys Ser Met Lys Val Thr
```

```
1               5                   10                  15

Val Ala Phe Asn
            20

<210> SEQ ID NO 234
<211> LENGTH: 19
<212> TYPE: PRT
<213> ORGANISM: Artificial Sequence
<220> FEATURE:
<223> OTHER INFORMATION: Cryptomeria japonica Cry j 1 precursor epitope

<400> SEQUENCE: 234

Ser Gly Lys Tyr Glu Gly Gly Asn Ile Tyr Thr Lys Lys Glu Ala Phe
1               5                   10                  15

Asn Val Glu

<210> SEQ ID NO 235
<211> LENGTH: 11
<212> TYPE: PRT
<213> ORGANISM: Artificial Sequence
<220> FEATURE:
<223> OTHER INFORMATION: Cochliobolus lunatus Cytochrome c epitope

<400> SEQUENCE: 235

Glu Asn Pro Lys Lys Tyr Ile Pro Gly Thr Lys
1               5                   10

<210> SEQ ID NO 236
<211> LENGTH: 11
<212> TYPE: PRT
<213> ORGANISM: Artificial Sequence
<220> FEATURE:
<223> OTHER INFORMATION: Cochliobolus lunatus Cytochrome c epitope

<400> SEQUENCE: 236

Gly Leu Phe Gly Arg Lys Thr Gly Ser Val Ala
1               5                   10

<210> SEQ ID NO 237
<211> LENGTH: 9
<212> TYPE: PRT
<213> ORGANISM: Artificial Sequence
<220> FEATURE:
<223> OTHER INFORMATION: Cochliobolus lunatus Cytochrome c epitope

<400> SEQUENCE: 237

Lys Ile Gly Pro Glu Leu His Gly Leu
1               5

<210> SEQ ID NO 238
<211> LENGTH: 12
<212> TYPE: PRT
<213> ORGANISM: Artificial Sequence
<220> FEATURE:
<223> OTHER INFORMATION: Cochliobolus lunatus Cytochrome c epitope

<400> SEQUENCE: 238

Leu Lys Ala Gly Glu Gly Asn Lys Ile Gly Pro Glu
1               5                   10

<210> SEQ ID NO 239
<211> LENGTH: 11
<212> TYPE: PRT
<213> ORGANISM: Artificial Sequence
<220> FEATURE:
<223> OTHER INFORMATION: Cochliobolus lunatus Cytochrome c epitope
```

```
<400> SEQUENCE: 239

Leu Lys Lys Pro Lys Asp Arg Asn Asp Leu Ile
1               5                  10

<210> SEQ ID NO 240
<211> LENGTH: 18
<212> TYPE: PRT
<213> ORGANISM: Artificial Sequence
<220> FEATURE:
<223> OTHER INFORMATION: Dermatophagoides farinae Der f 2 allergen
      epitope

<400> SEQUENCE: 240

Gly Leu Glu Ile Asp Val Pro Gly Ile Asp Thr Asn Ala Cys His Phe
1               5                  10                  15

Val Lys

<210> SEQ ID NO 241
<211> LENGTH: 20
<212> TYPE: PRT
<213> ORGANISM: Artificial Sequence
<220> FEATURE:
<223> OTHER INFORMATION: Dermatophagoides farinae Der f 2 allergen
      epitope

<400> SEQUENCE: 241

Pro Gly Ile Asp Thr Asn Ala Cys His Phe Val Lys Cys Pro Leu Val
1               5                  10                  15

Lys Gly Gln Gln
            20

<210> SEQ ID NO 242
<211> LENGTH: 19
<212> TYPE: PRT
<213> ORGANISM: Artificial Sequence
<220> FEATURE:
<223> OTHER INFORMATION: Dermatophagoides pteronyssinus Der p 1 allergen
      epitope

<400> SEQUENCE: 242

Arg Phe Gly Ile Ser Asn Tyr Cys Gln Ile Tyr Pro Pro Asn Ala Asn
1               5                  10                  15

Lys Ile Arg

<210> SEQ ID NO 243
<211> LENGTH: 15
<212> TYPE: PRT
<213> ORGANISM: Artificial Sequence
<220> FEATURE:
<223> OTHER INFORMATION: Dermatophagoides pteronyssinus Der p 1 allergen
      epitope

<400> SEQUENCE: 243

Ala Val Asn Ile Val Gly Tyr Ser Asn Ala Gln Gly Val Asp Tyr
1               5                  10                  15

<210> SEQ ID NO 244
<211> LENGTH: 20
<212> TYPE: PRT
<213> ORGANISM: Artificial Sequence
<220> FEATURE:
<223> OTHER INFORMATION: Chironomus thummi globin Ctt 3-1 epitope

<400> SEQUENCE: 244
```

```
Phe Ala Gly Lys Asp Leu Glu Ser Ile Lys Gly Thr Ala Pro Phe Glu
1               5                   10                  15

Thr His Ala Asn
            20

<210> SEQ ID NO 245
<211> LENGTH: 11
<212> TYPE: PRT
<213> ORGANISM: Artificial Sequence
<220> FEATURE:
<223> OTHER INFORMATION: Chironomus thummi globin Ctt 3-1 epitope

<400> SEQUENCE: 245

Gly Thr Ala Pro Phe Glu Thr His Ala Asn Arg
1               5                   10

<210> SEQ ID NO 246
<211> LENGTH: 21
<212> TYPE: PRT
<213> ORGANISM: Artificial Sequence
<220> FEATURE:
<223> OTHER INFORMATION: Chironomus thummi globin Ctt 3-1 epitope

<400> SEQUENCE: 246

Lys Gly Thr Ala Pro Phe Glu Thr His Ala Asn Arg Ile Val Gly Phe
1               5                   10                  15

Phe Ser Lys Ile Ile
            20

<210> SEQ ID NO 247
<211> LENGTH: 21
<212> TYPE: PRT
<213> ORGANISM: Artificial Sequence
<220> FEATURE:
<223> OTHER INFORMATION: Chironomus thummi thummi Globin CTT-III epitope

<400> SEQUENCE: 247

Ala His Thr Asp Phe Ala Gly Ala Glu Ala Ala Trp Gly Ala Thr Leu
1               5                   10                  15

Asp Thr Phe Phe Gly
            20

<210> SEQ ID NO 248
<211> LENGTH: 20
<212> TYPE: PRT
<213> ORGANISM: Artificial Sequence
<220> FEATURE:
<223> OTHER INFORMATION: Chironomus thummi thummi Globin CTT-III epitope

<400> SEQUENCE: 248

Phe Ala Gly Lys Asp Leu Glu Ser Ile Lys Gly Thr Ala Pro Phe Glu
1               5                   10                  15

Ile His Ala Asn
            20

<210> SEQ ID NO 249
<211> LENGTH: 21
<212> TYPE: PRT
<213> ORGANISM: Artificial Sequence
<220> FEATURE:
<223> OTHER INFORMATION: Chironomus thummi thummi Globin CTT-III epitope

<400> SEQUENCE: 249

Val Asn Thr Phe Val Ala Ser His Lys Pro Arg Gly Val Thr His Asp
1               5                   10                  15
```

Gln Leu Asn Asn Phe
            20

<210> SEQ ID NO 250
<211> LENGTH: 8
<212> TYPE: PRT
<213> ORGANISM: Artificial Sequence
<220> FEATURE:
<223> OTHER INFORMATION: Chironomus thummi thummi Globin CTT-III
      precursor epitope

<400> SEQUENCE: 250

Ala Asp Pro Ser Ile Met Ala Lys
1               5

<210> SEQ ID NO 251
<211> LENGTH: 21
<212> TYPE: PRT
<213> ORGANISM: Artificial Sequence
<220> FEATURE:
<223> OTHER INFORMATION: Chironomus thummi thummi Globin CTT-III
      precursor epitope

<400> SEQUENCE: 251

Ala Asp Pro Ser Ile Met Ala Lys Phe Thr Gln Phe Ala Gly Lys Asp
1               5                   10                  15

Leu Glu Ser Ile Lys
            20

<210> SEQ ID NO 252
<211> LENGTH: 5
<212> TYPE: PRT
<213> ORGANISM: Artificial Sequence
<220> FEATURE:
<223> OTHER INFORMATION: Chironomus thummi thummi Globin CTT-III
      precursor epitope

<400> SEQUENCE: 252

Ala Glu Ala Ala Trp
1               5

<210> SEQ ID NO 253
<211> LENGTH: 20
<212> TYPE: PRT
<213> ORGANISM: Artificial Sequence
<220> FEATURE:
<223> OTHER INFORMATION: Chironomus thummi thummi Globin CTT-III
      precursor epitope

<400> SEQUENCE: 253

Ala Glu Ala Ala Trp Gly Ala Thr Leu Asp Thr Phe Phe Gly Met Ile
1               5                   10                  15

Phe Ser Lys Met
            20

<210> SEQ ID NO 254
<211> LENGTH: 8
<212> TYPE: PRT
<213> ORGANISM: Artificial Sequence
<220> FEATURE:
<223> OTHER INFORMATION: Chironomus thummi thummi Globin CTT-III
      precursor epitope

<400> SEQUENCE: 254

Ala Gly Phe Val Ser Tyr Met Lys
1               5

<210> SEQ ID NO 255
<211> LENGTH: 15
<212> TYPE: PRT
<213> ORGANISM: Artificial Sequence
<220> FEATURE:
<223> OTHER INFORMATION: Phaseolus vulgaris Glycine-rich cell wall
      structural protein 1.8 precursor epitope

<400> SEQUENCE: 255

Gly Gly Tyr Gly Asp Gly Gly Ala His Gly Gly Gly Tyr Gly Gly
1               5                   10                  15

<210> SEQ ID NO 256
<211> LENGTH: 15
<212> TYPE: PRT
<213> ORGANISM: Artificial Sequence
<220> FEATURE:
<223> OTHER INFORMATION: Phleum pratense Group V allergen Phl p 5
      epitope

<400> SEQUENCE: 256

Ala Thr Pro Glu Ala Lys Tyr Asp Ala Tyr Val Ala Thr Leu Ser
1               5                   10                  15

<210> SEQ ID NO 257
<211> LENGTH: 15
<212> TYPE: PRT
<213> ORGANISM: Artificial Sequence
<220> FEATURE:
<223> OTHER INFORMATION: Phleum pratense Group V allergen Phl p 5
      epitope

<400> SEQUENCE: 257

Phe Thr Val Phe Glu Ala Ala Phe Asn Asn Ala Ile Lys Ala Gly
1               5                   10                  15

<210> SEQ ID NO 258
<211> LENGTH: 15
<212> TYPE: PRT
<213> ORGANISM: Artificial Sequence
<220> FEATURE:
<223> OTHER INFORMATION: Phleum pratense Group V allergen Phl p 5
      epitope

<400> SEQUENCE: 258

Lys Tyr Asp Ala Tyr Val Ala Thr Leu Ser Glu Ala Leu Arg Ile
1               5                   10                  15

<210> SEQ ID NO 259
<211> LENGTH: 15
<212> TYPE: PRT
<213> ORGANISM: Artificial Sequence
<220> FEATURE:
<223> OTHER INFORMATION: Phleum pratense Group V allergen Phl p 5
      epitope

<400> SEQUENCE: 259

Pro Ala Asn Asp Lys Phe Thr Val Phe Glu Ala Ala Phe Asn Asn
1               5                   10                  15

<210> SEQ ID NO 260
<211> LENGTH: 15
<212> TYPE: PRT
<213> ORGANISM: Artificial Sequence
<220> FEATURE:
<223> OTHER INFORMATION: Phleum pratense Group V allergen Phl p 5
      epitope

<400> SEQUENCE: 260

Pro Lys Gly Gly Ala Glu Ser Ser Ser Lys Ala Ala Leu Thr Ser
1               5                   10                  15

<210> SEQ ID NO 261
<211> LENGTH: 16
<212> TYPE: PRT
<213> ORGANISM: Artificial Sequence
<220> FEATURE:
<223> OTHER INFORMATION: Homo sapiens KIAA1224 protein epitope

<400> SEQUENCE: 261

Asp Leu Glu Ser Tyr Leu Gln Leu Asn Cys Glu Arg Gly Thr Trp Arg
1               5                   10                  15

<210> SEQ ID NO 262
<211> LENGTH: 15
<212> TYPE: PRT
<213> ORGANISM: Artificial Sequence
<220> FEATURE:
<223> OTHER INFORMATION: Lepidoglyphus destructor Lep D 2 precursor
      epitope

<400> SEQUENCE: 262

Lys Gly Glu Ala Leu Asp Phe Asn Tyr Gly Met Thr Ile Pro Ala
1               5                   10                  15

<210> SEQ ID NO 263
<211> LENGTH: 12
<212> TYPE: PRT
<213> ORGANISM: Artificial Sequence
<220> FEATURE:
<223> OTHER INFORMATION: Corylus avellana lipid transfer protein
      precursor epitope

<400> SEQUENCE: 263

Ala Gly Leu Pro Gly Lys Cys Gly Val Asn Ile Pro
1               5                   10

<210> SEQ ID NO 264
<211> LENGTH: 12
<212> TYPE: PRT
<213> ORGANISM: Artificial Sequence
<220> FEATURE:
<223> OTHER INFORMATION: Corylus avellana lipid transfer protein
      precursor epitope

<400> SEQUENCE: 264

Ala Lys Gly Ile Ala Gly Leu Asn Pro Asn Leu Ala
1               5                   10

<210> SEQ ID NO 265
<211> LENGTH: 12
<212> TYPE: PRT
<213> ORGANISM: Artificial Sequence
<220> FEATURE:
<223> OTHER INFORMATION: Corylus avellana lipid transfer protein
      precursor epitope

<400> SEQUENCE: 265

Cys Gly Val Asn Ile Pro Tyr Lys Ile Ser Pro Ser
1               5                   10

<210> SEQ ID NO 266
<211> LENGTH: 12
<212> TYPE: PRT

-continued

<213> ORGANISM: Artificial Sequence
<220> FEATURE:
<223> OTHER INFORMATION: Corylus avellana lipid transfer protein
      precursor epitope

<400> SEQUENCE: 266

Cys Lys Gly Val Arg Ala Val Asn Asp Ala Ser Arg
1               5                   10

<210> SEQ ID NO 267
<211> LENGTH: 12
<212> TYPE: PRT
<213> ORGANISM: Artificial Sequence
<220> FEATURE:
<223> OTHER INFORMATION: Corylus avellana lipid transfer protein
      precursor epitope

<400> SEQUENCE: 267

Cys Val Leu Tyr Leu Lys Asn Gly Gly Val Leu Pro
1               5                   10

<210> SEQ ID NO 268
<211> LENGTH: 16
<212> TYPE: PRT
<213> ORGANISM: Artificial Sequence
<220> FEATURE:
<223> OTHER INFORMATION: Homo sapiens Lipocalin 1 (tear prealbumin)
      epitope

<400> SEQUENCE: 268

Lys Pro Val Arg Gly Val Lys Leu Val Gly Arg Asp Pro Lys Asn Asn
1               5                   10                  15

<210> SEQ ID NO 269
<211> LENGTH: 15
<212> TYPE: PRT
<213> ORGANISM: Artificial Sequence
<220> FEATURE:
<223> OTHER INFORMATION: Dermatophagoides farinae Mag3 epitope

<400> SEQUENCE: 269

Glu Phe Asn Thr Glu Phe Thr Ile His Ala Asp Lys Asn Asn Leu
1               5                   10                  15

<210> SEQ ID NO 270
<211> LENGTH: 15
<212> TYPE: PRT
<213> ORGANISM: Artificial Sequence
<220> FEATURE:
<223> OTHER INFORMATION: Dermatophagoides farinae Mag3 epitope

<400> SEQUENCE: 270

Phe Thr Ile His Ala Asp Lys Asn Asn Leu Lys Met His Met Asp
1               5                   10                  15

<210> SEQ ID NO 271
<211> LENGTH: 15
<212> TYPE: PRT
<213> ORGANISM: Artificial Sequence
<220> FEATURE:
<223> OTHER INFORMATION: Dermatophagoides farinae Mag3 epitope

<400> SEQUENCE: 271

Lys Met His Met Asp Phe Pro Asn Val Phe Gln Ala Asp Leu Thr
1               5                   10                  15

<210> SEQ ID NO 272

```
<211> LENGTH: 13
<212> TYPE: PRT
<213> ORGANISM: Artificial Sequence
<220> FEATURE:
<223> OTHER INFORMATION: Apium graveolens Major allergen Api g 1 epitope

<400> SEQUENCE: 272

Ala Leu Phe Lys Ala Leu Glu Ala Tyr Leu Ile Ala Asn
1               5                   10

<210> SEQ ID NO 273
<211> LENGTH: 12
<212> TYPE: PRT
<213> ORGANISM: Artificial Sequence
<220> FEATURE:
<223> OTHER INFORMATION: Apium graveolens Major allergen Api g 1 epitope

<400> SEQUENCE: 273

Asp Ala Val Val Pro Glu Glu Asn Ile Lys Tyr Ala
1               5                   10

<210> SEQ ID NO 274
<211> LENGTH: 12
<212> TYPE: PRT
<213> ORGANISM: Artificial Sequence
<220> FEATURE:
<223> OTHER INFORMATION: Apium graveolens Major allergen Api g 1 epitope

<400> SEQUENCE: 274

Asp Ile Leu Leu Gly Phe Ile Glu Ser Ile Glu Asn
1               5                   10

<210> SEQ ID NO 275
<211> LENGTH: 12
<212> TYPE: PRT
<213> ORGANISM: Artificial Sequence
<220> FEATURE:
<223> OTHER INFORMATION: Apium graveolens Major allergen Api g 1 epitope

<400> SEQUENCE: 275

Gly Gly Ser Ile Cys Lys Thr Thr Ala Ile Phe His
1               5                   10

<210> SEQ ID NO 276
<211> LENGTH: 12
<212> TYPE: PRT
<213> ORGANISM: Artificial Sequence
<220> FEATURE:
<223> OTHER INFORMATION: Apium graveolens Major allergen Api g 1 epitope

<400> SEQUENCE: 276

Gly Val Gln Thr His Val Leu Glu Leu Thr Ser Ser
1               5                   10

<210> SEQ ID NO 277
<211> LENGTH: 15
<212> TYPE: PRT
<213> ORGANISM: Artificial Sequence
<220> FEATURE:
<223> OTHER INFORMATION: Aspergillus fumigatus Major allergen Asp f 2
      precursor epitope

<400> SEQUENCE: 277

Phe Gly Asn Arg Pro Thr Met Glu Ala Val Gly Ala Tyr Asp Val
1               5                   10                  15

<210> SEQ ID NO 278
```

```
<211> LENGTH: 15
<212> TYPE: PRT
<213> ORGANISM: Artificial Sequence
<220> FEATURE:
<223> OTHER INFORMATION: Aspergillus fumigatus Major allergen Asp f 2
      precursor epitope

<400> SEQUENCE: 278

Met Glu Ala Val Gly Ala Tyr Asp Val Ile Val Asn Gly Asp Lys
1               5                   10                  15

<210> SEQ ID NO 279
<211> LENGTH: 16
<212> TYPE: PRT
<213> ORGANISM: Artificial Sequence
<220> FEATURE:
<223> OTHER INFORMATION: Canis lupus familiaris Major allergen Can f 1
      precursor epitope

<400> SEQUENCE: 279

Ala Leu Glu Asp Phe Arg Glu Phe Ser Arg Ala Lys Gly Leu Asn Gln
1               5                   10                  15

<210> SEQ ID NO 280
<211> LENGTH: 16
<212> TYPE: PRT
<213> ORGANISM: Artificial Sequence
<220> FEATURE:
<223> OTHER INFORMATION: Canis lupus familiaris Major allergen Can f 1
      precursor epitope

<400> SEQUENCE: 280

Asp Gln Glu Val Pro Glu Lys Pro Asp Ser Val Thr Pro Met Ile Leu
1               5                   10                  15

<210> SEQ ID NO 281
<211> LENGTH: 12
<212> TYPE: PRT
<213> ORGANISM: Artificial Sequence
<220> FEATURE:
<223> OTHER INFORMATION: Corylus avellana major allergen Cor a 1.0401
      epitope

<400> SEQUENCE: 281

Ala Gly Lys Glu Lys Ala Ala Gly Leu Phe Lys Ala
1               5                   10

<210> SEQ ID NO 282
<211> LENGTH: 12
<212> TYPE: PRT
<213> ORGANISM: Artificial Sequence
<220> FEATURE:
<223> OTHER INFORMATION: Corylus avellana major allergen Cor a 1.0401
      epitope

<400> SEQUENCE: 282

Ala Gly Leu Phe Lys Ala Val Glu Ala Tyr Leu Leu
1               5                   10

<210> SEQ ID NO 283
<211> LENGTH: 12
<212> TYPE: PRT
<213> ORGANISM: Artificial Sequence
<220> FEATURE:
<223> OTHER INFORMATION: Corylus avellana major allergen Cor a 1.0401
      epitope

<400> SEQUENCE: 283
```

Ala Pro Gln His Phe Thr Ser Ala Glu Asn Leu Glu
1               5                   10

<210> SEQ ID NO 284
<211> LENGTH: 12
<212> TYPE: PRT
<213> ORGANISM: Artificial Sequence
<220> FEATURE:
<223> OTHER INFORMATION: Corylus avellana major allergen Cor a 1.0401
      epitope

<400> SEQUENCE: 284

Ala Arg Leu Phe Lys Ser Phe Val Leu Asp Ala Asp
1               5                   10

<210> SEQ ID NO 285
<211> LENGTH: 12
<212> TYPE: PRT
<213> ORGANISM: Artificial Sequence
<220> FEATURE:
<223> OTHER INFORMATION: Corylus avellana major allergen Cor a 1.0401
      epitope

<400> SEQUENCE: 285

Glu Ile Asp His Ala Asn Phe Lys Tyr Cys Tyr Ser
1               5                   10

<210> SEQ ID NO 286
<211> LENGTH: 13
<212> TYPE: PRT
<213> ORGANISM: Artificial Sequence
<220> FEATURE:
<223> OTHER INFORMATION: Daucus carota Major allergen Dau c 1 epitope

<400> SEQUENCE: 286

Ala Leu Phe Lys Ala Ile Glu Ala Tyr Leu Ile Ala Asn
1               5                   10

<210> SEQ ID NO 287
<211> LENGTH: 16
<212> TYPE: PRT
<213> ORGANISM: Artificial Sequence
<220> FEATURE:
<223> OTHER INFORMATION: Equus caballus Major allergen Equ c 1 precursor
      epitope

<400> SEQUENCE: 287

Asp Gly Tyr Asn Val Phe Arg Ile Ser Glu Phe Glu Asn Asp Glu His
1               5                   10                  15

<210> SEQ ID NO 288
<211> LENGTH: 16
<212> TYPE: PRT
<213> ORGANISM: Artificial Sequence
<220> FEATURE:
<223> OTHER INFORMATION: Equus caballus Major allergen Equ c 1 precursor
      epitope

<400> SEQUENCE: 288

Asp Lys Asp Arg Pro Phe Gln Leu Phe Glu Phe Tyr Ala Arg Glu Pro
1               5                   10                  15

<210> SEQ ID NO 289
<211> LENGTH: 16
<212> TYPE: PRT
<213> ORGANISM: Artificial Sequence
<220> FEATURE:
<223> OTHER INFORMATION: Equus caballus Major allergen Equ c 1 precursor -continued epitope

<400> SEQUENCE: 289

Asp Leu Thr Lys Ile Asp Arg Cys Phe Gln Leu Arg Gly Asn Gly Val
1               5                   10                  15

<210> SEQ ID NO 290
<211> LENGTH: 16
<212> TYPE: PRT
<213> ORGANISM: Artificial Sequence
<220> FEATURE:
<223> OTHER INFORMATION: Equus caballus Major allergen Equ c 1 precursor
      epitope

<400> SEQUENCE: 290

Asp Arg Pro Phe Gln Leu Phe Glu Phe Tyr Ala Arg Glu Pro Asp Val
1               5                   10                  15

<210> SEQ ID NO 291
<211> LENGTH: 16
<212> TYPE: PRT
<213> ORGANISM: Artificial Sequence
<220> FEATURE:
<223> OTHER INFORMATION: Equus caballus Major allergen Equ c 1 precursor
      epitope

<400> SEQUENCE: 291

Asp Val Ser Pro Glu Ile Lys Glu Glu Phe Val Lys Ile Val Gln Lys
1               5                   10                  15

<210> SEQ ID NO 292
<211> LENGTH: 17
<212> TYPE: PRT
<213> ORGANISM: Artificial Sequence
<220> FEATURE:
<223> OTHER INFORMATION: Felis catus major allergen I epitope

<400> SEQUENCE: 292

Glu Asn Ala Arg Ile Leu Lys Asn Cys Val Asp Ala Lys Met Thr Glu
1               5                   10                  15

Glu

<210> SEQ ID NO 293
<211> LENGTH: 17
<212> TYPE: PRT
<213> ORGANISM: Artificial Sequence
<220> FEATURE:
<223> OTHER INFORMATION: Felis catus major allergen I epitope

<400> SEQUENCE: 293

Arg Asp Val Asp Leu Phe Leu Thr Gly Thr Pro Asp Glu Tyr Val Glu
1               5                   10                  15

Gln

<210> SEQ ID NO 294
<211> LENGTH: 17
<212> TYPE: PRT
<213> ORGANISM: Artificial Sequence
<220> FEATURE:
<223> OTHER INFORMATION: Felis catus major allergen I epitope

<400> SEQUENCE: 294

Thr Gly Thr Pro Asp Glu Tyr Val Glu Gln Val Ala Gln Tyr Lys Ala
1               5                   10                  15

Leu

<210> SEQ ID NO 295
<211> LENGTH: 17
<212> TYPE: PRT
<213> ORGANISM: Artificial Sequence
<220> FEATURE:
<223> OTHER INFORMATION: Felis catus Major allergen I polypeptide chain
      1 precursor epitope

<400> SEQUENCE: 295

Asp Val Asp Leu Phe Leu Thr Gly Thr Pro Asp Glu Tyr Val Glu Gln
1               5                   10                  15

Val

<210> SEQ ID NO 296
<211> LENGTH: 17
<212> TYPE: PRT
<213> ORGANISM: Artificial Sequence
<220> FEATURE:
<223> OTHER INFORMATION: Felis catus Major allergen I polypeptide chain
      1 precursor epitope

<400> SEQUENCE: 296

Glu Ile Cys Pro Ala Val Lys Arg Asp Val Asp Leu Phe Leu Thr Gly
1               5                   10                  15

Thr

<210> SEQ ID NO 297
<211> LENGTH: 16
<212> TYPE: PRT
<213> ORGANISM: Artificial Sequence
<220> FEATURE:
<223> OTHER INFORMATION: Felis catus Major allergen I polypeptide chain
      1 precursor epitope

<400> SEQUENCE: 297

Glu Gln Val Ala Gln Tyr Lys Ala Leu Pro Val Val Leu Glu Asn Ala
1               5                   10                  15

<210> SEQ ID NO 298
<211> LENGTH: 17
<212> TYPE: PRT
<213> ORGANISM: Artificial Sequence
<220> FEATURE:
<223> OTHER INFORMATION: Felis catus Major allergen I polypeptide chain
      1 precursor epitope

<400> SEQUENCE: 298

Lys Ala Leu Pro Val Val Leu Glu Asn Ala Arg Ile Leu Lys Asn Cys
1               5                   10                  15

Val

<210> SEQ ID NO 299
<211> LENGTH: 17
<212> TYPE: PRT
<213> ORGANISM: Artificial Sequence
<220> FEATURE:
<223> OTHER INFORMATION: Felis catus Major allergen I polypeptide chain
      1 precursor epitope

<400> SEQUENCE: 299

Leu Phe Leu Thr Gly Thr Pro Asp Glu Tyr Val Glu Gln Val Ala Gln
1               5                   10                  15

Tyr

```
<210> SEQ ID NO 300
<211> LENGTH: 16
<212> TYPE: PRT
<213> ORGANISM: Artificial Sequence
<220> FEATURE:
<223> OTHER INFORMATION: Felis catus major allergen I, polypeptide chain
      1 epitope

<400> SEQUENCE: 300

Lys Glu Asn Ala Leu Ser Leu Leu Asp Lys Ile Tyr Thr Ser Pro Leu
1               5                   10                  15

<210> SEQ ID NO 301
<211> LENGTH: 16
<212> TYPE: PRT
<213> ORGANISM: Artificial Sequence
<220> FEATURE:
<223> OTHER INFORMATION: Felis catus major allergen I, polypeptide chain
      1 epitope

<400> SEQUENCE: 301

Lys Met Thr Glu Glu Asp Lys Glu Asn Ala Leu Ser Leu Leu Asp Lys
1               5                   10                  15

<210> SEQ ID NO 302
<211> LENGTH: 15
<212> TYPE: PRT
<213> ORGANISM: Artificial Sequence
<220> FEATURE:
<223> OTHER INFORMATION: Malus x domestica Major allergen Mal d 1 epitope

<400> SEQUENCE: 302

Gly Leu Phe Lys Leu Ile Glu Ser Tyr Leu Lys Asp His Pro Asp
1               5                   10                  15

<210> SEQ ID NO 303
<211> LENGTH: 15
<212> TYPE: PRT
<213> ORGANISM: Artificial Sequence
<220> FEATURE:
<223> OTHER INFORMATION: Prunus avium Major allergen Pru av 1 epitope

<400> SEQUENCE: 303

Asn Leu Phe Lys Leu Ile Glu Thr Tyr Leu Lys Gly His Pro Asp
1               5                   10                  15

<210> SEQ ID NO 304
<211> LENGTH: 20
<212> TYPE: PRT
<213> ORGANISM: Artificial Sequence
<220> FEATURE:
<223> OTHER INFORMATION: Hevea brasiliensis Major latex allergen Hev b 5
      epitope

<400> SEQUENCE: 304

Ala Ala Pro Ala Glu Gly Glu Lys Pro Ala Glu Glu Lys Pro Ile
1               5                   10                  15

Thr Glu Ala Ala
            20

<210> SEQ ID NO 305
<211> LENGTH: 20
<212> TYPE: PRT
<213> ORGANISM: Artificial Sequence
<220> FEATURE:
<223> OTHER INFORMATION: Hevea brasiliensis Major latex allergen Hev b 5
      epitope
```

<400> SEQUENCE: 305

Ala Glu Glu Glu Lys Pro Ile Thr Glu Ala Ala Glu Thr Ala Thr Thr
1               5                   10                  15

Glu Val Pro Val
            20

<210> SEQ ID NO 306
<211> LENGTH: 20
<212> TYPE: PRT
<213> ORGANISM: Artificial Sequence
<220> FEATURE:
<223> OTHER INFORMATION: Hevea brasiliensis Major latex allergen Hev b 5
      epitope

<400> SEQUENCE: 306

Ala Pro Ala Glu Pro Glu Ala Pro Ala Pro Glu Thr Glu Lys Ala Glu
1               5                   10                  15

Glu Val Glu Lys
            20

<210> SEQ ID NO 307
<211> LENGTH: 20
<212> TYPE: PRT
<213> ORGANISM: Artificial Sequence
<220> FEATURE:
<223> OTHER INFORMATION: Hevea brasiliensis Major latex allergen Hev b 5
      epitope

<400> SEQUENCE: 307

Ala Pro Glu Ala Asp Gln Thr Thr Pro Glu Glu Lys Pro Ala Glu Pro
1               5                   10                  15

Glu Pro Val Ala
            20

<210> SEQ ID NO 308
<211> LENGTH: 20
<212> TYPE: PRT
<213> ORGANISM: Artificial Sequence
<220> FEATURE:
<223> OTHER INFORMATION: Hevea brasiliensis Major latex allergen Hev b 5
      epitope

<400> SEQUENCE: 308

Ala Ser Glu Gln Glu Thr Ala Asp Ala Thr Pro Glu Lys Glu Glu Pro
1               5                   10                  15

Thr Ala Ala Pro
            20

<210> SEQ ID NO 309
<211> LENGTH: 11
<212> TYPE: PRT
<213> ORGANISM: Artificial Sequence
<220> FEATURE:
<223> OTHER INFORMATION: Dermatophagoides pteronyssinus Major mite fecal
      allergen Der p 1 epitope

<400> SEQUENCE: 309

Tyr Ala Tyr Val Ala Arg Glu Gln Ser Cys Arg
1               5                   10

<210> SEQ ID NO 310
<211> LENGTH: 19
<212> TYPE: PRT
<213> ORGANISM: Artificial Sequence

```
<220> FEATURE:
<223> OTHER INFORMATION: Dermatophagoides pteronyssinus Major mite fecal
      allergen Der p 1 epitope

<400> SEQUENCE: 310

Ala Leu Ala Gln Thr His Thr Ala Ile Ala Val Ile Ile Gly Ile Lys
1               5                   10                  15

Asp Leu Asp

<210> SEQ ID NO 311
<211> LENGTH: 35
<212> TYPE: PRT
<213> ORGANISM: Artificial Sequence
<220> FEATURE:
<223> OTHER INFORMATION: Olea europaea Major pollen allergen epitope

<400> SEQUENCE: 311

Glu Asp Ile Pro Gln Pro Pro Val Ser Gln Phe His Ile Gln Gly Gln
1               5                   10                  15

Val Tyr Cys Asp Thr Cys Arg Ala Gly Phe Ile Thr Glu Leu Ser Glu
            20                  25                  30

Phe Ile Pro
        35

<210> SEQ ID NO 312
<211> LENGTH: 31
<212> TYPE: PRT
<213> ORGANISM: Artificial Sequence
<220> FEATURE:
<223> OTHER INFORMATION: Olea europaea Major pollen allergen epitope

<400> SEQUENCE: 312

Gly Ala Ser Leu Arg Leu Gln Cys Lys Asp Lys Glu Asn Gly Asp Val
1               5                   10                  15

Thr Phe Thr Glu Val Gly Tyr Thr Arg Ala Glu Gly Leu Tyr Ser
            20                  25                  30

<210> SEQ ID NO 313
<211> LENGTH: 34
<212> TYPE: PRT
<213> ORGANISM: Artificial Sequence
<220> FEATURE:
<223> OTHER INFORMATION: Olea europaea Major pollen allergen epitope

<400> SEQUENCE: 313

Gly Thr Thr Arg Thr Val Asn Pro Leu Gly Phe Phe Lys Lys Glu Ala
1               5                   10                  15

Leu Pro Lys Cys Ala Gln Val Tyr Asn Lys Leu Gly Met Tyr Pro Pro
            20                  25                  30

Asn Met

<210> SEQ ID NO 314
<211> LENGTH: 53
<212> TYPE: PRT
<213> ORGANISM: Artificial Sequence
<220> FEATURE:
<223> OTHER INFORMATION: Olea europaea Major pollen allergen epitope

<400> SEQUENCE: 314

Leu Val Glu Arg Asp His Lys Asn Glu Phe Cys Glu Ile Thr Leu Ile
1               5                   10                  15

Ser Ser Gly Arg Lys Asp Cys Asn Glu Ile Pro Thr Glu Gly Trp Ala
            20                  25                  30
```

```
Lys Pro Ser Leu Lys Phe Lys Leu Asn Thr Val Asn Gly Thr Thr Arg
        35                  40                  45

Thr Val Asn Pro Leu
    50

<210> SEQ ID NO 315
<211> LENGTH: 33
<212> TYPE: PRT
<213> ORGANISM: Artificial Sequence
<220> FEATURE:
<223> OTHER INFORMATION: Olea europaea Major pollen allergen epitope

<400> SEQUENCE: 315

Met Leu Val Glu Arg Asp His Lys Asn Glu Phe Cys Glu Ile Thr Leu
1               5                   10                  15

Ile Ser Ser Gly Arg Lys Asp Cys Asn Glu Ile Pro Thr Glu Gly Trp
            20                  25                  30

Ala

<210> SEQ ID NO 316
<211> LENGTH: 12
<212> TYPE: PRT
<213> ORGANISM: Artificial Sequence
<220> FEATURE:
<223> OTHER INFORMATION: Artemisia vulgaris Major pollen allergen Art v
      1 precursor epitope

<400> SEQUENCE: 316

Ala Gly Gly Ser Pro Ser Pro Pro Ala Asp Gly Gly
1               5                   10

<210> SEQ ID NO 317
<211> LENGTH: 12
<212> TYPE: PRT
<213> ORGANISM: Artificial Sequence
<220> FEATURE:
<223> OTHER INFORMATION: Artemisia vulgaris Major pollen allergen Art v
      1 precursor epitope

<400> SEQUENCE: 317

Ala Gly Ser Lys Leu Cys Glu Lys Thr Ser Lys Thr
1               5                   10

<210> SEQ ID NO 318
<211> LENGTH: 12
<212> TYPE: PRT
<213> ORGANISM: Artificial Sequence
<220> FEATURE:
<223> OTHER INFORMATION: Artemisia vulgaris Major pollen allergen Art v
      1 precursor epitope

<400> SEQUENCE: 318

Cys Asp Lys Lys Cys Ile Glu Trp Glu Lys Ala Gln
1               5                   10

<210> SEQ ID NO 319
<211> LENGTH: 12
<212> TYPE: PRT
<213> ORGANISM: Artificial Sequence
<220> FEATURE:
<223> OTHER INFORMATION: Artemisia vulgaris Major pollen allergen Art v
      1 precursor epitope

<400> SEQUENCE: 319

Asp Gly Gly Ser Pro Pro Pro Ala Asp Gly Gly
```

<210> SEQ ID NO 320
<211> LENGTH: 12
<212> TYPE: PRT
<213> ORGANISM: Artificial Sequence
<220> FEATURE:
<223> OTHER INFORMATION: Artemisia vulgaris Major pollen allergen Art v
      1 precursor epitope

<400> SEQUENCE: 320

Glu Lys Thr Ser Lys Thr Tyr Ser Gly Lys Cys Asp
1               5                   10

<210> SEQ ID NO 321
<211> LENGTH: 12
<212> TYPE: PRT
<213> ORGANISM: Artificial Sequence
<220> FEATURE:
<223> OTHER INFORMATION: Betula pendula Major pollen allergen Bet v 1-A
      epitope

<400> SEQUENCE: 321

Ala Ala Arg Leu Phe Lys Ala Phe Ile Leu Asp Gly
1               5                   10

<210> SEQ ID NO 322
<211> LENGTH: 15
<212> TYPE: PRT
<213> ORGANISM: Artificial Sequence
<220> FEATURE:
<223> OTHER INFORMATION: Betula pendula Major pollen allergen Bet v 1-A
      epitope

<400> SEQUENCE: 322

Ala Ala Arg Leu Phe Lys Ala Phe Ile Leu Asp Gly Asp Asn Leu
1               5                   10                  15

<210> SEQ ID NO 323
<211> LENGTH: 12
<212> TYPE: PRT
<213> ORGANISM: Artificial Sequence
<220> FEATURE:
<223> OTHER INFORMATION: Betula pendula Major pollen allergen Bet v 1-A
      epitope

<400> SEQUENCE: 323

Ala Glu Gln Val Lys Ala Ser Lys Glu Met Gly Glu
1               5                   10

<210> SEQ ID NO 324
<211> LENGTH: 21
<212> TYPE: PRT
<213> ORGANISM: Artificial Sequence
<220> FEATURE:
<223> OTHER INFORMATION: Betula pendula Major pollen allergen Bet v 1-A
      epitope

<400> SEQUENCE: 324

Ala Phe Ile Leu Asp Gly Asp Asn Leu Phe Pro Lys Val Ala Pro Gln
1               5                   10                  15

Ala Ile Ser Ser Val
            20

<210> SEQ ID NO 325
<211> LENGTH: 12
<212> TYPE: PRT

```
<213> ORGANISM: Artificial Sequence
<220> FEATURE:
<223> OTHER INFORMATION: Betula pendula Major pollen allergen Bet v 1-A
      epitope

<400> SEQUENCE: 325

Ala Ile Ser Ser Val Glu Asn Ile Glu Gly Asn Gly
1               5                   10

<210> SEQ ID NO 326
<211> LENGTH: 15
<212> TYPE: PRT
<213> ORGANISM: Artificial Sequence
<220> FEATURE:
<223> OTHER INFORMATION: Betula pendula Major pollen allergen Bet v 1-A
      epitope

<400> SEQUENCE: 326

Glu Thr Leu Leu Arg Ala Val Glu Ser Tyr Leu Leu Ala His Ser
1               5                   10                  15

<210> SEQ ID NO 327
<211> LENGTH: 16
<212> TYPE: PRT
<213> ORGANISM: Artificial Sequence
<220> FEATURE:
<223> OTHER INFORMATION: Betula pendula Major pollen allergen Bet v
      1-F/I epitope

<400> SEQUENCE: 327

Gly Glu Thr Leu Leu Arg Ala Val Glu Ser Tyr Leu Leu Ala His Ser
1               5                   10                  15

<210> SEQ ID NO 328
<211> LENGTH: 20
<212> TYPE: PRT
<213> ORGANISM: Artificial Sequence
<220> FEATURE:
<223> OTHER INFORMATION: Chamaecyparis obtusa Major pollen allergen Cha
      o 1 precursor epitope

<400> SEQUENCE: 328

Ala Asn Asn Asn Tyr Asp Pro Trp Ser Ile Tyr Ala Ile Gly Gly Ser
1               5                   10                  15
Ser Asn Pro Thr
            20

<210> SEQ ID NO 329
<211> LENGTH: 20
<212> TYPE: PRT
<213> ORGANISM: Artificial Sequence
<220> FEATURE:
<223> OTHER INFORMATION: Chamaecyparis obtusa Major pollen allergen Cha
      o 1 precursor epitope

<400> SEQUENCE: 329

Ala Ser Thr Gly Val Thr Ile Ser Asn Asn His Phe Phe Asn His His
1               5                   10                  15
Lys Val Met Leu
            20

<210> SEQ ID NO 330
<211> LENGTH: 20
<212> TYPE: PRT
<213> ORGANISM: Artificial Sequence
<220> FEATURE:
<223> OTHER INFORMATION: Chamaecyparis obtusa Major pollen allergen Cha
``` o 1 precursor epitope

<400> SEQUENCE: 330

Cys Ala Asn Trp Val Trp Arg Ser Thr Gln Asp Ser Phe Asn Asn Gly
1               5                   10                  15

Ala Tyr Phe Val
            20

<210> SEQ ID NO 331
<211> LENGTH: 20
<212> TYPE: PRT
<213> ORGANISM: Artificial Sequence
<220> FEATURE:
<223> OTHER INFORMATION: Chamaecyparis obtusa Major pollen allergen Cha
      o 1 precursor epitope

<400> SEQUENCE: 331

Asp Ala Ile Thr Met Arg Asn Val Thr Asp Val Trp Ile Asp His Asn
1               5                   10                  15

Ser Leu Ser Asp
            20

<210> SEQ ID NO 332
<211> LENGTH: 20
<212> TYPE: PRT
<213> ORGANISM: Artificial Sequence
<220> FEATURE:
<223> OTHER INFORMATION: Chamaecyparis obtusa Major pollen allergen Cha
      o 1 precursor epitope

<400> SEQUENCE: 332

Asp Ala Asn Trp Asp Gln Asn Arg Met Lys Leu Ala Asp Cys Ala Val
1               5                   10                  15

Gly Phe Gly Ser
            20

<210> SEQ ID NO 333
<211> LENGTH: 20
<212> TYPE: PRT
<213> ORGANISM: Artificial Sequence
<220> FEATURE:
<223> OTHER INFORMATION: Cynodon dactylon Major pollen allergen Cyn d 1
      epitope

<400> SEQUENCE: 333

Ala Ile Gly Asp Lys Pro Gly Pro Asn Ile Thr Ala Thr Tyr Gly Asn
1               5                   10                  15

Lys Trp Leu Glu
            20

<210> SEQ ID NO 334
<211> LENGTH: 20
<212> TYPE: PRT
<213> ORGANISM: Artificial Sequence
<220> FEATURE:
<223> OTHER INFORMATION: Cynodon dactylon Major pollen allergen Cyn d 1
      epitope

<400> SEQUENCE: 334

Cys Tyr Glu Ile Lys Cys Lys Glu Pro Val Glu Cys Ser Gly Glu Pro
1               5                   10                  15

Val Leu Val Lys
            20

```
<210> SEQ ID NO 335
<211> LENGTH: 20
<212> TYPE: PRT
<213> ORGANISM: Artificial Sequence
<220> FEATURE:
<223> OTHER INFORMATION: Cynodon dactylon Major pollen allergen Cyn d 1
      epitope

<400> SEQUENCE: 335

Asp His Gly Gly Ala Cys Gly Tyr Lys Asp Val Asp Lys Pro Pro Phe
1               5                   10                  15

Asp Gly Met Thr
            20

<210> SEQ ID NO 336
<211> LENGTH: 20
<212> TYPE: PRT
<213> ORGANISM: Artificial Sequence
<220> FEATURE:
<223> OTHER INFORMATION: Cynodon dactylon Major pollen allergen Cyn d 1
      epitope

<400> SEQUENCE: 336

Glu Gly Gly Ala His Leu Val Gln Asp Asp Val Ile Pro Ala Asn Trp
1               5                   10                  15

Lys Pro Asp Thr
            20

<210> SEQ ID NO 337
<211> LENGTH: 20
<212> TYPE: PRT
<213> ORGANISM: Artificial Sequence
<220> FEATURE:
<223> OTHER INFORMATION: Cynodon dactylon Major pollen allergen Cyn d 1
      epitope

<400> SEQUENCE: 337

Phe Lys Asp Gly Leu Gly Cys Gly Ala Cys Tyr Glu Ile Lys Cys Lys
1               5                   10                  15

Glu Pro Val Glu
            20

<210> SEQ ID NO 338
<211> LENGTH: 15
<212> TYPE: PRT
<213> ORGANISM: Artificial Sequence
<220> FEATURE:
<223> OTHER INFORMATION: Phleum pratense Major pollen allergen Phl p 4
      precursor epitope

<400> SEQUENCE: 338

Phe Ala Glu Tyr Lys Ser Asp Tyr Val Tyr Gln Pro Phe Pro Lys
1               5                   10                  15

<210> SEQ ID NO 339
<211> LENGTH: 15
<212> TYPE: PRT
<213> ORGANISM: Artificial Sequence
<220> FEATURE:
<223> OTHER INFORMATION: Phleum pratense Major pollen allergen Phl p 4
      precursor epitope

<400> SEQUENCE: 339

Met Leu Leu Arg Lys Tyr Gly Ile Ala Ala Glu Asn Val Ile Asp
1               5                   10                  15
```

-continued

```
<210> SEQ ID NO 340
<211> LENGTH: 15
<212> TYPE: PRT
<213> ORGANISM: Artificial Sequence
<220> FEATURE:
<223> OTHER INFORMATION: Phleum pratense Major pollen allergen Phl p 4
      precursor epitope

<400> SEQUENCE: 340

Asn Ser Phe Lys Pro Phe Ala Glu Tyr Lys Ser Asp Tyr Val Tyr
1               5                   10                  15

<210> SEQ ID NO 341
<211> LENGTH: 20
<212> TYPE: PRT
<213> ORGANISM: Artificial Sequence
<220> FEATURE:
<223> OTHER INFORMATION: Rattus norvegicus Major urinary protein
      precursor epitope

<400> SEQUENCE: 341

Ala Ser Asn Lys Arg Glu Lys Ile Glu Glu Asn Gly Ser Met Arg Val
1               5                   10                  15

Phe Met Gln His
            20

<210> SEQ ID NO 342
<211> LENGTH: 20
<212> TYPE: PRT
<213> ORGANISM: Artificial Sequence
<220> FEATURE:
<223> OTHER INFORMATION: Rattus norvegicus Major urinary protein
      precursor epitope

<400> SEQUENCE: 342

Asp Ile Lys Glu Lys Phe Ala Lys Leu Cys Glu Ala His Gly Ile Thr
1               5                   10                  15

Arg Asp Asn Ile
            20

<210> SEQ ID NO 343
<211> LENGTH: 20
<212> TYPE: PRT
<213> ORGANISM: Artificial Sequence
<220> FEATURE:
<223> OTHER INFORMATION: Rattus norvegicus Major urinary protein
      precursor epitope

<400> SEQUENCE: 343

Glu Glu Ala Ser Ser Thr Arg Gly Asn Leu Asp Val Ala Lys Leu Asn
1               5                   10                  15

Gly Asp Trp Phe
            20

<210> SEQ ID NO 344
<211> LENGTH: 20
<212> TYPE: PRT
<213> ORGANISM: Artificial Sequence
<220> FEATURE:
<223> OTHER INFORMATION: Rattus norvegicus Major urinary protein
      precursor epitope

<400> SEQUENCE: 344

Glu Glu Asn Gly Ser Met Arg Val Phe Met Gln His Ile Asp Val Leu
1               5                   10                  15

Glu Asn Ser Leu
```

20

<210> SEQ ID NO 345
<211> LENGTH: 20
<212> TYPE: PRT
<213> ORGANISM: Artificial Sequence
<220> FEATURE:
<223> OTHER INFORMATION: Rattus norvegicus Major urinary protein
    precursor epitope

<400> SEQUENCE: 345

Glu Asn Ser Leu Gly Phe Lys Phe Arg Ile Lys Glu Asn Gly Glu Cys
1               5                   10                  15

Arg Glu Leu Tyr
            20

<210> SEQ ID NO 346
<211> LENGTH: 21
<212> TYPE: PRT
<213> ORGANISM: Artificial Sequence
<220> FEATURE:
<223> OTHER INFORMATION: Dermatophagoides farinae Mite group 2 allergen
    Der f 2 precursor epitope

<400> SEQUENCE: 346

Asp Ile Lys Tyr Thr Trp Asn Val Pro Lys Ile Ala Pro Lys Ser Glu
1               5                   10                  15

Asn Val Val Val Thr
            20

<210> SEQ ID NO 347
<211> LENGTH: 17
<212> TYPE: PRT
<213> ORGANISM: Artificial Sequence
<220> FEATURE:
<223> OTHER INFORMATION: Dermatophagoides farinae Mite group 2 allergen
    Der f 2 precursor epitope

<400> SEQUENCE: 347

Asp Asn Gly Val Leu Ala Cys Ala Ile Ala Thr His Gly Lys Ile Arg
1               5                   10                  15

Asp

<210> SEQ ID NO 348
<211> LENGTH: 21
<212> TYPE: PRT
<213> ORGANISM: Artificial Sequence
<220> FEATURE:
<223> OTHER INFORMATION: Dermatophagoides farinae Mite group 2 allergen
    Der f 2 precursor epitope

<400> SEQUENCE: 348

Glu Ala Leu Phe Asp Ala Asn Gln Asn Thr Lys Thr Ala Lys Ile Glu
1               5                   10                  15

Ile Lys Ala Ser Leu
            20

<210> SEQ ID NO 349
<211> LENGTH: 45
<212> TYPE: PRT
<213> ORGANISM: Artificial Sequence
<220> FEATURE:
<223> OTHER INFORMATION: Dermatophagoides farinae Mite group 2 allergen
    Der f 2 precursor epitope

<400> SEQUENCE: 349

```
Gln Tyr Asp Ile Lys Tyr Thr Trp Asn Val Pro Lys Ile Ala Pro Lys
1               5                   10                  15

Ser Glu Asn Val Val Thr Val Lys Leu Ile Gly Asp Asn Gly Val
                20                  25                  30

Leu Ala Cys Ala Ile Ala Thr His Gly Lys Ile Arg Asp
        35                  40                  45

<210> SEQ ID NO 350
<211> LENGTH: 19
<212> TYPE: PRT
<213> ORGANISM: Artificial Sequence
<220> FEATURE:
<223> OTHER INFORMATION: Dermatophagoides farinae Mite group 2 allergen
      Der f 2 precursor epitope

<400> SEQUENCE: 350

Thr Lys Thr Ala Lys Ile Glu Ile Lys Ala Ser Leu Asp Gly Leu Glu
1               5                   10                  15

Ile Asp Val

<210> SEQ ID NO 351
<211> LENGTH: 14
<212> TYPE: PRT
<213> ORGANISM: Artificial Sequence
<220> FEATURE:
<223> OTHER INFORMATION: Dermatophagoides pteronyssinus Mite group 2
      allergen Der p 2 epitope

<400> SEQUENCE: 351

Ala Ser Ile Asp Gly Leu Gly Val Asp Val Pro Gly Ile Asp
1               5                   10

<210> SEQ ID NO 352
<211> LENGTH: 15
<212> TYPE: PRT
<213> ORGANISM: Artificial Sequence
<220> FEATURE:
<223> OTHER INFORMATION: Dermatophagoides pteronyssinus Mite group 2
      allergen Der p 2 epitope

<400> SEQUENCE: 352

Phe Glu Ala Val Gln Asn Thr Lys Thr Ala Lys Ile Glu Ile Lys
1               5                   10                  15

<210> SEQ ID NO 353
<211> LENGTH: 17
<212> TYPE: PRT
<213> ORGANISM: Artificial Sequence
<220> FEATURE:
<223> OTHER INFORMATION: Dermatophagoides pteronyssinus Mite group 2
      allergen Der p 2 epitope

<400> SEQUENCE: 353

Arg Gly Lys Pro Pro Gln Leu Glu Ala Val Phe Glu Ala Val Gln Asn
1               5                   10                  15

Thr

<210> SEQ ID NO 354
<211> LENGTH: 15
<212> TYPE: PRT
<213> ORGANISM: Artificial Sequence
<220> FEATURE:
<223> OTHER INFORMATION: Dermatophagoides pteronyssinus Mite group 2
      allergen Der p 2 precursor epitope
```

<400> SEQUENCE: 354

Cys His Gly Ser Glu Pro Cys Ile Ile His Arg Gly Lys Pro Phe
1               5                   10                  15

<210> SEQ ID NO 355
<211> LENGTH: 27
<212> TYPE: PRT
<213> ORGANISM: Artificial Sequence
<220> FEATURE:
<223> OTHER INFORMATION: Dermatophagoides pteronyssinus Mite group 2
      allergen Der p 2 precursor epitope

<400> SEQUENCE: 355

Cys Pro Leu Val Lys Gly Gln Gln Tyr Asp Ile Lys Tyr Thr Trp Asn
1               5                   10                  15

Val Pro Lys Ile Ala Pro Lys Ser Glu Asn Val
            20                  25

<210> SEQ ID NO 356
<211> LENGTH: 26
<212> TYPE: PRT
<213> ORGANISM: Artificial Sequence
<220> FEATURE:
<223> OTHER INFORMATION: Dermatophagoides pteronyssinus Mite group 2
      allergen Der p 2 precursor epitope

<400> SEQUENCE: 356

Asp Ile Lys Tyr Thr Trp Asn Val Pro Lys Ile Ala Pro Lys Ser Glu
1               5                   10                  15

Asn Val Val Val Thr Val Lys Val Met Gly
            20                  25

<210> SEQ ID NO 357
<211> LENGTH: 15
<212> TYPE: PRT
<213> ORGANISM: Artificial Sequence
<220> FEATURE:
<223> OTHER INFORMATION: Dermatophagoides pteronyssinus Mite group 2
      allergen Der p 2 precursor epitope

<400> SEQUENCE: 357

Asp Gln Val Asp Val Lys Asp Cys Ala Asn His Glu Ile Lys Lys
1               5                   10                  15

<210> SEQ ID NO 358
<211> LENGTH: 20
<212> TYPE: PRT
<213> ORGANISM: Artificial Sequence
<220> FEATURE:
<223> OTHER INFORMATION: Dermatophagoides pteronyssinus Mite group 2
      allergen Der p 2 precursor epitope

<400> SEQUENCE: 358

Asp Gln Val Asp Val Lys Asp Cys Ala Asn His Glu Ile Lys Lys Val
1               5                   10                  15

Leu Val Pro Gly
            20

<210> SEQ ID NO 359
<211> LENGTH: 15
<212> TYPE: PRT
<213> ORGANISM: Artificial Sequence
<220> FEATURE:
<223> OTHER INFORMATION: Dermatophagoides pteronyssinus Mite group 2
      allergen Der p 2 precursor epitope

```
<400> SEQUENCE: 359

Cys His Gly Ser Glu Pro Cys Ile Ile His Arg Gly Lys Pro Phe
1               5                   10                  15

<210> SEQ ID NO 360
<211> LENGTH: 15
<212> TYPE: PRT
<213> ORGANISM: Artificial Sequence
<220> FEATURE:
<223> OTHER INFORMATION: Lepidoglyphus destructor Mite group 2 allergen
      Lep d 2 precursor epitope

<400> SEQUENCE: 360

Asp His Gly Val Met Ala Cys Gly Thr Val His Gly Gln Val Glu
1               5                   10                  15

<210> SEQ ID NO 361
<211> LENGTH: 15
<212> TYPE: PRT
<213> ORGANISM: Artificial Sequence
<220> FEATURE:
<223> OTHER INFORMATION: Lepidoglyphus destructor Mite group 2 allergen
      Lep d 2 precursor epitope

<400> SEQUENCE: 361

Gly Cys Lys Phe Ile Lys Cys Pro Val Lys Lys Gly Glu Ala Leu
1               5                   10                  15

<210> SEQ ID NO 362
<211> LENGTH: 15
<212> TYPE: PRT
<213> ORGANISM: Artificial Sequence
<220> FEATURE:
<223> OTHER INFORMATION: Lepidoglyphus destructor Mite group 2 allergen
      Lep d 2 precursor epitope

<400> SEQUENCE: 362

Gly Glu Lys Met Thr Leu Glu Ala Lys Phe Ala Ala Asn Gln Asp
1               5                   10                  15

<210> SEQ ID NO 363
<211> LENGTH: 15
<212> TYPE: PRT
<213> ORGANISM: Artificial Sequence
<220> FEATURE:
<223> OTHER INFORMATION: Lepidoglyphus destructor Mite group 2 allergen
      Lep d 2 precursor epitope

<400> SEQUENCE: 363

Gly Glu Val Thr Glu Leu Asp Ile Thr Gly Cys Ser Gly Asp Thr
1               5                   10                  15

<210> SEQ ID NO 364
<211> LENGTH: 15
<212> TYPE: PRT
<213> ORGANISM: Artificial Sequence
<220> FEATURE:
<223> OTHER INFORMATION: Lepidoglyphus destructor Mite group 2 allergen
      Lep d 2 precursor epitope

<400> SEQUENCE: 364

Gly Lys Met Thr Phe Lys Asp Cys Gly His Gly Glu Val Thr Glu
1               5                   10                  15

<210> SEQ ID NO 365
<211> LENGTH: 16
<212> TYPE: PRT
```

```
<213> ORGANISM: Artificial Sequence
<220> FEATURE:
<223> OTHER INFORMATION: Homo sapiens Neurofilament heavy polypeptide
      (NF-H) (Neurofilament triplet H protein) (200 kDa neurofilament
      protein) epitope

<400> SEQUENCE: 365

Tyr Gln Glu Ala Ile Gln Gln Leu Asp Ala Glu Leu Arg Asn Thr Lys
1               5                   10                  15

<210> SEQ ID NO 366
<211> LENGTH: 10
<212> TYPE: PRT
<213> ORGANISM: Artificial Sequence
<220> FEATURE:
<223> OTHER INFORMATION: Prunus persica Non-specific lipid-transfer
      protein 1 epitope

<400> SEQUENCE: 366

Ala Ala Ala Leu Pro Gly Lys Cys Gly Val
1               5                   10

<210> SEQ ID NO 367
<211> LENGTH: 10
<212> TYPE: PRT
<213> ORGANISM: Artificial Sequence
<220> FEATURE:
<223> OTHER INFORMATION: Prunus persica Non-specific lipid-transfer
      protein 1 epitope

<400> SEQUENCE: 367

Ala Cys Cys Asn Gly Ile Arg Asn Val Asn
1               5                   10

<210> SEQ ID NO 368
<211> LENGTH: 10
<212> TYPE: PRT
<213> ORGANISM: Artificial Sequence
<220> FEATURE:
<223> OTHER INFORMATION: Prunus persica Non-specific lipid-transfer
      protein 1 epitope

<400> SEQUENCE: 368

Ala Pro Cys Ile Pro Tyr Val Arg Gly Gly
1               5                   10

<210> SEQ ID NO 369
<211> LENGTH: 10
<212> TYPE: PRT
<213> ORGANISM: Artificial Sequence
<220> FEATURE:
<223> OTHER INFORMATION: Prunus persica Non-specific lipid-transfer
      protein 1 epitope

<400> SEQUENCE: 369

Ile Arg Asn Val Asn Asn Leu Ala Arg Thr
1               5                   10

<210> SEQ ID NO 370
<211> LENGTH: 11
<212> TYPE: PRT
<213> ORGANISM: Artificial Sequence
<220> FEATURE:
<223> OTHER INFORMATION: Prunus persica Non-specific lipid-transfer
      protein 1 epitope

<400> SEQUENCE: 370

Ile Ser Ala Ser Thr Asn Cys Ala Thr Val Lys
```

<210> SEQ ID NO 371
<211> LENGTH: 10
<212> TYPE: PRT
<213> ORGANISM: Artificial Sequence
<220> FEATURE:
<223> OTHER INFORMATION: Prunus persica Non-specific lipid-transfer
      protein 1 epitope

<400> SEQUENCE: 371

Asn Leu Ala Arg Thr Thr Pro Asp Arg Gln
1               5                   10

<210> SEQ ID NO 372
<211> LENGTH: 10
<212> TYPE: PRT
<213> ORGANISM: Artificial Sequence
<220> FEATURE:
<223> OTHER INFORMATION: Gallus gallus Ovalbumin epitope

<400> SEQUENCE: 372

Cys Phe Asp Val Phe Lys Glu Leu Lys Val
1               5                   10

<210> SEQ ID NO 373
<211> LENGTH: 10
<212> TYPE: PRT
<213> ORGANISM: Artificial Sequence
<220> FEATURE:
<223> OTHER INFORMATION: Gallus gallus Ovalbumin epitope

<400> SEQUENCE: 373

Gly Ser Ile Gly Ala Ala Ser Met Glu Phe
1               5                   10

<210> SEQ ID NO 374
<211> LENGTH: 18
<212> TYPE: PRT
<213> ORGANISM: Artificial Sequence
<220> FEATURE:
<223> OTHER INFORMATION: Gallus gallus Ovalbumin epitope

<400> SEQUENCE: 374

Ile Gly Leu Phe Arg Val Ala Ser Met Ala Ser Glu Lys Met Lys Ile
1               5                   10                  15

Leu Glu

<210> SEQ ID NO 375
<211> LENGTH: 18
<212> TYPE: PRT
<213> ORGANISM: Artificial Sequence
<220> FEATURE:
<223> OTHER INFORMATION: Gallus gallus Ovalbumin epitope

<400> SEQUENCE: 375

Ile Lys His Ile Ala Thr Asn Ala Val Leu Phe Phe Gly Arg Cys Val
1               5                   10                  15

Ser Pro

<210> SEQ ID NO 376
<211> LENGTH: 13
<212> TYPE: PRT
<213> ORGANISM: Artificial Sequence
<220> FEATURE:
<223> OTHER INFORMATION: Gallus gallus Ovalbumin epitope

```
<400> SEQUENCE: 376

Ile Met Ser Ala Leu Ala Met Val Tyr Leu Gly Ala Lys
1               5                   10

<210> SEQ ID NO 377
<211> LENGTH: 14
<212> TYPE: PRT
<213> ORGANISM: Artificial Sequence
<220> FEATURE:
<223> OTHER INFORMATION: Gallus gallus Ovomucoid precursor epitope

<400> SEQUENCE: 377

Ala Glu Val Asp Cys Ser Arg Phe Pro Asn Ala Thr Asp Lys
1               5                   10

<210> SEQ ID NO 378
<211> LENGTH: 14
<212> TYPE: PRT
<213> ORGANISM: Artificial Sequence
<220> FEATURE:
<223> OTHER INFORMATION: Gallus gallus Ovomucoid precursor epitope

<400> SEQUENCE: 378

Ala Thr Asp Lys Glu Gly Lys Asp Val Leu Val Cys Asn Lys
1               5                   10

<210> SEQ ID NO 379
<211> LENGTH: 17
<212> TYPE: PRT
<213> ORGANISM: Artificial Sequence
<220> FEATURE:
<223> OTHER INFORMATION: Gallus gallus Ovomucoid precursor epitope

<400> SEQUENCE: 379

Ala Val Val Glu Ser Asn Gly Thr Leu Thr Leu Ser His Phe Gly Lys
1               5                   10                  15

Cys

<210> SEQ ID NO 380
<211> LENGTH: 16
<212> TYPE: PRT
<213> ORGANISM: Artificial Sequence
<220> FEATURE:
<223> OTHER INFORMATION: Gallus gallus Ovomucoid precursor epitope

<400> SEQUENCE: 380

Cys Leu Leu Cys Ala Tyr Ser Ile Glu Phe Gly Thr Asn Ile Ser Lys
1               5                   10                  15

<210> SEQ ID NO 381
<211> LENGTH: 20
<212> TYPE: PRT
<213> ORGANISM: Artificial Sequence
<220> FEATURE:
<223> OTHER INFORMATION: Gallus gallus Ovomucoid precursor epitope

<400> SEQUENCE: 381

Asp Asn Glu Cys Leu Leu Cys Ala His Lys Val Glu Gln Gly Ala Ser
1               5                   10                  15

Val Asp Lys Arg
            20

<210> SEQ ID NO 382
<211> LENGTH: 16
```

```
<212> TYPE: PRT
<213> ORGANISM: Artificial Sequence
<220> FEATURE:
<223> OTHER INFORMATION: Musa acuminata pectate lyase epitope

<400> SEQUENCE: 382

Gly His Ser Asp Glu Leu Thr Ser Asp Lys Ser Met Gln Val Thr Ile
1               5                   10                  15

<210> SEQ ID NO 383
<211> LENGTH: 16
<212> TYPE: PRT
<213> ORGANISM: Artificial Sequence
<220> FEATURE:
<223> OTHER INFORMATION: Zinnia violacea Pectate lyase precursor epitope

<400> SEQUENCE: 383

Gly His Ser Asp Ser Tyr Thr Gln Asp Lys Asn Met Gln Val Thr Ile
1               5                   10                  15

<210> SEQ ID NO 384
<211> LENGTH: 21
<212> TYPE: PRT
<213> ORGANISM: Artificial Sequence
<220> FEATURE:
<223> OTHER INFORMATION: Dermatophagoides farinae Peptidase 1 precursor
      (Major mite fecal allergen Der f 1) (Allergen Der f I) epitope

<400> SEQUENCE: 384

Asp Gly Arg Thr Ile Ile Gln His Asp Asn Gly Tyr Gln Pro Asn Tyr
1               5                   10                  15

His Ala Val Asn Ile
            20

<210> SEQ ID NO 385
<211> LENGTH: 19
<212> TYPE: PRT
<213> ORGANISM: Artificial Sequence
<220> FEATURE:
<223> OTHER INFORMATION: Dermatophagoides farinae Peptidase 1 precursor
      (Major mite fecal allergen Der f 1) (Allergen Der f I) epitope

<400> SEQUENCE: 385

Asp Leu Arg Ser Leu Arg Thr Val Thr Pro Ile Arg Met Gln Gly Gly
1               5                   10                  15

Cys Gly Ser

<210> SEQ ID NO 386
<211> LENGTH: 19
<212> TYPE: PRT
<213> ORGANISM: Artificial Sequence
<220> FEATURE:
<223> OTHER INFORMATION: Dermatophagoides farinae Peptidase 1 precursor
      (Major mite fecal allergen Der f 1) (Allergen Der f I) epitope

<400> SEQUENCE: 386

Gly Cys Gly Ser Cys Trp Ala Phe Ser Gly Val Ala Ala Thr Glu Ser
1               5                   10                  15

Ala Tyr Leu

<210> SEQ ID NO 387
<211> LENGTH: 21
<212> TYPE: PRT
<213> ORGANISM: Artificial Sequence
<220> FEATURE:
<223> OTHER INFORMATION: Dermatophagoides farinae Peptidase 1 precursor
```

(Major mite fecal allergen Der f 1) (Allergen Der f I) epitope

<400> SEQUENCE: 387

Ile Arg Glu Ala Leu Thr Gln Thr His Thr Ala Ile Ala Val Ile Ile
1               5                   10                  15

Gly Ile Lys Asp Leu
            20

<210> SEQ ID NO 388
<211> LENGTH: 19
<212> TYPE: PRT
<213> ORGANISM: Artificial Sequence
<220> FEATURE:
<223> OTHER INFORMATION: Dermatophagoides farinae Peptidase 1 precursor
      (Major mite fecal allergen Der f 1) (Allergen Der f I) epitope

<400> SEQUENCE: 388

Ile Arg Met Gln Gly Gly Cys Gly Ser Cys Trp Ala Phe Ser Gly Val
1               5                   10                  15

Ala Ala Thr

<210> SEQ ID NO 389
<211> LENGTH: 19
<212> TYPE: PRT
<213> ORGANISM: Artificial Sequence
<220> FEATURE:
<223> OTHER INFORMATION: Euroglyphus maynei Peptidase 1 precursor (Mite
      group 1 allergen Eur m 1) (Allergen Eur m I) epitope

<400> SEQUENCE: 389

Phe Arg His Tyr Asp Gly Arg Thr Ile Met Gln His Asp Asn Gly Tyr
1               5                   10                  15

Gln Pro Asn

<210> SEQ ID NO 390
<211> LENGTH: 19
<212> TYPE: PRT
<213> ORGANISM: Artificial Sequence
<220> FEATURE:
<223> OTHER INFORMATION: Euroglyphus maynei Peptidase 1 precursor (Mite
      group 1 allergen Eur m 1) (Allergen Eur m I) epitope

<400> SEQUENCE: 390

Gly Arg Thr Ile Met Gln His Asp Asn Gly Tyr Gln Pro Asn Tyr His
1               5                   10                  15

Ala Val Asn

<210> SEQ ID NO 391
<211> LENGTH: 19
<212> TYPE: PRT
<213> ORGANISM: Artificial Sequence
<220> FEATURE:
<223> OTHER INFORMATION: Euroglyphus maynei Peptidase 1 precursor (Mite
      group 1 allergen Eur m 1) (Allergen Eur m I) epitope

<400> SEQUENCE: 391

His Ala Val Asn Ile Val Gly Tyr Gly Asn Thr Gln Gly Val Asp Tyr
1               5                   10                  15

Trp Ile Val

<210> SEQ ID NO 392
<211> LENGTH: 19
<212> TYPE: PRT
<213> ORGANISM: Artificial Sequence

```
<220> FEATURE:
<223> OTHER INFORMATION: Euroglyphus maynei Peptidase 1 precursor (Mite
      group 1 allergen Eur m 1) (Allergen Eur m I) epitope

<400> SEQUENCE: 392

Asn Lys Ile Arg Gln Ala Leu Thr Gln Thr His Thr Ala Val Ala Val
1               5                   10                  15

Ile Ile Gly

<210> SEQ ID NO 393
<211> LENGTH: 19
<212> TYPE: PRT
<213> ORGANISM: Artificial Sequence
<220> FEATURE:
<223> OTHER INFORMATION: Euroglyphus maynei Peptidase 1 precursor (Mite
      group 1 allergen Eur m 1) (Allergen Eur m I) epitope

<400> SEQUENCE: 393

Pro Tyr Val Ala Arg Glu Gln Ser Cys His Arg Pro Asn Ala Gln Arg
1               5                   10                  15

Tyr Gly Leu

<210> SEQ ID NO 394
<211> LENGTH: 15
<212> TYPE: PRT
<213> ORGANISM: Artificial Sequence
<220> FEATURE:
<223> OTHER INFORMATION: Phleum pratense Phl p 3 allergen epitope

<400> SEQUENCE: 394

Ala Val Gln Val Thr Phe Thr Val Gln Lys Gly Ser Asp Pro Lys
1               5                   10                  15

<210> SEQ ID NO 395
<211> LENGTH: 15
<212> TYPE: PRT
<213> ORGANISM: Artificial Sequence
<220> FEATURE:
<223> OTHER INFORMATION: Phleum pratense Phl p 3 allergen epitope

<400> SEQUENCE: 395

Glu Glu Trp Glu Pro Leu Thr Lys Lys Gly Asn Val Trp Glu Val
1               5                   10                  15

<210> SEQ ID NO 396
<211> LENGTH: 15
<212> TYPE: PRT
<213> ORGANISM: Artificial Sequence
<220> FEATURE:
<223> OTHER INFORMATION: Phleum pratense Phl p 3 allergen epitope

<400> SEQUENCE: 396

Phe Thr Val Gln Lys Gly Ser Asp Pro Lys Lys Leu Val Leu Asp
1               5                   10                  15

<210> SEQ ID NO 397
<211> LENGTH: 15
<212> TYPE: PRT
<213> ORGANISM: Artificial Sequence
<220> FEATURE:
<223> OTHER INFORMATION: Phleum pratense Phl p 3 allergen epitope

<400> SEQUENCE: 397

Phe Thr Val Gln Lys Gly Ser Asp Pro Lys Lys Leu Val Leu Asn
1               5                   10                  15
```

```
<210> SEQ ID NO 398
<211> LENGTH: 15
<212> TYPE: PRT
<213> ORGANISM: Artificial Sequence
<220> FEATURE:
<223> OTHER INFORMATION: Phleum pratense Phl p 3 allergen epitope

<400> SEQUENCE: 398

Gly Ser Asp Pro Lys Lys Leu Val Leu Asp Ile Lys Tyr Thr Arg
1               5                   10                  15

<210> SEQ ID NO 399
<211> LENGTH: 15
<212> TYPE: PRT
<213> ORGANISM: Artificial Sequence
<220> FEATURE:
<223> OTHER INFORMATION: Apis mellifera Phospholipase A2 precursor
      epitope

<400> SEQUENCE: 399

Cys Asp Cys Asp Asp Lys Phe Tyr Asp Cys Leu Lys Asn Ser Ala
1               5                   10                  15

<210> SEQ ID NO 400
<211> LENGTH: 12
<212> TYPE: PRT
<213> ORGANISM: Artificial Sequence
<220> FEATURE:
<223> OTHER INFORMATION: Apis mellifera Phospholipase A2 precursor
      epitope

<400> SEQUENCE: 400

Cys Leu His Tyr Thr Val Asp Lys Ser Lys Pro Lys
1               5                   10

<210> SEQ ID NO 401
<211> LENGTH: 15
<212> TYPE: PRT
<213> ORGANISM: Artificial Sequence
<220> FEATURE:
<223> OTHER INFORMATION: Apis mellifera Phospholipase A2 precursor
      epitope

<400> SEQUENCE: 401

Cys Arg Thr His Asp Met Cys Pro Asp Val Met Ser Ala Gly Glu
1               5                   10                  15

<210> SEQ ID NO 402
<211> LENGTH: 18
<212> TYPE: PRT
<213> ORGANISM: Artificial Sequence
<220> FEATURE:
<223> OTHER INFORMATION: Apis mellifera Phospholipase A2 precursor
      epitope

<400> SEQUENCE: 402

Asp Thr Ile Ser Ser Tyr Phe Val Gly Lys Met Tyr Phe Asn Leu Ile
1               5                   10                  15

Asp Thr

<210> SEQ ID NO 403
<211> LENGTH: 18
<212> TYPE: PRT
<213> ORGANISM: Artificial Sequence
<220> FEATURE:
<223> OTHER INFORMATION: Apis mellifera Phospholipase A2 precursor
      epitope
```

```
<400> SEQUENCE: 403

Glu Arg Thr Glu Gly Arg Cys Leu His Tyr Thr Val Asp Lys Ser Lys
1               5                   10                  15

Pro Lys

<210> SEQ ID NO 404
<211> LENGTH: 16
<212> TYPE: PRT
<213> ORGANISM: Artificial Sequence
<220> FEATURE:
<223> OTHER INFORMATION: Spiroplasma citri plectrovirus spv1-r8a2b orf
      14 transmembrane protein epitope

<400> SEQUENCE: 404

His Val Ile Glu Val Gln Gln Ile Asn Ser Glu Arg Ser Trp Phe Phe
1               5                   10                  15

<210> SEQ ID NO 405
<211> LENGTH: 20
<212> TYPE: PRT
<213> ORGANISM: Artificial Sequence
<220> FEATURE:
<223> OTHER INFORMATION: Lolium perenne pollen allergen epitope

<400> SEQUENCE: 405

Cys Gly Tyr Lys Asp Val Asp Lys Ala Pro Phe Asn Gly Met Thr Gly
1               5                   10                  15

Cys Gly Asn Thr
            20

<210> SEQ ID NO 406
<211> LENGTH: 20
<212> TYPE: PRT
<213> ORGANISM: Artificial Sequence
<220> FEATURE:
<223> OTHER INFORMATION: Lolium perenne pollen allergen epitope

<400> SEQUENCE: 406

Gly Ala Gly Pro Lys Asp Asn Gly Gly Ala Cys Gly Tyr Lys Asp Val
1               5                   10                  15

Asp Lys Ala Pro
            20

<210> SEQ ID NO 407
<211> LENGTH: 20
<212> TYPE: PRT
<213> ORGANISM: Artificial Sequence
<220> FEATURE:
<223> OTHER INFORMATION: Lolium perenne pollen allergen epitope

<400> SEQUENCE: 407

Ser Glu Val Glu Asp Val Ile Pro Glu Gly Trp Lys Ala Asp Thr Ser
1               5                   10                  15

Tyr Ser Ala Lys
            20

<210> SEQ ID NO 408
<211> LENGTH: 20
<212> TYPE: PRT
<213> ORGANISM: Artificial Sequence
<220> FEATURE:
<223> OTHER INFORMATION: Lolium perenne pollen allergen epitope

<400> SEQUENCE: 408
```

-continued

```
Val Glu Lys Gly Ser Asn Pro Asn Tyr Leu Ala Ile Leu Val Lys Tyr
1               5                   10                  15

Val Asp Gly Asp
            20

<210> SEQ ID NO 409
<211> LENGTH: 20
<212> TYPE: PRT
<213> ORGANISM: Artificial Sequence
<220> FEATURE:
<223> OTHER INFORMATION: Lolium perenne pollen allergen epitope

<400> SEQUENCE: 409

Tyr Pro Asp Asp Thr Lys Pro Thr Phe His Val Glu Lys Gly Ser Asn
1               5                   10                  15

Pro Asn Tyr Leu
            20

<210> SEQ ID NO 410
<211> LENGTH: 16
<212> TYPE: PRT
<213> ORGANISM: Artificial Sequence
<220> FEATURE:
<223> OTHER INFORMATION: Ambrosia artemisiifolia Pollen allergen Amb
      a 1.1 precursor epitope

<400> SEQUENCE: 410

Gly Ala Gly Asp Glu Asn Ile Glu Asp Arg Gly Met Leu Ala Thr Val
1               5                   10                  15

<210> SEQ ID NO 411
<211> LENGTH: 16
<212> TYPE: PRT
<213> ORGANISM: Artificial Sequence
<220> FEATURE:
<223> OTHER INFORMATION: Ambrosia artemisiifolia Pollen allergen Amb a
      1.1 precursor epitope

<400> SEQUENCE: 411

Gly Ala Gly Asp Glu Asn Ile Glu Asp Arg Gly Met Leu Ala Thr Val
1               5                   10                  15

<210> SEQ ID NO 412
<211> LENGTH: 16
<212> TYPE: PRT
<213> ORGANISM: Artificial Sequence
<220> FEATURE:
<223> OTHER INFORMATION: Ambrosia artemisiifolia Pollen allergen Amb a
      2 precursor epitope

<400> SEQUENCE: 412

Gly Ala Ser Asp Thr His Phe Gln Asp Leu Lys Met His Val Thr Leu
1               5                   10                  15

<210> SEQ ID NO 413
<211> LENGTH: 16
<212> TYPE: PRT
<213> ORGANISM: Artificial Sequence
<220> FEATURE:
<223> OTHER INFORMATION: Ambrosia artemisiifolia Pollen allergen Amb a
      2 precursor epitope

<400> SEQUENCE: 413

Gly Ala Ser Asp Thr His Phe Gln Asp Leu Lys Met His Val Thr Leu
1               5                   10                  15
```

```
<210> SEQ ID NO 414
<211> LENGTH: 11
<212> TYPE: PRT
<213> ORGANISM: Artificial Sequence
<220> FEATURE:
<223> OTHER INFORMATION: Ambrosia artemisiifolia var. elatior Pollen
      allergen Amb a 3 epitope

<400> SEQUENCE: 414

Glu Glu Ala Tyr His Ala Cys Asp Ile Lys Asp
1               5                   10

<210> SEQ ID NO 415
<211> LENGTH: 15
<212> TYPE: PRT
<213> ORGANISM: Artificial Sequence
<220> FEATURE:
<223> OTHER INFORMATION: Ambrosia artemisiifolia var. elatior Pollen
      allergen Amb a 3 epitope

<400> SEQUENCE: 415

Gly Lys Val Tyr Leu Val Gly Gly Pro Glu Leu Gly Gly Trp Lys
1               5                   10                  15

<210> SEQ ID NO 416
<211> LENGTH: 15
<212> TYPE: PRT
<213> ORGANISM: Artificial Sequence
<220> FEATURE:
<223> OTHER INFORMATION: Ambrosia artemisiifolia var. elatior Pollen
      allergen Amb a 3 epitope

<400> SEQUENCE: 416

Leu Gly Gly Trp Lys Leu Gln Ser Asp Pro Arg Ala Tyr Ala Leu
1               5                   10                  15

<210> SEQ ID NO 417
<211> LENGTH: 15
<212> TYPE: PRT
<213> ORGANISM: Artificial Sequence
<220> FEATURE:
<223> OTHER INFORMATION: Ambrosia artemisiifolia var. elatior Pollen
      allergen Amb a 3 epitope

<400> SEQUENCE: 417

Pro Gly Gly Pro Asp Arg Phe Thr Leu Leu Thr Pro Gly Ser His
1               5                   10                  15

<210> SEQ ID NO 418
<211> LENGTH: 15
<212> TYPE: PRT
<213> ORGANISM: Artificial Sequence
<220> FEATURE:
<223> OTHER INFORMATION: Ambrosia artemisiifolia var. elatior Pollen
      allergen Amb a 5 epitope

<400> SEQUENCE: 418

Ala Tyr Cys Cys Ser Asp Pro Gly Arg Tyr Cys Pro Trp Gln Val
1               5                   10                  15

<210> SEQ ID NO 419
<211> LENGTH: 20
<212> TYPE: PRT
<213> ORGANISM: Artificial Sequence
<220> FEATURE:
<223> OTHER INFORMATION: Ambrosia artemisiifolia var. elatior Pollen
      allergen Amb a 5 epitope
```

```
<400> SEQUENCE: 419

Cys Gly Glu Lys Arg Ala Tyr Cys Cys Ser Asp Pro Gly Arg Tyr Cys
1               5                   10                  15

Pro Trp Gln Val
            20

<210> SEQ ID NO 420
<211> LENGTH: 17
<212> TYPE: PRT
<213> ORGANISM: Artificial Sequence
<220> FEATURE:
<223> OTHER INFORMATION: Ambrosia artemisiifolia var. elatior Pollen
      allergen Amb a 5 epitope

<400> SEQUENCE: 420

Asp Pro Gly Arg Tyr Cys Pro Trp Gln Val Val Cys Tyr Glu Ser Ser
1               5                   10                  15

Glu

<210> SEQ ID NO 421
<211> LENGTH: 20
<212> TYPE: PRT
<213> ORGANISM: Artificial Sequence
<220> FEATURE:
<223> OTHER INFORMATION: Ambrosia artemisiifolia var. elatior Pollen
      allergen Amb a 5 epitope

<400> SEQUENCE: 421

Asp Pro Gly Arg Tyr Cys Pro Trp Gln Val Val Cys Tyr Glu Ser Ser
1               5                   10                  15

Glu Ile Cys Ser
            20

<210> SEQ ID NO 422
<211> LENGTH: 15
<212> TYPE: PRT
<213> ORGANISM: Artificial Sequence
<220> FEATURE:
<223> OTHER INFORMATION: Ambrosia artemisiifolia var. elatior Pollen
      allergen Amb a 5 epitope

<400> SEQUENCE: 422

Gly Asn Val Cys Gly Glu Lys Arg Ala Tyr Cys Cys Ser Asp Pro
1               5                   10                  15

<210> SEQ ID NO 423
<211> LENGTH: 15
<212> TYPE: PRT
<213> ORGANISM: Artificial Sequence
<220> FEATURE:
<223> OTHER INFORMATION: Ambrosia artemisiifolia var. elatior Pollen
      allergen Amb a 5 epitope

<400> SEQUENCE: 423

Leu Val Pro Cys Ala Trp Ala Gly Asn Val Cys Gly Glu Lys Arg
1               5                   10                  15

<210> SEQ ID NO 424
<211> LENGTH: 20
<212> TYPE: PRT
<213> ORGANISM: Artificial Sequence
<220> FEATURE:
<223> OTHER INFORMATION: Ambrosia artemisiifolia var. elatior Pollen
      allergen Amb a 5 epitope

<400> SEQUENCE: 424
```

```
Leu Val Pro Cys Ala Trp Ala Gly Asn Val Cys Gly Glu Lys Arg Ala
1               5                   10                  15

Tyr Cys Cys Ser
            20

<210> SEQ ID NO 425
<211> LENGTH: 15
<212> TYPE: PRT
<213> ORGANISM: Artificial Sequence
<220> FEATURE:
<223> OTHER INFORMATION: Ambrosia artemisiifolia var. elatior Pollen
      allergen Amb a 5 epitope

<400> SEQUENCE: 425

Val Cys Tyr Glu Ser Ser Glu Ile Cys Ser Lys Lys Cys Gly Lys
1               5                   10                  15

<210> SEQ ID NO 426
<211> LENGTH: 20
<212> TYPE: PRT
<213> ORGANISM: Artificial Sequence
<220> FEATURE:
<223> OTHER INFORMATION: Ambrosia trifida Pollen allergen Amb t 5
      precursor epitope

<400> SEQUENCE: 426

Cys Gly Lys Val Gly Lys Tyr Cys Cys Ser Pro Ile Gly Lys Tyr Cys
1               5                   10                  15

Val Cys Tyr Asp
            20

<210> SEQ ID NO 427
<211> LENGTH: 20
<212> TYPE: PRT
<213> ORGANISM: Artificial Sequence
<220> FEATURE:
<223> OTHER INFORMATION: Ambrosia trifida Pollen allergen Amb t 5
      precursor epitope

<400> SEQUENCE: 427

Asp Asp Gly Leu Cys Tyr Glu Gly Thr Asn Cys Gly Lys Val Gly Lys
1               5                   10                  15

Tyr Cys Cys Ser
            20

<210> SEQ ID NO 428
<211> LENGTH: 12
<212> TYPE: PRT
<213> ORGANISM: Artificial Sequence
<220> FEATURE:
<223> OTHER INFORMATION: Ambrosia trifida Pollen allergen Amb t 5
      precursor epitope

<400> SEQUENCE: 428

Gly Lys Tyr Cys Val Cys Tyr Asp Ser Lys Ala Ile
1               5                   10

<210> SEQ ID NO 429
<211> LENGTH: 14
<212> TYPE: PRT
<213> ORGANISM: Artificial Sequence
<220> FEATURE:
<223> OTHER INFORMATION: Ambrosia trifida Pollen allergen Amb t 5
      precursor epitope

<400> SEQUENCE: 429
```

```
Pro Ile Gly Lys Tyr Cys Val Cys Tyr Asp Ser Lys Ala Ile
1               5                   10

<210> SEQ ID NO 430
<211> LENGTH: 20
<212> TYPE: PRT
<213> ORGANISM: Artificial Sequence
<220> FEATURE:
<223> OTHER INFORMATION: Ambrosia trifida Pollen allergen Amb t 5
      precursor epitope

<400> SEQUENCE: 430

Pro Ile Gly Lys Tyr Cys Val Cys Tyr Asp Ser Lys Ala Ile Cys Asn
1               5                   10                  15

Lys Asn Cys Thr
            20

<210> SEQ ID NO 431
<211> LENGTH: 14
<212> TYPE: PRT
<213> ORGANISM: Artificial Sequence
<220> FEATURE:
<223> OTHER INFORMATION: Ambrosia trifida Pollen allergen Amb t 5
      precursor epitope

<400> SEQUENCE: 431

Val Cys Tyr Asp Ser Lys Ala Ile Cys Asn Lys Asn Cys Thr
1               5                   10

<210> SEQ ID NO 432
<211> LENGTH: 15
<212> TYPE: PRT
<213> ORGANISM: Artificial Sequence
<220> FEATURE:
<223> OTHER INFORMATION: Betula pendula pollen allergen Bet v 1 epitope

<400> SEQUENCE: 432

His Glu Val Lys Ala Glu Gln Val Lys Ala Thr Lys Glu Met Gly
1               5                   10                  15

<210> SEQ ID NO 433
<211> LENGTH: 20
<212> TYPE: PRT
<213> ORGANISM: Artificial Sequence
<220> FEATURE:
<223> OTHER INFORMATION: Poa pratensis Pollen allergen KBG 60 precursor
      epitope

<400> SEQUENCE: 433

Ala Ala Asn Lys Tyr Lys Thr Phe Val Ala Thr Phe Gly Ala Ala Ser
1               5                   10                  15

Asn Lys Ala Phe
            20

<210> SEQ ID NO 434
<211> LENGTH: 20
<212> TYPE: PRT
<213> ORGANISM: Artificial Sequence
<220> FEATURE:
<223> OTHER INFORMATION: Poa pratensis Pollen allergen KBG 60 precursor
      epitope

<400> SEQUENCE: 434

Ala Ala Pro Ala Asn Asp Lys Phe Thr Val Phe Glu Ala Ala Phe Asn
1               5                   10                  15
```

```
Asp Ala Ile Lys
            20

<210> SEQ ID NO 435
<211> LENGTH: 20
<212> TYPE: PRT
<213> ORGANISM: Artificial Sequence
<220> FEATURE:
<223> OTHER INFORMATION: Poa pratensis Pollen allergen KBG 60 precursor
      epitope

<400> SEQUENCE: 435

Ala Ala Val Asp Ser Ser Lys Ala Ala Leu Thr Ser Lys Leu Asp Ala
1               5                   10                  15

Ala Tyr Lys Leu
            20

<210> SEQ ID NO 436
<211> LENGTH: 20
<212> TYPE: PRT
<213> ORGANISM: Artificial Sequence
<220> FEATURE:
<223> OTHER INFORMATION: Poa pratensis Pollen allergen KBG 60 precursor
      epitope

<400> SEQUENCE: 436

Ala Glu Glu Val Lys Ala Thr Pro Ala Gly Glu Leu Gln Val Ile Asp
1               5                   10                  15

Lys Val Asp Ala
            20

<210> SEQ ID NO 437
<211> LENGTH: 20
<212> TYPE: PRT
<213> ORGANISM: Artificial Sequence
<220> FEATURE:
<223> OTHER INFORMATION: Poa pratensis Pollen allergen KBG 60 precursor
      epitope

<400> SEQUENCE: 437

Ala Phe Lys Val Ala Ala Thr Ala Ala Asn Ala Ala Pro Ala Asn Asp
1               5                   10                  15

Lys Phe Thr Val
            20

<210> SEQ ID NO 438
<211> LENGTH: 20
<212> TYPE: PRT
<213> ORGANISM: Artificial Sequence
<220> FEATURE:
<223> OTHER INFORMATION: Lolium perenne Pollen allergen Lol p 1
      precursor epitope

<400> SEQUENCE: 438

Ala Phe Gly Ser Met Ala Lys Lys Gly Glu Glu Gln Asn Val Arg Ser
1               5                   10                  15

Ala Gly Glu Leu
            20

<210> SEQ ID NO 439
<211> LENGTH: 20
<212> TYPE: PRT
<213> ORGANISM: Artificial Sequence
<220> FEATURE:
<223> OTHER INFORMATION: Lolium perenne Pollen allergen Lol p 1
      precursor epitope
```

<400> SEQUENCE: 439

Ala Gly Glu Leu Glu Leu Gln Phe Arg Arg Val Lys Cys Lys Tyr Pro
1               5                   10                  15

Asp Asp Thr Lys
            20

<210> SEQ ID NO 440
<211> LENGTH: 20
<212> TYPE: PRT
<213> ORGANISM: Artificial Sequence
<220> FEATURE:
<223> OTHER INFORMATION: Lolium perenne Pollen allergen Lol p 1
      precursor epitope

<400> SEQUENCE: 440

Ala Lys Ser Thr Trp Tyr Gly Lys Pro Thr Gly Ala Gly Pro Lys Asp
1               5                   10                  15

Asn Gly Gly Ala
            20

<210> SEQ ID NO 441
<211> LENGTH: 20
<212> TYPE: PRT
<213> ORGANISM: Artificial Sequence
<220> FEATURE:
<223> OTHER INFORMATION: Lolium perenne Pollen allergen Lol p 1
      precursor epitope

<400> SEQUENCE: 441

Ala Pro Tyr His Phe Asp Leu Ser Gly His Ala Phe Gly Ser Met Ala
1               5                   10                  15

Lys Lys Gly Glu
            20

<210> SEQ ID NO 442
<211> LENGTH: 12
<212> TYPE: PRT
<213> ORGANISM: Artificial Sequence
<220> FEATURE:
<223> OTHER INFORMATION: Lolium perenne Pollen allergen Lol p 1
      precursor epitope

<400> SEQUENCE: 442

Ile Ala Pro Tyr His Phe Asp Leu Ser Gly His Ala
1               5                   10

<210> SEQ ID NO 443
<211> LENGTH: 20
<212> TYPE: PRT
<213> ORGANISM: Artificial Sequence
<220> FEATURE:
<223> OTHER INFORMATION: Lolium perenne Pollen allergen Lol p VA
      precursor epitope

<400> SEQUENCE: 443

Ala Ala Leu Thr Lys Ala Ile Thr Ala Met Thr Gln Ala Gln Lys Ala
1               5                   10                  15

Gly Lys Pro Ala
            20

<210> SEQ ID NO 444
<211> LENGTH: 20
<212> TYPE: PRT
<213> ORGANISM: Artificial Sequence

```
<220> FEATURE:
<223> OTHER INFORMATION: Lolium perenne Pollen allergen Lol p VA
      precursor epitope

<400> SEQUENCE: 444

Ala Ala Asn Ala Ala Pro Thr Asn Asp Lys Phe Thr Val Phe Glu Ser
1               5                   10                  15

Ala Phe Asn Lys
            20

<210> SEQ ID NO 445
<211> LENGTH: 20
<212> TYPE: PRT
<213> ORGANISM: Artificial Sequence
<220> FEATURE:
<223> OTHER INFORMATION: Lolium perenne Pollen allergen Lol p VA
      precursor epitope

<400> SEQUENCE: 445

Ala Asp Lys Phe Lys Ile Phe Glu Ala Ala Phe Ser Glu Ser Ser Lys
1               5                   10                  15

Gly Leu Leu Ala
            20

<210> SEQ ID NO 446
<211> LENGTH: 20
<212> TYPE: PRT
<213> ORGANISM: Artificial Sequence
<220> FEATURE:
<223> OTHER INFORMATION: Lolium perenne Pollen allergen Lol p VA
      precursor epitope

<400> SEQUENCE: 446

Ala Phe Ser Glu Ser Ser Lys Gly Leu Leu Ala Thr Ser Ala Ala Lys
1               5                   10                  15

Ala Pro Gly Leu
            20

<210> SEQ ID NO 447
<211> LENGTH: 20
<212> TYPE: PRT
<213> ORGANISM: Artificial Sequence
<220> FEATURE:
<223> OTHER INFORMATION: Lolium perenne Pollen allergen Lol p VA
      precursor epitope

<400> SEQUENCE: 447

Ala Tyr Ala Ala Thr Val Ala Ala Ala Pro Glu Val Lys Tyr Ala Val
1               5                   10                  15

Phe Glu Ala Ala
            20

<210> SEQ ID NO 448
<211> LENGTH: 12
<212> TYPE: PRT
<213> ORGANISM: Artificial Sequence
<220> FEATURE:
<223> OTHER INFORMATION: Phleum pratense Pollen allergen Phl p 1 epitope

<400> SEQUENCE: 448

Ala Cys Ser Gly Glu Pro Val Val Val His Ile Thr
1               5                   10

<210> SEQ ID NO 449
<211> LENGTH: 12
```

```
<212> TYPE: PRT
<213> ORGANISM: Artificial Sequence
<220> FEATURE:
<223> OTHER INFORMATION: Phleum pratense Pollen allergen Phl p 1 epitope

<400> SEQUENCE: 449

Ala Glu Asp Val Ile Pro Glu Gly Trp Lys Ala Asp
1               5                   10

<210> SEQ ID NO 450
<211> LENGTH: 12
<212> TYPE: PRT
<213> ORGANISM: Artificial Sequence
<220> FEATURE:
<223> OTHER INFORMATION: Phleum pratense Pollen allergen Phl p 1 epitope

<400> SEQUENCE: 450

Ala Gly Glu Leu Glu Leu Gln Phe Arg Arg Val Lys
1               5                   10

<210> SEQ ID NO 451
<211> LENGTH: 12
<212> TYPE: PRT
<213> ORGANISM: Artificial Sequence
<220> FEATURE:
<223> OTHER INFORMATION: Phleum pratense Pollen allergen Phl p 1 epitope

<400> SEQUENCE: 451

Asp Lys Trp Ile Glu Leu Lys Glu Ser Trp Gly Ala
1               5                   10

<210> SEQ ID NO 452
<211> LENGTH: 12
<212> TYPE: PRT
<213> ORGANISM: Artificial Sequence
<220> FEATURE:
<223> OTHER INFORMATION: Phleum pratense Pollen allergen Phl p 1 epitope

<400> SEQUENCE: 452

Asp Lys Trp Leu Asp Ala Lys Ser Thr Trp Tyr Gly
1               5                   10

<210> SEQ ID NO 453
<211> LENGTH: 12
<212> TYPE: PRT
<213> ORGANISM: Artificial Sequence
<220> FEATURE:
<223> OTHER INFORMATION: Phleum pratense Pollen allergen Phl p 1
      precursor epitope

<400> SEQUENCE: 453

Phe Glu Ile Lys Cys Thr Lys Pro Glu Ala Cys Ser
1               5                   10

<210> SEQ ID NO 454
<211> LENGTH: 12
<212> TYPE: PRT
<213> ORGANISM: Artificial Sequence
<220> FEATURE:
<223> OTHER INFORMATION: Phleum pratense Pollen allergen Phl p 1
      precursor epitope

<400> SEQUENCE: 454

Tyr His Phe Asp Leu Ser Gly His Ala Phe Gly Ala
1               5                   10

<210> SEQ ID NO 455
```

```
<211> LENGTH: 15
<212> TYPE: PRT
<213> ORGANISM: Artificial Sequence
<220> FEATURE:
<223> OTHER INFORMATION: Phleum pratense Pollen allergen Phl p 1
      precursor epitope

<400> SEQUENCE: 455

Glu Leu Lys Glu Ser Trp Gly Ala Ile Trp Arg Ile Asp Thr Pro
1               5                   10                  15

<210> SEQ ID NO 456
<211> LENGTH: 15
<212> TYPE: PRT
<213> ORGANISM: Artificial Sequence
<220> FEATURE:
<223> OTHER INFORMATION: Phleum pratense Pollen allergen Phl p 1
      precursor epitope

<400> SEQUENCE: 456

Glu Pro Ile Ala Pro Tyr His Phe Asp Leu Ser Gly His Ala Phe
1               5                   10                  15

<210> SEQ ID NO 457
<211> LENGTH: 15
<212> TYPE: PRT
<213> ORGANISM: Artificial Sequence
<220> FEATURE:
<223> OTHER INFORMATION: Phleum pratense Pollen allergen Phl p 1
      precursor epitope

<400> SEQUENCE: 457

Phe Glu Ile Lys Cys Thr Lys Pro Glu Ala Cys Ser Gly Glu Pro
1               5                   10                  15

<210> SEQ ID NO 458
<211> LENGTH: 15
<212> TYPE: PRT
<213> ORGANISM: Artificial Sequence
<220> FEATURE:
<223> OTHER INFORMATION: Phleum pratense Pollen allergen Phl p 1
      precursor epitope

<400> SEQUENCE: 458

Trp Gly Ala Ile Trp Arg Ile Asp Thr Pro Asp Lys Leu Thr Gly
1               5                   10                  15

<210> SEQ ID NO 459
<211> LENGTH: 15
<212> TYPE: PRT
<213> ORGANISM: Artificial Sequence
<220> FEATURE:
<223> OTHER INFORMATION: Phleum pratense Pollen allergen Phl p 11
      epitope

<400> SEQUENCE: 459

Arg Tyr Ala Asn Pro Ile Ala Phe Phe Arg Lys Glu Pro Leu Lys
1               5                   10                  15

<210> SEQ ID NO 460
<211> LENGTH: 15
<212> TYPE: PRT
<213> ORGANISM: Artificial Sequence
<220> FEATURE:
<223> OTHER INFORMATION: Phleum pratense Pollen allergen Phl p 2 epitope

<400> SEQUENCE: 460

Glu His Gly Ser Asp Glu Trp Val Ala Met Thr Lys Gly Glu Gly
```

<210> SEQ ID NO 461
<211> LENGTH: 15
<212> TYPE: PRT
<213> ORGANISM: Artificial Sequence
<220> FEATURE:
<223> OTHER INFORMATION: Phleum pratense Pollen allergen Phl p 2 epitope

<400> SEQUENCE: 461

Glu Trp Val Ala Met Thr Lys Gly Glu Gly Gly Val Trp Thr Phe
1               5                   10                  15

<210> SEQ ID NO 462
<211> LENGTH: 15
<212> TYPE: PRT
<213> ORGANISM: Artificial Sequence
<220> FEATURE:
<223> OTHER INFORMATION: Phleum pratense Pollen allergen Phl p 2 epitope

<400> SEQUENCE: 462

Gly Val Trp Thr Phe Asp Ser Glu Glu Pro Leu Gln Gly Pro Phe
1               5                   10                  15

<210> SEQ ID NO 463
<211> LENGTH: 15
<212> TYPE: PRT
<213> ORGANISM: Artificial Sequence
<220> FEATURE:
<223> OTHER INFORMATION: Phleum pratense Pollen allergen Phl p 2 epitope

<400> SEQUENCE: 463

Lys Asn Val Phe Asp Asp Val Val Pro Glu Lys Tyr Thr Ile Gly
1               5                   10                  15

<210> SEQ ID NO 464
<211> LENGTH: 15
<212> TYPE: PRT
<213> ORGANISM: Artificial Sequence
<220> FEATURE:
<223> OTHER INFORMATION: Phleum pratense Pollen allergen Phl p 2 epitope

<400> SEQUENCE: 464

Leu Gln Gly Pro Phe Asn Phe Arg Phe Leu Thr Glu Lys Gly Met
1               5                   10                  15

<210> SEQ ID NO 465
<211> LENGTH: 15
<212> TYPE: PRT
<213> ORGANISM: Artificial Sequence
<220> FEATURE:
<223> OTHER INFORMATION: Phleum pratense Pollen allergen Phl p 4 epitope

<400> SEQUENCE: 465

Phe Lys Pro Phe Ala Glu Tyr Lys Ser Asp Tyr Val Tyr Glu Pro
1               5                   10                  15

<210> SEQ ID NO 466
<211> LENGTH: 15
<212> TYPE: PRT
<213> ORGANISM: Artificial Sequence
<220> FEATURE:
<223> OTHER INFORMATION: Phleum pratense Pollen allergen Phl p 4 epitope

<400> SEQUENCE: 466

Phe Pro Lys Glu Val Trp Glu Gln Ile Phe Ser Thr Trp Leu Leu
1               5                   10                  15

<210> SEQ ID NO 467
<211> LENGTH: 15
<212> TYPE: PRT
<213> ORGANISM: Artificial Sequence
<220> FEATURE:
<223> OTHER INFORMATION: Phleum pratense Pollen allergen Phl p 4 epitope

<400> SEQUENCE: 467

Phe Val His Leu Gly His Arg Asp Asn Ile Glu Asp Asp Leu Leu
1               5                   10                  15

<210> SEQ ID NO 468
<211> LENGTH: 15
<212> TYPE: PRT
<213> ORGANISM: Artificial Sequence
<220> FEATURE:
<223> OTHER INFORMATION: Phleum pratense Pollen allergen Phl p 4 epitope

<400> SEQUENCE: 468

Gly Ile Val Val Ala Trp Lys Val Arg Leu Leu Pro Val Pro Pro
1               5                   10                  15

<210> SEQ ID NO 469
<211> LENGTH: 15
<212> TYPE: PRT
<213> ORGANISM: Artificial Sequence
<220> FEATURE:
<223> OTHER INFORMATION: Phleum pratense Pollen allergen Phl p 4 epitope

<400> SEQUENCE: 469

Asn Arg Asn Asn Thr Phe Lys Pro Phe Ala Glu Tyr Lys Ser Asp
1               5                   10                  15

<210> SEQ ID NO 470
<211> LENGTH: 12
<212> TYPE: PRT
<213> ORGANISM: Artificial Sequence
<220> FEATURE:
<223> OTHER INFORMATION: Phleum pratense Pollen allergen Phl p 5a
      epitope

<400> SEQUENCE: 470

Glu Val Lys Tyr Thr Val Phe Glu Thr Ala Leu Lys
1               5                   10

<210> SEQ ID NO 471
<211> LENGTH: 19
<212> TYPE: PRT
<213> ORGANISM: Artificial Sequence
<220> FEATURE:
<223> OTHER INFORMATION: Phleum pratense Pollen allergen Phl p 5a
      epitope

<400> SEQUENCE: 471

Asn Ala Gly Phe Lys Ala Ala Leu Ala Gly Ala Gly Val Gln Pro Ala
1               5                   10                  15

Asp Lys Tyr

<210> SEQ ID NO 472
<211> LENGTH: 27
<212> TYPE: PRT
<213> ORGANISM: Artificial Sequence
<220> FEATURE:
<223> OTHER INFORMATION: Phleum pratense Pollen allergen Phl p 5b
      precursor epitope

```
<400> SEQUENCE: 472

Ala Ala Gly Lys Ala Thr Thr Glu Glu Gln Lys Leu Ile Glu Asp Ile
1               5                   10                  15

Asn Val Gly Phe Lys Ala Ala Val Ala Ala Ala
            20                  25

<210> SEQ ID NO 473
<211> LENGTH: 33
<212> TYPE: PRT
<213> ORGANISM: Artificial Sequence
<220> FEATURE:
<223> OTHER INFORMATION: Phleum pratense Pollen allergen Phl p 5b
      precursor epitope

<400> SEQUENCE: 473

Ala Ala Gly Lys Ala Thr Thr Glu Glu Gln Lys Leu Ile Glu Asp Ile
1               5                   10                  15

Asn Val Gly Phe Lys Ala Ala Val Ala Ala Ala Ser Val Pro Ala
            20                  25                  30

Ala

<210> SEQ ID NO 474
<211> LENGTH: 19
<212> TYPE: PRT
<213> ORGANISM: Artificial Sequence
<220> FEATURE:
<223> OTHER INFORMATION: Phleum pratense Pollen allergen Phl p 5b
      precursor epitope

<400> SEQUENCE: 474

Ala Ala Val Ala Ala Ala Ala Ser Val Pro Ala Ala Asp Lys Phe Lys
1               5                   10                  15

Thr Phe Glu

<210> SEQ ID NO 475
<211> LENGTH: 27
<212> TYPE: PRT
<213> ORGANISM: Artificial Sequence
<220> FEATURE:
<223> OTHER INFORMATION: Phleum pratense Pollen allergen Phl p 5b
      precursor epitope

<400> SEQUENCE: 475

Ala Lys Phe Asp Ser Phe Val Ala Ser Leu Thr Glu Ala Leu Arg Val
1               5                   10                  15

Ile Ala Gly Ala Leu Glu Val His Ala Val Lys
            20                  25

<210> SEQ ID NO 476
<211> LENGTH: 19
<212> TYPE: PRT
<213> ORGANISM: Artificial Sequence
<220> FEATURE:
<223> OTHER INFORMATION: Phleum pratense Pollen allergen Phl p 5b
      precursor epitope

<400> SEQUENCE: 476

Ala Met Ser Glu Val Gln Lys Val Ser Gln Pro Ala Thr Gly Ala Ala
1               5                   10                  15

Thr Val Ala

<210> SEQ ID NO 477
<211> LENGTH: 20
```

-continued

```
<212> TYPE: PRT
<213> ORGANISM: Artificial Sequence
<220> FEATURE:
<223> OTHER INFORMATION: Chamaecyparis obtusa Polygalacturonase epitope

<400> SEQUENCE: 477

Ala Arg Trp Lys Asn Ser Lys Ile Trp Leu Gln Phe Ala Gln Leu Thr
1               5                   10                  15

Asp Phe Asn Leu
            20

<210> SEQ ID NO 478
<211> LENGTH: 20
<212> TYPE: PRT
<213> ORGANISM: Artificial Sequence
<220> FEATURE:
<223> OTHER INFORMATION: Chamaecyparis obtusa Polygalacturonase epitope

<400> SEQUENCE: 478

Ala Val Leu Leu Val Pro Ala Asn Lys Lys Phe Phe Val Asn Asn Leu
1               5                   10                  15

Val Phe Arg Gly
            20

<210> SEQ ID NO 479
<211> LENGTH: 20
<212> TYPE: PRT
<213> ORGANISM: Artificial Sequence
<220> FEATURE:
<223> OTHER INFORMATION: Chamaecyparis obtusa Polygalacturonase epitope

<400> SEQUENCE: 479

Asp Gly Thr Ile Val Ala Gln Pro Asp Pro Ala Arg Trp Lys Asn Ser
1               5                   10                  15

Lys Ile Trp Leu
            20

<210> SEQ ID NO 480
<211> LENGTH: 20
<212> TYPE: PRT
<213> ORGANISM: Artificial Sequence
<220> FEATURE:
<223> OTHER INFORMATION: Chamaecyparis obtusa Polygalacturonase epitope

<400> SEQUENCE: 480

Phe Phe Val Asn Asn Leu Val Phe Arg Gly Pro Cys Gln Pro His Leu
1               5                   10                  15

Ser Phe Lys Val
            20

<210> SEQ ID NO 481
<211> LENGTH: 20
<212> TYPE: PRT
<213> ORGANISM: Artificial Sequence
<220> FEATURE:
<223> OTHER INFORMATION: Chamaecyparis obtusa Polygalacturonase epitope

<400> SEQUENCE: 481

Phe Gly Glu Cys Glu Gly Val Lys Ile Gln Gly Leu Lys Ile Lys Ala
1               5                   10                  15

Pro Arg Asp Ser
            20

<210> SEQ ID NO 482
```

-continued

```
<211> LENGTH: 15
<212> TYPE: PRT
<213> ORGANISM: Artificial Sequence
<220> FEATURE:
<223> OTHER INFORMATION: Cryptomeria japonica Polygalacturonase
      precursor epitope

<400> SEQUENCE: 482

Ala Ala Tyr Gln Asn Pro Ala Ser Trp Lys Asn Asn Arg Ile Trp
1               5                   10                  15

<210> SEQ ID NO 483
<211> LENGTH: 15
<212> TYPE: PRT
<213> ORGANISM: Artificial Sequence
<220> FEATURE:
<223> OTHER INFORMATION: Cryptomeria japonica Polygalacturonase
      precursor epitope

<400> SEQUENCE: 483

Ala Cys Lys Lys Pro Ser Ala Met Leu Leu Val Pro Gly Asn Lys
1               5                   10                  15

<210> SEQ ID NO 484
<211> LENGTH: 15
<212> TYPE: PRT
<213> ORGANISM: Artificial Sequence
<220> FEATURE:
<223> OTHER INFORMATION: Cryptomeria japonica Polygalacturonase
      precursor epitope

<400> SEQUENCE: 484

Ala Ile Lys Phe Asp Phe Ser Thr Gly Leu Ile Ile Gln Gly Leu
1               5                   10                  15

<210> SEQ ID NO 485
<211> LENGTH: 15
<212> TYPE: PRT
<213> ORGANISM: Artificial Sequence
<220> FEATURE:
<223> OTHER INFORMATION: Cryptomeria japonica Polygalacturonase
      precursor epitope

<400> SEQUENCE: 485

Ala Ile Asn Ile Phe Asn Val Glu Lys Tyr Gly Ala Val Gly Asp
1               5                   10                  15

<210> SEQ ID NO 486
<211> LENGTH: 15
<212> TYPE: PRT
<213> ORGANISM: Artificial Sequence
<220> FEATURE:
<223> OTHER INFORMATION: Cryptomeria japonica Polygalacturonase
      precursor epitope

<400> SEQUENCE: 486

Ala Asn Gly Tyr Phe Ser Gly His Val Ile Pro Ala Cys Lys Asn
1               5                   10                  15

<210> SEQ ID NO 487
<211> LENGTH: 16
<212> TYPE: PRT
<213> ORGANISM: Artificial Sequence
<220> FEATURE:
<223> OTHER INFORMATION: Arabidopsis thaliana Probable pectate lyase
      18 precursor epitope

<400> SEQUENCE: 487
```

```
Gly His Ser Asp Thr Tyr Ser Arg Asp Lys Asn Met Gln Val Thr Ile
1               5                   10                  15
```

<210> SEQ ID NO 488
<211> LENGTH: 15
<212> TYPE: PRT
<213> ORGANISM: Artificial Sequence
<220> FEATURE:
<223> OTHER INFORMATION: Phleum pratense Profilin-2/4 epitope

<400> SEQUENCE: 488

```
Leu Gly His Asp Gly Thr Val Trp Ala Gln Ser Ala Asp Phe Pro
1               5                   10                  15
```

<210> SEQ ID NO 489
<211> LENGTH: 20
<212> TYPE: PRT
<213> ORGANISM: Artificial Sequence
<220> FEATURE:
<223> OTHER INFORMATION: Hevea brasiliensis Pro-hevein precursor epitope

<400> SEQUENCE: 489

```
Asp Glu Tyr Cys Ser Pro Asp His Asn Cys Gln Ser Asn Cys Lys Asp
1               5                   10                  15

Ser Gly Glu Gly
            20
```

<210> SEQ ID NO 490
<211> LENGTH: 20
<212> TYPE: PRT
<213> ORGANISM: Artificial Sequence
<220> FEATURE:
<223> OTHER INFORMATION: Hevea brasiliensis Pro-hevein precursor epitope

<400> SEQUENCE: 490

```
Glu Gln Cys Gly Arg Gln Ala Gly Gly Lys Leu Cys Pro Asn Asn Leu
1               5                   10                  15

Cys Cys Ser Gln
            20
```

<210> SEQ ID NO 491
<211> LENGTH: 43
<212> TYPE: PRT
<213> ORGANISM: Artificial Sequence
<220> FEATURE:
<223> OTHER INFORMATION: Hevea brasiliensis Pro-hevein precursor epitope

<400> SEQUENCE: 491

```
Glu Gln Cys Gly Arg Gln Ala Gly Gly Lys Leu Cys Pro Asn Asn Leu
1               5                   10                  15

Cys Cys Ser Gln Trp Gly Trp Cys Gly Ser Thr Asp Glu Tyr Cys Ser
            20                  25                  30

Pro Asp His Asn Cys Gln Ser Asn Cys Lys Asp
        35                  40
```

<210> SEQ ID NO 492
<211> LENGTH: 20
<212> TYPE: PRT
<213> ORGANISM: Artificial Sequence
<220> FEATURE:
<223> OTHER INFORMATION: Hevea brasiliensis Pro-hevein precursor epitope

<400> SEQUENCE: 492

```
Lys Leu Cys Pro Asn Asn Leu Cys Cys Ser Gln Trp Gly Trp Cys Gly
1               5                   10                  15
```

```
Ser Thr Asp Glu
        20

<210> SEQ ID NO 493
<211> LENGTH: 20
<212> TYPE: PRT
<213> ORGANISM: Artificial Sequence
<220> FEATURE:
<223> OTHER INFORMATION: Hevea brasiliensis Pro-hevein precursor epitope

<400> SEQUENCE: 493

Asn Gly Gly Leu Asp Leu Asp Val Asn Val Phe Arg Gln Leu Asp Thr
1               5                   10                  15

Asp Gly Lys Gly
        20

<210> SEQ ID NO 494
<211> LENGTH: 10
<212> TYPE: PRT
<213> ORGANISM: Artificial Sequence
<220> FEATURE:
<223> OTHER INFORMATION: Prunus persica pru p 1 epitope

<400> SEQUENCE: 494

Gly Lys Cys Gly Val Ser Ile Pro Tyr Lys
1               5                   10

<210> SEQ ID NO 495
<211> LENGTH: 10
<212> TYPE: PRT
<213> ORGANISM: Artificial Sequence
<220> FEATURE:
<223> OTHER INFORMATION: Prunus persica pru p 1 epitope

<400> SEQUENCE: 495

Ile Thr Cys Gly Gln Val Ser Ser Ser Leu
1               5                   10

<210> SEQ ID NO 496
<211> LENGTH: 10
<212> TYPE: PRT
<213> ORGANISM: Artificial Sequence
<220> FEATURE:
<223> OTHER INFORMATION: Prunus persica pru p 1 epitope

<400> SEQUENCE: 496

Ser Ile Pro Tyr Lys Ile Ser Ala Ser Thr
1               5                   10

<210> SEQ ID NO 497
<211> LENGTH: 15
<212> TYPE: PRT
<213> ORGANISM: Artificial Sequence
<220> FEATURE:
<223> OTHER INFORMATION: Prunus persica pru p 1 epitope

<400> SEQUENCE: 497

Asp Arg Gln Ala Ala Cys Asn Cys Leu Lys Gln Leu Ser Ala Ser
1               5                   10                  15

<210> SEQ ID NO 498
<211> LENGTH: 15
<212> TYPE: PRT
<213> ORGANISM: Artificial Sequence
<220> FEATURE:
<223> OTHER INFORMATION: Prunus persica pru p 1 epitope
```

-continued

<400> SEQUENCE: 498

Val Asn Pro Asn Asn Ala Ala Ala Leu Pro Gly Lys Cys Gly Val
1               5                   10                  15

<210> SEQ ID NO 499
<211> LENGTH: 16
<212> TYPE: PRT
<213> ORGANISM: Artificial Sequence
<220> FEATURE:
<223> OTHER INFORMATION: Arabidopsis thaliana Putative pectate lyase 17
      precursor epitope

<400> SEQUENCE: 499

Gly His Asn Asp Asn Phe Val Lys Asp Val Lys Met Lys Val Thr Val
1               5                   10                  15

<210> SEQ ID NO 500
<211> LENGTH: 16
<212> TYPE: PRT
<213> ORGANISM: Artificial Sequence
<220> FEATURE:
<223> OTHER INFORMATION: Homo sapiens RAD51-like 1 isoform 1 epitope

<400> SEQUENCE: 500

Thr Arg Leu Ile Leu Gln Tyr Leu Asp Ser Glu Arg Arg Gln Ile Leu
1               5                   10                  15

<210> SEQ ID NO 501
<211> LENGTH: 16
<212> TYPE: PRT
<213> ORGANISM: Artificial Sequence
<220> FEATURE:
<223> OTHER INFORMATION: Aspergillus fumigatus Ribonuclease mitogillin
      precursor epitope

<400> SEQUENCE: 501

Asp Pro Gly Pro Ala Arg Val Ile Tyr Thr Tyr Pro Asn Lys Val Phe
1               5                   10                  15

<210> SEQ ID NO 502
<211> LENGTH: 20
<212> TYPE: PRT
<213> ORGANISM: Artificial Sequence
<220> FEATURE:
<223> OTHER INFORMATION: Aspergillus fumigatus Ribonuclease mitogillin
      precursor epitope

<400> SEQUENCE: 502

Ala Thr Trp Thr Cys Ile Asn Gln Gln Leu Asn Pro Lys Thr Asn Lys
1               5                   10                  15

Trp Glu Asp Lys
            20

<210> SEQ ID NO 503
<211> LENGTH: 20
<212> TYPE: PRT
<213> ORGANISM: Artificial Sequence
<220> FEATURE:
<223> OTHER INFORMATION: Aspergillus fumigatus Ribonuclease mitogillin
      precursor epitope

<400> SEQUENCE: 503

His Tyr Leu Leu Glu Phe Pro Thr Phe Pro Asp Gly His Asp Tyr Lys
1               5                   10                  15

Phe Asp Ser Lys

-continued

```
          20

<210> SEQ ID NO 504
<211> LENGTH: 20
<212> TYPE: PRT
<213> ORGANISM: Artificial Sequence
<220> FEATURE:
<223> OTHER INFORMATION: Aspergillus fumigatus Ribonuclease mitogillin
      precursor epitope

<400> SEQUENCE: 504

Lys Phe Asp Ser Lys Lys Pro Lys Glu Asp Pro Gly Pro Ala Arg Val
1               5                   10                  15

Ile Tyr Thr Tyr
          20

<210> SEQ ID NO 505
<211> LENGTH: 20
<212> TYPE: PRT
<213> ORGANISM: Artificial Sequence
<220> FEATURE:
<223> OTHER INFORMATION: Aspergillus fumigatus Ribonuclease mitogillin
      precursor epitope

<400> SEQUENCE: 505

Leu Ile Lys Gly Arg Thr Pro Ile Lys Phe Gly Lys Ala Asp Cys Asp
1               5                   10                  15

Arg Pro Pro Lys
          20

<210> SEQ ID NO 506
<211> LENGTH: 20
<212> TYPE: PRT
<213> ORGANISM: Artificial Sequence
<220> FEATURE:
<223> OTHER INFORMATION: Aspergillus fumigatus Ribonuclease mitogillin
      precursor epitope

<400> SEQUENCE: 506

Ser Tyr Pro His Trp Phe Thr Asn Gly Tyr Asp Gly Asn Gly Lys Leu
1               5                   10                  15

Ile Lys Gly Arg
          20

<210> SEQ ID NO 507
<211> LENGTH: 19
<212> TYPE: PRT
<213> ORGANISM: Artificial Sequence
<220> FEATURE:
<223> OTHER INFORMATION: Hevea brasiliensis Rubber elongation factor
      protein epitope

<400> SEQUENCE: 507

Ala Glu Asp Glu Asp Asn Gln Gln Gly Gln Gly Glu Gly Leu Lys Tyr
1               5                   10                  15

Leu Gly Phe

<210> SEQ ID NO 508
<211> LENGTH: 19
<212> TYPE: PRT
<213> ORGANISM: Artificial Sequence
<220> FEATURE:
<223> OTHER INFORMATION: Hevea brasiliensis Rubber elongation factor
      protein epitope

<400> SEQUENCE: 508
```

```
Phe Ser Asn Val Tyr Leu Phe Ala Lys Asp Lys Ser Gly Pro Leu Gln
1               5                   10                  15

Pro Gly Val

<210> SEQ ID NO 509
<211> LENGTH: 19
<212> TYPE: PRT
<213> ORGANISM: Artificial Sequence
<220> FEATURE:
<223> OTHER INFORMATION: Hevea brasiliensis Rubber elongation factor
      protein epitope

<400> SEQUENCE: 509

Lys Phe Val Asp Ser Thr Val Val Ala Ser Val Thr Ile Ile Asp Arg
1               5                   10                  15

Ser Leu Pro

<210> SEQ ID NO 510
<211> LENGTH: 19
<212> TYPE: PRT
<213> ORGANISM: Artificial Sequence
<220> FEATURE:
<223> OTHER INFORMATION: Hevea brasiliensis Rubber elongation factor
      protein epitope

<400> SEQUENCE: 510

Gln Pro Gly Val Asp Ile Ile Glu Gly Pro Val Lys Asn Val Ala Val
1               5                   10                  15

Pro Leu Tyr

<210> SEQ ID NO 511
<211> LENGTH: 19
<212> TYPE: PRT
<213> ORGANISM: Artificial Sequence
<220> FEATURE:
<223> OTHER INFORMATION: Hevea brasiliensis Rubber elongation factor
      protein epitope

<400> SEQUENCE: 511

Arg Ser Leu Pro Pro Ile Val Lys Asp Ala Ser Ile Gln Val Val Ser
1               5                   10                  15

Ala Ile Arg

<210> SEQ ID NO 512
<211> LENGTH: 17
<212> TYPE: PRT
<213> ORGANISM: Artificial Sequence
<220> FEATURE:
<223> OTHER INFORMATION: Bos taurus Serum albumin precursor epitope

<400> SEQUENCE: 512

Asp Asp Ser Pro Asp Leu Pro Lys Leu Lys Pro Asp Pro Asn Thr Leu
1               5                   10                  15

Cys

<210> SEQ ID NO 513
<211> LENGTH: 20
<212> TYPE: PRT
<213> ORGANISM: Artificial Sequence
<220> FEATURE:
<223> OTHER INFORMATION: Bos taurus Serum albumin precursor epitope

<400> SEQUENCE: 513
```

```
Glu Lys Asp Ala Ile Pro Glu Asn Leu Pro Pro Leu Thr Ala Asp Phe
1               5                   10                  15

Ala Glu Asp Lys
            20

<210> SEQ ID NO 514
<211> LENGTH: 9
<212> TYPE: PRT
<213> ORGANISM: Artificial Sequence
<220> FEATURE:
<223> OTHER INFORMATION: Bos taurus Serum albumin precursor epitope

<400> SEQUENCE: 514

Glu Ser His Ala Gly Cys Glu Lys Ser
1               5

<210> SEQ ID NO 515
<211> LENGTH: 10
<212> TYPE: PRT
<213> ORGANISM: Artificial Sequence
<220> FEATURE:
<223> OTHER INFORMATION: Bos taurus Serum albumin precursor epitope

<400> SEQUENCE: 515

His Pro Glu Tyr Ala Val Ser Val Leu Leu
1               5                   10

<210> SEQ ID NO 516
<211> LENGTH: 9
<212> TYPE: PRT
<213> ORGANISM: Artificial Sequence
<220> FEATURE:
<223> OTHER INFORMATION: Bos taurus Serum albumin precursor epitope

<400> SEQUENCE: 516

Leu Ser Leu Ile Leu Asn Arg Leu Cys
1               5

<210> SEQ ID NO 517
<211> LENGTH: 12
<212> TYPE: PRT
<213> ORGANISM: Artificial Sequence
<220> FEATURE:
<223> OTHER INFORMATION: Hevea brasiliensis Small rubber particle
      protein epitope

<400> SEQUENCE: 517

Asp Phe Val Arg Ala Ala Gly Val Tyr Ala Val Asp
1               5                   10

<210> SEQ ID NO 518
<211> LENGTH: 12
<212> TYPE: PRT
<213> ORGANISM: Artificial Sequence
<220> FEATURE:
<223> OTHER INFORMATION: Hevea brasiliensis Small rubber particle
      protein epitope

<400> SEQUENCE: 518

Lys Tyr Leu Asp Phe Val Arg Ala Ala Gly Val Tyr
1               5                   10

<210> SEQ ID NO 519
<211> LENGTH: 12
<212> TYPE: PRT
<213> ORGANISM: Artificial Sequence
<220> FEATURE:
```

<223> OTHER INFORMATION: Hevea brasiliensis Small rubber particle
      protein epitope

<400> SEQUENCE: 519

Asn Val Val Lys Thr Val Val Thr Pro Val Tyr Tyr
1               5                   10

<210> SEQ ID NO 520
<211> LENGTH: 12
<212> TYPE: PRT
<213> ORGANISM: Artificial Sequence
<220> FEATURE:
<223> OTHER INFORMATION: Hevea brasiliensis Small rubber particle
      protein epitope

<400> SEQUENCE: 520

Pro Arg Ile Val Leu Asp Val Ala Ser Ser Val Phe
1               5                   10

<210> SEQ ID NO 521
<211> LENGTH: 12
<212> TYPE: PRT
<213> ORGANISM: Artificial Sequence
<220> FEATURE:
<223> OTHER INFORMATION: Hevea brasiliensis Small rubber particle
      protein epitope

<400> SEQUENCE: 521

Gln Gly Tyr Arg Val Ser Ser Tyr Leu Pro Leu Leu
1               5                   10

<210> SEQ ID NO 522
<211> LENGTH: 15
<212> TYPE: PRT
<213> ORGANISM: Artificial Sequence
<220> FEATURE:
<223> OTHER INFORMATION: Glycine max Stress-induced protein SAM22
      epitope

<400> SEQUENCE: 522

Ala Leu Phe Lys Ala Ile Glu Ala Tyr Leu Leu Ala His Pro Asp
1               5                   10                  15

<210> SEQ ID NO 523
<211> LENGTH: 15
<212> TYPE: PRT
<213> ORGANISM: Artificial Sequence
<220> FEATURE:
<223> OTHER INFORMATION: Cryptomeria japonica Sugi basic protein
      precursor epitope

<400> SEQUENCE: 523

Ala Phe Asn Val Glu Asn Gly Asn Ala Thr Pro Gln Leu Thr Lys
1               5                   10                  15

<210> SEQ ID NO 524
<211> LENGTH: 15
<212> TYPE: PRT
<213> ORGANISM: Artificial Sequence
<220> FEATURE:
<223> OTHER INFORMATION: Cryptomeria japonica Sugi basic protein
      precursor epitope

<400> SEQUENCE: 524

Ala Asn Asn Asn Tyr Asp Pro Trp Thr Ile Tyr Ala Ile Gly Gly
1               5                   10                  15

```
<210> SEQ ID NO 525
<211> LENGTH: 15
<212> TYPE: PRT
<213> ORGANISM: Artificial Sequence
<220> FEATURE:
<223> OTHER INFORMATION: Cryptomeria japonica Sugi basic protein
      precursor epitope

<400> SEQUENCE: 525

Ala Tyr Ser Asp Asp Lys Ser Met Lys Val Thr Val Ala Phe Asn
1               5                   10                  15

<210> SEQ ID NO 526
<211> LENGTH: 15
<212> TYPE: PRT
<213> ORGANISM: Artificial Sequence
<220> FEATURE:
<223> OTHER INFORMATION: Cryptomeria japonica Sugi basic protein
      precursor epitope

<400> SEQUENCE: 526

Cys Gly Gln Arg Met Pro Arg Ala Arg Tyr Gly Leu Val His Val
1               5                   10                  15

<210> SEQ ID NO 527
<211> LENGTH: 15
<212> TYPE: PRT
<213> ORGANISM: Artificial Sequence
<220> FEATURE:
<223> OTHER INFORMATION: Cryptomeria japonica Sugi basic protein
      precursor epitope

<400> SEQUENCE: 527

Cys Ser Asn Trp Val Trp Gln Ser Thr Gln Asp Val Phe Tyr Asn
1               5                   10                  15

<210> SEQ ID NO 528
<211> LENGTH: 20
<212> TYPE: PRT
<213> ORGANISM: Artificial Sequence
<220> FEATURE:
<223> OTHER INFORMATION: Trichophyton rubrum Tri r 2 allergen epitope

<400> SEQUENCE: 528

Ala Asp Phe Ser Asn Tyr Gly Ala Val Val Asp Val Tyr Ala Pro Gly
1               5                   10                  15

Lys Asp Ile Thr
            20

<210> SEQ ID NO 529
<211> LENGTH: 20
<212> TYPE: PRT
<213> ORGANISM: Artificial Sequence
<220> FEATURE:
<223> OTHER INFORMATION: Trichophyton rubrum Tri r 2 allergen epitope

<400> SEQUENCE: 529

Ala Lys Gly Val Ser Leu Val Ala Val Lys Val Leu Asp Cys Asp Gly
1               5                   10                  15

Ser Gly Ser Asn
            20

<210> SEQ ID NO 530
<211> LENGTH: 20
<212> TYPE: PRT
<213> ORGANISM: Artificial Sequence
<220> FEATURE:
```

```
<223> OTHER INFORMATION: Trichophyton rubrum Tri r 2 allergen epitope

<400> SEQUENCE: 530

Ala Ser Asn Gln Ala Ala Lys Ala Ile Ser Asp Ala Gly Ile Phe Met
1               5                   10                  15
Ala Val Ala Ala
            20

<210> SEQ ID NO 531
<211> LENGTH: 20
<212> TYPE: PRT
<213> ORGANISM: Artificial Sequence
<220> FEATURE:
<223> OTHER INFORMATION: Trichophyton rubrum Tri r 2 allergen epitope

<400> SEQUENCE: 531

Asp Cys Asn Gly His Gly Thr His Val Ala Gly Thr Val Gly Gly Thr
1               5                   10                  15
Lys Tyr Gly Leu
            20

<210> SEQ ID NO 532
<211> LENGTH: 20
<212> TYPE: PRT
<213> ORGANISM: Artificial Sequence
<220> FEATURE:
<223> OTHER INFORMATION: Trichophyton rubrum Tri r 2 allergen epitope

<400> SEQUENCE: 532

Asp Pro Ser Ala Gly Lys Gly Val Thr Ala Tyr Ile Ile Asp Thr Gly
1               5                   10                  15
Ile Asp Ile Asp
            20

<210> SEQ ID NO 533
<211> LENGTH: 12
<212> TYPE: PRT
<213> ORGANISM: Artificial Sequence
<220> FEATURE:
<223> OTHER INFORMATION: Vespula vulgaris Venom allergen 5 precursor
      epitope

<400> SEQUENCE: 533

Ala Cys Lys Tyr Gly Ser Leu Lys Pro Asn Cys Gly
1               5                   10

<210> SEQ ID NO 534
<211> LENGTH: 12
<212> TYPE: PRT
<213> ORGANISM: Artificial Sequence
<220> FEATURE:
<223> OTHER INFORMATION: Vespula vulgaris Venom allergen 5 precursor
      epitope

<400> SEQUENCE: 534

Cys Asn Tyr Gly Pro Ser Gly Asn Phe Met Asn Glu
1               5                   10

<210> SEQ ID NO 535
<211> LENGTH: 12
<212> TYPE: PRT
<213> ORGANISM: Artificial Sequence
<220> FEATURE:
<223> OTHER INFORMATION: Vespula vulgaris Venom allergen 5 precursor
      epitope
```

```
<400> SEQUENCE: 535

Asp Val Ala Lys Tyr Gln Val Gly Gln Asn Val Ala
1               5                   10

<210> SEQ ID NO 536
<211> LENGTH: 12
<212> TYPE: PRT
<213> ORGANISM: Artificial Sequence
<220> FEATURE:
<223> OTHER INFORMATION: Vespula vulgaris Venom allergen 5 precursor
      epitope

<400> SEQUENCE: 536

Glu Lys Trp His Lys His Tyr Leu Val Cys Asn Tyr
1               5                   10

<210> SEQ ID NO 537
<211> LENGTH: 12
<212> TYPE: PRT
<213> ORGANISM: Artificial Sequence
<220> FEATURE:
<223> OTHER INFORMATION: Vespula vulgaris Venom allergen 5 precursor
      epitope

<400> SEQUENCE: 537

Glu Leu Ala Tyr Val Ala Gln Val Trp Ala Asn Gln
1               5                   10

<210> SEQ ID NO 538
<211> LENGTH: 15
<212> TYPE: PRT
<213> ORGANISM: Artificial Sequence
<220> FEATURE:
<223> OTHER INFORMATION: Corylus avellana 11S globulin-like protein
      epitope

<400> SEQUENCE: 538

Ala Phe Gln Ile Ser Arg Glu Glu Ala Arg Arg Leu Lys Tyr Asn
1               5                   10                  15

<210> SEQ ID NO 539
<211> LENGTH: 12
<212> TYPE: PRT
<213> ORGANISM: Artificial Sequence
<220> FEATURE:
<223> OTHER INFORMATION: Carya illinoinensis 11S legumin protein epitope

<400> SEQUENCE: 539

Glu Glu Ser Gln Arg Gln Ser Gln Gln Gly Gln Arg
1               5                   10

<210> SEQ ID NO 540
<211> LENGTH: 18
<212> TYPE: PRT
<213> ORGANISM: Artificial Sequence
<220> FEATURE:
<223> OTHER INFORMATION: Fagopyrum esculentum 13S globulin epitope

<400> SEQUENCE: 540

Asp Ala His Gln Pro Thr Arg Arg Val Arg Lys Gly Asp Val Val Ala
1               5                   10                  15

Leu Pro

<210> SEQ ID NO 541
<211> LENGTH: 12
<212> TYPE: PRT
```

```
<213> ORGANISM: Artificial Sequence
<220> FEATURE:
<223> OTHER INFORMATION: Fagopyrum esculentum 13S globulin seed storage
      protein 1 precursor (Legumin-like protein 1) epitope

<400> SEQUENCE: 541

Phe Lys Gln Asn Val Asn Arg Pro Ser Arg Ala Asp
1               5                   10

<210> SEQ ID NO 542
<211> LENGTH: 12
<212> TYPE: PRT
<213> ORGANISM: Artificial Sequence
<220> FEATURE:
<223> OTHER INFORMATION: Fagopyrum esculentum 13S globulin seed storage
      protein 3 precursor (Legumin-like protein 3) (Allergen Fag e 1)
      epitope

<400> SEQUENCE: 542

Asp Ile Ser Thr Lys Glu Ala Phe Arg Leu Lys Asn
1               5                   10

<210> SEQ ID NO 543
<211> LENGTH: 12
<212> TYPE: PRT
<213> ORGANISM: Artificial Sequence
<220> FEATURE:
<223> OTHER INFORMATION: Anacardium occidentale 2s albumin epitope

<400> SEQUENCE: 543

Cys Gln Arg Gln Phe Glu Glu Gln Gln Arg Phe Arg
1               5                   10

<210> SEQ ID NO 544
<211> LENGTH: 10
<212> TYPE: PRT
<213> ORGANISM: Artificial Sequence
<220> FEATURE:
<223> OTHER INFORMATION: Sesamum indicum 2S seed storage protein 1
      epitope

<400> SEQUENCE: 544

His Phe Arg Glu Cys Cys Asn Glu Ile Arg
1               5                   10

<210> SEQ ID NO 545
<211> LENGTH: 10
<212> TYPE: PRT
<213> ORGANISM: Artificial Sequence
<220> FEATURE:
<223> OTHER INFORMATION: Sesamum indicum 2S seed storage protein 1
      precursor epitope

<400> SEQUENCE: 545

Cys Met Gln Trp Met Arg Ser Met Arg Gly
1               5                   10

<210> SEQ ID NO 546
<211> LENGTH: 14
<212> TYPE: PRT
<213> ORGANISM: Artificial Sequence
<220> FEATURE:
<223> OTHER INFORMATION: Bertholletia excelsa 2S sulfur-rich seed
      storage protein precursor (Allergen Ber e 1) epitope

<400> SEQUENCE: 546

Cys Arg Cys Glu Gly Leu Arg Met Met Met Met Arg Met Gln
1               5                   10
```

```
<210> SEQ ID NO 547
<211> LENGTH: 40
<212> TYPE: PRT
<213> ORGANISM: Artificial Sequence
<220> FEATURE:
<223> OTHER INFORMATION: Homo sapiens 52 kDa Ro protein epitope

<400> SEQUENCE: 547

Leu Glu Lys Asp Glu Arg Glu Gln Leu Arg Ile Leu Gly Glu Lys Glu
1               5                   10                  15

Ala Lys Leu Ala Gln Gln Ser Gln Ala Leu Gln Glu Leu Ile Ser Glu
            20                  25                  30

Leu Asp Arg Arg Cys His Ser Ser
        35                  40

<210> SEQ ID NO 548
<211> LENGTH: 10
<212> TYPE: PRT
<213> ORGANISM: Artificial Sequence
<220> FEATURE:
<223> OTHER INFORMATION: Homo sapiens 52-kD SS-A/Ro autoantigen epitope

<400> SEQUENCE: 548

Gln Glu Lys Leu Gln Val Ala Leu Gly Glu
1               5                   10

<210> SEQ ID NO 549
<211> LENGTH: 21
<212> TYPE: PRT
<213> ORGANISM: Artificial Sequence
<220> FEATURE:
<223> OTHER INFORMATION: Homo sapiens 5-hydroxytryptamine (serotonin)
      receptor 4 epitope

<400> SEQUENCE: 549

Gly Ile Ile Asp Leu Ile Glu Lys Arg Lys Phe Asn Gln Asn Ser Asn
1               5                   10                  15

Ser Thr Tyr Cys Val
            20

<210> SEQ ID NO 550
<211> LENGTH: 10
<212> TYPE: PRT
<213> ORGANISM: Artificial Sequence
<220> FEATURE:
<223> OTHER INFORMATION: Homo sapiens 60 kDa heat shock protein,
      mitochondrial precursor
      epitope

<400> SEQUENCE: 550

Asp Gly Val Ala Val Leu Lys Val Gly Gly
1               5                   10

<210> SEQ ID NO 551
<211> LENGTH: 22
<212> TYPE: PRT
<213> ORGANISM: Artificial Sequence
<220> FEATURE:
<223> OTHER INFORMATION: Homo sapiens 60 kDa SS-A/Ro ribonucleoprotein
      epitope

<400> SEQUENCE: 551

Glu Leu Tyr Lys Glu Lys Ala Leu Ser Val Glu Thr Glu Lys Leu Leu
1               5                   10                  15
```

```
Lys Tyr Leu Glu Ala Val
            20

<210> SEQ ID NO 552
<211> LENGTH: 22
<212> TYPE: PRT
<213> ORGANISM: Artificial Sequence
<220> FEATURE:
<223> OTHER INFORMATION: Homo sapiens 60S acidic ribosomal protein P0
      epitope

<400> SEQUENCE: 552

Ala Lys Val Glu Ala Lys Glu Glu Ser Glu Glu Ser Asp Glu Asp Met
1               5                   10                  15

Gly Phe Gly Leu Phe Asp
            20

<210> SEQ ID NO 553
<211> LENGTH: 13
<212> TYPE: PRT
<213> ORGANISM: Artificial Sequence
<220> FEATURE:
<223> OTHER INFORMATION: Homo sapiens 60S acidic ribosomal protein P2
      epitope

<400> SEQUENCE: 553

Glu Glu Ser Asp Asp Asp Met Gly Phe Gly Leu Phe Asp
1               5                   10

<210> SEQ ID NO 554
<211> LENGTH: 50
<212> TYPE: PRT
<213> ORGANISM: Artificial Sequence
<220> FEATURE:
<223> OTHER INFORMATION: Homo sapiens 64 Kd autoantigen epitope

<400> SEQUENCE: 554

Ala Thr Lys Lys Glu Glu Glu Lys Lys Gly Gly Asp Arg Asn Thr Gly
1               5                   10                  15

Leu Ser Arg Asp Lys Asp Lys Lys Arg Glu Glu Met Lys Glu Val Ala
            20                  25                  30

Lys Lys Glu Asp Asp Glu Lys Val Lys Gly Glu Arg Arg Asn Thr Asp
        35                  40                  45

Thr Arg
    50

<210> SEQ ID NO 555
<211> LENGTH: 19
<212> TYPE: PRT
<213> ORGANISM: Artificial Sequence
<220> FEATURE:
<223> OTHER INFORMATION: Homo sapiens 65 kDa heat shock protein epitope

<400> SEQUENCE: 555

Ala Leu Leu Arg Cys Ile Pro Ala Leu Asp Ser Leu Thr Pro Ala Asn
1               5                   10                  15

Glu Asp Cys

<210> SEQ ID NO 556
<211> LENGTH: 14
<212> TYPE: PRT
<213> ORGANISM: Artificial Sequence
<220> FEATURE:
<223> OTHER INFORMATION: Homo sapiens Acetylcholine receptor subunit
      alpha precursor epitope
```

-continued

```
<400> SEQUENCE: 556

Ala Ile Asn Pro Glu Ser Asp Gln Pro Asp Leu Ser Asn Phe
1               5                   10

<210> SEQ ID NO 557
<211> LENGTH: 21
<212> TYPE: PRT
<213> ORGANISM: Artificial Sequence
<220> FEATURE:
<223> OTHER INFORMATION: Cynodon dactylon acidic Cyn d 1 isoallergen
      isoform 1 precursor epitope

<400> SEQUENCE: 557

Gln Asp Asp Val Ile Pro Glu Asp Trp Lys Pro Asp Thr Val Tyr Lys
1               5                   10                  15

Ser Lys Ile Gln Phe
            20

<210> SEQ ID NO 558
<211> LENGTH: 50
<212> TYPE: PRT
<213> ORGANISM: Artificial Sequence
<220> FEATURE:
<223> OTHER INFORMATION: Cynodon dactylon acidic Cyn d 1 isoallergen
      isoform 3 precursor epitope

<400> SEQUENCE: 558

Glu Glu Asp Lys Leu Arg Lys Ala Gly Glu Leu Met Leu Gln Phe Arg
1               5                   10                  15

Arg Val Lys Cys Glu Tyr Pro Ser Asp Thr Lys Ile Thr Phe His Val
                20                  25                  30

Glu Lys Gly Ser Ser Pro Asn Tyr Leu Ala Leu Leu Val Lys Tyr Ala
            35                  40                  45

Ala Gly
    50

<210> SEQ ID NO 559
<211> LENGTH: 8
<212> TYPE: PRT
<213> ORGANISM: Artificial Sequence
<220> FEATURE:
<223> OTHER INFORMATION: Homo sapiens acidic ribosomal phosphoprotein
      (P0) epitope

<400> SEQUENCE: 559

Ala Ala Ala Ala Ala Pro Ala Lys
1               5

<210> SEQ ID NO 560
<211> LENGTH: 15
<212> TYPE: PRT
<213> ORGANISM: Artificial Sequence
<220> FEATURE:
<223> OTHER INFORMATION: Homo sapiens acidic ribosomal phosphoprotein
      (P1) epitope

<400> SEQUENCE: 560

Glu Ser Glu Glu Ser Asp Asp Asp Met Gly Phe Gly Leu Phe Asp
1               5                   10                  15

<210> SEQ ID NO 561
<211> LENGTH: 15
<212> TYPE: PRT
<213> ORGANISM: Artificial Sequence
```

```
<220> FEATURE:
<223> OTHER INFORMATION: Homo sapiens acidic ribosomal phosphoprotein
      (P2) epitope

<400> SEQUENCE: 561

Ala Pro Ala Ala Gly Ser Ala Pro Ala Ala Glu Glu Lys Lys
1               5                   10                  15

<210> SEQ ID NO 562
<211> LENGTH: 16
<212> TYPE: PRT
<213> ORGANISM: Artificial Sequence
<220> FEATURE:
<223> OTHER INFORMATION: Homo sapiens Adrenergic, beta-2-, receptor,
      surface epitope

<400> SEQUENCE: 562

His Trp Tyr Arg Ala Thr His Gln Glu Ala Ile Asn Cys Tyr Ala Asn
1               5                   10                  15

<210> SEQ ID NO 563
<211> LENGTH: 10
<212> TYPE: PRT
<213> ORGANISM: Artificial Sequence
<220> FEATURE:
<223> OTHER INFORMATION: Homo sapiens Alanyl-tRNA synthetase,
      cytoplasmic epitope

<400> SEQUENCE: 563

Phe Ile Asp Glu Pro Arg Arg Arg Pro Ile
1               5                   10

<210> SEQ ID NO 564
<211> LENGTH: 7
<212> TYPE: PRT
<213> ORGANISM: Artificial Sequence
<220> FEATURE:
<223> OTHER INFORMATION: Bos taurus albumin epitope

<400> SEQUENCE: 564

Pro Val Glu Ser Lys Val Thr
1               5

<210> SEQ ID NO 565
<211> LENGTH: 13
<212> TYPE: PRT
<213> ORGANISM: Artificial Sequence
<220> FEATURE:
<223> OTHER INFORMATION: Juglans regia Albumin seed storage protein
      epitope

<400> SEQUENCE: 565

Gly Leu Arg Gly Glu Glu Met Glu Glu Met Val Gln Ser
1               5                   10

<210> SEQ ID NO 566
<211> LENGTH: 18
<212> TYPE: PRT
<213> ORGANISM: Artificial Sequence
<220> FEATURE:
<223> OTHER INFORMATION: Cochliobolus lunatus alcohol dehydrogenase
      epitope

<400> SEQUENCE: 566

Ala Val Asn Gly Asp Trp Pro Leu Pro Thr Lys Leu Pro Leu Val Gly
1               5                   10                  15

Gly His
```

<210> SEQ ID NO 567
<211> LENGTH: 37
<212> TYPE: PRT
<213> ORGANISM: Artificial Sequence
<220> FEATURE:
<223> OTHER INFORMATION: Penicillium chrysogenum alkaline serine
      protease epitope

<400> SEQUENCE: 567

Ala Asn Val Val Gln Arg Asn Ala Pro Ser Trp Gly Leu Ser Arg Ile
1               5                   10                  15

Ser Ser Lys Lys Ser Gly Ala Thr Asp Tyr Val Tyr Asp Ser Thr Ala
            20                  25                  30

Gly Glu Gly Ile Val
        35

<210> SEQ ID NO 568
<211> LENGTH: 10
<212> TYPE: PRT
<213> ORGANISM: Artificial Sequence
<220> FEATURE:
<223> OTHER INFORMATION: Arachis hypogaea allergen epitope

<400> SEQUENCE: 568

Asp Asp Gln Cys Gln Arg Gln Leu Gln Arg
1               5                   10

<210> SEQ ID NO 569
<211> LENGTH: 15
<212> TYPE: PRT
<213> ORGANISM: Artificial Sequence
<220> FEATURE:
<223> OTHER INFORMATION: Anacardium occidentale allergen Ana o 2 epitope

<400> SEQUENCE: 569

Glu Glu Ser Glu Asp Glu Lys Arg Arg Trp Gly Gln Arg Asp Asn
1               5                   10                  15

<210> SEQ ID NO 570
<211> LENGTH: 10
<212> TYPE: PRT
<213> ORGANISM: Artificial Sequence
<220> FEATURE:
<223> OTHER INFORMATION: Arachis hypogaea Allergen Ara h 1, clone P41B
      precursor epitope

<400> SEQUENCE: 570

Ala Lys Ser Ser Pro Tyr Gln Lys Lys Thr
1               5                   10

<210> SEQ ID NO 571
<211> LENGTH: 15
<212> TYPE: PRT
<213> ORGANISM: Artificial Sequence
<220> FEATURE:
<223> OTHER INFORMATION: Arachis hypogaea allergen Arah3/Arah4 epitope

<400> SEQUENCE: 571

Ala Gly Val Ala Leu Ser Arg Leu Val Leu Arg Arg Asn Ala Leu
1               5                   10                  15

<210> SEQ ID NO 572
<211> LENGTH: 10
<212> TYPE: PRT
<213> ORGANISM: Artificial Sequence

```
<220> FEATURE:
<223> OTHER INFORMATION: Arachis hypogaea allergen Arah6 epitope

<400> SEQUENCE: 572

Asp Arg Gln Met Val Gln His Phe Lys Arg
1               5                   10

<210> SEQ ID NO 573
<211> LENGTH: 11
<212> TYPE: PRT
<213> ORGANISM: Artificial Sequence
<220> FEATURE:
<223> OTHER INFORMATION: Periplaneta americana Allergen Cr-PI epitope

<400> SEQUENCE: 573

Ile Pro Lys Gly Lys Lys Gly Gly Gln Ala Tyr
1               5                   10

<210> SEQ ID NO 574
<211> LENGTH: 8
<212> TYPE: PRT
<213> ORGANISM: Artificial Sequence
<220> FEATURE:
<223> OTHER INFORMATION: Aspergillus fumigatus allergen I/a; Asp f I/a
      epitope

<400> SEQUENCE: 574

Ile Asn Gln Gln Leu Asn Pro Lys
1               5

<210> SEQ ID NO 575
<211> LENGTH: 10
<212> TYPE: PRT
<213> ORGANISM: Artificial Sequence
<220> FEATURE:
<223> OTHER INFORMATION: Arachis hypogaea Allergen II epitope

<400> SEQUENCE: 575

Asp Arg Leu Gln Gly Arg Gln Gln Glu Gln
1               5                   10

<210> SEQ ID NO 576
<211> LENGTH: 15
<212> TYPE: PRT
<213> ORGANISM: Artificial Sequence
<220> FEATURE:
<223> OTHER INFORMATION: Lens culinaris allergen Len c 1.0101 epitope

<400> SEQUENCE: 576

Ala Ile Asn Ala Ser Ser Asp Leu Asn Leu Ile Gly Phe Gly Ile
1               5                   10                  15

<210> SEQ ID NO 577
<211> LENGTH: 12
<212> TYPE: PRT
<213> ORGANISM: Artificial Sequence
<220> FEATURE:
<223> OTHER INFORMATION: Dermatophagoides farinae Allergen Mag epitope

<400> SEQUENCE: 577

Asp Val Glu Leu Ser Leu Arg Ser Ser Asp Ile Ala
1               5                   10

<210> SEQ ID NO 578
<211> LENGTH: 31
<212> TYPE: PRT
<213> ORGANISM: Artificial Sequence
```

```
<220> FEATURE:
<223> OTHER INFORMATION: Penicillium chrysogenum Allergen Pen n 18
      epitope

<400> SEQUENCE: 578

Ala His Ile Lys Lys Ser Lys Lys Gly Asp Lys Lys Phe Lys Gly Ser
1               5                   10                  15

Val Ala Asn Met Ser Leu Gly Gly Gly Ser Ser Arg Thr Leu Asp
            20                  25                  30

<210> SEQ ID NO 579
<211> LENGTH: 14
<212> TYPE: PRT
<213> ORGANISM: Artificial Sequence
<220> FEATURE:
<223> OTHER INFORMATION: Sinapis alba Allergen Sin a 1 epitope

<400> SEQUENCE: 579

Gln Gly Pro His Val Ile Ser Arg Ile Tyr Gln Thr Ala Thr
1               5                   10

<210> SEQ ID NO 580
<211> LENGTH: 12
<212> TYPE: PRT
<213> ORGANISM: Artificial Sequence
<220> FEATURE:
<223> OTHER INFORMATION: Ziziphus mauritiana allergen Ziz m 1 epitope

<400> SEQUENCE: 580

Lys Thr Asn Tyr Ser Ser Ser Ile Ile Leu Glu Tyr
1               5                   10

<210> SEQ ID NO 581
<211> LENGTH: 37
<212> TYPE: PRT
<213> ORGANISM: Artificial Sequence
<220> FEATURE:
<223> OTHER INFORMATION: Fagopyrum tataricum allergenic protein epitope

<400> SEQUENCE: 581

Asp Ile Ser Thr Glu Glu Ala Tyr Lys Leu Lys Asn Gly Arg Gln Glu
1               5                   10                  15

Val Glu Val Phe Arg Pro Phe Gln Ser Arg Tyr Glu Lys Glu Glu Glu
            20                  25                  30

Lys Glu Arg Glu Arg
        35

<210> SEQ ID NO 582
<211> LENGTH: 14
<212> TYPE: PRT
<213> ORGANISM: Artificial Sequence
<220> FEATURE:
<223> OTHER INFORMATION: Homo sapiens alpha 2 interferon epitope

<400> SEQUENCE: 582

Glu Val Val Arg Ala Glu Ile Met Arg Ser Phe Ser Leu Ser
1               5                   10

<210> SEQ ID NO 583
<211> LENGTH: 30
<212> TYPE: PRT
<213> ORGANISM: Artificial Sequence
<220> FEATURE:
<223> OTHER INFORMATION: Bos taurus alpha S1 casein epitope

<400> SEQUENCE: 583
```

```
Glu Asp Gln Ala Met Glu Asp Ile Lys Gln Met Glu Ala Glu Ser Ile
1               5                   10                  15

Ser Ser Ser Glu Glu Ile Val Pro Asn Ser Val Glu Gln Lys
            20                  25                  30

<210> SEQ ID NO 584
<211> LENGTH: 10
<212> TYPE: PRT
<213> ORGANISM: Artificial Sequence
<220> FEATURE:
<223> OTHER INFORMATION: Triticum aestivum Alpha/beta-gliadin A-II
      precursor epitope

<400> SEQUENCE: 584

Gln Val Ser Phe Gln Gln Pro Gln Gln Gln
1               5                   10

<210> SEQ ID NO 585
<211> LENGTH: 10
<212> TYPE: PRT
<213> ORGANISM: Artificial Sequence
<220> FEATURE:
<223> OTHER INFORMATION: Triticum aestivum Alpha/beta-gliadin A-V
      epitope

<400> SEQUENCE: 585

Leu Ala Leu Gln Thr Leu Pro Ala Met Cys
1               5                   10

<210> SEQ ID NO 586
<211> LENGTH: 10
<212> TYPE: PRT
<213> ORGANISM: Artificial Sequence
<220> FEATURE:
<223> OTHER INFORMATION: Homo sapiens alpha-1 type IV collagen epitope

<400> SEQUENCE: 586

Ser Arg Cys Gln Val Cys Met Arg Arg Thr
1               5                   10

<210> SEQ ID NO 587
<211> LENGTH: 12
<212> TYPE: PRT
<213> ORGANISM: Artificial Sequence
<220> FEATURE:
<223> OTHER INFORMATION: Homo sapiens alpha1A-voltage-dependent calcium
      channel epitope

<400> SEQUENCE: 587

Glu Asp Ser Asp Glu Asp Glu Phe Gln Ile Thr Glu
1               5                   10

<210> SEQ ID NO 588
<211> LENGTH: 15
<212> TYPE: PRT
<213> ORGANISM: Artificial Sequence
<220> FEATURE:
<223> OTHER INFORMATION: Homo sapiens alpha-2 type XI collagen epitope

<400> SEQUENCE: 588

Gly Ser Leu Asp Ser Leu Arg Arg Glu Ile Glu Gln Met Arg Arg
1               5                   10                  15

<210> SEQ ID NO 589
<211> LENGTH: 20
<212> TYPE: PRT
```

```
<213> ORGANISM: Artificial Sequence
<220> FEATURE:
<223> OTHER INFORMATION: Bos taurus alpha2(I) collagen epitope

<400> SEQUENCE: 589

Leu Pro Gly Leu Lys Gly His Asn Gly Leu Gln Gly Leu Pro Gly Leu
1               5                   10                  15

Ala Gly His His
            20

<210> SEQ ID NO 590
<211> LENGTH: 5
<212> TYPE: PRT
<213> ORGANISM: Artificial Sequence
<220> FEATURE:
<223> OTHER INFORMATION: Triticum aestivum Alpha-amylase inhibitor 0.28
      precursor (CIII) (WMAI-1) epitope

<400> SEQUENCE: 590

Ala Tyr Pro Asp Val
1               5

<210> SEQ ID NO 591
<211> LENGTH: 17
<212> TYPE: PRT
<213> ORGANISM: Artificial Sequence
<220> FEATURE:
<223> OTHER INFORMATION: Homo sapiens Alpha-enolase epitope

<400> SEQUENCE: 591

Lys Ile His Ala Arg Glu Ile Phe Asp Ser Arg Gly Asn Pro Thr Val
1               5                   10                  15

Glu

<210> SEQ ID NO 592
<211> LENGTH: 15
<212> TYPE: PRT
<213> ORGANISM: Artificial Sequence
<220> FEATURE:
<223> OTHER INFORMATION: Homo sapiens alpha-fibrinogen precursor epitope

<400> SEQUENCE: 592

Gly Pro Arg Val Val Glu Arg His Gln Ser Ala Cys Lys Asp Ser
1               5                   10                  15

<210> SEQ ID NO 593
<211> LENGTH: 12
<212> TYPE: PRT
<213> ORGANISM: Artificial Sequence
<220> FEATURE:
<223> OTHER INFORMATION: Triticum aestivum Alpha-gliadin epitope

<400> SEQUENCE: 593

Leu Gly Gln Gly Ser Phe Arg Pro Ser Gln Gln Asn
1               5                   10

<210> SEQ ID NO 594
<211> LENGTH: 10
<212> TYPE: PRT
<213> ORGANISM: Artificial Sequence
<220> FEATURE:
<223> OTHER INFORMATION: Bos taurus Alpha-lactalbumin epitope

<400> SEQUENCE: 594

Lys Asp Leu Lys Gly Tyr Gly Gly Val Ser
1               5                   10
```

<210> SEQ ID NO 595
<211> LENGTH: 14
<212> TYPE: PRT
<213> ORGANISM: Artificial Sequence
<220> FEATURE:
<223> OTHER INFORMATION: Bos taurus Alpha-lactalbumin precursor epitope

<400> SEQUENCE: 595

Lys Cys Glu Val Phe Arg Glu Leu Lys Asp Leu Lys Gly Tyr
1               5                   10

<210> SEQ ID NO 596
<211> LENGTH: 20
<212> TYPE: PRT
<213> ORGANISM: Artificial Sequence
<220> FEATURE:
<223> OTHER INFORMATION: Bos taurus alpha-S1-casein epitope

<400> SEQUENCE: 596

Leu Asn Glu Asn Leu Leu Arg Phe Phe Val Ala Pro Phe Pro Gln Val
1               5                   10                  15

Phe Gly Lys Glu
            20

<210> SEQ ID NO 597
<211> LENGTH: 10
<212> TYPE: PRT
<213> ORGANISM: Artificial Sequence
<220> FEATURE:
<223> OTHER INFORMATION: Bos taurus Alpha-S1-casein precursor epitope

<400> SEQUENCE: 597

Ala Met Glu Asp Ile Lys Gln Met Glu Ala
1               5                   10

<210> SEQ ID NO 598
<211> LENGTH: 10
<212> TYPE: PRT
<213> ORGANISM: Artificial Sequence
<220> FEATURE:
<223> OTHER INFORMATION: Bos taurus Alpha-S2-casein precursor epitope

<400> SEQUENCE: 598

Glu Asn Leu Cys Ser Thr Phe Cys Lys Glu
1               5                   10

<210> SEQ ID NO 599
<211> LENGTH: 7
<212> TYPE: PRT
<213> ORGANISM: Artificial Sequence
<220> FEATURE:
<223> OTHER INFORMATION: Homo sapiens anti-beta-amyloid peptide
     immunoglobulin heavy chain variable region epitope

<400> SEQUENCE: 599

Ala His Ile Trp Trp Asn Asp
1               5

<210> SEQ ID NO 600
<211> LENGTH: 24
<212> TYPE: PRT
<213> ORGANISM: Artificial Sequence
<220> FEATURE:
<223> OTHER INFORMATION: Homo sapiens Aquaporin-4 epitope

<400> SEQUENCE: 600

```
Phe Cys Pro Asp Val Glu Phe Lys Arg Arg Phe Lys Glu Ala Phe Ser
1               5                   10                  15

Lys Ala Ala Gln Gln Thr Lys Gly
            20

<210> SEQ ID NO 601
<211> LENGTH: 15
<212> TYPE: PRT
<213> ORGANISM: Artificial Sequence
<220> FEATURE:
<223> OTHER INFORMATION: Arachis hypogaea Ara h 2.01 allergen epitope

<400> SEQUENCE: 601

Cys Cys Asn Glu Leu Asn Glu Phe Glu Asn Asn Gln Arg Cys Met
1               5                   10                  15

<210> SEQ ID NO 602
<211> LENGTH: 20
<212> TYPE: PRT
<213> ORGANISM: Artificial Sequence
<220> FEATURE:
<223> OTHER INFORMATION: Homo sapiens ATP-dependent DNA helicase 2
      subunit 2 epitope

<400> SEQUENCE: 602

Glu Glu Ala Ser Gly Ser Ser Val Thr Ala Glu Glu Ala Lys Lys Phe
1               5                   10                  15

Leu Ala Pro Lys
            20

<210> SEQ ID NO 603
<211> LENGTH: 28
<212> TYPE: PRT
<213> ORGANISM: Artificial Sequence
<220> FEATURE:
<223> OTHER INFORMATION: Homo sapiens autoantigen epitope

<400> SEQUENCE: 603

Glu Ile Arg Val Arg Leu Gln Ser Ala Ser Pro Ser Thr Arg Trp Thr
1               5                   10                  15

Glu Leu Asp Asp Val Lys Arg Leu Leu Lys Gly Ser
            20                  25

<210> SEQ ID NO 604
<211> LENGTH: 16
<212> TYPE: PRT
<213> ORGANISM: Artificial Sequence
<220> FEATURE:
<223> OTHER INFORMATION: Homo sapiens Band 3 anion transport protein
      epitope

<400> SEQUENCE: 604

Leu Phe Lys Pro Pro Lys Tyr His Pro Asp Val Pro Tyr Val Lys Arg
1               5                   10                  15

<210> SEQ ID NO 605
<211> LENGTH: 15
<212> TYPE: PRT
<213> ORGANISM: Artificial Sequence
<220> FEATURE:
<223> OTHER INFORMATION: Glycine max Bd 30K (34 kDa maturing seed
      protein) epitope

<400> SEQUENCE: 605

Glu Asp Trp Gly Glu Asp Gly Tyr Ile Trp Ile Gln Arg Asn Thr
```

<210> SEQ ID NO 606
<211> LENGTH: 7
<212> TYPE: PRT
<213> ORGANISM: Artificial Sequence
<220> FEATURE:
<223> OTHER INFORMATION: Homo sapiens Bence Jones protein HAG epitope

<400> SEQUENCE: 606

Ala Trp His Gln Gln Gln Pro
1               5

<210> SEQ ID NO 607
<211> LENGTH: 8
<212> TYPE: PRT
<213> ORGANISM: Artificial Sequence
<220> FEATURE:
<223> OTHER INFORMATION: Betula pendula Bet v 4 epitope

<400> SEQUENCE: 607

Phe Ala Arg Ala Asn Arg Gly Leu
1               5

<210> SEQ ID NO 608
<211> LENGTH: 9
<212> TYPE: PRT
<213> ORGANISM: Artificial Sequence
<220> FEATURE:
<223> OTHER INFORMATION: Musa acuminata beta-1, 3-glucananse epitope

<400> SEQUENCE: 608

Gly Leu Phe Tyr Pro Asn Lys Gln Pro
1               5

<210> SEQ ID NO 609
<211> LENGTH: 15
<212> TYPE: PRT
<213> ORGANISM: Artificial Sequence
<220> FEATURE:
<223> OTHER INFORMATION: Hevea brasiliensis beta-1,3-glucanase epitope

<400> SEQUENCE: 609

Gly Leu Phe Phe Pro Asp Lys Arg Pro Lys Tyr Asn Leu Asn Phe
1               5                   10                  15

<210> SEQ ID NO 610
<211> LENGTH: 12
<212> TYPE: PRT
<213> ORGANISM: Artificial Sequence
<220> FEATURE:
<223> OTHER INFORMATION: Olea europaea beta-1,3-glucanase-like protein
      epitope

<400> SEQUENCE: 610

Ala Gly Arg Asn Ser Trp Asn Cys Asp Phe Ser Gln
1               5                   10

<210> SEQ ID NO 611
<211> LENGTH: 6
<212> TYPE: PRT
<213> ORGANISM: Artificial Sequence
<220> FEATURE:
<223> OTHER INFORMATION: Homo sapiens beta-2-glycoprotein 1 precursor
      epitope

<400> SEQUENCE: 611

Leu Lys Thr Pro Arg Val
1               5

<210> SEQ ID NO 612
<211> LENGTH: 6
<212> TYPE: PRT
<213> ORGANISM: Artificial Sequence
<220> FEATURE:
<223> OTHER INFORMATION: Homo sapiens beta-2-glycoprotein I epitope

<400> SEQUENCE: 612

Thr Leu Arg Val Tyr Lys
1               5

<210> SEQ ID NO 613
<211> LENGTH: 13
<212> TYPE: PRT
<213> ORGANISM: Artificial Sequence
<220> FEATURE:
<223> OTHER INFORMATION: Bos taurus beta-casein epitope

<400> SEQUENCE: 613

Gln Ser Lys Val Leu Pro Val Pro Gln Lys Ala Val Pro
1               5                   10

<210> SEQ ID NO 614
<211> LENGTH: 12
<212> TYPE: PRT
<213> ORGANISM: Artificial Sequence
<220> FEATURE:
<223> OTHER INFORMATION: Bos taurus Beta-casein precursor epitope

<400> SEQUENCE: 614

Asp Glu Leu Gln Asp Lys Ile His Pro Phe Ala Gln
1               5                   10

<210> SEQ ID NO 615
<211> LENGTH: 10
<212> TYPE: PRT
<213> ORGANISM: Artificial Sequence
<220> FEATURE:
<223> OTHER INFORMATION: Bos taurus Beta-lactoglobulin epitope

<400> SEQUENCE: 615

Ala Gln Lys Lys Ile Ile Ala Glu Lys Thr
1               5                   10

<210> SEQ ID NO 616
<211> LENGTH: 16
<212> TYPE: PRT
<213> ORGANISM: Artificial Sequence
<220> FEATURE:
<223> OTHER INFORMATION: Bos taurus Beta-lactoglobulin precursor epitope

<400> SEQUENCE: 616

Ala Ala Ser Asp Ile Ser Leu Leu Asp Ala Gln Ser Ala Pro Leu Arg
1               5                   10                  15

<210> SEQ ID NO 617
<211> LENGTH: 7
<212> TYPE: PRT
<213> ORGANISM: Artificial Sequence
<220> FEATURE:
<223> OTHER INFORMATION: Homo sapiens Botulinum neurotoxin type E
      epitope

<400> SEQUENCE: 617

Trp Lys Ala Pro Ser Ser Pro
1               5

<210> SEQ ID NO 618
<211> LENGTH: 19
<212> TYPE: PRT
<213> ORGANISM: Artificial Sequence
<220> FEATURE:
<223> OTHER INFORMATION: Homo sapiens bullous pemphigoid antigen epitope

<400> SEQUENCE: 618

Lys Ser Thr Ala Lys Asp Cys Thr Phe Lys Pro Asp Phe Glu Met Thr
1               5                   10                  15

Val Lys Glu

<210> SEQ ID NO 619
<211> LENGTH: 20
<212> TYPE: PRT
<213> ORGANISM: Artificial Sequence
<220> FEATURE:
<223> OTHER INFORMATION: Homo sapiens Bullous pemphigoid antigen 1,
      isoforms 1/2/3/4/5/8 epitope

<400> SEQUENCE: 619

Leu Thr Asp Thr Lys Thr Gly Leu His Phe Asn Ile Asn Glu Ala Ile
1               5                   10                  15

Glu Gln Gly Thr
            20

<210> SEQ ID NO 620
<211> LENGTH: 8
<212> TYPE: PRT
<213> ORGANISM: Artificial Sequence
<220> FEATURE:
<223> OTHER INFORMATION: Fagopyrum esculentum BW 16kDa allergen epitope

<400> SEQUENCE: 620

Glu Gly Val Arg Asp Leu Lys Glu
1               5

<210> SEQ ID NO 621
<211> LENGTH: 17
<212> TYPE: PRT
<213> ORGANISM: Artificial Sequence
<220> FEATURE:
<223> OTHER INFORMATION: Homo sapiens calcium channel, alpha 1A subunit
      isoform 3 epitope

<400> SEQUENCE: 621

Gly Asn Ile Gly Ile Asp Val Glu Asp Glu Ser Asp Glu Asp Glu
1               5                   10                  15

Phe

<210> SEQ ID NO 622
<211> LENGTH: 15
<212> TYPE: PRT
<213> ORGANISM: Artificial Sequence
<220> FEATURE:
<223> OTHER INFORMATION: Homo sapiens Calpastatin epitope

<400> SEQUENCE: 622

Ala Val Cys Arg Thr Ser Met Cys Ser Ile Gln Ser Ala Pro Pro
1               5                   10                  15

<210> SEQ ID NO 623

```
<211> LENGTH: 18
<212> TYPE: PRT
<213> ORGANISM: Artificial Sequence
<220> FEATURE:
<223> OTHER INFORMATION: Homo sapiens Calreticulin precursor epitope

<400> SEQUENCE: 623

Lys Glu Gln Phe Leu Asp Gly Asp Gly Trp Thr Ser Arg Trp Ile Glu
1               5                   10                  15

Ser Lys

<210> SEQ ID NO 624
<211> LENGTH: 13
<212> TYPE: PRT
<213> ORGANISM: Artificial Sequence
<220> FEATURE:
<223> OTHER INFORMATION: Homo sapiens Ca-sensing receptor epitope

<400> SEQUENCE: 624

Phe Val Ala Gln Asn Lys Ile Asp Ser Leu Asn Leu Asp
1               5                   10

<210> SEQ ID NO 625
<211> LENGTH: 9
<212> TYPE: PRT
<213> ORGANISM: Artificial Sequence
<220> FEATURE:
<223> OTHER INFORMATION: Homo sapiens Caspase-8 precursor epitope

<400> SEQUENCE: 625

Asp Arg Asn Gly Thr His Leu Asp Ala
1               5

<210> SEQ ID NO 626
<211> LENGTH: 14
<212> TYPE: PRT
<213> ORGANISM: Artificial Sequence
<220> FEATURE:
<223> OTHER INFORMATION: Homo sapiens centromere protein A isoform a
      epitope

<400> SEQUENCE: 626

Gly Pro Ser Arg Arg Gly Pro Ser Leu Gly Ala Ser Ser His
1               5                   10

<210> SEQ ID NO 627
<211> LENGTH: 10
<212> TYPE: PRT
<213> ORGANISM: Artificial Sequence
<220> FEATURE:
<223> OTHER INFORMATION: Homo sapiens centromere protein B, 80kDa
      epitope

<400> SEQUENCE: 627

Met Gly Pro Lys Arg Arg Gln Leu Thr Phe
1               5                   10

<210> SEQ ID NO 628
<211> LENGTH: 10
<212> TYPE: PRT
<213> ORGANISM: Artificial Sequence
<220> FEATURE:
<223> OTHER INFORMATION: Homo sapiens centromere protein-A epitope

<400> SEQUENCE: 628

Glu Ala Pro Arg Arg Arg Ser Pro Ser Pro
1               5                   10
```

-continued

```
<210> SEQ ID NO 629
<211> LENGTH: 17
<212> TYPE: PRT
<213> ORGANISM: Artificial Sequence
<220> FEATURE:
<223> OTHER INFORMATION: Betula pendula Chain A, Birch Pollen Profilin
      epitope

<400> SEQUENCE: 629

Ala Gln Ser Ser Ser Phe Pro Gln Phe Lys Pro Gln Glu Ile Thr Gly
1               5                   10                  15

Ile

<210> SEQ ID NO 630
<211> LENGTH: 5
<212> TYPE: PRT
<213> ORGANISM: Artificial Sequence
<220> FEATURE:
<223> OTHER INFORMATION: Homo sapiens Chain A, Crystal Structure Of The
      Glycosylated Five-Domain Human Beta2-Glycoprotein I Purified From
      Blood Plasma epitope

<400> SEQUENCE: 630

Arg Gly Gly Met Arg
1               5

<210> SEQ ID NO 631
<211> LENGTH: 7
<212> TYPE: PRT
<213> ORGANISM: Artificial Sequence
<220> FEATURE:
<223> OTHER INFORMATION: Homo sapiens Chain H, Three-Dimensional
      Structure Of A Human Immunoglobulin With A Hinge Deletion epitope

<400> SEQUENCE: 631

Ala Leu Pro Ala Pro Ile Glu
1               5

<210> SEQ ID NO 632
<211> LENGTH: 27
<212> TYPE: PRT
<213> ORGANISM: Artificial Sequence
<220> FEATURE:
<223> OTHER INFORMATION: Homo sapiens cholesterol side-chain cleavage
      enzyme P450scc (EC 1.14.15.67) epitope

<400> SEQUENCE: 632

Phe Asp Pro Glu Asn Phe Asp Pro Thr Arg Trp Leu Ser Lys Asp Lys
1               5                   10                  15

Asn Ile Thr Tyr Phe Arg Asn Leu Gly Phe Gly
            20                  25

<210> SEQ ID NO 633
<211> LENGTH: 10
<212> TYPE: PRT
<213> ORGANISM: Artificial Sequence
<220> FEATURE:
<223> OTHER INFORMATION: Homo sapiens citrate synthase epitope

<400> SEQUENCE: 633

Ala Leu Lys His Leu Pro Asn Asp Pro Met
1               5                   10

<210> SEQ ID NO 634
<211> LENGTH: 5
```

```
<212> TYPE: PRT
<213> ORGANISM: Artificial Sequence
<220> FEATURE:
<223> OTHER INFORMATION: Homo sapiens claudin 11 epitope

<400> SEQUENCE: 634

Ala His Arg Glu Thr
1               5

<210> SEQ ID NO 635
<211> LENGTH: 11
<212> TYPE: PRT
<213> ORGANISM: Artificial Sequence
<220> FEATURE:
<223> OTHER INFORMATION: Homo sapiens Coagulation factor VIII precursor
      epitope

<400> SEQUENCE: 635

Ala Pro Asp Asp Arg Ser Tyr Lys Ser Gln Tyr
1               5                   10

<210> SEQ ID NO 636
<211> LENGTH: 20
<212> TYPE: PRT
<213> ORGANISM: Artificial Sequence
<220> FEATURE:
<223> OTHER INFORMATION: Oncorhynchus mykiss collagen a2(I) epitope

<400> SEQUENCE: 636

Met Lys Gly Leu Arg Gly His Gly Gly Leu Gln Gly Met Pro Gly Pro
1               5                   10                  15

Asn Gly Pro Ser
            20

<210> SEQ ID NO 637
<211> LENGTH: 14
<212> TYPE: PRT
<213> ORGANISM: Artificial Sequence
<220> FEATURE:
<223> OTHER INFORMATION: Homo sapiens Collagen alpha-1(II) chain epitope

<400> SEQUENCE: 637

Ala Arg Gly Ala Gln Gly Pro Pro Gly Ala Thr Gly Phe Pro
1               5                   10

<210> SEQ ID NO 638
<211> LENGTH: 8
<212> TYPE: PRT
<213> ORGANISM: Artificial Sequence
<220> FEATURE:
<223> OTHER INFORMATION: Homo sapiens collagen alpha-1(VII) chain
      precursor epitope

<400> SEQUENCE: 638

Gly Thr Leu His Val Val Gln Arg
1               5

<210> SEQ ID NO 639
<211> LENGTH: 23
<212> TYPE: PRT
<213> ORGANISM: Artificial Sequence
<220> FEATURE:
<223> OTHER INFORMATION: Homo sapiens Collagen alpha-1(XVII) chain
      epitope

<400> SEQUENCE: 639

Arg Ser Ile Leu Pro Tyr Gly Asp Ser Met Asp Arg Ile Glu Lys Asp
```

```
                1               5                   10                  15
Arg Leu Gln Gly Met Ala Pro
            20

<210> SEQ ID NO 640
<211> LENGTH: 15
<212> TYPE: PRT
<213> ORGANISM: Artificial Sequence
<220> FEATURE:
<223> OTHER INFORMATION: Homo sapiens Collagen alpha-3(IV) chain epitope

<400> SEQUENCE: 640

Thr Ala Ile Pro Ser Cys Pro Glu Gly Thr Val Pro Leu Tyr Ser
1               5                   10                  15

<210> SEQ ID NO 641
<211> LENGTH: 8
<212> TYPE: PRT
<213> ORGANISM: Artificial Sequence
<220> FEATURE:
<223> OTHER INFORMATION: Homo sapiens collagen VII epitope

<400> SEQUENCE: 641

Ile Ile Trp Arg Ser Thr Gln Gly
1               5

<210> SEQ ID NO 642
<211> LENGTH: 46
<212> TYPE: PRT
<213> ORGANISM: Artificial Sequence
<220> FEATURE:
<223> OTHER INFORMATION: Bos taurus collagen, type I, alpha 2 epitope

<400> SEQUENCE: 642

Ala Pro Gly Pro Asp Gly Asn Asn Gly Ala Gln Gly Pro Pro Gly Leu
1               5                   10                  15

Gln Gly Val Gln Gly Gly Lys Gly Glu Gln Gly Pro Ala Gly Pro Pro
            20                  25                  30

Gly Phe Gln Gly Leu Pro Gly Pro Ala Gly Thr Ala Gly Glu
        35                  40                  45

<210> SEQ ID NO 643
<211> LENGTH: 9
<212> TYPE: PRT
<213> ORGANISM: Artificial Sequence
<220> FEATURE:
<223> OTHER INFORMATION: Homo sapiens collagen, type II, alpha 1 epitope

<400> SEQUENCE: 643

Pro Pro Gly Pro Thr Gly Ala Ser Gly
1               5

<210> SEQ ID NO 644
<211> LENGTH: 11
<212> TYPE: PRT
<213> ORGANISM: Artificial Sequence
<220> FEATURE:
<223> OTHER INFORMATION: Homo sapiens collagen, type II, alpha 1 isoform
      1 precursor epitope

<400> SEQUENCE: 644

Ala Arg Gly Leu Thr Gly Arg Pro Gly Asp Ala
1               5                   10

<210> SEQ ID NO 645
```

```
<211> LENGTH: 11
<212> TYPE: PRT
<213> ORGANISM: Artificial Sequence
<220> FEATURE:
<223> OTHER INFORMATION: Homo sapiens collagen, type II, alpha 1 isoform
      2 precursor epitope

<400> SEQUENCE: 645

Leu Val Gly Pro Arg Gly Glu Arg Gly Phe Pro
1               5                   10

<210> SEQ ID NO 646
<211> LENGTH: 9
<212> TYPE: PRT
<213> ORGANISM: Artificial Sequence
<220> FEATURE:
<223> OTHER INFORMATION: Homo sapiens Complement C1q subcomponent
      subunit A epitope

<400> SEQUENCE: 646

Lys Gly Glu Gln Gly Glu Pro Gly Ala
1               5

<210> SEQ ID NO 647
<211> LENGTH: 10
<212> TYPE: PRT
<213> ORGANISM: Artificial Sequence
<220> FEATURE:
<223> OTHER INFORMATION: Homo sapiens Condensin-2 complex subunit D3
      epitope

<400> SEQUENCE: 647

Pro Thr Pro Glu Thr Gly Pro Leu Gln Arg
1               5                   10

<210> SEQ ID NO 648
<211> LENGTH: 15
<212> TYPE: PRT
<213> ORGANISM: Artificial Sequence
<220> FEATURE:
<223> OTHER INFORMATION: Arachis hypogaea Conglutin-7 precursor epitope

<400> SEQUENCE: 648

Ala Ala His Ala Ser Ala Arg Gln Gln Trp Glu Leu Gln Gly Asp
1               5                   10                  15

<210> SEQ ID NO 649
<211> LENGTH: 8
<212> TYPE: PRT
<213> ORGANISM: Artificial Sequence
<220> FEATURE:
<223> OTHER INFORMATION: Periplaneta americana Cr-PII allergen epitope

<400> SEQUENCE: 649

Ile Arg Ser Trp Phe Gly Leu Pro
1               5

<210> SEQ ID NO 650
<211> LENGTH: 11
<212> TYPE: PRT
<213> ORGANISM: Artificial Sequence
<220> FEATURE:
<223> OTHER INFORMATION: Cochliobolus lunatus Cytochrome c epitope

<400> SEQUENCE: 650

Glu Asn Pro Lys Lys Tyr Ile Pro Gly Thr Lys
1               5                   10
```

```
<210> SEQ ID NO 651
<211> LENGTH: 10
<212> TYPE: PRT
<213> ORGANISM: Artificial Sequence
<220> FEATURE:
<223> OTHER INFORMATION: Rattus norvegicus Cytochrome P450 3A1 epitope

<400> SEQUENCE: 651

Asp Met Val Leu Asn Glu Thr Leu Arg Leu
1               5                   10

<210> SEQ ID NO 652
<211> LENGTH: 15
<212> TYPE: PRT
<213> ORGANISM: Artificial Sequence
<220> FEATURE:
<223> OTHER INFORMATION: Homo sapiens cytoskeleton-associated protein
      5 isoform b epitope

<400> SEQUENCE: 652

Cys Gln Ala Leu Val Arg Met Leu Ala Lys Lys Pro Gly Trp Lys
1               5                   10                  15

<210> SEQ ID NO 653
<211> LENGTH: 9
<212> TYPE: PRT
<213> ORGANISM: Artificial Sequence
<220> FEATURE:
<223> OTHER INFORMATION: Dermatophagoides farinae Der f 2 epitope

<400> SEQUENCE: 653

Ile Ala Thr His Ala Lys Ile Arg Asp
1               5

<210> SEQ ID NO 654
<211> LENGTH: 15
<212> TYPE: PRT
<213> ORGANISM: Artificial Sequence
<220> FEATURE:
<223> OTHER INFORMATION: Dermatophagoides farinae Der f 7 allergen
      epitope

<400> SEQUENCE: 654

His Ile Gly Gly Leu Ser Ile Leu Asp Pro Ile Phe Gly Val Leu
1               5                   10                  15

<210> SEQ ID NO 655
<211> LENGTH: 43
<212> TYPE: PRT
<213> ORGANISM: Artificial Sequence
<220> FEATURE:
<223> OTHER INFORMATION: Dermatophagoides pteronyssinus Der p 1 allergen
      epitope

<400> SEQUENCE: 655

Ala Arg Glu Gln Ser Cys Arg Arg Pro Asn Ala Gln Arg Phe Gly Ile
1               5                   10                  15

Ser Asn Tyr Cys Gln Ile Tyr Pro Pro Asn Ala Asn Lys Ile Arg Glu
            20                  25                  30

Ala Leu Ala Gln Thr His Ser Ala Ile Ala Val
        35                  40

<210> SEQ ID NO 656
<211> LENGTH: 15
<212> TYPE: PRT
<213> ORGANISM: Artificial Sequence
```

```
<220> FEATURE:
<223> OTHER INFORMATION: Dermatophagoides pteronyssinus Der p 7
      allergen polypeptide epitope

<400> SEQUENCE: 656

His Ile Gly Gly Leu Ser Ile Leu Asp Pro Ile Phe Ala Val Leu
1               5                   10                  15

<210> SEQ ID NO 657
<211> LENGTH: 12
<212> TYPE: PRT
<213> ORGANISM: Artificial Sequence
<220> FEATURE:
<223> OTHER INFORMATION: Homo sapiens Desmoglein-1 epitope

<400> SEQUENCE: 657

Arg Glu Trp Ile Lys Phe Ala Ala Ala Cys Arg Glu
1               5                   10

<210> SEQ ID NO 658
<211> LENGTH: 12
<212> TYPE: PRT
<213> ORGANISM: Artificial Sequence
<220> FEATURE:
<223> OTHER INFORMATION: Homo sapiens Desmoglein-3 precursor epitope

<400> SEQUENCE: 658

Arg Glu Trp Val Lys Phe Ala Lys Pro Cys Arg Glu
1               5                   10

<210> SEQ ID NO 659
<211> LENGTH: 30
<212> TYPE: PRT
<213> ORGANISM: Artificial Sequence
<220> FEATURE:
<223> OTHER INFORMATION: Homo sapiens desmoglein-3 preproprotein epitope

<400> SEQUENCE: 659

Ser Gln Glu Pro Ala Gly Thr Pro Met Phe Leu Leu Ser Arg Asn Thr
1               5                   10                  15

Gly Glu Val Arg Thr Leu Thr Asn Ser Leu Asp Arg Glu Gln
            20                  25                  30

<210> SEQ ID NO 660
<211> LENGTH: 12
<212> TYPE: PRT
<213> ORGANISM: Artificial Sequence
<220> FEATURE:
<223> OTHER INFORMATION: Homo sapiens desmoplakin epitope

<400> SEQUENCE: 660

Gly Asn Ser Ser Tyr Ser Tyr Ser Tyr Ser Phe Ser
1               5                   10

<210> SEQ ID NO 661
<211> LENGTH: 20
<212> TYPE: PRT
<213> ORGANISM: Artificial Sequence
<220> FEATURE:
<223> OTHER INFORMATION: Homo sapiens desmoplakin isoform II epitope

<400> SEQUENCE: 661

Leu Val Asp Arg Lys Thr Gly Ser Gln Tyr Asp Ile Gln Asp Ala Ile
1               5                   10                  15

Asp Lys Gly Leu
            20
```

<210> SEQ ID NO 662
<211> LENGTH: 18
<212> TYPE: PRT
<213> ORGANISM: Artificial Sequence
<220> FEATURE:
<223> OTHER INFORMATION: Homo sapiens dihydrolipoamide
      S-acetyltransferase (E2 component of pyruvate dehydrogenase
      complex), isoform CRA_a epitope

<400> SEQUENCE: 662

Ala Glu Ile Glu Thr Asp Lys Ala Thr Ile Gly Phe Glu Val Gln Glu
1               5                   10                  15

Glu Gly

<210> SEQ ID NO 663
<211> LENGTH: 17
<212> TYPE: PRT
<213> ORGANISM: Artificial Sequence
<220> FEATURE:
<223> OTHER INFORMATION: Homo sapiens DNA topoisomerase 1 epitope

<400> SEQUENCE: 663

Gly Val Pro Ile Glu Lys Ile Tyr Asn Lys Thr Gln Arg Glu Lys Phe
1               5                   10                  15

Ala

<210> SEQ ID NO 664
<211> LENGTH: 20
<212> TYPE: PRT
<213> ORGANISM: Artificial Sequence
<220> FEATURE:
<223> OTHER INFORMATION: Homo sapiens DNA topoisomerase I epitope

<400> SEQUENCE: 664

Glu Leu Asp Gly Gln Glu Tyr Val Val Glu Phe Asp Phe Leu Gly Lys
1               5                   10                  15

Asp Ser Ile Arg
            20

<210> SEQ ID NO 665
<211> LENGTH: 20
<212> TYPE: PRT
<213> ORGANISM: Artificial Sequence
<220> FEATURE:
<223> OTHER INFORMATION: Homo sapiens DNA topoisomerase II beta epitope

<400> SEQUENCE: 665

His Pro Met Leu Pro Asn Tyr Lys Asn Phe Lys Gly Thr Ile Gln Glu
1               5                   10                  15

Leu Gly Gln Asn
            20

<210> SEQ ID NO 666
<211> LENGTH: 7
<212> TYPE: PRT
<213> ORGANISM: Artificial Sequence
<220> FEATURE:
<223> OTHER INFORMATION: Homo sapiens DNA-directed RNA polymerase II
      subunit RPB1 epitope

<400> SEQUENCE: 666

Tyr Ser Pro Thr Ser Pro Ser
1               5

<210> SEQ ID NO 667
<211> LENGTH: 36
<212> TYPE: PRT
<213> ORGANISM: Artificial Sequence
<220> FEATURE:
<223> OTHER INFORMATION: Homo sapiens E3 ubiquitin-protein ligase TRIM9
      isoform 2 epitope

<400> SEQUENCE: 667

Ala Phe Asn Lys Thr Gly Val Ser Pro Tyr Ser Lys Thr Leu Val Leu
1               5                   10                  15

Gln Thr Ser Glu Gly Lys Ala Leu Gln Gln Tyr Pro Ser Glu Arg Glu
            20                  25                  30

Leu Arg Gly Ile
        35

<210> SEQ ID NO 668
<211> LENGTH: 39
<212> TYPE: PRT
<213> ORGANISM: Artificial Sequence
<220> FEATURE:
<223> OTHER INFORMATION: Candida albicans Enolase 1 (2-phosphoglycerate
      dehydratase) (2-phospho-D-glycerate hydro-lyase) epitope

<400> SEQUENCE: 668

Gln Ala Ala Asn Asp Ser Tyr Ala Ala Gly Trp Gly Val Met Val Ser
1               5                   10                  15

His Arg Ser Gly Glu Thr Glu Asp Thr Phe Ile Ala Asp Leu Ser Val
            20                  25                  30

Gly Leu Arg Ser Gly Gln Ile
        35

<210> SEQ ID NO 669
<211> LENGTH: 16
<212> TYPE: PRT
<213> ORGANISM: Artificial Sequence
<220> FEATURE:
<223> OTHER INFORMATION: Homo sapiens enolase 1 variant epitope

<400> SEQUENCE: 669

Lys Ile His Ala Arg Glu Ile Phe Asp Ser Arg Gly Asn Pro Thr Val
1               5                   10                  15

<210> SEQ ID NO 670
<211> LENGTH: 21
<212> TYPE: PRT
<213> ORGANISM: Artificial Sequence
<220> FEATURE:
<223> OTHER INFORMATION: Hevea brasiliensis ENSP-like protein epitope

<400> SEQUENCE: 670

Phe Pro Leu Ile Thr Cys Cys Gly Tyr Gly Gly Lys Tyr Asn Phe Ser
1               5                   10                  15

Val Thr Ala Pro Cys
            20

<210> SEQ ID NO 671
<211> LENGTH: 20
<212> TYPE: PRT
<213> ORGANISM: Artificial Sequence
<220> FEATURE:
<223> OTHER INFORMATION: Homo sapiens envoplakin epitope

<400> SEQUENCE: 671

```
Ala Gly Glu Thr Lys Pro Ser Ser Ser Leu Ser Ile Gly Ser Ile Ile
1               5                   10                  15

Ser Lys Ser Pro
            20

<210> SEQ ID NO 672
<211> LENGTH: 12
<212> TYPE: PRT
<213> ORGANISM: Artificial Sequence
<220> FEATURE:
<223> OTHER INFORMATION: Fagopyrum esculentum Fag e 1 epitope

<400> SEQUENCE: 672

Ala Val Val Leu Lys Ala Gly Asn Glu Gly Leu Glu
1               5                   10

<210> SEQ ID NO 673
<211> LENGTH: 3
<212> TYPE: PRT
<213> ORGANISM: Artificial Sequence
<220> FEATURE:
<223> OTHER INFORMATION: Homo sapiens Fas AMA epitope

<400> SEQUENCE: 673

Cys Val Pro
1

<210> SEQ ID NO 674
<211> LENGTH: 18
<212> TYPE: PRT
<213> ORGANISM: Artificial Sequence
<220> FEATURE:
<223> OTHER INFORMATION: Homo sapiens FGA protein epitope

<400> SEQUENCE: 674

Ser Arg Ala Leu Ala Arg Glu Val Asp Leu Lys Asp Tyr Glu Asp Gln
1               5                   10                  15

Gln Lys

<210> SEQ ID NO 675
<211> LENGTH: 20
<212> TYPE: PRT
<213> ORGANISM: Artificial Sequence
<220> FEATURE:
<223> OTHER INFORMATION: Homo sapiens FGB protein epitope

<400> SEQUENCE: 675

Ala Arg Gly His Arg Pro Leu Asp Lys Lys Arg Glu Glu Ala Pro Ser
1               5                   10                  15

Leu Arg Pro Ala
            20

<210> SEQ ID NO 676
<211> LENGTH: 19
<212> TYPE: PRT
<213> ORGANISM: Artificial Sequence
<220> FEATURE:
<223> OTHER INFORMATION: Homo sapiens fibrin beta epitope

<400> SEQUENCE: 676

Ala Asn Lys Tyr Gln Ile Ser Val Asn Lys Tyr Arg Gly Thr Ala Gly
1               5                   10                  15

Asn Ala Leu
```

```
<210> SEQ ID NO 677
<211> LENGTH: 15
<212> TYPE: PRT
<213> ORGANISM: Artificial Sequence
<220> FEATURE:
<223> OTHER INFORMATION: Homo sapiens fibrinogen alpha chain isoform
      alpha preproprotein epitope

<400> SEQUENCE: 677

Asp Ser Pro Gly Ser Gly Asn Ala Arg Pro Asn Asn Pro Asp Trp
1               5                   10                  15

<210> SEQ ID NO 678
<211> LENGTH: 17
<212> TYPE: PRT
<213> ORGANISM: Artificial Sequence
<220> FEATURE:
<223> OTHER INFORMATION: Homo sapiens Fibrinogen alpha chain precursor
      epitope

<400> SEQUENCE: 678

Phe Leu Ala Glu Gly Gly Gly Val Arg Gly Pro Arg Val Val Glu Arg
1               5                   10                  15

His

<210> SEQ ID NO 679
<211> LENGTH: 20
<212> TYPE: PRT
<213> ORGANISM: Artificial Sequence
<220> FEATURE:
<223> OTHER INFORMATION: Homo sapiens fibrinogen alpha chain
      preproprotein, isoform alpha epitope

<400> SEQUENCE: 679

Asp His Glu Gly Thr His Ser Thr Lys Arg Gly His Ala Lys Ser Arg
1               5                   10                  15

Pro Val Arg Gly
            20

<210> SEQ ID NO 680
<211> LENGTH: 15
<212> TYPE: PRT
<213> ORGANISM: Artificial Sequence
<220> FEATURE:
<223> OTHER INFORMATION: Homo sapiens fibrinogen beta chain epitope

<400> SEQUENCE: 680

Pro Arg Lys Gln Cys Ser Lys Glu Asp Gly Gly Gly Trp Trp Tyr
1               5                   10                  15

<210> SEQ ID NO 681
<211> LENGTH: 17
<212> TYPE: PRT
<213> ORGANISM: Artificial Sequence
<220> FEATURE:
<223> OTHER INFORMATION: Homo sapiens fibrinogen beta chain, isoform
      CRA_d epitope

<400> SEQUENCE: 681

Asn Glu Glu Gly Phe Phe Ser Ala Arg Gly His Arg Pro Leu Asp Lys
1               5                   10                  15

Lys

<210> SEQ ID NO 682
<211> LENGTH: 24
<212> TYPE: PRT
```

-continued

```
<213> ORGANISM: Artificial Sequence
<220> FEATURE:
<223> OTHER INFORMATION: Homo sapiens fibrinogen beta chain, isoform
      CRA_i epitope

<400> SEQUENCE: 682

Glu Glu Ala Pro Ser Leu Arg Pro Ala Pro Pro Pro Ile Ser Gly Gly
1               5                   10                  15

Gly Tyr Arg Ala Arg Pro Ala Lys
            20

<210> SEQ ID NO 683
<211> LENGTH: 6
<212> TYPE: PRT
<213> ORGANISM: Artificial Sequence
<220> FEATURE:
<223> OTHER INFORMATION: Homo sapiens Fibronectin precursor epitope

<400> SEQUENCE: 683

Leu Thr Ser Arg Pro Ala
1               5

<210> SEQ ID NO 684
<211> LENGTH: 18
<212> TYPE: PRT
<213> ORGANISM: Artificial Sequence
<220> FEATURE:
<223> OTHER INFORMATION: Homo sapiens filaggrin epitope

<400> SEQUENCE: 684

Asp Ser Gly His Arg Gly Tyr Ser Gly Ser Gln Ala Ser Asp Asn Glu
1               5                   10                  15

Gly His

<210> SEQ ID NO 685
<211> LENGTH: 8
<212> TYPE: PRT
<213> ORGANISM: Artificial Sequence
<220> FEATURE:
<223> OTHER INFORMATION: Homo sapiens Follistatin-related protein 1
      epitope

<400> SEQUENCE: 685

Leu Lys Phe Val Glu Gln Asn Glu
1               5

<210> SEQ ID NO 686
<211> LENGTH: 10
<212> TYPE: PRT
<213> ORGANISM: Artificial Sequence
<220> FEATURE:
<223> OTHER INFORMATION: Homo sapiens Forkhead box protein E3 epitope

<400> SEQUENCE: 686

Pro Thr Pro Ala Pro Gly Pro Gly Arg Arg
1               5                   10

<210> SEQ ID NO 687
<211> LENGTH: 7
<212> TYPE: PRT
<213> ORGANISM: Artificial Sequence
<220> FEATURE:
<223> OTHER INFORMATION: Homo sapiens GAD65 autoantigen glutamic acid
      decarboxylase epitope

<400> SEQUENCE: 687
```

```
Ala Pro Ala Met Ile Pro Pro
1               5
```

<210> SEQ ID NO 688
<211> LENGTH: 10
<212> TYPE: PRT
<213> ORGANISM: Artificial Sequence
<220> FEATURE:
<223> OTHER INFORMATION: Triticum aestivum Gamma-gliadin precursor
      epitope

<400> SEQUENCE: 688

```
Leu Gln Pro Gln Gln Pro Phe Pro Gln Gln
1               5                   10
```

<210> SEQ ID NO 689
<211> LENGTH: 21
<212> TYPE: PRT
<213> ORGANISM: Artificial Sequence
<220> FEATURE:
<223> OTHER INFORMATION: Chironomus thummi thummi Globin CTT-III epitope

<400> SEQUENCE: 689

```
Ala His Thr Asp Phe Ala Gly Ala Glu Ala Ala Trp Gly Ala Thr Leu
1               5                   10                  15

Asp Thr Phe Phe Gly
            20
```

<210> SEQ ID NO 690
<211> LENGTH: 11
<212> TYPE: PRT
<213> ORGANISM: Artificial Sequence
<220> FEATURE:
<223> OTHER INFORMATION: Chironomus thummi thummi Globin CTT-III
      precursor epitope

<400> SEQUENCE: 690

```
Gly Val Thr His Asp Gln Leu Asn Asn Phe Arg
1               5                   10
```

<210> SEQ ID NO 691
<211> LENGTH: 23
<212> TYPE: PRT
<213> ORGANISM: Artificial Sequence
<220> FEATURE:
<223> OTHER INFORMATION: Chironomus thummi thummi Globin CTT-IV
      precursor epitope

<400> SEQUENCE: 691

```
Lys Ala His Thr Asp Phe Ala Gly Ala Glu Ala Ala Trp Gly Ala Thr
1               5                   10                  15

Leu Asp Ala Phe Phe Gly Met
            20
```

<210> SEQ ID NO 692
<211> LENGTH: 35
<212> TYPE: PRT
<213> ORGANISM: Artificial Sequence
<220> FEATURE:
<223> OTHER INFORMATION: Chironomus thummi thummi Globin CTT-VI
      precursor epitope

<400> SEQUENCE: 692

```
Ile Val Ser Phe Leu Ser Glu Val Ile Ser Leu Ala Gly Ser Asp Ala
1               5                   10                  15

Asn Ile Pro Ala Ile Gln Asn Leu Ala Lys Glu Leu Ala Thr Ser His
```

-continued

```
              20                  25                  30

Lys Pro Arg
        35

<210> SEQ ID NO 693
<211> LENGTH: 35
<212> TYPE: PRT
<213> ORGANISM: Artificial Sequence
<220> FEATURE:
<223> OTHER INFORMATION: Chironomus thummi thummi Globin CTT-VIII
      epitope

<400> SEQUENCE: 693

Ile Val Gly Phe Phe Ser Glu Val Ile Gly Leu Ile Gly Asn Pro Glu
1               5                   10                  15

Asn Arg Pro Ala Leu Lys Thr Leu Ile Asp Gly Leu Ala Ser Ser His
            20                  25                  30

Lys Ala Arg
        35

<210> SEQ ID NO 694
<211> LENGTH: 9
<212> TYPE: PRT
<213> ORGANISM: Artificial Sequence
<220> FEATURE:
<223> OTHER INFORMATION: Hevea brasiliensis Glucan endo-1,3-beta-
      glucosidase, basic vacuolar isoform epitope

<400> SEQUENCE: 694

Ala Trp Leu Ala Gln Phe Val Leu Pro
1               5

<210> SEQ ID NO 695
<211> LENGTH: 20
<212> TYPE: PRT
<213> ORGANISM: Artificial Sequence
<220> FEATURE:
<223> OTHER INFORMATION: Homo sapiens glutamate decarboxylase epitope

<400> SEQUENCE: 695

Phe Arg Glu Arg Gln Ser Ser Lys Asn Leu Leu Ser Cys Glu Asn Ser
1               5                   10                  15

Asp Arg Asp Ala
            20

<210> SEQ ID NO 696
<211> LENGTH: 20
<212> TYPE: PRT
<213> ORGANISM: Artificial Sequence
<220> FEATURE:
<223> OTHER INFORMATION: Homo sapiens Glutamate decarboxylase 1 epitope

<400> SEQUENCE: 696

Met Ala Ser Ser Thr Pro Ser Ser Ser Ala Thr Ser Ser Asn Ala Gly
1               5                   10                  15

Ala Asp Pro Asn
            20

<210> SEQ ID NO 697
<211> LENGTH: 19
<212> TYPE: PRT
<213> ORGANISM: Artificial Sequence
<220> FEATURE:
<223> OTHER INFORMATION: Homo sapiens Glutamate decarboxylase 2 epitope
```

```
<400> SEQUENCE: 697

Pro Gly Ser Gly Phe Trp Ser Phe Gly Ser Glu Asp Gly Ser Gly Asp
1               5                   10                  15

Ser Glu Asn

<210> SEQ ID NO 698
<211> LENGTH: 15
<212> TYPE: PRT
<213> ORGANISM: Artificial Sequence
<220> FEATURE:
<223> OTHER INFORMATION: Homo sapiens glutamate receptor, ionotropic,
      N-methyl D-aspartate 2A epitope

<400> SEQUENCE: 698

Ser Val Ser Tyr Asp Asp Trp Asp Tyr Ser Leu Glu Ala Arg Val
1               5                   10                  15

<210> SEQ ID NO 699
<211> LENGTH: 14
<212> TYPE: PRT
<213> ORGANISM: Artificial Sequence
<220> FEATURE:
<223> OTHER INFORMATION: Homo sapiens glutathione peroxidase-GI epitope

<400> SEQUENCE: 699

Asn Glu His Pro Val Phe Ala Tyr Leu Lys Asp Lys Leu Pro
1               5                   10

<210> SEQ ID NO 700
<211> LENGTH: 14
<212> TYPE: PRT
<213> ORGANISM: Artificial Sequence
<220> FEATURE:
<223> OTHER INFORMATION: Triticum aestivum Glutenin, high molecular
      weight subunit DX5 epitope

<400> SEQUENCE: 700

Ala Gln Gly Gln Gln Pro Gly Gln Gly Gln Gln Gly Gln Gln
1               5                   10

<210> SEQ ID NO 701
<211> LENGTH: 5
<212> TYPE: PRT
<213> ORGANISM: Artificial Sequence
<220> FEATURE:
<223> OTHER INFORMATION: Triticum aestivum Glutenin, high molecular
      weight subunit DX5 precursor epitope

<400> SEQUENCE: 701

Gln Gln Pro Gly Gln
1               5

<210> SEQ ID NO 702
<211> LENGTH: 5
<212> TYPE: PRT
<213> ORGANISM: Artificial Sequence
<220> FEATURE:
<223> OTHER INFORMATION: Triticum aestivum Glutenin, low molecular
      weight subunit precursor epitope

<400> SEQUENCE: 702

Gln Gln Gln Pro Pro
1               5

<210> SEQ ID NO 703
<211> LENGTH: 15
```

```
<212> TYPE: PRT
<213> ORGANISM: Artificial Sequence
<220> FEATURE:
<223> OTHER INFORMATION: Phaseolus vulgaris Glycine-rich cell wall
      structural protein 1.8 precursor epitope

<400> SEQUENCE: 703

Gly Gly Tyr Gly Asp Gly Gly Ala His Gly Gly Gly Tyr Gly Gly
1               5                   10                  15

<210> SEQ ID NO 704
<211> LENGTH: 15
<212> TYPE: PRT
<213> ORGANISM: Artificial Sequence
<220> FEATURE:
<223> OTHER INFORMATION: Arachis hypogaea Glycinin epitope

<400> SEQUENCE: 704

Ala Leu Ser Arg Leu Val Leu Arg Arg Asn Ala Leu Arg Arg Pro
1               5                   10                  15

<210> SEQ ID NO 705
<211> LENGTH: 13
<212> TYPE: PRT
<213> ORGANISM: Artificial Sequence
<220> FEATURE:
<223> OTHER INFORMATION: Glycine max Glycinin G1 precursor epitope

<400> SEQUENCE: 705

Gly Ala Ile Val Thr Val Lys Gly Gly Leu Ser Val Ile
1               5                   10

<210> SEQ ID NO 706
<211> LENGTH: 15
<212> TYPE: PRT
<213> ORGANISM: Artificial Sequence
<220> FEATURE:
<223> OTHER INFORMATION: Glycine max Glycinin G2 precursor epitope

<400> SEQUENCE: 706

Ala Leu Ser Arg Cys Thr Leu Asn Arg Asn Ala Leu Arg Arg Pro
1               5                   10                  15

<210> SEQ ID NO 707
<211> LENGTH: 15
<212> TYPE: PRT
<213> ORGANISM: Artificial Sequence
<220> FEATURE:
<223> OTHER INFORMATION: Holcus lanatus group V allergen epitope

<400> SEQUENCE: 707

Ala Asn Val Pro Pro Ala Asp Lys Tyr Lys Thr Phe Glu Ala Ala
1               5                   10                  15

<210> SEQ ID NO 708
<211> LENGTH: 38
<212> TYPE: PRT
<213> ORGANISM: Artificial Sequence
<220> FEATURE:
<223> OTHER INFORMATION: Homo sapiens Gu protein epitope

<400> SEQUENCE: 708

Ile Asp Ala Pro Lys Pro Lys Met Lys Lys Glu Lys Glu Met Asn
1               5                   10                  15

Gly Glu Thr Arg Glu Lys Ser Pro Lys Leu Lys Asn Gly Phe Pro His
            20                  25                  30
```

Pro Glu Pro Asp Cys Asn
        35

<210> SEQ ID NO 709
<211> LENGTH: 17
<212> TYPE: PRT
<213> ORGANISM: Artificial Sequence
<220> FEATURE:
<223> OTHER INFORMATION: Homo sapiens H1 histone family, member 0
      epitope

<400> SEQUENCE: 709

Lys Glu Ile Lys Lys Val Ala Thr Pro Lys Lys Ala Ser Lys Pro Lys
1               5                   10                  15

Lys

<210> SEQ ID NO 710
<211> LENGTH: 12
<212> TYPE: PRT
<213> ORGANISM: Artificial Sequence
<220> FEATURE:
<223> OTHER INFORMATION: Homo sapiens heat shock 60kDa protein 1
      (chaperonin) epitope

<400> SEQUENCE: 710

Ala Tyr Ala Lys Asp Val Lys Phe Gly Ala Asp Ala
1               5                   10

<210> SEQ ID NO 711
<211> LENGTH: 6
<212> TYPE: PRT
<213> ORGANISM: Artificial Sequence
<220> FEATURE:
<223> OTHER INFORMATION: Homo sapiens Heat shock protein HSP 90-beta
      epitope

<400> SEQUENCE: 711

Gly Leu Glu Leu Pro Glu
1               5

<210> SEQ ID NO 712
<211> LENGTH: 15
<212> TYPE: PRT
<213> ORGANISM: Artificial Sequence
<220> FEATURE:
<223> OTHER INFORMATION: Homo sapiens high mobility group protein 17
      epitope

<400> SEQUENCE: 712

Lys Lys Ala Pro Ala Lys Lys Gly Glu Lys Val Pro Lys Gly Lys
1               5                   10                  15

<210> SEQ ID NO 713
<211> LENGTH: 22
<212> TYPE: PRT
<213> ORGANISM: Artificial Sequence
<220> FEATURE:
<223> OTHER INFORMATION: Homo sapiens High mobility group protein B1
      epitope

<400> SEQUENCE: 713

Ala Lys Gly Lys Pro Asp Ala Ala Lys Lys Gly Val Val Lys Ala Glu
1               5                   10                  15

Lys Ser Lys Lys Lys Lys
            20

```
<210> SEQ ID NO 714
<211> LENGTH: 15
<212> TYPE: PRT
<213> ORGANISM: Artificial Sequence
<220> FEATURE:
<223> OTHER INFORMATION: Homo sapiens high-mobility group box 2 epitope

<400> SEQUENCE: 714

Phe Glu Asp Met Ala Lys Ser Asp Lys Ala Arg Tyr Asp Arg Glu
1               5                   10                  15

<210> SEQ ID NO 715
<211> LENGTH: 43
<212> TYPE: PRT
<213> ORGANISM: Artificial Sequence
<220> FEATURE:
<223> OTHER INFORMATION: Homo sapiens histidyl-tRNA synthetase,
      cytoplasmic epitope

<400> SEQUENCE: 715

Ala Glu Arg Ala Ala Leu Glu Glu Leu Val Lys Leu Gln Gly Glu Arg
1               5                   10                  15

Val Arg Gly Leu Lys Gln Gln Lys Ala Ser Ala Glu Leu Ile Glu Glu
            20                  25                  30

Glu Val Ala Lys Leu Leu Lys Leu Lys Ala Gln
        35                  40

<210> SEQ ID NO 716
<211> LENGTH: 16
<212> TYPE: PRT
<213> ORGANISM: Artificial Sequence
<220> FEATURE:
<223> OTHER INFORMATION: Homo sapiens Histone H1.4 epitope

<400> SEQUENCE: 716

Ser Glu Thr Ala Pro Ala Ala Pro Ala Ala Pro Ala Pro Ala Glu Lys
1               5                   10                  15

<210> SEQ ID NO 717
<211> LENGTH: 15
<212> TYPE: PRT
<213> ORGANISM: Artificial Sequence
<220> FEATURE:
<223> OTHER INFORMATION: Homo sapiens histone H1b epitope

<400> SEQUENCE: 717

Lys Pro Lys Ala Ala Lys Pro Lys Ala Ala Ala Lys Lys Lys
1               5                   10                  15

<210> SEQ ID NO 718
<211> LENGTH: 20
<212> TYPE: PRT
<213> ORGANISM: Artificial Sequence
<220> FEATURE:
<223> OTHER INFORMATION: Homo sapiens Histone H2A.Z epitope

<400> SEQUENCE: 718

Gly Lys Ala Lys Thr Lys Ala Val Ser Arg Ser Gln Arg Ala Gly Leu
1               5                   10                  15

Gln Phe Pro Val
            20

<210> SEQ ID NO 719
<211> LENGTH: 15
<212> TYPE: PRT
<213> ORGANISM: Artificial Sequence
```

```
<220> FEATURE:
<223> OTHER INFORMATION: Homo sapiens histone H3 epitope

<400> SEQUENCE: 719

Leu Pro Phe Gln Arg Leu Val Arg Glu Ile Ala Gln Asp Phe Lys
1               5                   10                  15

<210> SEQ ID NO 720
<211> LENGTH: 10
<212> TYPE: PRT
<213> ORGANISM: Artificial Sequence
<220> FEATURE:
<223> OTHER INFORMATION: Homo sapiens Histone H3-like centromeric
      protein A epitope

<400> SEQUENCE: 720

Lys Pro Glu Ala Pro Arg Arg Arg Ser Pro
1               5                   10

<210> SEQ ID NO 721
<211> LENGTH: 8
<212> TYPE: PRT
<213> ORGANISM: Artificial Sequence
<220> FEATURE:
<223> OTHER INFORMATION: Homo sapiens HLA class I histocompatibility
      antigen, B-27 alpha chain precursor epitope

<400> SEQUENCE: 721

Lys Ala Lys Ala Gln Thr Asp Arg
1               5

<210> SEQ ID NO 722
<211> LENGTH: 16
<212> TYPE: PRT
<213> ORGANISM: Artificial Sequence
<220> FEATURE:
<223> OTHER INFORMATION: Homo sapiens HLA-B27 epitope

<400> SEQUENCE: 722

Ala Lys Ala Gln Thr Asp Arg Glu Asp Leu Arg Thr Leu Leu Arg Tyr
1               5                   10                  15

<210> SEQ ID NO 723
<211> LENGTH: 20
<212> TYPE: PRT
<213> ORGANISM: Artificial Sequence
<220> FEATURE:
<223> OTHER INFORMATION: Homo sapiens HLA-DR3 epitope

<400> SEQUENCE: 723

Arg Pro Asp Ala Glu Tyr Trp Asn Ser Gln Lys Asp Leu Leu Glu Gln
1               5                   10                  15

Lys Arg Gly Arg
            20

<210> SEQ ID NO 724
<211> LENGTH: 15
<212> TYPE: PRT
<213> ORGANISM: Artificial Sequence
<220> FEATURE:
<223> OTHER INFORMATION: Homo sapiens HMG-17 epitope

<400> SEQUENCE: 724

Asp Gly Lys Ala Lys Val Lys Asp Glu Pro Gln Arg Arg Ser Ala
1               5                   10                  15
```

```
<210> SEQ ID NO 725
<211> LENGTH: 13
<212> TYPE: PRT
<213> ORGANISM: Artificial Sequence
<220> FEATURE:
<223> OTHER INFORMATION: Homo sapiens HNRNPA2B1 protein epitope

<400> SEQUENCE: 725

Glu Thr Thr Glu Glu Ser Leu Arg Asn Tyr Tyr Glu Gln
1               5                   10

<210> SEQ ID NO 726
<211> LENGTH: 35
<212> TYPE: PRT
<213> ORGANISM: Artificial Sequence
<220> FEATURE:
<223> OTHER INFORMATION: Homo sapiens hypothetical protein epitope

<400> SEQUENCE: 726

Ala Asn Glu Asp Ala Ala Gln Gly Ile Ala Asn Trp Asp Ala Val Gln
1               5                   10                  15

Asp Ile Ala Asn Glu Asp Gly Phe His Gly Ile Asp Ile Glu Asp Ala
            20                  25                  30

Ala Gln Gly
        35

<210> SEQ ID NO 727
<211> LENGTH: 12
<212> TYPE: PRT
<213> ORGANISM: Artificial Sequence
<220> FEATURE:
<223> OTHER INFORMATION: Oryza sativa Japonica Group hypothetical
      protein epitope

<400> SEQUENCE: 727

Ala Phe Asn His Phe Gly Ile Gln Leu Val Gln Arg
1               5                   10

<210> SEQ ID NO 728
<211> LENGTH: 20
<212> TYPE: PRT
<213> ORGANISM: Artificial Sequence
<220> FEATURE:
<223> OTHER INFORMATION: Homo sapiens Ig alpha-1 chain C region epitope

<400> SEQUENCE: 728

Pro Val Pro Ser Thr Pro Pro Thr Pro Ser Pro Ser Thr Pro Pro Thr
1               5                   10                  15

Pro Ser Pro Ser
            20

<210> SEQ ID NO 729
<211> LENGTH: 7
<212> TYPE: PRT
<213> ORGANISM: Artificial Sequence
<220> FEATURE:
<223> OTHER INFORMATION: Homo sapiens Ig gamma-1 chain C region epitope

<400> SEQUENCE: 729

Lys Phe Asn Trp Tyr Val Asp
1               5

<210> SEQ ID NO 730
<211> LENGTH: 7
<212> TYPE: PRT
<213> ORGANISM: Artificial Sequence
```

```
<220> FEATURE:
<223> OTHER INFORMATION: Homo sapiens Ig gamma-3 chain C region epitope

<400> SEQUENCE: 730

Asp Gly Ser Phe Phe Leu Tyr
1               5

<210> SEQ ID NO 731
<211> LENGTH: 7
<212> TYPE: PRT
<213> ORGANISM: Artificial Sequence
<220> FEATURE:
<223> OTHER INFORMATION: Homo sapiens Ig heavy chain V-III region (ART)
      epitope

<400> SEQUENCE: 731

Cys Ser Val Met His Glu Gly
1               5

<210> SEQ ID NO 732
<211> LENGTH: 16
<212> TYPE: PRT
<213> ORGANISM: Artificial Sequence
<220> FEATURE:
<223> OTHER INFORMATION: Homo sapiens Ig lambda chain V-II region MGC
      epitope

<400> SEQUENCE: 732

Ser Gly Leu Gln Ala Glu Asp Glu Ala Asp Tyr Tyr Cys Ser Ser Tyr
1               5                   10                  15

<210> SEQ ID NO 733
<211> LENGTH: 7
<212> TYPE: PRT
<213> ORGANISM: Artificial Sequence
<220> FEATURE:
<223> OTHER INFORMATION: Homo sapiens Ig L-chain V-region epitope

<400> SEQUENCE: 733

Ala Pro Ser Val Thr Leu Phe
1               5

<210> SEQ ID NO 734
<211> LENGTH: 7
<212> TYPE: PRT
<213> ORGANISM: Artificial Sequence
<220> FEATURE:
<223> OTHER INFORMATION: Homo sapiens Immunoglobulin heavy chain epitope

<400> SEQUENCE: 734

Asp Lys Ser Arg Trp Gln Glu
1               5

<210> SEQ ID NO 735
<211> LENGTH: 16
<212> TYPE: PRT
<213> ORGANISM: Artificial Sequence
<220> FEATURE:
<223> OTHER INFORMATION: Homo sapiens immunoglobulin light chain epitope

<400> SEQUENCE: 735

Lys Ala Thr Leu Val Cys Leu Ile Ser Asp Phe Tyr Pro Gly Ala Val
1               5                   10                  15

<210> SEQ ID NO 736
<211> LENGTH: 7
<212> TYPE: PRT
```

```
<213> ORGANISM: Artificial Sequence
<220> FEATURE:
<223> OTHER INFORMATION: Homo sapiens immunoglobulin light chain
      variable region epitope

<400> SEQUENCE: 736

Ala Gly Glu Lys Val Thr Met
1               5

<210> SEQ ID NO 737
<211> LENGTH: 3
<212> TYPE: PRT
<213> ORGANISM: Artificial Sequence
<220> FEATURE:
<223> OTHER INFORMATION: Homo sapiens Insulin precursor epitope

<400> SEQUENCE: 737

Thr Ser Ile
1

<210> SEQ ID NO 738
<211> LENGTH: 14
<212> TYPE: PRT
<213> ORGANISM: Artificial Sequence
<220> FEATURE:
<223> OTHER INFORMATION: Homo sapiens Integrin alpha-6 epitope

<400> SEQUENCE: 738

Leu Lys Arg Asp Met Lys Ser Ala His Leu Leu Pro Glu His
1               5                   10

<210> SEQ ID NO 739
<211> LENGTH: 18
<212> TYPE: PRT
<213> ORGANISM: Artificial Sequence
<220> FEATURE:
<223> OTHER INFORMATION: Homo sapiens Integrin beta-3 precursor epitope

<400> SEQUENCE: 739

Cys Ala Pro Glu Ser Ile Glu Phe Pro Val Ser Glu Ala Arg Val Leu
1               5                   10                  15

Glu Asp

<210> SEQ ID NO 740
<211> LENGTH: 14
<212> TYPE: PRT
<213> ORGANISM: Artificial Sequence
<220> FEATURE:
<223> OTHER INFORMATION: Homo sapiens interferon alpha 2 epitope

<400> SEQUENCE: 740

Cys Asp Leu Pro Gln Thr His Ser Leu Gly Ser Arg Arg Thr
1               5                   10

<210> SEQ ID NO 741
<211> LENGTH: 14
<212> TYPE: PRT
<213> ORGANISM: Artificial Sequence
<220> FEATURE:
<223> OTHER INFORMATION: Homo sapiens interferon alpha A epitope

<400> SEQUENCE: 741

Glu Asp Ser Ile Leu Ala Val Arg Lys Tyr Phe Gln Arg Ile
1               5                   10

<210> SEQ ID NO 742
```

```
<211> LENGTH: 12
<212> TYPE: PRT
<213> ORGANISM: Artificial Sequence
<220> FEATURE:
<223> OTHER INFORMATION: Homo sapiens interferon beta precursor epitope

<400> SEQUENCE: 742

His Leu Lys Arg Tyr Tyr Gly Arg Ile Leu His Tyr
1               5                   10

<210> SEQ ID NO 743
<211> LENGTH: 14
<212> TYPE: PRT
<213> ORGANISM: Artificial Sequence
<220> FEATURE:
<223> OTHER INFORMATION: Homo sapiens interferon-alpha 2 epitope

<400> SEQUENCE: 743

Leu Met Leu Leu Ala Gln Met Arg Arg Ile Ser Leu Phe Ser
1               5                   10

<210> SEQ ID NO 744
<211> LENGTH: 37
<212> TYPE: PRT
<213> ORGANISM: Artificial Sequence
<220> FEATURE:
<223> OTHER INFORMATION: Homo sapiens Islet amyloid polypeptide
      precursor epitope

<400> SEQUENCE: 744

Met Gly Ile Leu Lys Leu Gln Val Phe Leu Ile Val Leu Ser Val Ala
1               5                   10                  15

Leu Asn His Leu Lys Ala Thr Pro Ile Glu Ser His Gln Val Glu Lys
            20                  25                  30

Arg Lys Cys Asn Thr
        35

<210> SEQ ID NO 745
<211> LENGTH: 14
<212> TYPE: PRT
<213> ORGANISM: Artificial Sequence
<220> FEATURE:
<223> OTHER INFORMATION: Bos taurus Kappa-casein precursor epitope

<400> SEQUENCE: 745

Ala Lys Tyr Ile Pro Ile Gln Tyr Val Leu Ser Arg Tyr Pro
1               5                   10

<210> SEQ ID NO 746
<211> LENGTH: 10
<212> TYPE: PRT
<213> ORGANISM: Artificial Sequence
<220> FEATURE:
<223> OTHER INFORMATION: Homo sapiens Ku antigen epitope

<400> SEQUENCE: 746

Arg Gly Asp Gly Pro Phe Arg Leu Gly Gly
1               5                   10

<210> SEQ ID NO 747
<211> LENGTH: 15
<212> TYPE: PRT
<213> ORGANISM: Artificial Sequence
<220> FEATURE:
<223> OTHER INFORMATION: Homo sapiens leukotriene B4 receptor 2 epitope

<400> SEQUENCE: 747
```

```
Gly Arg Gly Asn Gly Asp Pro Gly Gly Gly Met Glu Lys Asp Gly
1               5                   10                  15

<210> SEQ ID NO 748
<211> LENGTH: 14
<212> TYPE: PRT
<213> ORGANISM: Artificial Sequence
<220> FEATURE:
<223> OTHER INFORMATION: Homo sapiens liver histone H1e epitope

<400> SEQUENCE: 748

Ile Lys Lys Val Ala Thr Pro Lys Lys Ala Ser Pro Lys Lys
1               5                   10

<210> SEQ ID NO 749
<211> LENGTH: 23
<212> TYPE: PRT
<213> ORGANISM: Artificial Sequence
<220> FEATURE:
<223> OTHER INFORMATION: Homo sapiens Lupus La protein epitope

<400> SEQUENCE: 749

Ala Gln Pro Gly Ser Gly Lys Gly Lys Val Gln Phe Gln Gly Lys Lys
1               5                   10                  15

Thr Lys Phe Ala Ser Asp Asp
            20

<210> SEQ ID NO 750
<211> LENGTH: 30
<212> TYPE: PRT
<213> ORGANISM: Artificial Sequence
<220> FEATURE:
<223> OTHER INFORMATION: Homo sapiens lymphocyte activation gene 3
      protein precursor epitope

<400> SEQUENCE: 750

Gly Pro Pro Ala Ala Ala Pro Gly His Pro Leu Ala Pro Gly Pro His
1               5                   10                  15

Pro Ala Ala Pro Ser Ser Trp Gly Pro Arg Pro Arg Arg Tyr
            20                  25                  30

<210> SEQ ID NO 751
<211> LENGTH: 10
<212> TYPE: PRT
<213> ORGANISM: Artificial Sequence
<220> FEATURE:
<223> OTHER INFORMATION: Homo sapiens m3 muscarinic cholinergic receptor
      epitope

<400> SEQUENCE: 751

Glu Pro Thr Ile Thr Phe Gly Thr Ala Ile
1               5                   10

<210> SEQ ID NO 752
<211> LENGTH: 20
<212> TYPE: PRT
<213> ORGANISM: Artificial Sequence
<220> FEATURE:
<223> OTHER INFORMATION: Alternaria alternata Major allergen Alt a 1
      precursor epitope

<400> SEQUENCE: 752

Ala Asp Pro Val Thr Thr Glu Gly Asp Tyr Val Val Lys Ile Ser Glu
1               5                   10                  15

Phe Tyr Gly Arg
```

<210> SEQ ID NO 753
<211> LENGTH: 15
<212> TYPE: PRT
<213> ORGANISM: Artificial Sequence
<220> FEATURE:
<223> OTHER INFORMATION: Anisakis simplex Major allergen Ani s 1 epitope

<400> SEQUENCE: 753

```
Cys Lys Met Pro Asp Arg Gly Ala Cys Ala Leu Gly Lys Lys Pro
1               5                   10                  15
```

<210> SEQ ID NO 754
<211> LENGTH: 13
<212> TYPE: PRT
<213> ORGANISM: Artificial Sequence
<220> FEATURE:
<223> OTHER INFORMATION: Aspergillus fumigatus Major allergen Asp f 1
      epitope

<400> SEQUENCE: 754

```
Leu Asn Pro Lys Thr Asn Lys Trp Glu Asp Lys Arg Tyr
1               5                   10
```

<210> SEQ ID NO 755
<211> LENGTH: 10
<212> TYPE: PRT
<213> ORGANISM: Artificial Sequence
<220> FEATURE:
<223> OTHER INFORMATION: Aspergillus fumigatus Major allergen Asp f 2
      epitope

<400> SEQUENCE: 755

```
Ala His Ile Leu Arg Trp Gly Asn Glu Ser
1               5                   10
```

<210> SEQ ID NO 756
<211> LENGTH: 20
<212> TYPE: PRT
<213> ORGANISM: Artificial Sequence
<220> FEATURE:
<223> OTHER INFORMATION: Bos taurus major allergen beta-lactoglobulin
      epitope

<400> SEQUENCE: 756

```
Leu Gln Lys Trp Glu Asn Asp Glu Cys Ala Gln Lys Lys Ile Ile Ala
1               5                   10                  15

Glu Lys Thr Lys
            20
```

<210> SEQ ID NO 757
<211> LENGTH: 14
<212> TYPE: PRT
<213> ORGANISM: Artificial Sequence
<220> FEATURE:
<223> OTHER INFORMATION: Felis catus Major allergen I polypeptide chain
      1 precursor epitope

<400> SEQUENCE: 757

```
Asp Ala Lys Met Thr Glu Glu Asp Lys Glu Asn Ala Leu Ser
1               5                   10
```

<210> SEQ ID NO 758
<211> LENGTH: 14
<212> TYPE: PRT
<213> ORGANISM: Artificial Sequence

```
<220> FEATURE:
<223> OTHER INFORMATION: Felis catus Major allergen I polypeptide chain
      2 precursor epitope

<400> SEQUENCE: 758

Glu Pro Glu Arg Thr Ala Met Lys Lys Ile Gln Asp Cys Tyr
1               5                   10

<210> SEQ ID NO 759
<211> LENGTH: 11
<212> TYPE: PRT
<213> ORGANISM: Artificial Sequence
<220> FEATURE:
<223> OTHER INFORMATION: Felis catus major allergen I, polypeptide chain
      1 epitope

<400> SEQUENCE: 759

Leu Leu Asp Lys Ile Tyr Thr Ser Pro Leu Cys
1               5                   10

<210> SEQ ID NO 760
<211> LENGTH: 29
<212> TYPE: PRT
<213> ORGANISM: Artificial Sequence
<220> FEATURE:
<223> OTHER INFORMATION: Turbo cornutus major allergen Tur c1 - Turbo
      cornutus epitope

<400> SEQUENCE: 760

Leu Glu Asp Glu Leu Leu Ala Glu Lys Glu Lys Tyr Lys Ala Ile Ser
1               5                   10                  15

Asp Glu Leu Asp Gln Thr Phe Ala Glu Leu Ala Gly Tyr
            20                  25

<210> SEQ ID NO 761
<211> LENGTH: 25
<212> TYPE: PRT
<213> ORGANISM: Artificial Sequence
<220> FEATURE:
<223> OTHER INFORMATION: Dermatophagoides pteronyssinus major house dust
      allergen epitope

<400> SEQUENCE: 761

Leu Ala His Arg Asn Gln Ser Leu Asp Leu Ala Glu Gln Glu Leu Val
1               5                   10                  15

Asp Cys Ala Ser Gln His Gly Cys His
            20                  25

<210> SEQ ID NO 762
<211> LENGTH: 9
<212> TYPE: PRT
<213> ORGANISM: Artificial Sequence
<220> FEATURE:
<223> OTHER INFORMATION: Hevea brasiliensis Major latex allergen Hev b 5
      epitope

<400> SEQUENCE: 762

Ala Pro Pro Ala Ser Glu Gln Glu Thr
1               5

<210> SEQ ID NO 763
<211> LENGTH: 43
<212> TYPE: PRT
<213> ORGANISM: Artificial Sequence
<220> FEATURE:
<223> OTHER INFORMATION: Dermatophagoides pteronyssinus Major mite fecal
      allergen Der p 1 epitope
```

<400> SEQUENCE: 763

Ala Arg Glu Gln Ser Cys Arg Arg Pro Asn Ala Gln Arg Phe Gly Ile
1               5                   10                  15

Ser Asn Tyr Cys Gln Ile Tyr Pro Pro Asn Ala Asn Lys Ile Arg Glu
            20                  25                  30

Ala Leu Ala Gln Pro Gln Arg Tyr Cys Arg His
        35                  40

<210> SEQ ID NO 764
<211> LENGTH: 12
<212> TYPE: PRT
<213> ORGANISM: Artificial Sequence
<220> FEATURE:
<223> OTHER INFORMATION: Olea europaea Major pollen allergen epitope

<400> SEQUENCE: 764

Phe Thr Glu Val Gly Tyr Thr Arg Ala Glu Gly Leu
1               5                   10

<210> SEQ ID NO 765
<211> LENGTH: 10
<212> TYPE: PRT
<213> ORGANISM: Artificial Sequence
<220> FEATURE:
<223> OTHER INFORMATION: Betula pendula Major pollen allergen Bet v 1-A
      epitope

<400> SEQUENCE: 765

Asp Gly Asp Asn Leu Phe Pro Lys Val Ala
1               5                   10

<210> SEQ ID NO 766
<211> LENGTH: 11
<212> TYPE: PRT
<213> ORGANISM: Artificial Sequence
<220> FEATURE:
<223> OTHER INFORMATION: Chamaecyparis obtusa Major pollen allergen Cha
      o 1 precursor epitope

<400> SEQUENCE: 766

Trp Arg Ser Thr Gln Asp Ser Phe Asn Asn Gly
1               5                   10

<210> SEQ ID NO 767
<211> LENGTH: 17
<212> TYPE: PRT
<213> ORGANISM: Artificial Sequence
<220> FEATURE:
<223> OTHER INFORMATION: Corylus avellana Major pollen allergen Cor a 1
      epitope

<400> SEQUENCE: 767

Tyr Val Leu Asp Gly Asp Lys Leu Leu Pro Lys Val Ala Pro Gln Ala
1               5                   10                  15

Leu

<210> SEQ ID NO 768
<211> LENGTH: 27
<212> TYPE: PRT
<213> ORGANISM: Artificial Sequence
<220> FEATURE:
<223> OTHER INFORMATION: Holcus lanatus Major pollen allergen Hol l 1
      precursor epitope

<400> SEQUENCE: 768

```
Ala Lys Ser Thr Trp Tyr Gly Lys Pro Thr Gly Ala Gly Pro Lys Asp
1               5                   10                  15

Asn Gly Gly Ala Cys Gly Tyr Lys Asp Val Asp
            20                  25

<210> SEQ ID NO 769
<211> LENGTH: 12
<212> TYPE: PRT
<213> ORGANISM: Artificial Sequence
<220> FEATURE:
<223> OTHER INFORMATION: Juniperus ashei Major pollen allergen Jun a 1
      precursor epitope

<400> SEQUENCE: 769

Ala Phe Asn Gln Phe Gly Pro Asn Ala Gly Gln Arg
1               5                   10

<210> SEQ ID NO 770
<211> LENGTH: 34
<212> TYPE: PRT
<213> ORGANISM: Artificial Sequence
<220> FEATURE:
<223> OTHER INFORMATION: Olea europaea major pollen allergen Ole e 1
      epitope

<400> SEQUENCE: 770

Ser Gly Arg Lys Asp Cys Asn Glu Ile Pro Thr Glu Gly Trp Val Lys
1               5                   10                  15

Pro Ser Leu Lys Phe Ile Leu Asn Thr Val Asn Gly Thr Thr Arg Thr
            20                  25                  30

Val Asn

<210> SEQ ID NO 771
<211> LENGTH: 9
<212> TYPE: PRT
<213> ORGANISM: Artificial Sequence
<220> FEATURE:
<223> OTHER INFORMATION: Malus x domestica mal d 3 epitope

<400> SEQUENCE: 771

Arg Thr Thr Ala Asp Arg Gln Thr Ala
1               5

<210> SEQ ID NO 772
<211> LENGTH: 15
<212> TYPE: PRT
<213> ORGANISM: Artificial Sequence
<220> FEATURE:
<223> OTHER INFORMATION: Homo sapiens MBP protein epitope

<400> SEQUENCE: 772

Glu Asn Pro Val Val His Phe Phe Lys Asn Ile Val Thr Pro Arg
1               5                   10                  15

<210> SEQ ID NO 773
<211> LENGTH: 30
<212> TYPE: PRT
<213> ORGANISM: Artificial Sequence
<220> FEATURE:
<223> OTHER INFORMATION: Homo sapiens melanin-concentrating hormone
      receptor 1, isoform CRA_a epitope

<400> SEQUENCE: 773

Ala Glu His Ala Ser Arg Met Ser Val Leu Arg Ala Lys Pro Met Ser
1               5                   10                  15
```

```
Asn Ser Gln Arg Leu Leu Leu Ser Pro Gly Ser Pro Pro
            20                  25                  30

<210> SEQ ID NO 774
<211> LENGTH: 16
<212> TYPE: PRT
<213> ORGANISM: Artificial Sequence
<220> FEATURE:
<223> OTHER INFORMATION: Homo sapiens Melanocyte protein Pmel 17
      precursor epitope

<400> SEQUENCE: 774

Gln Val Pro Thr Thr Glu Val Val Gly Thr Thr Pro Gly Gln Ala Pro
1               5                   10                  15

<210> SEQ ID NO 775
<211> LENGTH: 6
<212> TYPE: PRT
<213> ORGANISM: Artificial Sequence
<220> FEATURE:
<223> OTHER INFORMATION: Homo sapiens MHC classII HLA-DRB1 epitope

<400> SEQUENCE: 775

Glu Gln Arg Arg Ala Ala
1               5

<210> SEQ ID NO 776
<211> LENGTH: 20
<212> TYPE: PRT
<213> ORGANISM: Artificial Sequence
<220> FEATURE:
<223> OTHER INFORMATION: Homo sapiens MHC HLA-DR1-beta epitope

<400> SEQUENCE: 776

Arg Pro Asp Ala Glu Tyr Trp Asn Ser Gln Lys Asp Leu Leu Glu Gln
1               5                   10                  15

Arg Arg Ala Ala
            20

<210> SEQ ID NO 777
<211> LENGTH: 16
<212> TYPE: PRT
<213> ORGANISM: Artificial Sequence
<220> FEATURE:
<223> OTHER INFORMATION: Blomia tropicalis Mite allergen Blo t 5 epitope

<400> SEQUENCE: 777

Glu Glu Ala Gln Thr Leu Ser Lys Ile Leu Leu Lys Asp Leu Lys Glu
1               5                   10                  15

<210> SEQ ID NO 778
<211> LENGTH: 5
<212> TYPE: PRT
<213> ORGANISM: Artificial Sequence
<220> FEATURE:
<223> OTHER INFORMATION: Dermatophagoides farinae Mite group 2 allergen
      Der f 2 precursor epitope

<400> SEQUENCE: 778

Asp Pro Cys Ile Ile
1               5

<210> SEQ ID NO 779
<211> LENGTH: 15
<212> TYPE: PRT
<213> ORGANISM: Artificial Sequence
```

```
<220> FEATURE:
<223> OTHER INFORMATION: Dermatophagoides pteronyssinus Mite group 2
      allergen Der p 2 precursor epitope

<400> SEQUENCE: 779

Asp Gln Val Asp Val Lys Asp Cys Ala Asn His Glu Ile Lys Lys
1               5                   10                  15

<210> SEQ ID NO 780
<211> LENGTH: 33
<212> TYPE: PRT
<213> ORGANISM: Artificial Sequence
<220> FEATURE:
<223> OTHER INFORMATION: Lepidoglyphus destructor Mite group 2 allergen
      Lep d 2 precursor epitope

<400> SEQUENCE: 780

Ala Ala Asn Gln Asp Thr Ala Lys Val Thr Ile Lys Val Leu Ala Lys
1               5                   10                  15

Val Ala Gly Thr Thr Ile Gln Val Pro Gly Leu Glu Thr Asp Gly Cys
            20                  25                  30

Lys

<210> SEQ ID NO 781
<211> LENGTH: 6
<212> TYPE: PRT
<213> ORGANISM: Artificial Sequence
<220> FEATURE:
<223> OTHER INFORMATION: Triticum aestivum monomeric alpha-amylase
      inhibitor epitope

<400> SEQUENCE: 781

Ala Ala Ser Val Pro Glu
1               5

<210> SEQ ID NO 782
<211> LENGTH: 21
<212> TYPE: PRT
<213> ORGANISM: Artificial Sequence
<220> FEATURE:
<223> OTHER INFORMATION: Homo sapiens Muscarinic acetylcholine receptor
      M1 epitope

<400> SEQUENCE: 782

Gln Tyr Leu Val Gly Glu Arg Thr Val Leu Ala Gly Gln Cys Tyr Ile
1               5                   10                  15

Gln Phe Leu Ser Gln
            20

<210> SEQ ID NO 783
<211> LENGTH: 17
<212> TYPE: PRT
<213> ORGANISM: Artificial Sequence
<220> FEATURE:
<223> OTHER INFORMATION: Homo sapiens myelin associated glycoprotein
      epitope

<400> SEQUENCE: 783

Asp Ser Tyr Thr Leu Thr Glu Glu Leu Ala Tyr Ala Glu Ile Arg Val
1               5                   10                  15

Lys

<210> SEQ ID NO 784
<211> LENGTH: 13
<212> TYPE: PRT
```

```
<213> ORGANISM: Artificial Sequence
<220> FEATURE:
<223> OTHER INFORMATION: Homo sapiens Myelin basic protein epitope

<400> SEQUENCE: 784

Ile Val Thr Pro Arg Thr Pro Pro Ser Gln Gly Lys
1               5                   10

<210> SEQ ID NO 785
<211> LENGTH: 26
<212> TYPE: PRT
<213> ORGANISM: Artificial Sequence
<220> FEATURE:
<223> OTHER INFORMATION: Homo sapiens myelin oligodendrocyte
      glycoprotein epitope

<400> SEQUENCE: 785

Ala Leu Val Gly Asp Glu Val Glu Leu Pro Cys Arg Ile Ser Pro Gly
1               5                   10                  15

Lys Asn Ala Thr Gly Met Glu Leu Gly Trp
            20                  25

<210> SEQ ID NO 786
<211> LENGTH: 5
<212> TYPE: PRT
<213> ORGANISM: Artificial Sequence
<220> FEATURE:
<223> OTHER INFORMATION: Homo sapiens myelin oligodendrocyte
      glycoprotein isoform alpha6 precursor epitope

<400> SEQUENCE: 786

His Arg Thr Phe Glu
1               5

<210> SEQ ID NO 787
<211> LENGTH: 5
<212> TYPE: PRT
<213> ORGANISM: Artificial Sequence
<220> FEATURE:
<223> OTHER INFORMATION: Homo sapiens myelin proteolipid protein epitope

<400> SEQUENCE: 787

Ala Asp Ala Arg Met
1               5

<210> SEQ ID NO 788
<211> LENGTH: 21
<212> TYPE: PRT
<213> ORGANISM: Artificial Sequence
<220> FEATURE:
<223> OTHER INFORMATION: Homo sapiens Myelin-associated glycoprotein
      precursor epitope

<400> SEQUENCE: 788

Gly His Trp Gly Ala Trp Met Pro Ser Ser Ile Ser Ala Phe Glu Gly
1               5                   10                  15

Thr Cys Val Ser Ile
            20

<210> SEQ ID NO 789
<211> LENGTH: 26
<212> TYPE: PRT
<213> ORGANISM: Artificial Sequence
<220> FEATURE:
<223> OTHER INFORMATION: Homo sapiens Myelin-oligodendrocyte
      glycoprotein precursor epitope
```

```
<400> SEQUENCE: 789

Gly Gln Phe Arg Val Ile Gly Pro Arg His Pro Ile Arg Ala Leu Val
1               5                   10                  15

Gly Asp Glu Val Glu Leu Pro Cys Arg Ile
            20                  25

<210> SEQ ID NO 790
<211> LENGTH: 8
<212> TYPE: PRT
<213> ORGANISM: Artificial Sequence
<220> FEATURE:
<223> OTHER INFORMATION: Homo sapiens Myeloblastin precursor epitope

<400> SEQUENCE: 790

Ala His Arg Pro Pro Ser Pro Ala
1               5

<210> SEQ ID NO 791
<211> LENGTH: 10
<212> TYPE: PRT
<213> ORGANISM: Artificial Sequence
<220> FEATURE:
<223> OTHER INFORMATION: Homo sapiens Myeloperoxidase epitope

<400> SEQUENCE: 791

Gly Ser Ala Ser Pro Met Glu Leu Leu Ser
1               5                   10

<210> SEQ ID NO 792
<211> LENGTH: 20
<212> TYPE: PRT
<213> ORGANISM: Artificial Sequence
<220> FEATURE:
<223> OTHER INFORMATION: Homo sapiens Myosin-11 epitope

<400> SEQUENCE: 792

Ala Leu Lys Thr Glu Leu Glu Asp Thr Leu Asp Ser Thr Ala Thr Gln
1               5                   10                  15

Gln Glu Leu Arg
            20

<210> SEQ ID NO 793
<211> LENGTH: 8
<212> TYPE: PRT
<213> ORGANISM: Artificial Sequence
<220> FEATURE:
<223> OTHER INFORMATION: Homo sapiens Neurofilament heavy polypeptide
      (NF-H) (Neurofilament triplet H protein) (200 kDa neurofilament
      protein) epitope

<400> SEQUENCE: 793

Ala Lys Ser Pro Glu Lys Ala Lys
1               5

<210> SEQ ID NO 794
<211> LENGTH: 16
<212> TYPE: PRT
<213> ORGANISM: Artificial Sequence
<220> FEATURE:
<223> OTHER INFORMATION: Homo sapiens nicotinic acetylcholine receptor
      alpha subunit hR alpha subunit epitope

<400> SEQUENCE: 794

Glu Val Asn Gln Ile Val Thr Thr Asn Val Arg Leu Lys Gln Gln Trp
1               5                   10                  15
```

<210> SEQ ID NO 795
<211> LENGTH: 10
<212> TYPE: PRT
<213> ORGANISM: Artificial Sequence
<220> FEATURE:
<223> OTHER INFORMATION: Homo sapiens Non-histone chromosomal protein
      HMG-17 epitope

<400> SEQUENCE: 795

Val Lys Asp Glu Pro Gln Arg Arg Ser Ala
1               5                   10

<210> SEQ ID NO 796
<211> LENGTH: 9
<212> TYPE: PRT
<213> ORGANISM: Artificial Sequence
<220> FEATURE:
<223> OTHER INFORMATION: Prunus armeniaca Non-specific lipid-transfer
      protein 1 epitope

<400> SEQUENCE: 796

Val Asn Pro Asn Asn Ala Ala Ala Leu
1               5

<210> SEQ ID NO 797
<211> LENGTH: 15
<212> TYPE: PRT
<213> ORGANISM: Artificial Sequence
<220> FEATURE:
<223> OTHER INFORMATION: Prunus armeniaca Non-specific lipid-transfer
      protein 1 (LTP 1) (Major allergen Pru ar 3) epitope

<400> SEQUENCE: 797

Leu Ala Arg Thr Thr Pro Asp Arg Arg Thr Ala Cys Asn Cys Leu
1               5                   10                  15

<210> SEQ ID NO 798
<211> LENGTH: 18
<212> TYPE: PRT
<213> ORGANISM: Artificial Sequence
<220> FEATURE:
<223> OTHER INFORMATION: Prunus domestica Non-specific lipid-transfer
      protein 1 (LTP 1) (Major allergen Pru d 3) epitope

<400> SEQUENCE: 798

Leu Ala Arg Thr Thr Ala Asp Arg Arg Ala Ala Cys Asn Cys Leu Lys
1               5                   10                  15

Gln Leu

<210> SEQ ID NO 799
<211> LENGTH: 15
<212> TYPE: PRT
<213> ORGANISM: Artificial Sequence
<220> FEATURE:
<223> OTHER INFORMATION: Malus x domestica Non-specific lipid-transfer
      protein precursor (LTP) (Allergen Mal d 3) epitope

<400> SEQUENCE: 799

Ala Asp Arg Gln Thr Ala Cys Asn Cys Leu Lys Asn Leu Ala Gly
1               5                   10                  15

<210> SEQ ID NO 800
<211> LENGTH: 10
<212> TYPE: PRT
<213> ORGANISM: Artificial Sequence
<220> FEATURE:
<223> OTHER INFORMATION: Homo sapiens NR2 subunit NMDA receptor epitope -continued

<400> SEQUENCE: 800

Asp Trp Glu Tyr Ser Val Trp Leu Ser Asn
1               5                   10

<210> SEQ ID NO 801
<211> LENGTH: 8
<212> TYPE: PRT
<213> ORGANISM: Artificial Sequence
<220> FEATURE:
<223> OTHER INFORMATION: Homo sapiens nuclear autoantigen Sp-100 isoform
      1 epitope

<400> SEQUENCE: 801

Glu Val Phe Ile Ser Ala Pro Arg
1               5

<210> SEQ ID NO 802
<211> LENGTH: 12
<212> TYPE: PRT
<213> ORGANISM: Artificial Sequence
<220> FEATURE:
<223> OTHER INFORMATION: Olea europaea Ole e 1 protein epitope

<400> SEQUENCE: 802

Glu Asp Val Pro Gln Pro Pro Val Ser Gln Phe His
1               5                   10

<210> SEQ ID NO 803
<211> LENGTH: 25
<212> TYPE: PRT
<213> ORGANISM: Artificial Sequence
<220> FEATURE:
<223> OTHER INFORMATION: Olea europaea Ole e 1.0102 protein epitope

<400> SEQUENCE: 803

Glu Asp Val Pro Gln Pro Pro Val Ser Gln Phe His Ile Gln Gly Gln
1               5                   10                  15

Val Tyr Cys Asp Thr Cys Arg Ala Gly
            20                  25

<210> SEQ ID NO 804
<211> LENGTH: 10
<212> TYPE: PRT
<213> ORGANISM: Artificial Sequence
<220> FEATURE:
<223> OTHER INFORMATION: Triticum aestivum Omega gliadin storage protein
      epitope

<400> SEQUENCE: 804

Gln Gln Pro Gln Gln Ser Phe Pro Gln Gln
1               5                   10

<210> SEQ ID NO 805
<211> LENGTH: 7
<212> TYPE: PRT
<213> ORGANISM: Artificial Sequence
<220> FEATURE:
<223> OTHER INFORMATION: Triticum aestivum omega-5 gliadin epitope

<400> SEQUENCE: 805

Gln Gln Phe His Gln Gln Gln
1               5

<210> SEQ ID NO 806
<211> LENGTH: 35

```
<212> TYPE: PRT
<213> ORGANISM: Artificial Sequence
<220> FEATURE:
<223> OTHER INFORMATION: Aspergillus fumigatus Oryzin precursor epitope

<400> SEQUENCE: 806

Ala Ser Asn Thr Ser Pro Ala Ser Ala Pro Asn Ala Leu Thr Val Ala
1               5                   10                  15

Ala Ile Asn Lys Ser Asn Ala Arg Ala Ser Phe Ser Asn Tyr Gly Ser
            20                  25                  30

Val Val Asp
        35

<210> SEQ ID NO 807
<211> LENGTH: 9
<212> TYPE: PRT
<213> ORGANISM: Artificial Sequence
<220> FEATURE:
<223> OTHER INFORMATION: Gallus gallus Ovalbumin epitope

<400> SEQUENCE: 807

Cys Phe Asp Val Phe Lys Glu Leu Lys
1               5

<210> SEQ ID NO 808
<211> LENGTH: 10
<212> TYPE: PRT
<213> ORGANISM: Artificial Sequence
<220> FEATURE:
<223> OTHER INFORMATION: Gallus gallus Ovomucoid epitope

<400> SEQUENCE: 808

Cys Asn Phe Cys Asn Ala Val Val Glu Ser
1               5                   10

<210> SEQ ID NO 809
<211> LENGTH: 14
<212> TYPE: PRT
<213> ORGANISM: Artificial Sequence
<220> FEATURE:
<223> OTHER INFORMATION: Gallus gallus Ovomucoid precursor epitope

<400> SEQUENCE: 809

Ala Glu Val Asp Cys Ser Arg Phe Pro Asn Ala Thr Asp Lys
1               5                   10

<210> SEQ ID NO 810
<211> LENGTH: 10
<212> TYPE: PRT
<213> ORGANISM: Artificial Sequence
<220> FEATURE:
<223> OTHER INFORMATION: Glycine max P34 probable thiol protease
      precursor epitope

<400> SEQUENCE: 810

Ala Ser Trp Asp Trp Arg Lys Lys Gly Val
1               5                   10

<210> SEQ ID NO 811
<211> LENGTH: 10
<212> TYPE: PRT
<213> ORGANISM: Artificial Sequence
<220> FEATURE:
<223> OTHER INFORMATION: Glycine max P34 probable thiol protease
      precursor; Gly m 1 epitope

<400> SEQUENCE: 811
```

```
Pro Gln Glu Phe Ser Lys Lys Thr Tyr Gln
1               5                   10

<210> SEQ ID NO 812
<211> LENGTH: 9
<212> TYPE: PRT
<213> ORGANISM: Artificial Sequence
<220> FEATURE:
<223> OTHER INFORMATION: Homo sapiens p70 autoantigen epitope

<400> SEQUENCE: 812

Glu Ala Leu Thr Lys His Phe Gln Asp
1               5

<210> SEQ ID NO 813
<211> LENGTH: 20
<212> TYPE: PRT
<213> ORGANISM: Artificial Sequence
<220> FEATURE:
<223> OTHER INFORMATION: Homo sapiens PADI-H protein epitope

<400> SEQUENCE: 813

Lys Ala Ala Ser Gly Ser Thr Gly Asp Gln Lys Val Gln Ile Ser Tyr
1               5                   10                  15

Tyr Gly Pro Lys
            20

<210> SEQ ID NO 814
<211> LENGTH: 9
<212> TYPE: PRT
<213> ORGANISM: Artificial Sequence
<220> FEATURE:
<223> OTHER INFORMATION: Parietaria judaica Par j epitope

<400> SEQUENCE: 814

Gly Thr Ser Ser Cys Arg Leu Val Pro
1               5

<210> SEQ ID NO 815
<211> LENGTH: 47
<212> TYPE: PRT
<213> ORGANISM: Artificial Sequence
<220> FEATURE:
<223> OTHER INFORMATION: Blomia tropicalis Paramyosin epitope

<400> SEQUENCE: 815

Glu Lys Leu Arg Asp Gln Lys Glu Ala Leu Ala Arg Glu Asn Lys Lys
1               5                   10                  15

Leu Ala Asp Asp Leu Ala Glu Ala Lys Ser Gln Leu Asn Asp Ala His
            20                  25                  30

Arg Arg Ile His Glu Gln Glu Ile Glu Ile Lys Arg Leu Glu Asn
        35                  40                  45

<210> SEQ ID NO 816
<211> LENGTH: 8
<212> TYPE: PRT
<213> ORGANISM: Artificial Sequence
<220> FEATURE:
<223> OTHER INFORMATION: Gadus morhua callarias Parvalbumin beta epitope

<400> SEQUENCE: 816

Ala Ala Glu Ala Ala Cys Phe Lys
1               5
```

```
<210> SEQ ID NO 817
<211> LENGTH: 15
<212> TYPE: PRT
<213> ORGANISM: Artificial Sequence
<220> FEATURE:
<223> OTHER INFORMATION: Salmo salar parvalbumin like 1 epitope

<400> SEQUENCE: 817

Ala Asp Ile Lys Thr Ala Leu Glu Ala Arg Lys Ala Ala Asp Thr
1               5                   10                  15

<210> SEQ ID NO 818
<211> LENGTH: 12
<212> TYPE: PRT
<213> ORGANISM: Artificial Sequence
<220> FEATURE:
<223> OTHER INFORMATION: Juniperus ashei Pathogenesis-related protein
      precursor epitope

<400> SEQUENCE: 818

Ala Asp Ile Asn Ala Val Cys Pro Ser Glu Leu Lys
1               5                   10

<210> SEQ ID NO 819
<211> LENGTH: 12
<212> TYPE: PRT
<213> ORGANISM: Artificial Sequence
<220> FEATURE:
<223> OTHER INFORMATION: Nicotiana tabacum Pectate lyase epitope

<400> SEQUENCE: 819

Ala Tyr Asn His Phe Gly Lys Arg Leu Asp Gln Arg
1               5                   10

<210> SEQ ID NO 820
<211> LENGTH: 12
<212> TYPE: PRT
<213> ORGANISM: Artificial Sequence
<220> FEATURE:
<223> OTHER INFORMATION: Musa acuminata AAA Group pectate lyase 2
      epitope

<400> SEQUENCE: 820

Ala Phe Asn His Phe Gly Glu Gly Leu Ile Gln Arg
1               5                   10

<210> SEQ ID NO 821
<211> LENGTH: 15
<212> TYPE: PRT
<213> ORGANISM: Artificial Sequence
<220> FEATURE:
<223> OTHER INFORMATION: Farfantepenaeus aztecus Pen a 1 allergen
      epitope

<400> SEQUENCE: 821

Ala Asn Ile Gln Leu Val Glu Lys Asp Lys Ala Leu Ser Asn Ala
1               5                   10                  15

<210> SEQ ID NO 822
<211> LENGTH: 43
<212> TYPE: PRT
<213> ORGANISM: Artificial Sequence
<220> FEATURE:
<223> OTHER INFORMATION: Dermatophagoides pteronyssinus Peptidase 1
      precursor (Major mite fecal allergen Der p 1) (Allergen Der p I)
      epitope

<400> SEQUENCE: 822
```

-continued

Ala Arg Glu Gln Ser Cys Arg Arg Pro Asn Ala Gln Arg Phe Gly Ile
1               5                   10                  15

Ser Asn Tyr Cys Gln Ile Tyr Pro Pro Asn Val Asn Lys Ile Arg Glu
            20                  25                  30

Ala Leu Ala Gln Thr His Ser Ala Ile Ala Val
        35                  40

<210> SEQ ID NO 823
<211> LENGTH: 3
<212> TYPE: PRT
<213> ORGANISM: Artificial Sequence
<220> FEATURE:
<223> OTHER INFORMATION: Homo sapiens pericentriolar material 1 protein
      epitope

<400> SEQUENCE: 823

Lys Asp Cys
1

<210> SEQ ID NO 824
<211> LENGTH: 20
<212> TYPE: PRT
<213> ORGANISM: Artificial Sequence
<220> FEATURE:
<223> OTHER INFORMATION: Homo sapiens Periplakin epitope

<400> SEQUENCE: 824

Ile His Asp Arg Lys Ser Gly Lys Lys Phe Ser Ile Glu Glu Ala Leu
1               5                   10                  15

Gln Ser Gly Arg
            20

<210> SEQ ID NO 825
<211> LENGTH: 45
<212> TYPE: PRT
<213> ORGANISM: Artificial Sequence
<220> FEATURE:
<223> OTHER INFORMATION: Apis mellifera Phospholipase A2 precursor
      epitope

<400> SEQUENCE: 825

Leu Ile Asp Thr Lys Cys Tyr Lys Leu Glu His Pro Val Thr Gly Cys
1               5                   10                  15

Gly Glu Arg Thr Glu Gly Arg Cys Leu His Tyr Thr Val Asp Lys Ser
            20                  25                  30

Lys Pro Lys Val Tyr Gln Trp Phe Asp Leu Arg Lys Tyr
        35                  40                  45

<210> SEQ ID NO 826
<211> LENGTH: 14
<212> TYPE: PRT
<213> ORGANISM: Artificial Sequence
<220> FEATURE:
<223> OTHER INFORMATION: Myrmecia pilosula Pilosulin-1 precursor (Major
      allergen Myr p 1) (Myr p I) epitope

<400> SEQUENCE: 826

Lys Glu Ala Ile Pro Met Ala Val Glu Met Ala Lys Ser Gln
1               5                   10

<210> SEQ ID NO 827
<211> LENGTH: 8
<212> TYPE: PRT
<213> ORGANISM: Artificial Sequence
<220> FEATURE:

-continued

```
<223> OTHER INFORMATION: Homo sapiens plasma protease C1 inhibitor
      precursor epitope

<400> SEQUENCE: 827

Ala Ser Ala Ile Ser Val Ala Arg
1               5

<210> SEQ ID NO 828
<211> LENGTH: 6
<212> TYPE: PRT
<213> ORGANISM: Artificial Sequence
<220> FEATURE:
<223> OTHER INFORMATION: Homo sapiens platelet glycoprotein IIIa epitope

<400> SEQUENCE: 828

Arg Ala Arg Ala Lys Trp
1               5

<210> SEQ ID NO 829
<211> LENGTH: 12
<212> TYPE: PRT
<213> ORGANISM: Artificial Sequence
<220> FEATURE:
<223> OTHER INFORMATION: Homo sapiens plexin domain containing 1,
      isoform CRA_b epitope

<400> SEQUENCE: 829

Asn Cys Ser Trp Cys His Val Leu Gln Arg Cys Ser
1               5                   10

<210> SEQ ID NO 830
<211> LENGTH: 15
<212> TYPE: PRT
<213> ORGANISM: Artificial Sequence
<220> FEATURE:
<223> OTHER INFORMATION: Homo sapiens PM/Scl 100kD nucleolar protein
      epitope

<400> SEQUENCE: 830

Cys Ile Ala Ala Lys Lys Ile Lys Gln Ser Val Gly Asn Lys Ser
1               5                   10                  15

<210> SEQ ID NO 831
<211> LENGTH: 8
<212> TYPE: PRT
<213> ORGANISM: Artificial Sequence
<220> FEATURE:
<223> OTHER INFORMATION: Betula pendula Polcalcin Bet v 4 epitope

<400> SEQUENCE: 831

Phe Gly Arg Ala Asn Arg Gly Leu
1               5

<210> SEQ ID NO 832
<211> LENGTH: 36
<212> TYPE: PRT
<213> ORGANISM: Artificial Sequence
<220> FEATURE:
<223> OTHER INFORMATION: Phleum pratense Polcalcin Phl p 7 (Calcium-
      binding pollen allergen Phl p 7) (P7) epitope

<400> SEQUENCE: 832

Ala Asp Asp Met Glu Arg Ile Phe Lys Arg Phe Asp Thr Asn Gly Asp
1               5                   10                  15

Gly Lys Ile Ser Leu Ser Glu Leu Thr Asp Ala Leu Arg Thr Leu Gly
            20                  25                  30
```

Ser Thr Ser Ala
          35

<210> SEQ ID NO 833
<211> LENGTH: 25
<212> TYPE: PRT
<213> ORGANISM: Artificial Sequence
<220> FEATURE:
<223> OTHER INFORMATION: Lolium perenne pollen allergen epitope

<400> SEQUENCE: 833

Glu Gly Gly Thr Lys Ser Glu Val Glu Asp Val Ile Pro Glu Gly Trp
1               5                   10                  15

Lys Ala Asp Thr Ser Tyr Ser Ala Lys
            20                  25

<210> SEQ ID NO 834
<211> LENGTH: 12
<212> TYPE: PRT
<213> ORGANISM: Artificial Sequence
<220> FEATURE:
<223> OTHER INFORMATION: Ambrosia artemisiifolia Pollen allergen Amb a
      1.4 epitope

<400> SEQUENCE: 834

Ala Phe Asn Lys Phe Thr Asp Asn Val Asp Gln Arg
1               5                   10

<210> SEQ ID NO 835
<211> LENGTH: 8
<212> TYPE: PRT
<213> ORGANISM: Artificial Sequence
<220> FEATURE:
<223> OTHER INFORMATION: Ambrosia artemisiifolia Pollen allergen Amb a
      2 precursor epitope

<400> SEQUENCE: 835

Met Pro Arg Cys Arg Phe Gly Phe
1               5

<210> SEQ ID NO 836
<211> LENGTH: 15
<212> TYPE: PRT
<213> ORGANISM: Artificial Sequence
<220> FEATURE:
<223> OTHER INFORMATION: Ambrosia artemisiifolia var. elatior Pollen
      allergen Amb a 3 epitope

<400> SEQUENCE: 836

Cys Asp Ile Lys Asp Pro Ile Arg Leu Glu Pro Gly Gly Pro Asp
1               5                   10                  15

<210> SEQ ID NO 837
<211> LENGTH: 31
<212> TYPE: PRT
<213> ORGANISM: Artificial Sequence
<220> FEATURE:
<223> OTHER INFORMATION: Betula pendula pollen allergen Bet v 1 epitope

<400> SEQUENCE: 837

Lys Ala Glu Gln Val Lys Ala Ser Lys Glu Met Gly Glu Thr Leu Leu
1               5                   10                  15

Arg Ala Val Glu Ser Tyr Leu Leu Ala His Ser Asp Ala Tyr Asn
            20                  25                  30

<210> SEQ ID NO 838

-continued

```
<211> LENGTH: 20
<212> TYPE: PRT
<213> ORGANISM: Artificial Sequence
<220> FEATURE:
<223> OTHER INFORMATION: Poa pratensis Pollen allergen KBG 60 precursor
      epitope

<400> SEQUENCE: 838

Ala Ala Asn Lys Tyr Lys Thr Phe Val Ala Thr Phe Gly Ala Ala Ser
1               5                   10                  15

Asn Lys Ala Phe
            20

<210> SEQ ID NO 839
<211> LENGTH: 25
<212> TYPE: PRT
<213> ORGANISM: Artificial Sequence
<220> FEATURE:
<223> OTHER INFORMATION: Lolium perenne Pollen allergen Lol p 2-A (Lol p
      II-A) epitope

<400> SEQUENCE: 839

Glu Lys Gly Met Arg Asn Val Phe Asp Asp Val Val Pro Ala Asp Phe
1               5                   10                  15

Lys Val Gly Thr Thr Tyr Lys Pro Glu
            20                  25

<210> SEQ ID NO 840
<211> LENGTH: 27
<212> TYPE: PRT
<213> ORGANISM: Artificial Sequence
<220> FEATURE:
<223> OTHER INFORMATION: Lolium perenne Pollen allergen Lol p 3 (Lol p
      III) epitope

<400> SEQUENCE: 840

Lys Gly Gly Met Lys Asn Val Phe Asp Glu Val Ile Pro Thr Ala Phe
1               5                   10                  15

Thr Val Gly Lys Thr Tyr Thr Pro Glu Tyr Asn
            20                  25

<210> SEQ ID NO 841
<211> LENGTH: 12
<212> TYPE: PRT
<213> ORGANISM: Artificial Sequence
<220> FEATURE:
<223> OTHER INFORMATION: Lolium perenne Pollen allergen Lol p VA
      precursor epitope

<400> SEQUENCE: 841

Ala Ala Glu Gly Ala Thr Pro Glu Ala Lys Tyr Asp
1               5                   10

<210> SEQ ID NO 842
<211> LENGTH: 15
<212> TYPE: PRT
<213> ORGANISM: Artificial Sequence
<220> FEATURE:
<223> OTHER INFORMATION: Phleum pratense Pollen allergen Phl p 1
      precursor epitope

<400> SEQUENCE: 842

Ala Pro Tyr His Phe Asp Leu Ser Gly His Ala Phe Gly Ala Met
1               5                   10                  15

<210> SEQ ID NO 843
```

```
<211> LENGTH: 8
<212> TYPE: PRT
<213> ORGANISM: Artificial Sequence
<220> FEATURE:
<223> OTHER INFORMATION: Zea mays pollen allergen Phl p 11 epitope

<400> SEQUENCE: 843

Arg Asp Arg Ala Arg Val Pro Leu
1               5

<210> SEQ ID NO 844
<211> LENGTH: 12
<212> TYPE: PRT
<213> ORGANISM: Artificial Sequence
<220> FEATURE:
<223> OTHER INFORMATION: Phleum pratense pollen allergen Phl pI epitope

<400> SEQUENCE: 844

Ile Pro Lys Val Pro Pro Gly Pro Asn Ile Thr Ala
1               5                   10

<210> SEQ ID NO 845
<211> LENGTH: 20
<212> TYPE: PRT
<213> ORGANISM: Artificial Sequence
<220> FEATURE:
<223> OTHER INFORMATION: Cryptomeria japonica Polygalacturonase
      precursor epitope

<400> SEQUENCE: 845

Gly Gln Cys Lys Trp Val Asn Gly Arg Glu Ile Cys Asn Asp Arg Asp
1               5                   10                  15

Arg Pro Thr Ala
            20

<210> SEQ ID NO 846
<211> LENGTH: 30
<212> TYPE: PRT
<213> ORGANISM: Artificial Sequence
<220> FEATURE:
<223> OTHER INFORMATION: Parietaria judaica Probable non-specific lipid-
      transfer protein epitope

<400> SEQUENCE: 846

Gln Glu Thr Cys Gly Thr Met Val Arg Ala Leu Met Pro Cys Leu Pro
1               5                   10                  15

Phe Val Gln Gly Lys Glu Lys Glu Pro Ser Lys Gly Cys Cys
            20                  25                  30

<210> SEQ ID NO 847
<211> LENGTH: 10
<212> TYPE: PRT
<213> ORGANISM: Artificial Sequence
<220> FEATURE:
<223> OTHER INFORMATION: Parietaria judaica Probable non-specific lipid-
      transfer protein 2 epitope

<400> SEQUENCE: 847

Ala Glu Val Pro Lys Lys Cys Asp Ile Lys
1               5                   10

<210> SEQ ID NO 848
<211> LENGTH: 30
<212> TYPE: PRT
<213> ORGANISM: Artificial Sequence
<220> FEATURE:
<223> OTHER INFORMATION: Parietaria judaica Probable non-specific lipid-
``` transfer protein 2 precursor epitope

<400> SEQUENCE: 848

Glu Ala Cys Gly Lys Val Val Gln Asp Ile Met Pro Cys Leu His Phe
1               5                   10                  15

Val Lys Gly Glu Glu Lys Glu Pro Ser Lys Glu Cys Cys Ser
            20                  25                  30

<210> SEQ ID NO 849
<211> LENGTH: 12
<212> TYPE: PRT
<213> ORGANISM: Artificial Sequence
<220> FEATURE:
<223> OTHER INFORMATION: Solanum lycopersicum Probable pectate lyase P59
      epitope

<400> SEQUENCE: 849

Ala Phe Asn His Phe Gly Lys Arg Leu Ile Gln Arg
1               5                   10

<210> SEQ ID NO 850
<211> LENGTH: 11
<212> TYPE: PRT
<213> ORGANISM: Artificial Sequence
<220> FEATURE:
<223> OTHER INFORMATION: Homo sapiens profilaggrin epitope

<400> SEQUENCE: 850

Gly Gly Gln Gly Ser Arg His Gln Gln Ala Arg
1               5                   10

<210> SEQ ID NO 851
<211> LENGTH: 10
<212> TYPE: PRT
<213> ORGANISM: Artificial Sequence
<220> FEATURE:
<223> OTHER INFORMATION: Cucumis melo profilin epitope

<400> SEQUENCE: 851

Ala Phe Arg Leu Glu Glu Ile Ala Ala Ile
1               5                   10

<210> SEQ ID NO 852
<211> LENGTH: 56
<212> TYPE: PRT
<213> ORGANISM: Artificial Sequence
<220> FEATURE:
<223> OTHER INFORMATION: Glycine max Profilin-1 epitope

<400> SEQUENCE: 852

Trp Ala Gln Ser Thr Asp Phe Pro Gln Phe Lys Pro Glu Glu Ile Thr
1               5                   10                  15

Ala Ile Met Asn Asp Phe Asn Glu Pro Gly Ser Leu Ala Pro Thr Gly
            20                  25                  30

Leu Tyr Leu Gly Gly Thr Lys Tyr Met Val Ile Gln Gly Glu Pro Gly
        35                  40                  45

Ala Val Ile Arg Gly Lys Lys Gly
    50                  55

<210> SEQ ID NO 853
<211> LENGTH: 43
<212> TYPE: PRT
<213> ORGANISM: Artificial Sequence
<220> FEATURE:
<223> OTHER INFORMATION: Hevea brasiliensis Pro-hevein precursor epitope

```
<400> SEQUENCE: 853

Glu Gln Cys Gly Arg Gln Ala Gly Gly Lys Leu Cys Pro Asn Asn Leu
1               5                   10                  15

Cys Cys Ser Gln Trp Gly Trp Cys Gly Ser Thr Asp Glu Tyr Cys Ser
            20                  25                  30

Pro Asp His Asn Cys Gln Ser Asn Cys Lys Asp
        35                  40

<210> SEQ ID NO 854
<211> LENGTH: 15
<212> TYPE: PRT
<213> ORGANISM: Artificial Sequence
<220> FEATURE:
<223> OTHER INFORMATION: Homo sapiens Proliferating cell nuclear antigen
      epitope

<400> SEQUENCE: 854

Leu Lys Tyr Tyr Leu Ala Pro Lys Ile Glu Asp Glu Glu Gly Ser
1               5                   10                  15

<210> SEQ ID NO 855
<211> LENGTH: 9
<212> TYPE: PRT
<213> ORGANISM: Artificial Sequence
<220> FEATURE:
<223> OTHER INFORMATION: Homo sapiens Proline-rich transmembrane protein
      2 epitope

<400> SEQUENCE: 855

His Ser Glu Ala Glu Thr Gly Pro Pro
1               5

<210> SEQ ID NO 856
<211> LENGTH: 15
<212> TYPE: PRT
<213> ORGANISM: Artificial Sequence
<220> FEATURE:
<223> OTHER INFORMATION: Homo sapiens proteasome (prosome, macropain)
      activator subunit 3 (PA28 gamma; Ki), isoform CRA_a epitope

<400> SEQUENCE: 856

Leu Asp Gly Pro Thr Tyr Lys Arg Arg Leu Asp Glu Cys Glu Glu
1               5                   10                  15

<210> SEQ ID NO 857
<211> LENGTH: 13
<212> TYPE: PRT
<213> ORGANISM: Artificial Sequence
<220> FEATURE:
<223> OTHER INFORMATION: Homo sapiens protein tyrosine phosphatase-like
      autoantigen epitope

<400> SEQUENCE: 857

Gly Ala His Gly Asp Thr Thr Pro Glu Tyr Gln Asp Leu
1               5                   10

<210> SEQ ID NO 858
<211> LENGTH: 20
<212> TYPE: PRT
<213> ORGANISM: Artificial Sequence
<220> FEATURE:
<223> OTHER INFORMATION: Homo sapiens protein-arginine deiminase type-4
      epitope

<400> SEQUENCE: 858
```

```
Ala Phe Phe Pro Asn Met Val Asn Met Leu Val Leu Gly Lys His Leu
1               5                   10                  15

Gly Ile Pro Lys
            20

<210> SEQ ID NO 859
<211> LENGTH: 15
<212> TYPE: PRT
<213> ORGANISM: Artificial Sequence
<220> FEATURE:
<223> OTHER INFORMATION: Homo sapiens proteinase 3 epitope

<400> SEQUENCE: 859

Cys Ala Thr Arg Leu Phe Pro Asp Phe Phe Thr Arg Val Ala Leu
1               5                   10                  15

<210> SEQ ID NO 860
<211> LENGTH: 10
<212> TYPE: PRT
<213> ORGANISM: Artificial Sequence
<220> FEATURE:
<223> OTHER INFORMATION: Prunus persica pru p 1 epitope

<400> SEQUENCE: 860

Gly Lys Cys Gly Val Ser Ile Pro Tyr Lys
1               5                   10

<210> SEQ ID NO 861
<211> LENGTH: 15
<212> TYPE: PRT
<213> ORGANISM: Artificial Sequence
<220> FEATURE:
<223> OTHER INFORMATION: Prunus dulcis prunin 1 precursor epitope

<400> SEQUENCE: 861

Glu Glu Ser Gln Gln Ser Ser Gln Gln Gly Arg Gln Gln Glu Gln
1               5                   10                  15

<210> SEQ ID NO 862
<211> LENGTH: 15
<212> TYPE: PRT
<213> ORGANISM: Artificial Sequence
<220> FEATURE:
<223> OTHER INFORMATION: Prunus dulcis prunin 2 precursor epitope

<400> SEQUENCE: 862

Asp Ser Gln Pro Gln Gln Phe Gln Gln Gln Gln Gln Gln Gln Gln
1               5                   10                  15

<210> SEQ ID NO 863
<211> LENGTH: 11
<212> TYPE: PRT
<213> ORGANISM: Artificial Sequence
<220> FEATURE:
<223> OTHER INFORMATION: Hesperocyparis arizonica putative allergen Cup
      a 1 epitope

<400> SEQUENCE: 863

Trp Arg Phe Thr Arg Asp Ala Phe Thr Asn Gly
1               5                   10

<210> SEQ ID NO 864
<211> LENGTH: 11
<212> TYPE: PRT
<213> ORGANISM: Artificial Sequence
<220> FEATURE:
<223> OTHER INFORMATION: Homo sapiens Putative HTLV-1-related endogenous
``` sequence (p25) epitope

<400> SEQUENCE: 864

Pro Thr Arg Ala Pro Ser Gly Pro Arg Pro Pro
1               5                   10

<210> SEQ ID NO 865
<211> LENGTH: 8
<212> TYPE: PRT
<213> ORGANISM: Artificial Sequence
<220> FEATURE:
<223> OTHER INFORMATION: Homo sapiens Putative small nuclear
      ribonucleoprotein polypeptide E-like protein 1 epitope

<400> SEQUENCE: 865

Glu Ile His Ser Lys Thr Lys Ser
1               5

<210> SEQ ID NO 866
<211> LENGTH: 18
<212> TYPE: PRT
<213> ORGANISM: Artificial Sequence
<220> FEATURE:
<223> OTHER INFORMATION: Homo sapiens Receptor tyrosine-protein kinase
      erbB-2 precursor epitope

<400> SEQUENCE: 866

Pro Glu Ser Phe Asp Gly Asp Pro Ala Ser Asn Thr Ala Pro Leu Gln
1               5                   10                  15

Pro Glu

<210> SEQ ID NO 867
<211> LENGTH: 13
<212> TYPE: PRT
<213> ORGANISM: Artificial Sequence
<220> FEATURE:
<223> OTHER INFORMATION: Homo sapiens Receptor-type tyrosine-protein
      phosphatase-like N precursor epitope

<400> SEQUENCE: 867

Lys Glu Arg Leu Ala Ala Leu Gly Pro Glu Gly Ala His
1               5                   10

<210> SEQ ID NO 868
<211> LENGTH: 11
<212> TYPE: PRT
<213> ORGANISM: Artificial Sequence
<220> FEATURE:
<223> OTHER INFORMATION: Homo sapiens recombinant IgG2 heavy chain
      epitope

<400> SEQUENCE: 868

Glu Pro Gln Val Val Thr Leu Pro Pro Ser Arg
1               5                   10

<210> SEQ ID NO 869
<211> LENGTH: 20
<212> TYPE: PRT
<213> ORGANISM: Artificial Sequence
<220> FEATURE:
<223> OTHER INFORMATION: Homo sapiens Replication protein A 32 kDa
      subunit epitope

<400> SEQUENCE: 869

Arg Ser Phe Gln Asn Lys Lys Ser Leu Val Ala Phe Lys Ile Met Pro
1               5                   10                  15

Leu Glu Asp Met
        20

<210> SEQ ID NO 870
<211> LENGTH: 10
<212> TYPE: PRT
<213> ORGANISM: Artificial Sequence
<220> FEATURE:
<223> OTHER INFORMATION: Aspergillus fumigatus Ribonuclease mitogillin
      precursor epitope

<400> SEQUENCE: 870

Phe Pro Thr Phe Pro Asp Gly His Asp Tyr
1               5                   10

<210> SEQ ID NO 871
<211> LENGTH: 23
<212> TYPE: PRT
<213> ORGANISM: Artificial Sequence
<220> FEATURE:
<223> OTHER INFORMATION: Homo sapiens ribosomal protein L7 epitope

<400> SEQUENCE: 871

Glu Leu Lys Ile Lys Arg Leu Arg Lys Lys Phe Ala Gln Lys Met Leu
1               5                   10                  15

Arg Lys Ala Arg Arg Lys Leu
            20

<210> SEQ ID NO 872
<211> LENGTH: 14
<212> TYPE: PRT
<213> ORGANISM: Artificial Sequence
<220> FEATURE:
<223> OTHER INFORMATION: Homo sapiens ribosomal protein P2 epitope

<400> SEQUENCE: 872

Ser Glu Glu Ser Asp Asp Asp Met Gly Phe Gly Leu Phe Asp
1               5                   10

<210> SEQ ID NO 873
<211> LENGTH: 12
<212> TYPE: PRT
<213> ORGANISM: Artificial Sequence
<220> FEATURE:
<223> OTHER INFORMATION: Mangifera indica ripening-related pectate lyase
      epitope

<400> SEQUENCE: 873

Ala Tyr Asn His Phe Gly Glu Gly Leu Ile Gln Arg
1               5                   10

<210> SEQ ID NO 874
<211> LENGTH: 21
<212> TYPE: PRT
<213> ORGANISM: Artificial Sequence
<220> FEATURE:
<223> OTHER INFORMATION: Homo sapiens RNA binding protein, autoantigenic
      (hnRNP-associated with lethal yellow homolog (mouse)), isoform
      CRA_c epitope

<400> SEQUENCE: 874

Gly Gly Gly Gly Gly Gly Ser Gly Gly Gly Ser Gly Gly Gly Gly
1               5                   10                  15

Gly Gly Gly Ser Ser
            20

-continued

```
<210> SEQ ID NO 875
<211> LENGTH: 21
<212> TYPE: PRT
<213> ORGANISM: Artificial Sequence
<220> FEATURE:
<223> OTHER INFORMATION: Homo sapiens Ro ribonucleoprotein epitope

<400> SEQUENCE: 875

Asp Gly Tyr Val Trp Gln Val Thr Asp Met Asn Arg Leu His Arg Phe
1               5                   10                  15

Leu Cys Phe Gly Ser
            20

<210> SEQ ID NO 876
<211> LENGTH: 10
<212> TYPE: PRT
<213> ORGANISM: Artificial Sequence
<220> FEATURE:
<223> OTHER INFORMATION: Hevea brasiliensis Rubber elongation factor
      protein epitope

<400> SEQUENCE: 876

Ala Glu Asp Glu Asp Asn Gln Gln Gly Gln
1               5                   10

<210> SEQ ID NO 877
<211> LENGTH: 14
<212> TYPE: PRT
<213> ORGANISM: Artificial Sequence
<220> FEATURE:
<223> OTHER INFORMATION: Homo sapiens S-arrestin epitope

<400> SEQUENCE: 877

Phe Leu Gly Glu Leu Thr Ser Ser Glu Val Ala Thr Glu Val
1               5                   10

<210> SEQ ID NO 878
<211> LENGTH: 15
<212> TYPE: PRT
<213> ORGANISM: Artificial Sequence
<220> FEATURE:
<223> OTHER INFORMATION: Juglans regia seed storage protein epitope

<400> SEQUENCE: 878

Asp Asp Asn Gly Leu Glu Glu Thr Ile Cys Thr Leu Arg Leu Arg
1               5                   10                  15

<210> SEQ ID NO 879
<211> LENGTH: 15
<212> TYPE: PRT
<213> ORGANISM: Artificial Sequence
<220> FEATURE:
<223> OTHER INFORMATION: Arachis hypogaea seed storage protein SSP2
      epitope

<400> SEQUENCE: 879

Cys Gly Leu Arg Ala Pro Gln Arg Cys Asp Leu Asp Val Glu Ser
1               5                   10                  15

<210> SEQ ID NO 880
<211> LENGTH: 8
<212> TYPE: PRT
<213> ORGANISM: Artificial Sequence
<220> FEATURE:
<223> OTHER INFORMATION: Gallus gallus serine (or cysteine) proteinase
      inhibitor, clade B (ovalbumin), member 3 epitope

<400> SEQUENCE: 880
```

```
Arg Pro Asn Ala Thr Tyr Ser Leu
1               5

<210> SEQ ID NO 881
<211> LENGTH: 8
<212> TYPE: PRT
<213> ORGANISM: Artificial Sequence
<220> FEATURE:
<223> OTHER INFORMATION: Gallus gallus Serum albumin epitope

<400> SEQUENCE: 881

Gln Ser Arg Ala Thr Leu Gly Ile
1               5

<210> SEQ ID NO 882
<211> LENGTH: 17
<212> TYPE: PRT
<213> ORGANISM: Artificial Sequence
<220> FEATURE:
<223> OTHER INFORMATION: Bos taurus Serum albumin precursor epitope

<400> SEQUENCE: 882

Asp Asp Ser Pro Asp Leu Pro Lys Leu Lys Pro Asp Pro Asn Thr Leu
1               5                   10                  15

Cys

<210> SEQ ID NO 883
<211> LENGTH: 8
<212> TYPE: PRT
<213> ORGANISM: Artificial Sequence
<220> FEATURE:
<223> OTHER INFORMATION: Homo sapiens small nuclear ribonucleoprotein
      epitope

<400> SEQUENCE: 883

Pro Pro Pro Gly Ile Arg Gly Pro
1               5

<210> SEQ ID NO 884
<211> LENGTH: 8
<212> TYPE: PRT
<213> ORGANISM: Artificial Sequence
<220> FEATURE:
<223> OTHER INFORMATION: Homo sapiens small nuclear ribonucleoprotein B'
      epitope

<400> SEQUENCE: 884

Pro Pro Pro Gly Met Arg Gly Pro
1               5

<210> SEQ ID NO 885
<211> LENGTH: 24
<212> TYPE: PRT
<213> ORGANISM: Artificial Sequence
<220> FEATURE:
<223> OTHER INFORMATION: Homo sapiens small nuclear ribonucleoprotein D1
      polypeptide epitope

<400> SEQUENCE: 885

Lys Met Thr Leu Lys Asn Arg Glu Pro Val Gln Leu Glu Thr Leu Ser
1               5                   10                  15

Ile Arg Gly Asn Arg Ile Arg Tyr
            20

<210> SEQ ID NO 886
```

```
<211> LENGTH: 23
<212> TYPE: PRT
<213> ORGANISM: Artificial Sequence
<220> FEATURE:
<223> OTHER INFORMATION: Homo sapiens small nuclear ribonucleoprotein D2
      isoform 1 epitope

<400> SEQUENCE: 886

Gly Lys Lys Lys Ser Lys Pro Val Asn Lys Asp Arg Tyr Ile Ser Lys
1               5                   10                  15

Met Phe Leu Arg Gly Asp Ser
            20

<210> SEQ ID NO 887
<211> LENGTH: 8
<212> TYPE: PRT
<213> ORGANISM: Artificial Sequence
<220> FEATURE:
<223> OTHER INFORMATION: Homo sapiens small nuclear ribonucleoprotein F
      epitope

<400> SEQUENCE: 887

Glu Glu Glu Glu Asp Gly Glu Met
1               5

<210> SEQ ID NO 888
<211> LENGTH: 8
<212> TYPE: PRT
<213> ORGANISM: Artificial Sequence
<220> FEATURE:
<223> OTHER INFORMATION: Homo sapiens small nuclear ribonucleoprotein G
      epitope

<400> SEQUENCE: 888

Trp Ser Lys Ala His Pro Pro Glu
1               5

<210> SEQ ID NO 889
<211> LENGTH: 9
<212> TYPE: PRT
<213> ORGANISM: Artificial Sequence
<220> FEATURE:
<223> OTHER INFORMATION: Homo sapiens small nuclear ribonucleoprotein
      polypeptide A epitope

<400> SEQUENCE: 889

Ala Met Lys Ile Ser Phe Ala Lys Lys
1               5

<210> SEQ ID NO 890
<211> LENGTH: 7
<212> TYPE: PRT
<213> ORGANISM: Artificial Sequence
<220> FEATURE:
<223> OTHER INFORMATION: Homo sapiens small nuclear ribonucleoprotein
      polypeptide B epitope

<400> SEQUENCE: 890

Pro Pro Gly Met Arg Pro Pro
1               5

<210> SEQ ID NO 891
<211> LENGTH: 12
<212> TYPE: PRT
<213> ORGANISM: Artificial Sequence
<220> FEATURE:
<223> OTHER INFORMATION: Homo sapiens small nuclear ribonucleoprotein
      polypeptide B/B' isoform B epitope
```

```
<400> SEQUENCE: 891

Met Gly Arg Gly Ala Pro Pro Gly Met Met Gly
1               5                   10

<210> SEQ ID NO 892
<211> LENGTH: 7
<212> TYPE: PRT
<213> ORGANISM: Artificial Sequence
<220> FEATURE:
<223> OTHER INFORMATION: Homo sapiens small nuclear ribonucleoprotein
      polypeptide C, isoform CRA_b epitope

<400> SEQUENCE: 892

Ala Pro Gly Met Arg Pro Pro
1               5

<210> SEQ ID NO 893
<211> LENGTH: 15
<212> TYPE: PRT
<213> ORGANISM: Artificial Sequence
<220> FEATURE:
<223> OTHER INFORMATION: Homo sapiens small nuclear ribonucleoprotein
      polypeptide D3 epitope

<400> SEQUENCE: 893

Ala Ala Arg Gly Arg Gly Arg Gly Met Gly Arg Gly Asn Ile Phe
1               5                   10                  15

<210> SEQ ID NO 894
<211> LENGTH: 12
<212> TYPE: PRT
<213> ORGANISM: Artificial Sequence
<220> FEATURE:
<223> OTHER INFORMATION: Homo sapiens small nuclear ribonucleoprotein
      polypeptide N variant epitope

<400> SEQUENCE: 894

Val Gly Arg Ala Thr Pro Pro Pro Gly Ile Met Ala
1               5                   10

<210> SEQ ID NO 895
<211> LENGTH: 23
<212> TYPE: PRT
<213> ORGANISM: Artificial Sequence
<220> FEATURE:
<223> OTHER INFORMATION: Homo sapiens Small nuclear ribonucleoprotein
      Sm D1 epitope

<400> SEQUENCE: 895

Gly Arg Gly Arg Gly Arg Gly Arg Gly Arg Gly Arg Gly Arg Gly Arg
1               5                   10                  15

Gly Arg Gly Gly Pro Arg Arg
            20

<210> SEQ ID NO 896
<211> LENGTH: 8
<212> TYPE: PRT
<213> ORGANISM: Artificial Sequence
<220> FEATURE:
<223> OTHER INFORMATION: Homo sapiens Small nuclear ribonucleoprotein
      Sm D2 epitope

<400> SEQUENCE: 896

Glu Glu Leu Gln Lys Arg Glu Glu
1               5
```

<210> SEQ ID NO 897
<211> LENGTH: 8
<212> TYPE: PRT
<213> ORGANISM: Artificial Sequence
<220> FEATURE:
<223> OTHER INFORMATION: Homo sapiens Small nuclear ribonucleoprotein-
      associated proteins B and B' epitope

<400> SEQUENCE: 897

Arg Gly Val Gly Gly Pro Ser Gln
1               5

<210> SEQ ID NO 898
<211> LENGTH: 10
<212> TYPE: PRT
<213> ORGANISM: Artificial Sequence
<220> FEATURE:
<223> OTHER INFORMATION: Hevea brasiliensis Small rubber particle
      protein epitope

<400> SEQUENCE: 898

Ala Glu Glu Val Glu Glu Glu Arg Leu Lys
1               5                   10

<210> SEQ ID NO 899
<211> LENGTH: 20
<212> TYPE: PRT
<213> ORGANISM: Artificial Sequence
<220> FEATURE:
<223> OTHER INFORMATION: Homo sapiens Smoothelin epitope

<400> SEQUENCE: 899

Gly Ser Thr Met Met Gln Thr Lys Thr Phe Ser Ser Ser Ser Ser
1               5                   10                  15

Lys Lys Met Gly
            20

<210> SEQ ID NO 900
<211> LENGTH: 15
<212> TYPE: PRT
<213> ORGANISM: Artificial Sequence
<220> FEATURE:
<223> OTHER INFORMATION: Homo sapiens snRNP polypeptide B epitope

<400> SEQUENCE: 900

Pro Pro Gly Met Arg Pro Pro Met Gly Pro Met Gly Ile Pro Pro
1               5                   10                  15

<210> SEQ ID NO 901
<211> LENGTH: 14
<212> TYPE: PRT
<213> ORGANISM: Artificial Sequence
<220> FEATURE:
<223> OTHER INFORMATION: Homo sapiens spectrin, alpha, non-erythrocytic
      1 (alpha-fodrin), isoform CRA_e epitope

<400> SEQUENCE: 901

Phe Gln Phe Phe Gln Arg Asp Ala Glu Glu Leu Glu Lys Trp
1               5                   10

<210> SEQ ID NO 902
<211> LENGTH: 43
<212> TYPE: PRT
<213> ORGANISM: Artificial Sequence
<220> FEATURE:
<223> OTHER INFORMATION: Homo sapiens steroid 17-alpha-hydroxylase/17,20
      lyase epitope

```
<400> SEQUENCE: 902

Glu Val Pro Asp Asp Gly Gln Leu Pro Ser Leu Glu Gly Ile Pro Lys
1               5                   10                  15

Val Val Phe Leu Ile Asp Ser Phe Lys Val Lys Ile Lys Val Arg Gln
            20                  25                  30

Ala Trp Arg Glu Ala Gln Ala Glu Gly Ser Thr
        35                  40

<210> SEQ ID NO 903
<211> LENGTH: 15
<212> TYPE: PRT
<213> ORGANISM: Artificial Sequence
<220> FEATURE:
<223> OTHER INFORMATION: Homo sapiens Sucrase-isomaltase, intestinal
      epitope

<400> SEQUENCE: 903

Asp Phe Thr Tyr Asp Gln Val Ala Phe Asn Gly Leu Pro Gln Phe
1               5                   10                  15

<210> SEQ ID NO 904
<211> LENGTH: 12
<212> TYPE: PRT
<213> ORGANISM: Artificial Sequence
<220> FEATURE:
<223> OTHER INFORMATION: Cryptomeria japonica Sugi basic protein
      precursor epitope

<400> SEQUENCE: 904

Asp Ala Leu Thr Leu Arg Thr Ala Thr Asn Ile Trp
1               5                   10

<210> SEQ ID NO 905
<211> LENGTH: 48
<212> TYPE: PRT
<213> ORGANISM: Artificial Sequence
<220> FEATURE:
<223> OTHER INFORMATION: Aspergillus fumigatus Superoxide dismutase
      epitope

<400> SEQUENCE: 905

Tyr Thr Leu Pro Pro Leu Pro Tyr Pro Tyr Asp Ala Leu Gln Pro Tyr
1               5                   10                  15

Ile Ser Gln Gln Ile Met Glu Leu His His Lys Lys His His Gln Thr
            20                  25                  30

Tyr Val Asn Gly Leu Asn Ala Ala Leu Glu Ala Gln Lys Lys Ala Ala
        35                  40                  45

<210> SEQ ID NO 906
<211> LENGTH: 11
<212> TYPE: PRT
<213> ORGANISM: Artificial Sequence
<220> FEATURE:
<223> OTHER INFORMATION: Homo sapiens T cell receptor beta variable 20
      epitope

<400> SEQUENCE: 906

Arg Ser Leu Asp Phe Gln Ala Thr Thr Met Phe
1               5                   10

<210> SEQ ID NO 907
<211> LENGTH: 18
<212> TYPE: PRT
<213> ORGANISM: Artificial Sequence
```

```
<220> FEATURE:
<223> OTHER INFORMATION: Homo sapiens T cell receptor beta variable 5
      epitope

<400> SEQUENCE: 907

Ala Leu Gly Gln Gly Pro Gln Phe Ile Phe Gln Tyr Tyr Glu Glu Glu
1               5                   10                  15

Glu Arg

<210> SEQ ID NO 908
<211> LENGTH: 15
<212> TYPE: PRT
<213> ORGANISM: Artificial Sequence
<220> FEATURE:
<223> OTHER INFORMATION: Homo sapiens Tax1-binding protein 1 epitope

<400> SEQUENCE: 908

Glu Phe Lys Lys Arg Phe Ser Asp Ala Thr Ser Lys Ala His Gln
1               5                   10                  15

<210> SEQ ID NO 909
<211> LENGTH: 16
<212> TYPE: PRT
<213> ORGANISM: Artificial Sequence
<220> FEATURE:
<223> OTHER INFORMATION: Homo sapiens T-cell receptor beta chain epitope

<400> SEQUENCE: 909

Gln Pro Leu Lys Glu Gln Pro Ala Leu Asn Asp Ser Arg Tyr Cys Leu
1               5                   10                  15

<210> SEQ ID NO 910
<211> LENGTH: 16
<212> TYPE: PRT
<213> ORGANISM: Artificial Sequence
<220> FEATURE:
<223> OTHER INFORMATION: Homo sapiens T-cell receptor beta chain C
      region epitope

<400> SEQUENCE: 910

Ser Ala Thr Phe Trp Gln Asn Pro Arg Asn His Phe Arg Cys Gln Val
1               5                   10                  15

<210> SEQ ID NO 911
<211> LENGTH: 16
<212> TYPE: PRT
<213> ORGANISM: Artificial Sequence
<220> FEATURE:
<223> OTHER INFORMATION: Homo sapiens T-cell receptor beta chain V
      region YT35 epitope

<400> SEQUENCE: 911

Cys Lys Pro Ile Ser Gly His Asn Ser Leu Phe Trp Tyr Arg Gln Thr
1               5                   10                  15

<210> SEQ ID NO 912
<211> LENGTH: 10
<212> TYPE: PRT
<213> ORGANISM: Artificial Sequence
<220> FEATURE:
<223> OTHER INFORMATION: Homo sapiens T-cell receptor beta-chain
      (V1-D-J-C) precursor epitope

<400> SEQUENCE: 912

Ser Pro Arg Ser Gly Asp Leu Ser Val Tyr
1               5                   10
```

<210> SEQ ID NO 913
<211> LENGTH: 21
<212> TYPE: PRT
<213> ORGANISM: Artificial Sequence
<220> FEATURE:
<223> OTHER INFORMATION: Homo sapiens TCR V-beta 6.1 epitope

<400> SEQUENCE: 913

Leu Gly Gln Gly Pro Glu Phe Leu Ile Tyr Phe Gln Gly Thr Gly Ala
1               5                   10                  15

Ala Asp Asp Ser Gly
            20

<210> SEQ ID NO 914
<211> LENGTH: 10
<212> TYPE: PRT
<213> ORGANISM: Artificial Sequence
<220> FEATURE:
<223> OTHER INFORMATION: Homo sapiens TCR V-beta 6.3 epitope

<400> SEQUENCE: 914

Asp Pro Ile Ser Gly His Val Ser Leu Phe
1               5                   10

<210> SEQ ID NO 915
<211> LENGTH: 20
<212> TYPE: PRT
<213> ORGANISM: Artificial Sequence
<220> FEATURE:
<223> OTHER INFORMATION: Homo sapiens Thyroglobulin epitope

<400> SEQUENCE: 915

Pro Pro Ala Arg Ala Leu Lys Arg Ser Leu Trp Val Glu Val Asp Leu
1               5                   10                  15

Leu Ile Gly Ser
            20

<210> SEQ ID NO 916
<211> LENGTH: 19
<212> TYPE: PRT
<213> ORGANISM: Artificial Sequence
<220> FEATURE:
<223> OTHER INFORMATION: Homo sapiens Thyroid peroxidase epitope

<400> SEQUENCE: 916

Gly Leu Pro Arg Leu Glu Thr Pro Ala Asp Leu Ser Thr Ala Ile Ala
1               5                   10                  15

Ser Arg Ser

<210> SEQ ID NO 917
<211> LENGTH: 15
<212> TYPE: PRT
<213> ORGANISM: Artificial Sequence
<220> FEATURE:
<223> OTHER INFORMATION: Homo sapiens thyroid stimulating hormone
      receptor epitope

<400> SEQUENCE: 917

Glu Ile Ile Gly Phe Gly Gln Glu Leu Lys Asn Pro Gln Glu Glu
1               5                   10                  15

<210> SEQ ID NO 918
<211> LENGTH: 16
<212> TYPE: PRT
<213> ORGANISM: Artificial Sequence

```
<220> FEATURE:
<223> OTHER INFORMATION: Homo sapiens thyroid stimulating hormone
      receptor variant epitope

<400> SEQUENCE: 918

Glu Glu Gln Glu Asp Glu Ile Ile Gly Phe Gly Gln Glu Leu Lys Asn
1               5                   10                  15

<210> SEQ ID NO 919
<211> LENGTH: 20
<212> TYPE: PRT
<213> ORGANISM: Artificial Sequence
<220> FEATURE:
<223> OTHER INFORMATION: Homo sapiens Thyrotropin receptor epitope

<400> SEQUENCE: 919

Gly Gln Glu Leu Lys Asn Pro Gln Glu Glu Thr Leu Gln Ala Phe Asp
1               5                   10                  15

Ser His Tyr Asp
            20

<210> SEQ ID NO 920
<211> LENGTH: 15
<212> TYPE: PRT
<213> ORGANISM: Artificial Sequence
<220> FEATURE:
<223> OTHER INFORMATION: Homo sapiens transaldolase 1 epitope

<400> SEQUENCE: 920

Ala Ala Ala Gln Met Pro Ala Tyr Gln Glu Leu Val Glu Glu Ala
1               5                   10                  15

<210> SEQ ID NO 921
<211> LENGTH: 20
<212> TYPE: PRT
<213> ORGANISM: Artificial Sequence
<220> FEATURE:
<223> OTHER INFORMATION: Trichophyton rubrum Tri r 2 allergen epitope

<400> SEQUENCE: 921

Asp Cys Asn Gly His Gly Thr His Val Ala Gly Thr Val Gly Gly Thr
1               5                   10                  15

Lys Tyr Gly Leu
            20

<210> SEQ ID NO 922
<211> LENGTH: 15
<212> TYPE: PRT
<213> ORGANISM: Artificial Sequence
<220> FEATURE:
<223> OTHER INFORMATION: Homo sapiens trinucleotide repeat containing
      6A, isoform CRA_b epitope

<400> SEQUENCE: 922

Ala Phe Leu Ser Val Asp His Leu Gly Gly Gly Gly Glu Ser Met
1               5                   10                  15

<210> SEQ ID NO 923
<211> LENGTH: 15
<212> TYPE: PRT
<213> ORGANISM: Artificial Sequence
<220> FEATURE:
<223> OTHER INFORMATION: Homo sapiens trinucleotide repeat containing
      6A, isoform CRA_c epitope

<400> SEQUENCE: 923
```

```
Trp Gly Ser Ser Ser Val Gly Pro Gln Ala Leu Ser Lys Ser Gly
1               5                   10                  15
```

<210> SEQ ID NO 924
<211> LENGTH: 36
<212> TYPE: PRT
<213> ORGANISM: Artificial Sequence
<220> FEATURE:
<223> OTHER INFORMATION: Homo sapiens tripartite motif-containing 67
      epitope

<400> SEQUENCE: 924

```
Leu Gly Gly Gly Ala Gly Gly Gly Asp His Ala Asp Lys Leu Ser
1               5                   10                  15

Leu Tyr Ser Glu Thr Asp Ser Gly Tyr Gly Ser Tyr Thr Pro Ser Leu
                20                  25                  30

Lys Ser Pro Asn
        35
```

<210> SEQ ID NO 925
<211> LENGTH: 10
<212> TYPE: PRT
<213> ORGANISM: Artificial Sequence
<220> FEATURE:
<223> OTHER INFORMATION: Triticum aestivum Triticum aestivum proteins
      epitope

<400> SEQUENCE: 925

```
Leu Pro Gln Gln Gln Ile Pro Gln Gln Pro
1               5                   10
```

<210> SEQ ID NO 926
<211> LENGTH: 9
<212> TYPE: PRT
<213> ORGANISM: Artificial Sequence
<220> FEATURE:
<223> OTHER INFORMATION: Penaeus tropomyosin epitope

<400> SEQUENCE: 926

```
Phe Leu Ala Glu Glu Ala Asp Arg Lys
1               5
```

<210> SEQ ID NO 927
<211> LENGTH: 20
<212> TYPE: PRT
<213> ORGANISM: Artificial Sequence
<220> FEATURE:
<223> OTHER INFORMATION: Homo sapiens TSHR protein epitope

<400> SEQUENCE: 927

```
Cys His Gln Glu Glu Asp Phe Arg Val Thr Cys Lys Asp Ile Gln Arg
1               5                   10                  15

Ile Pro Ser Leu
            20
```

<210> SEQ ID NO 928
<211> LENGTH: 14
<212> TYPE: PRT
<213> ORGANISM: Artificial Sequence
<220> FEATURE:
<223> OTHER INFORMATION: Homo sapiens tubulin beta-6 chain epitope

<400> SEQUENCE: 928

```
Ala Ala Cys Asp Pro Arg His Gly Arg Tyr Leu Thr Val Ala
1               5                   10
```

<210> SEQ ID NO 929
<211> LENGTH: 10
<212> TYPE: PRT
<213> ORGANISM: Artificial Sequence
<220> FEATURE:
<223> OTHER INFORMATION: Homo sapiens tumor necrosis factor ligand
      superfamily member 6 epitope

<400> SEQUENCE: 929

Glu Trp Glu Asp Thr Tyr Gly Ile Val Leu
1               5                   10

<210> SEQ ID NO 930
<211> LENGTH: 20
<212> TYPE: PRT
<213> ORGANISM: Artificial Sequence
<220> FEATURE:
<223> OTHER INFORMATION: Paralichthys olivaceus type 1 collagen alpha
      2 epitope

<400> SEQUENCE: 930

Met Lys Gly Leu Arg Gly His Pro Gly Leu Gln Gly Met Pro Gly Pro
1               5                   10                  15

Ser Gly Pro Ser
            20

<210> SEQ ID NO 931
<211> LENGTH: 10
<212> TYPE: PRT
<213> ORGANISM: Artificial Sequence
<220> FEATURE:
<223> OTHER INFORMATION: Triticum aestivum type 1 non-specific lipid
      transfer protein precursor epitope

<400> SEQUENCE: 931

Ala Arg Gly Thr Pro Leu Lys Cys Gly Val
1               5                   10

<210> SEQ ID NO 932
<211> LENGTH: 5
<212> TYPE: PRT
<213> ORGANISM: Artificial Sequence
<220> FEATURE:
<223> OTHER INFORMATION: Homo sapiens U1 small nuclear ribonucleoprotein
      70 kDa epitope

<400> SEQUENCE: 932

Glu Arg Lys Arg Arg
1               5

<210> SEQ ID NO 933
<211> LENGTH: 26
<212> TYPE: PRT
<213> ORGANISM: Artificial Sequence
<220> FEATURE:
<223> OTHER INFORMATION: Homo sapiens U1 small nuclear ribonucleoprotein
      A epitope

<400> SEQUENCE: 933

Ala Gly Ala Ala Arg Asp Ala Leu Gln Gly Phe Lys Ile Thr Gln Asn
1               5                   10                  15

Asn Ala Met Lys Ile Ser Phe Ala Lys Lys
            20                  25

<210> SEQ ID NO 934
<211> LENGTH: 8

```
<212> TYPE: PRT
<213> ORGANISM: Artificial Sequence
<220> FEATURE:
<223> OTHER INFORMATION: Homo sapiens U1 small nuclear ribonucleoprotein
      C epitope

<400> SEQUENCE: 934

Pro Ala Pro Gly Met Arg Pro Pro
1               5

<210> SEQ ID NO 935
<211> LENGTH: 18
<212> TYPE: PRT
<213> ORGANISM: Artificial Sequence
<220> FEATURE:
<223> OTHER INFORMATION: Anisakis simplex UA3-recognized allergen epitope

<400> SEQUENCE: 935

Met Cys Gln Cys Val Gln Lys Tyr Gly Thr Glu Phe Cys Lys Lys Arg
1               5                   10                  15

Leu Ala

<210> SEQ ID NO 936
<211> LENGTH: 9
<212> TYPE: PRT
<213> ORGANISM: Artificial Sequence
<220> FEATURE:
<223> OTHER INFORMATION: Homo sapiens unnamed protein product epitope

<400> SEQUENCE: 936

Ala Phe Gln Gln Gly Lys Ile Pro Pro
1               5

<210> SEQ ID NO 937
<211> LENGTH: 8
<212> TYPE: PRT
<213> ORGANISM: Artificial Sequence
<220> FEATURE:
<223> OTHER INFORMATION: Juglans nigra vicilin seed storage protein
      epitope

<400> SEQUENCE: 937

Ser Phe Glu Asp Gln Gly Arg Arg
1               5

<210> SEQ ID NO 938
<211> LENGTH: 15
<212> TYPE: PRT
<213> ORGANISM: Artificial Sequence
<220> FEATURE:
<223> OTHER INFORMATION: Anacardium occidentale Vicilin-like protein
      epitope

<400> SEQUENCE: 938

Ala Ile Met Gly Pro Pro Thr Lys Phe Ser Phe Ser Leu Phe Leu
1               5                   10                  15

<210> SEQ ID NO 939
<211> LENGTH: 10
<212> TYPE: PRT
<213> ORGANISM: Artificial Sequence
<220> FEATURE:
<223> OTHER INFORMATION: Juglans regia vicilin-like protein precursor
      epitope

<400> SEQUENCE: 939

Asp Gln Arg Ser Gln Glu Glu Arg Glu Arg
```

```
                       1               5                   10

<210> SEQ ID NO 940
<211> LENGTH: 20
<212> TYPE: PRT
<213> ORGANISM: Artificial Sequence
<220> FEATURE:
<223> OTHER INFORMATION: Homo sapiens Vimentin epitope

<400> SEQUENCE: 940

Arg Leu Arg Ser Ser Val Pro Gly Val Arg Leu Leu Gln Asp Ser Val
1               5                   10                  15

Asp Phe Ser Leu
            20

<210> SEQ ID NO 941
<211> LENGTH: 15
<212> TYPE: PRT
<213> ORGANISM: Artificial Sequence
<220> FEATURE:
<223> OTHER INFORMATION: Homo sapiens von Willebrand factor epitope

<400> SEQUENCE: 941

His Cys Gln Ile Cys His Cys Asp Val Val Asn Leu Thr Cys Glu
1               5                   10                  15

<210> SEQ ID NO 942
<211> LENGTH: 45
<212> TYPE: PRT
<213> ORGANISM: Artificial Sequence
<220> FEATURE:
<223> OTHER INFORMATION: Homo sapiens von Willebrand factor-cleaving
      protease precursor epitope

<400> SEQUENCE: 942

Pro Ser His Phe Gln Gln Ser Cys Leu Gln Ala Leu Glu Pro Gln Ala
1               5                   10                  15

Val Ser Ser Tyr Leu Ser Pro Gly Ala Pro Leu Lys Gly Arg Pro Pro
                20                  25                  30

Ser Pro Gly Phe Gln Arg Gln Arg Gln Arg Gln Arg Arg
            35                  40                  45

<210> SEQ ID NO 943
<211> LENGTH: 15
<212> TYPE: PRT
<213> ORGANISM: Artificial Sequence
<220> FEATURE:
<223> OTHER INFORMATION: Homo sapiens XRCC4 protein epitope

<400> SEQUENCE: 943

Val Ser Lys Asp Asp Ser Ile Ile Ser Ser Leu Asp Val Thr Asp
1               5                   10                  15
```

TOLEROGENIC SYNTHETIC NANOCARRIERS FOR INDUCING REGULATORY B CELLS

RELATED APPLICATIONS

This application is a continuation of U.S. patent application Ser. No. 13/458,179, filed Apr. 27, 2012, now allowed, which claims the benefit under 35 U.S.C. § 119 of U.S. Provisional Patent Application 61/480,946, filed Apr. 29, 2011, 61/513,514, filed Jul. 29, 2011, 61/531,147, filed Sep. 6, 2011, 61/531,153, filed Sep. 6, 2011, 61/531,164, filed Sep. 6, 2011, 61/531,168, filed Sep. 6, 2011, 61/531,175, filed Sep. 6, 2011, 61/531,180, filed Sep. 6, 2011, 61/531,194, filed Sep. 6, 2011, 61/531,204, filed Sep. 6, 2011, 61/531,209, filed Sep. 6, 2011, 61/531,215, filed Sep. 6, 2011, the entire contents of each of which are incorporated herein by reference.

FIELD OF THE INVENTION

This invention relates to methods of administering synthetic nanocarrier compositions with immunosuppressants and B cell and/or MHC Class II-restricted epitopes of an antigen wherein the compositions can generate regulatory B cells, and related compositions. The methods allow for efficient uptake by APCs to shift the immune response in favor of regulatory B cell development specific to antigens.

BACKGROUND OF THE INVENTION

Conventional strategies for generating immunosuppression associated with an undesired immune response are based on broad-acting immunosuppressive drugs. Additionally, in order to maintain immunosuppression, immunosuppressant drug therapy is generally a life-long proposition. Unfortunately, the use of broad-acting immunosuppressants are associated with a risk of severe side effects, such as tumors, infections, nephrotoxicity and metabolic disorders. Accordingly, new immunosuppressant therapies would be beneficial.

SUMMARY OF THE INVENTION

In one aspect, a method comprising administering to a subject a composition that comprises: (i) a first population of synthetic nanocarriers coupled to immunosuppressants, and (ii) a second population of synthetic nanocarriers coupled to comprise B cell and/or MHC Class II-restricted epitopes of an antigen is provided. In another aspect, a method comprising generating antigen-specific regulatory B cells in a subject by administering a composition that comprises (i) a first population of synthetic nanocarriers coupled to immunosuppressants, and (ii) a second population of synthetic nanocarriers coupled to B cell and/or MHC Class II-restricted epitopes of an antigen is provided. In another aspect, a method comprising: administering to a subject a composition according to a protocol that was previously shown to generate antigen-specific regulatory B cells in one or more test subjects; wherein the composition comprises: (i) a first population of synthetic nanocarriers coupled to immunosuppressants, and (ii) a second population of synthetic nanocarriers coupled to B cell and/or MHC Class II-restricted epitopes of an antigen is provided. In one embodiment, the composition is in an amount effective to generate antigen-specific regulatory B cells in the subject. In another embodiment, the composition is administered in an amount effective to generate antigen-specific regulatory B cells in the subject.

In one embodiment, the first population and the second population are the same population. In another embodiment, the first population and second population are different populations.

In another embodiment, the method further comprises providing or identifying the subject.

In another embodiment, the antigen is a therapeutic protein, an autoantigen or an allergen, or is associated with an inflammatory disease, an autoimmune disease, organ or tissue rejection or graft versus host disease.

In another embodiment, the method further comprises assessing the generation of antigen-specific regulatory B cells in the subject prior to and/or after the administration of the composition.

In another embodiment, the subject has or is at risk of having an inflammatory disease, an autoimmune disease, an allergy, organ or tissue rejection or graft versus host disease. In another embodiment, the subject has undergone or will undergo transplantation. In another embodiment, the subject has or is at risk of having an undesired immune response against a therapeutic protein that is being administered or will be administered to the subject.

In another embodiment, one or more maintenance doses of the composition comprising the first population and second population of synthetic nanocarriers is administered to the subject.

In another embodiment, the administering is by intravenous, intraperitoneal, transmucosal, oral, subcutaneous, pulmonary, intranasal, intradermal or intramuscular administration. In another embodiment, the administering is by inhalation or intravenous, subcutaneous or transmucosal administration.

In another embodiment, the method further comprises administering a transplantable graft or therapeutic protein. In another embodiment, the administering of the transplantable graft or therapeutic protein, when the therapeutic protein is provided as one or more cells, is by parenteral, intraarterial, intranasal or intravenous administration or by injection to lymph nodes or anterior chamber of the eye or by local administration to an organ or tissue of interest.

In another embodiment, the method further comprises collecting the generated antigen-specific regulatory B cells.

In another embodiment, the immunosuppressants comprise a statin, an mTOR inhibitor, a TGF-β signaling agent, a corticosteroid, an inhibitor of mitochondrial function, a P38 inhibitor, an NF-κβ inhibitor, an adenosine receptor agonist, a prostaglandin E2 agonist, a phosphodiesterasse 4 inhibitor, an HDAC inhibitor or a proteasome inhibitor. In another embodiment, the mTOR inhibitor is rapamycin or a rapamycin analog.

In another embodiment, the load of the immunosuppressants and/or antigens on average across the first and/or second population of synthetic nanocarriers is between 0.0001% and 50% (weight/weight). In another embodiment, the load of the immunosuppressants and/or antigens on average across the first and/or second population of synthetic nanocarriers is between 0.1% and 10% (weight/weight).

In another embodiment, the synthetic nanocarriers of the first population and/or second population comprise lipid nanoparticles, polymeric nanoparticles, metallic nanoparticles, surfactant-based emulsions, dendrimers, buckyballs, nanowires, virus-like particles or peptide or protein particles. In another embodiment, the synthetic nanocarriers of the first population and/or second population comprise lipid nanoparticles. In another embodiment, the synthetic nanocarriers of the first population and/or second population comprise liposomes. In another embodiment, the synthetic nanocarriers of the first population and/or second population comprise metallic nanoparticles. In another embodiment, the metallic nanoparticles comprise gold nanoparticles. In another embodiment, the synthetic nanocarriers of the first population and/or second population comprise polymeric nanoparticles. In another embodiment, the polymeric nanoparticle comprises polymer that is a non-methoxy-terminated, pluronic polymer. In another embodiment, the polymeric nanoparticles comprise a polyester, a polyester coupled to a polyether, polyamino acid, polycarbonate, polyacetal, polyketal, polysaccharide, polyethyloxazoline or polyethyleneimine. In another embodiment, the polyester comprises a poly(lactic acid), poly(glycolic acid), poly(lactic-co-glycolic acid) or polycaprolactone. In another embodiment, the polymeric nanoparticles comprise a polyester and a polyester coupled to a polyether. In another embodiment, the polyether comprises polyethylene glycol or polypropylene glycol.

In another embodiment, the mean of a particle size distribution obtained using dynamic light scattering of the synthetic nanocarriers of the first and/or second population is a diameter greater than 100 nm. In another embodiment, the diameter is greater than 150 nm. In another embodiment, the diameter is greater than 200 nm. In another embodiment, the diameter is greater than 250 nm. In another embodiment, the diameter is greater than 300 nm. In another embodiment, the aspect ratio of the synthetic nanocarriers of the first population and/or second population is greater than 1:1, 1:1.2, 1:1.5, 1:2, 1:3, 1:5, 1:7 or 1:10.

In another embodiment, the method further comprises making a dosage form comprising the collected antigen-specific regulatory B cells. In another embodiment, the method further comprises making the collected antigen-specific regulatory B cells available or dosage form available to a subject for administration.

In another embodiment, the second population of synthetic nanocarriers are also coupled to antigens that comprise MHC I-restricted epitopes.

In another aspect, a composition comprising the isolated antigen-specific regulatory B cells produced according to any of the methods provided herein is provided.

In another embodiment, the composition further comprises a pharmaceutically acceptable excipient.

In another aspect, a dosage form comprising the any of the compositions provided herein is provided.

In another aspect, a composition comprising isolated antigen-specific regulatory B cells for use in therapy or prophylaxis, said isolated antigen-specific regulatory B cells being obtainable by a process comprising the steps of: (a) generating antigen-specific regulatory B cells in a subject by administering a composition that comprises: (i) a first population of synthetic nanocarriers coupled to immunosuppressants, and (ii) a second population of synthetic nanocarriers coupled to B cell and/or MHC Class II-restricted epitopes of an antigen; and (b) collecting the generated antigen-specific regulatory B cells is provided. In one embodiment, the composition is any of the compositions provided herein or used in any of the methods provided.

In another aspect, a composition comprising: (i) a first population of synthetic nanocarriers coupled to immunosuppressants, and (ii) a second population of synthetic nanocarriers coupled to B cell and/or MHC Class II-restricted epitopes of an antigen, for use in therapy or prophylaxis is provided. In one embodiment, the composition is any of the compositions provided herein or used in any of the methods provided.

In another aspect, any of the compositions provided may be for use in therapy or prophylaxis.

In another aspect, any of the compositions provided may be for use in promoting a tolerogenic immune response or generating antigen-specific regulatory B cells in a subject.

In another aspect, a use of any of the compositions or dosage forms provided for the manufacture of a medicament for use in promoting a tolerogenic immune response or generating antigen-specific regulatory B cells in a subject is provided.

In another embodiment, the composition further comprises a transplantable graft or therapeutic protein.

In another aspect, a dosage form comprising any of the compositions provided is provided.

In another aspect, a method comprising: (i) producing a first population of synthetic nanocarriers coupled to immunosuppressants, and (ii) producing a second population of synthetic nanocarriers coupled to B cell and/or MHC Class II-restricted epitopes of an antigen is provided.

In one embodiment, the composition is in an amount effective to generate antigen-specific regulatory B cells in a subject. In another embodiment, the first population and second population are the same population. In another embodiment, the first population and second population are different populations.

In another embodiment, the method further comprises making a dosage form comprising the first population and second population of synthetic nanocarriers.

In another embodiment, the method further comprises making a composition comprising the first population and second population of synthetic nanocarriers or the dosage form available to a subject for administration.

In another embodiment, the method further comprises assessing the generation of antigen-specific regulatory B cells with a composition comprising the first population and second population of synthetic nanocarriers.

In another embodiment, the first population and second population of synthetic nanocarriers that are produced are as defined in any of the compositions and methods provided herein.

In another aspect, a process for producing a composition or dosage form comprising the steps of: (i) coupling a first population of synthetic nanocarriers to immunosuppressants, and (ii) coupling a second population of synthetic nanocarriers to B cell and/or MHC Class II-restricted epitopes of an antigen is provided. In one embodiment, the composition or dosage form is in an amount effective to generate regulatory B cells in a subject. In one embodiment, the steps are as defined in any of the methods provided herein.

In another aspect, a composition or dosage form obtainable by any of the methods or processes provided herein is provided.

In another embodiment, the methods further comprise including a transplantable graft or therapeutic protein with the collected antigen-specific regulatory B cells or dosage form.

In another embodiment, the first and/or second population of synthetic nanocarriers of any of the compositions or methods provided are also coupled to MHC Class I-restricted epitopes. In an embodiment of any of the compositions and methods provided herein, the antigens comprise substantially no MHC Class I-restricted epitopes.

In an embodiment of any of the compositions and methods provided herein, antigens that are proteins that comprise the aforementioned epitopes can be coupled to the synthetic nanocarriers. In another embodiment, polypeptides or peptides that comprise the aforementioned epitopes but additional amino acids that flank one or both ends of the epitope(s) can be coupled to the synthetic nanocarriers. In another embodiment, the epitopes themselves are coupled to the synthetic nanocarriers.

DETAILED DESCRIPTION OF THE INVENTION

Figure 1:
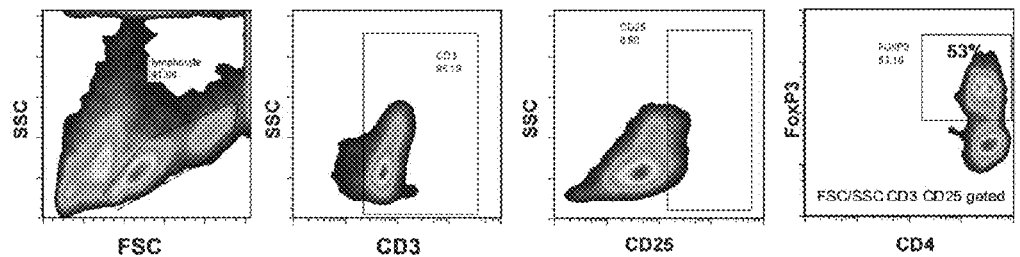
FIG. 1 provides a representative example of a flow cytometric analysis of Treg cells.

Before describing the present invention in detail, it is to be understood that this invention is not limited to particularly exemplified materials or process parameters as such may, of course, vary. It is also to be understood that the terminology used herein is for the purpose of describing particular embodiments of the invention only, and is not intended to be limiting of the use of alternative terminology to describe the present invention.

All publications, patents and patent applications cited herein, whether supra or infra, are hereby incorporated by reference in their entirety for all purposes.

As used in this specification and the appended claims, the singular forms "a," "an" and "the" include plural referents unless the content clearly dictates otherwise. For example, reference to "a polymer" includes a mixture of two or more such molecules or a mixture of differing molecular weights of a single polymer species, reference to "a synthetic nanocarrier" includes a mixture of two or more such synthetic nanocarriers or a plurality of such synthetic nanocarriers, reference to "a DNA molecule" includes a mixture of two or more such DNA molecules or a plurality of such DNA molecules, reference to "an immunosuppressant" includes a mixture of two or more such materials or a plurality of an immunosuppressant molecules, and the like.

As used herein, the term "comprise" or variations thereof such as "comprises" or "comprising" are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein, the term "comprising" is inclusive and does not exclude additional, unrecited integers or method/process steps.

In embodiments of any of the compositions and methods provided herein, "comprising" may be replaced with "consisting essentially of" or "consisting of". The phrase "consisting essentially of" is used herein to require the specified integer(s) or steps as well as those which do not materially affect the character or function of the claimed invention. As used herein, the term "consisting" is used to indicate the presence of the recited integer (e.g. a feature, element, characteristic, property, method/process step or limitation) or group of integers (e.g. features, element, characteristics, properties, method/process steps or limitations) alone.

A. Introduction

Delivering immunosuppressants and antigens via synthetic nanocarrier compositions that comprise B cell and/or MHC Class II-restricted epitopes more directly at the sites of action in cells of interest, in particular APCs, can stimulate regulatory B cells and result in beneficial tolerogenic immune responses specific to the antigens. As shown in the examples, synthetic nanocarrier compositions were found to be effective in generating CD24+ B cells that produce IL-10 and TGF-β and also recognize antigen, which speaks to the antigen-specific nature of the response. Additionally, the same synthetic nanocarrier compositions were found to decrease IgE production, which suggests a downstream result of the regulatory B cell production. The compositions provided, without being bound to any particular theory, can provide tolerogenic immune effects directly as a result of the recognition of epitopes, which may cause the generation of the regulatory cells, the switching of B cells to a regulatory phenotype, etc. The tolerogenic immune responses may also be a result of the production of cytokines and/or the production of other regulatory immune cells stimulated by such cytokines. The generation of regulatory B cells can also lead to downstream tolerogenic effects. For example, regulatory B cells can reduce the proliferative capacity of effector T cells, such as CD4+ T cells, and/or enhance FoxP3 and CTLA-4 expression in regulatory T cells. Regulatory B cells can also produce the regulatory cytokine, IL-10. In embodiments, the antigen-specific itDCs provided herein may have these effects, for example, on a subject.

The generation of such regulatory B cells evidences the ability of the compositions of the invention to generate antigen-specific tolerogenic immune responses that can have utility in the treatment or prophylaxis of a variety of diseases, disorders or conditions. Therefore, this invention is useful, for example, to promote tolerogenic immune responses in subjects who have or are at risk of having an allergy, autoimmune disease, an inflammatory disease, organ or tissue rejection or graft versus host disease. This invention is also useful for promoting tolerogenic immune responses in subjects who have undergone or will undergo transplantation. This invention is also useful for promoting tolerogenic immune responses in subjects that have received, are receiving or will receive a therapeutic protein against which undesired immune responses are generated or are expected to be generated. The present invention, in some embodiments, prevents or suppresses undesired immune responses that may neutralize the beneficial effect of certain therapeutic treatments.

The inventors have unexpectedly and surprisingly discovered that the problems and limitations noted above can be overcome by practicing the invention disclosed herein. In particular, the inventors have unexpectedly discovered that it is possible to provide synthetic nanocarrier compositions, and related methods, that induce a tolerogenic immune response through the increase in the number and/or activity of regulatory B cells. The method described herein include administering to a subject a composition that comprises (i) a first population of synthetic nanocarriers coupled to immunosuppressants, and (ii) a second population of synthetic nanocarriers coupled to B cell and/or MHC Class II-restricted epitopes of an antigen. Preferably, the composition is in an amount effective to effect antigen-specific regulatory B cell proliferation and/or activity in the subject. In another aspect, a method comprising generating antigen-specific regulatory B cells in a subject by administering a composition that comprises (i) a first population of synthetic nanocarriers coupled to immunosuppressants, and (ii) a second population of synthetic nanocarriers coupled to B cell and/or MHC Class II-restricted epitopes of an antigen is provided. In another aspect, a method comprising administering to a subject a composition according to a protocol that was previously shown to generate antigen-specific regulatory B cells in one or more test subjects wherein the composition comprises (i) a first population of synthetic nanocarriers coupled to immunosuppressants, and (ii) a second population of synthetic nanocarriers coupled to B cell and/or MHC Class II-restricted epitopes of an antigen is provided.

Transplantable grafts, therapeutic proteins, etc. may also be administered to the subjects as provided herein. Such compositions may be administered to a subject prior to, concomitantly with or after the administration of the first and second populations of synthetic nanocarriers. Such additional agents may or may not be coupled to the first or second population of synthetic nanocarriers or another population of synthetic nanocarriers. In embodiments, the compositions provided may also be administered as one or more maintenance doses to a subject. In such embodiments, the compositions provided are administered such that the generation of a desired immune response is maintained or an undesired immune response is reduced for a certain length of time. Examples of such lengths of time are provided elsewhere herein.

In another aspect, a composition comprising isolated antigen-specific regulatory B cells produced according to any of the methods provided is provided. In yet another aspect, the compositions comprising the first population and second population of synthetic nanocarriers are also provided. In embodiments, the compositions further comprise a transplantable graft or a therapeutic protein that may or may not be coupled to the first or second population of synthetic nanocarriers or another population of synthetic nanocarriers.

In another aspect, dosage forms of any of the compositions herein are provided. Such dosage forms may be administered to a subject, for example, one in need of antigen-specific regulatory B cell generation.

In yet another aspect, a method of (i) producing a first population of synthetic nanocarriers coupled to immunosuppressants, and (ii) producing a second population of synthetic nanocarriers coupled to B cell and/or MHC Class II-restricted epitopes of an antigen is provided. In one embodiment, the method further comprises producing a dosage form comprising the first and second populations of synthetic nanocarriers. In another embodiment, the method further comprises ensuring the second population of synthetic nanocarriers comprises B cell and/or MHC Class II-restricted epitopes of an antigen. In one embodiment, the presence of a B cell epitope and/or MHC Class II-restricted can be confirmed by the ability of such epitope to stimulate immune responses such as antibody production or B cell proliferation and/or activity for the B cell epitopes and CD4+ T cell immune responses for the MHC Class II-restricted epitopes. Methods for determining these activity are well known to those of ordinary skill in the art or are provided elsewhere herein. In still another embodiment, the method further comprises assessing the generation of regulatory B cells with a composition or dosage form comprising the first population and second population of synthetic nanocarriers. In one embodiment, this assessment is performed in vitro. In another embodiment, this assessment is performed in vivo, such as with a sample obtained from a subject. In yet another embodiment, the method further comprises making a composition comprising the first population and second population of synthetic nanocarriers or the dosage form available to a subject for administration.

In another aspect, the compositions or dosage forms produced by any of the methods provided herein are also provided.

The invention will now be described in more detail below.

B. Definitions

"Administering" or "administration" means providing a material to a subject in a manner that is pharmacologically useful.

"Allergens" are any substances that can cause an undesired (e.g., a Type 1 hypersensitive) immune response (i.e., an allergic response or reaction) in a subject. Allergens include, but are not limited to, plant allergens (e.g., pollen, ragweed allergen), insect allergens, insect sting allergens (e.g., bee sting allergens), animal allergens (e.g., pet allergens, such as animal dander or cat Fel d 1 antigen), latex allergens, mold allergens, fungal allergens, cosmetic allergens, drug allergens, food allergens, dust, insect venom, viruses, bacteria, etc. Food allergens include, but are not limited to milk allergens, egg allergens, nut allergens (e.g., peanut or tree nut allergens, etc. (e.g., walnuts, cashews, etc.)), fish allergens, shellfish allergens, soy allergens, legume allergens, seed allergens and wheat allergens. Insect sting allergens include allergens that are or are associated with bee stings, wasp stings, hornet stings, yellow jacket stings, etc. Insect allergens also include house dust mite allergens (e.g., Der P1 antigen) and cockroach allergens. Drug allergens include allergens that are or are associated with antibiotics, NSAIDs, anaesthetics, etc. Pollen allergens include grass allergens, tree allergens, weed allergens, flower allergens, etc. Subjects that develop or are at risk of developing an undesired immune response to any of the allergens provided herein may be treated with any of the compositions and methods provided herein. Subjects that may be treated with any of the compositions and methods provided also include those who have or are at risk of having an allergy to any of the allergens provided.

An "allergy" also referred to herein as an "allergic condition," is any condition where there is an undesired (e.g., a Type 1 hypersensitive) immune response (i.e., allergic response or reaction) to a substance. Such substances are referred to herein as allergens. Allergies or allergic conditions include, but are not limited to, allergic asthma, hay fever, hives, eczema, plant allergies, bee sting allergies, pet allergies, latex allergies, mold allergies, cosmetic allergies, food allergies, allergic rhinitis or coryza, topic allergic reactions, anaphylaxis, atopic dermatitis, hypersensitivity reactions and other allergic conditions. The allergic reaction may be the result of an immune reaction to any allergen. In some embodiments, the allergy is a food allergy. Food allergies include, but are not limited to, milk allergies, egg allergies, nut allergies, fish allergies, shellfish allergies, soy allergies or wheat allergies.

"Amount effective" in the context of a composition or dosage form for administration to a subject refers to an amount of the composition or dosage form that produces one or more desired immune responses in the subject, for example, the generation of regulatory B cells. Therefore, in some embodiments, an amount effective is any amount of a composition provided herein that produces such a desired immune response. This amount can be for in vitro or in vivo purposes. For in vivo purposes, the amount can be one that a clinician would believe may have a clinical benefit for a subject in need of antigen-specific tolerization. Such subjects include those that have or are at risk of having an inflammatory disease, an autoimmune disease, an allergy, organ or tissue rejection or graft versus host disease. Such subjects also include those that have undergone or will undergo transplantation. Such subjects further include those that have experienced, are experiencing or are expected to experience an undesired immune response against a therapeutic protein. Other subjects include those described elsewhere herein.

Amounts effective can involve only reducing the level of an undesired immune response, although in some embodiments, it involves preventing an undesired immune response altogether. Amounts effective can also involve delaying the occurrence of an undesired immune response. Amounts effective can also involve generating a desired immune response. An amount that is effective can also be an amount of a composition provided herein that produces a desired therapeutic endpoint or a desired therapeutic result. Amounts effective, preferably, result in a tolerogenic immune response in a subject to an antigen. Preferably, the amounts effective result in the increased proliferation and/or activity of regulatory B cells. The achievement of any of the foregoing can be monitored by routine methods.

In some embodiments of any of the compositions and methods provided, the amount effective is one in which the desired immune response persists in the subject for at least 1 week, at least 2 weeks, at least 1 month, at least 2 months, at least 3 months, at least 4 months, at least 5 months, at least 6 months, at least 9 months, at least 1 year, at least 2 years, at least 5 years, or longer. In other embodiments of any of the compositions and methods provided, the amount effective is one which produces a measurable desired immune response, for example, a measurable decrease in an immune response (e.g., to a specific antigen), for at least 1 week, at least 2 weeks, at least 1 month, at least 2 months, at least 3 months, at least 4 months, at least 5 months, at least 6 months, at least 9 months, at least 1 year, at least 2 years, at least 5 years, or longer.

Amounts effective will depend, of course, on the particular subject being treated; the severity of a condition, disease or disorder; the individual patient parameters including age, physical condition, size and weight; the duration of the treatment; the nature of concurrent therapy (if any); the specific route of administration and like factors within the knowledge and expertise of the health practitioner. These factors are well known to those of ordinary skill in the art and can be addressed with no more than routine experimentation. It is generally preferred that a maximum dose be used, that is, the highest safe dose according to sound medical judgment. It will be understood by those of ordinary skill in the art, however, that a patient may insist upon a lower dose or tolerable dose for medical reasons, psychological reasons or for virtually any other reason.

In general, doses of the immunosuppressants and/or antigens in the compositions of the invention can range from about 10 µg/kg to about 100,000 µg/kg. In some embodiments, the doses can range from about 0.1 mg/kg to about 100 mg/kg. In still other embodiments, the doses can range from about 0.1 mg/kg to about 25 mg/kg, about 25 mg/kg to about 50 mg/kg, about 50 mg/kg to about 75 mg/kg or about 75 mg/kg to about 100 mg/kg. Alternatively, the dose can be administered based on the number of synthetic nanocarriers that provide the desired amount of immunosuppressants and/or antigens. For example, useful doses include greater than $10^6$, $10^7$, $10^8$, $10^9$ or $10^{10}$ synthetic nanocarriers per dose. Other examples of useful doses include from about $1 \times 10^6$ to about $1 \times 10^{10}$, about $1 \times 10^7$ to about $1 \times 10^9$ or about $1 \times 10^8$ to about $1 \times 10^9$ synthetic nanocarriers per dose.

"Antigen" means a B cell antigen or T cell antigen. "Type(s) of antigens" means molecules that share the same, or substantially the same, antigenic characteristics. In some embodiments, antigens may be proteins, polypeptides, peptides, lipoproteins, glycolipids, polynucleotides, polysaccharides or are contained or expressed in cells. In some embodiments, such as when the antigens are not well defined or characterized, the antigens may be contained within a cell or tissue preparation, cell debris, cell exosomes, conditioned media, etc. An antigen can be combined with the synthetic nanocarriers in the same form as what a subject is exposed to that causes an undesired immune response but may also be a fragment or derivative thereof. When a fragment or derivative, however, a desired immune response to the form encountered by such a subject is the preferable result with the compositions and methods provided. Preferably, the antigens comprise epitopes such that regulatory B cells are generated, recruited or activated with the compositions provided herein. Whether or not this occurs can be established through measurement of cytokine production (e.g., IL-10) and/or regulatory B cell proliferation using conventional techniques.

"Antigen-specific" refers to any immune response that results from the presence of the antigen, or portion thereof, or that generates molecules that specifically recognize or bind the antigen. For example, where the immune response is antigen-specific antibody production, antibodies are produced that specifically bind the antigen. As another example, where the immune response is antigen-specific regulatory B cell proliferation and/or activity, the proliferation and/or activity results from recognition of the antigen, or portion thereof, alone or in complex with MHC molecules, by B cells, etc.

"Antigens associated" with a disease, disorder or condition provided herein are antigens that can generate an undesired immune response against, as a result of, or in conjunction with the disease, disorder or condition; the cause of the disease, disorder or condition (or a symptom or effect thereof); and/or can generate an undesired immune response that is a symptom, result or effect of the disease, disorder or condition. Preferably, in some embodiments, the use of an antigen associated with a disease, disorder or condition, etc. in the compositions and methods provided herein will lead to a tolerogenic immune response against the antigen and/or the cells, by, on or in which the antigen is expressed. The antigens can be in the same form as expressed in a subject with the disease, disorder or condition but may also be a fragment or derivative thereof. When a fragment or derivative, however, a desired immune response to the form expressed in such a subject is the preferable result with the compositions and methods provided.

In one embodiment, the antigen is an antigen associated with an inflammatory disease, autoimmune disease, organ or tissue rejection or graft versus host disease. Such antigens include autoantigens, such as myelin basic protein, collagen (e.g., collagen type 11), human cartilage gp 39, chromogranin A, gp130-RAPS, proteolipid protein, fibrillarin, nuclear proteins, nucleolar proteins (e.g., small nucleolar protein), thyroid stimulating factor receptor, histones, glycoprotein gp 70, ribosomal proteins, pyruvate dehydrogenase dehydrolipoamide acetyltransferase, hair follicle antigens, human tropomyosin isoform 5, mitochondrial proteins, pancreatic β-cell proteins, myelin oligodendrocyte glycoprotein, insulin, glutamic acid decarboxylase (GAD), gluten, and fragments or derivatives thereof. Other autoantigens are provided in Table 1 below.

Antigens also include those associated with organ or tissue rejection. Examples of such antigens include, but are not limited to, antigens from allogeneic cells, e.g., antigens from an allogeneic cell extract and antigens from other cells, such as endothelial cell antigens.

Antigens also include those associated with an allergy. Such antigens include the allergens described elsewhere herein.

Antigens also include those associated with a transplantable graft. Such antigens are associated with a transplantable graft, or an undesired immune response in a recipient of a transplantable graft that is generated as a result of the introduction of the transplantable graft in the recipient, that can be presented for recognition by cells of the immune system and that can generate an undesired immune response. Transplant antigens include those associated with organ or tissue rejection or graft versus host disease. Transplant antigens may be obtained or derived from cells of a biological material or from information related to a transplantable graft. Transplant antigens generally include proteins, polypeptides, peptides, lipoproteins, glycolipids, polynucleotides or are contained or expressed in cells. Information related to a transplantable graft is any information about a transplantable graft that can be used to obtain or derive transplant antigens. Such information includes information about antigens that would be expected to be present in or on cells of a transplantable graft such as, for example, sequence information, types or classes of antigens and/or their MHC Class I, MHC Class II or B cell presentation restrictions. Such information may also include information about the type of transplantable graft (e.g, autograft, allograft, xenograft), the molecular and cellular composition of the graft, the bodily location from which the graft is derived or to which the graft to be transplanted (e.g., whole or partial organ, skin, bone, nerves, tendon, neurons, blood vessels, fat, cornea, etc.).

Antigens also include antigens associated with a therapeutic protein that can be presented for recognition by cells of the immune system and that can generate an undesired immune response against the therapeutic protein. Therapeutic protein antigens generally include proteins, polypeptides, peptides, lipoproteins, or are contained or expressed in, by or on cells.

Antigens, can be antigens that are fully defined or characterized. However, in some embodiments, an antigen is not fully defined or characterized. Antigens, therefore, also include those that are contained within a cell or tissue preparation, cell debris, cell exosome or conditioned media and can be delivered in such form in some embodiments.

"Assessing an immune response" refers to any measurement or determination of the level, presence or absence, reduction, increase in, etc. of an immune response in vitro or in vivo. Such measurements or determinations may be performed on one or more samples obtained from a subject. Such assessing can be performed with any of the methods provided herein or otherwise known in the art.

An "at risk" subject is one in which a health practitioner believes has a chance of having a disease, disorder or condition as provided herein or is one a health practitioner believes has a chance of experiencing an undesired immune response as provided herein.

An "autoimmune disease" is any disease where the immune system mounts an undesired immune response against self (e.g., one or more autoantigens). In some embodiments, an autoimmune disease comprises an aberrant destruction of cells of the body as part of the self-targeted immune response. In some embodiments, the destruction of self manifests in the malfunction of an organ, for example, the colon or pancreas. Examples of autoimmune diseases are described elsewhere herein. Additional autoimmune diseases will be known to those of skill in the art and the invention is not limited in this respect.

"Average", as used herein, refers to the arithmetic mean unless otherwise noted.

"B cell antigen" means any antigen that triggers an immune response in a B cell (e.g., an antigen that is specifically recognized by a B cell or a receptor thereon). In some embodiments, an antigen that is a T cell antigen is also a B cell antigen. In other embodiments, the T cell antigen is not also a B cell antigen. B cell antigens include, but are not limited to proteins, peptides, small molecules, and carbohydrates. In some embodiments, the B cell antigen comprises a non-protein antigen (i.e., not a protein or peptide antigen). In some embodiments, the B cell antigen comprises a autoantigen. In other embodiments, the B cell antigen is obtained or derived from an allergen, autoantigen, therapeutic protein, or transplantable graft.

"Concomitantly" means administering two or more substances to a subject in a manner that is correlated in time, preferably sufficiently correlated in time so as to provide a modulation in an immune response. In embodiments, concomitant administration may occur through administration of two or more substances in the same dosage form. In other embodiments, concomitant administration may encompass administration of two or more substances in different dosage forms, but within a specified period of time, preferably within 1 month, more preferably within 1 week, still more preferably within 1 day, and even more preferably within 1 hour.

"Couple" or "Coupled" or "Couples" (and the like) means to chemically associate one entity (for example a moiety) with another. In some embodiments, the coupling is covalent, meaning that the coupling occurs in the context of the presence of a covalent bond between the two entities. In non-covalent embodiments, the non-covalent coupling is mediated by non-covalent interactions including but not limited to charge interactions, affinity interactions, metal coordination, physical adsorption, host-guest interactions, hydrophobic interactions, TT stacking interactions, hydrogen bonding interactions, van der Waals interactions, magnetic interactions, electrostatic interactions, dipole-dipole interactions, and/or combinations thereof. In embodiments, encapsulation is a form of coupling.

"Derived" means prepared from a material or information related to a material but is not "obtained" from the material. Such materials may be substantially modified or processed forms of materials taken directly from a biological material. Such materials also include materials produced from information related to a biological material.

"Dosage form" means a pharmacologically and/or immunologically active material in a medium, carrier, vehicle, or device suitable for administration to a subject.

"Encapsulate" means to enclose at least a portion of a substance within a synthetic nanocarrier. In some embodiments, a substance is enclosed completely within a synthetic nanocarrier. In other embodiments, most or all of a substance that is encapsulated is not exposed to the local environment external to the synthetic nanocarrier. In other embodiments, no more than 50%, 40%, 30%, 20%, 10% or 5% (weight/weight) is exposed to the local environment.

Encapsulation is distinct from absorption, which places most or all of a substance on a surface of a synthetic nanocarrier, and leaves the substance exposed to the local environment external to the synthetic nanocarrier.

"Epitope", also known as an antigenic determinant, is the part of an antigen that is recognized by the immune system, specifically by, for example, antibodies, B cells, or T cells. As used herein, "MHC Class I-restricted epitopes" are epitopes that are presented to immune cells by MHC class I molecules found on nucleated cells. "MHC Class II-restricted epitopes" are epitopes that are presented to immune cells by MHC class II molecules found on antigen-presenting cells (APCs), for example, on professional antigen-presenting immune cells, such as on macrophages, B cells, and dendritic cells, or on non-hematopoietic cells, such as hepatocytes. "B cell epitopes" are molecular structures that are recognized by antibodies or B cells. In some embodiments, the epitope itself is an antigen.

A number of epitopes are known to those of skill in the art, and exemplary epitopes suitable according to some aspects of this invention include, but are not limited to those listed in the Immune Epitope Database (www.immuneepitope.org, Vita R, Zarebski L, Greenbaum J A, Emami H, Hoof I, Salimi N, Damle R, Sette A, Peters B. The immune epitope database 2.0. Nucleic Acids Res. 2010 January; 38(Database issue):D854-62; the entire contents of which as well as all database entries of IEDB version 2.4, August 2011, and particularly all epitopes disclosed therein, are incorporated herein by reference). Epitopes can also be identified with publicly available algorithms, for example, the algorithms described in Wang P, Sidney J, Kim Y, Sette A, Lund O, Nielsen M, Peters B. 2010. peptide binding predictions for HLA DR, DP and DQ molecules. BMC Bioinformatics 2010, 11:568; Wang P, Sidney J, Dow C, Mothé B, Sette A, Peters B. 2008. A systematic assessment of MHC class II peptide binding predictions and evaluation of a consensus approach. PLoS Comput Biol. 4(4):e1000048; Nielsen M, Lund O. 2009. NN-align. An artificial neural network-based alignment algorithm for MHC class II peptide binding prediction. BMC Bioinformatics. 10:296; Nielsen M, Lundegaard C, Lund O. 2007. Prediction of MHC class II binding affinity using SMM-align, a novel stabilization matrix alignment method. BMC Bioinformatics. 8:238; Bui H H, Sidney J, Peters B, Sathiamurthy M, Sinichi A, Purton K A, Mothé B R, Chisari F V, Watkins D I, Sette A. 2005. Immunogenetics. 57:304-314; Sturniolo T, Bono E, Ding J, Raddrizzani L, Tuereci O, Sahin U, Braxenthaler M, Gallazzi F, Protti M P, Sinigaglia F, Hammer J. 1999. Generation of tissue-specific and promiscuous HLA ligand databases using DNA microarrays and virtual HLA class II matrices. Nat Biotechnol. 17(6):555-561; Nielsen M, Lundegaard C, Worning P, Lauemoller S L, Lamberth K, Buus S, Brunak S, Lund O. 2003. Reliable prediction of T-cell epitopes using neural networks with novel sequence representations. Protein Sci 12:1007-1017; Bui H H, Sidney J, Peters B, Sathiamurthy M, Sinichi A, Purton K A, Mothe B R, Chisari F V, Watkins D I, Sette A. 2005. Automated generation and evaluation of specific MHC binding predictive tools: ARB matrix applications. Immunogenetics 57:304-314; Peters B, Sette A. 2005. Generating quantitative models describing the sequence specificity of biological processes with the stabilized matrix method. BMC Bioinformatics 6:132; Chou P Y, Fasman G D. 1978. Prediction of the secondary structure of proteins from their amino acid sequence. Adv Enzymol Relat Areas Mol Biol 47:45-148; Emini E A, Hughes J V, Perlow D S, Boger J. 1985. Induction of hepatitis A virus-neutralizing antibody by a virus-specific synthetic peptide. J Virol 55:836-839; Karplus P A, Schulz G E. 1985. Prediction of chain flexibility in proteins. Naturwissenschaften 72:212-213; Kolaskar A S, Tongaonkar P C. 1990. A semi-empirical method for prediction of antigenic determinants on protein antigens. FEBS Lett 276:172-174; Parker J M, Guo D, Hodges R S. 1986. New hydrophilicity scale derived from high-performance liquid chromatography peptide retention data: correlation of predicted surface residues with antigenicity and X-ray-derived accessible sites. Biochemistry 25:5425-5432; Larsen J E, Lund O, Nielsen M. 2006. Improved method for predicting linear B-cell epitopes. Immunome Res 2:2; Ponomarenko J V, Bourne P E. 2007. Antibody-protein interactions: benchmark datasets and prediction tools evaluation. BMC Struct Biol 7:64; Haste Andersen P, Nielsen M, Lund O. 2006. Prediction of residues in discontinuous B-cell epitopes using protein 3D structures. Protein Sci 15:2558-2567; Ponomarenko J V, Bui H, Li W, Fusseder N, Bourne P E, Sette A, Peters B. 2008. ElliPro: a new structure-based tool for the prediction of antibody epitopes. BMC Bioinformatics 9:514; Nielsen M, Lundegaard C, Blicher T, Peters B, Sette A, Justesen S, Buus S, and Lund O. 2008. PLoS Comput Biol. 4(7)e1000107. Quantitative predictions of peptide binding to any HLA-DR molecule of known sequence: NetMHCIIpan; the entire contents of each of which are incorporated herein by reference for disclosure of methods and algorithms for the identification of epitopes.

Other examples of epitopes include any of the MHC Class I-restricted, MHC Class II-restricted and B cell epitopes as provided as SEQ ID NOs: 1-943. Without wishing to being bound by any particular theory, MHC Class I-restricted epitopes include those set forth in SEQ ID NOs: 1-186, MHC Class II-restricted epitopes include those set forth in SEQ ID NOs: 187-537, and B cell epitopes include those set forth in SEQ ID NOs: 538-943. These epitopes include MHC Class I-restricted autoantigens, MHC Class II-restricted epitopes of allergens and B cell epitopes of autoantigens and allergens.

"Generating" means causing an action, such as an immune response (e.g., a tolerogenic immune response) to occur, either directly oneself or indirectly, such as, but not limited to, an unrelated third party that takes an action through reliance on one's words or deeds.

"Identifying" is any action or set of actions that allows a clinician to recognize a subject as one who may benefit from the methods and compositions provided herein. Preferably, the identified subject is one who is in need of a tolerogenic immune response as provided herein. The action or set of actions may be either directly oneself or indirectly, such as, but not limited to, an unrelated third party that takes an action through reliance on one's words or deeds.

"Immunosuppressant" means a compound that causes an APC to have an immunosuppressive (e.g., tolerogenic effect). An immunosuppressive effect generally refers to the production or expression of cytokines or other factors by the APC that reduces, inhibits or prevents an undesired immune response but can also include the production or expression of cytokines or other factors by the APC that increases, stimulates or promotes a desired immune response. When the APC results in an immunosuppressive effect on immune cells that recognize an antigen presented by the APC, the immunosuppressive effect is said to be specific to the presented antigen. Such effect is also referred to herein as a tolerogenic effect. Without being bound by any particular theory, it is thought that the immunosuppressive or tolerogenic effect is a result of the immunosuppressant being delivered to the APC, preferably in the presence of an antigen (e.g., an administered antigen or one that is already present in vivo). Accordingly, the immunosuppressant includes compounds that provide a tolerogenic immune response to an antigen that may or may not be provided in the same composition or a different composition. In one embodiment, the immunosuppressant is one that causes an APC to promote a regulatory phenotype in one or more immune effector cells. For example, the regulatory phenotype may be characterized by the production, induction, stimulation or recruitment of Treg cells, etc. This may be the result of the conversion of B cells to a regulatory phenotype. This may also be the result of the stimulation, recruitment, etc. of regulatory B cells. This may also be the result of induction of FoxP3 in other immune cells, such as macrophages and iNKT cells. In one embodiment, the immunosuppressant is one that affects the response of the APC after it processes an antigen. In another embodiment, the immunosuppressant is not one that interferes with the processing of the antigen. In a further embodiment, the immunosuppressant is not an apoptotic-signaling molecule. In another embodiment, the immunosuppressant is not a phospholipid.

Immunosuppressants include, but are not limited to, statins; mTOR inhibitors, such as rapamycin or a rapamycin analog; TGF-β signaling agents; TGF-β receptor agonists; histone deacetylase inhibitors, such as Trichostatin A; corticosteroids; inhibitors of mitochondrial function, such as rotenone; P38 inhibitors; NF-κβ inhibitors, such as 6Bio, Dexamethasone, TCPA-1, IKK VII; adenosine receptor agonists; prostaglandin E2 agonists (PGE2), such as Misoprostol; phosphodiesterase inhibitors, such as phosphodiesterase 4 inhibitor (PDE4), such as Rolipram; proteasome inhibitors; kinase inhibitors; G-protein coupled receptor agonists; G-protein coupled receptor antagonists; glucocorticoids; retinoids; cytokine inhibitors; cytokine receptor inhibitors; cytokine receptor activators; peroxisome proliferator-activated receptor antagonists; peroxisome proliferator-activated receptor agonists; histone deacetylase inhibitors; calcineurin inhibitors; phosphatase inhibitors; PI3 KB inhibitors, such as TGX-221; autophagy inhibitors, such as 3-Methyladenine; aryl hydrocarbon receptor inhibitors; proteasome inhibitor I (PSI); and oxidized ATPs, such as P2X receptor blockers. Immunosuppressants also include IDO, vitamin D3, cyclosporins, such as cyclosporine A, aryl hydrocarbon receptor inhibitors, resveratrol, azathiopurine (Aza), 6-mercaptopurine (6-MP), 6-thioguanine (6-TG), FK506, sanglifehrin A, salmeterol, mycophenolate mofetil (MMF), aspirin and other COX inhibitors, niflumic acid, estriol and triptolide. In embodiments, the immunosuppressant may comprise any of the agents provided herein.

The immunosuppressant can be a compound that directly provides the immunosuppressive (e.g., tolerogenic) effect on APCs or it can be a compound that provides the immunosuppressive (e.g., tolerogenic) effect indirectly (i.e., after being processed in some way after administration). Immunosuppressants, therefore, include prodrug forms of any of the compounds provided herein.

Immunosuppressants also include nucleic acids that encode the peptides, polypeptides or proteins provided herein that result in an immunosuppressive (e.g., tolerogenic) immune response. In embodiments, therefore, the immunosuppressant is a nucleic acid that encodes a peptide, polypeptide or protein that results in an immunosuppressive (e.g., tolerogenic) immune response, and it is the nucleic acid that is coupled to the synthetic nanocarrier.

The nucleic acid may be DNA or RNA, such as mRNA. In embodiments, the inventive compositions comprise a complement, such as a full-length complement, or a degenerate (due to degeneracy of the genetic code) of any of the nucleic acids provided herein. In embodiments, the nucleic acid is an expression vector that can be transcribed when transfected into a cell line. In embodiments, the expression vector may comprise a plasmid, retrovirus, or an adenovirus amongst others. Nucleic acids can be isolated or synthesized using standard molecular biology approaches, for example by using a polymerase chain reaction to produce a nucleic acid fragment, which is then purified and cloned into an expression vector. Additional techniques useful in the practice of this invention may be found in Current Protocols in Molecular Biology 2007 by John Wiley and Sons, Inc.; Molecular Cloning: A Laboratory Manual (Third Edition) Joseph Sambrook, Peter MacCallum Cancer Institute, Melbourne, Australia; David Russell, University of Texas Southwestern Medical Center, Dallas, Cold Spring Harbor.

In embodiments, the immunosuppressants provided herein are coupled to synthetic nanocarriers. In preferable embodiments, the immunosuppressant is an element that is in addition to the material that makes up the structure of the synthetic nanocarrier. For example, in one embodiment, where the synthetic nanocarrier is made up of one or more polymers, the immunosuppressant is a compound that is in addition and coupled to the one or more polymers. As another example, in one embodiment, where the synthetic nanocarrier is made up of one or more lipids, the immunosuppressant is again in addition and coupled to the one or more lipids. In embodiments, such as where the material of the synthetic nanocarrier also results in an immunosuppressive (e.g., tolerogenic) effect, the immunosuppressant is an element present in addition to the material of the synthetic nanocarrier that results in an immunosuppressive (e.g., tolerogenic) effect.

Other exemplary immunosuppressants include, but are not limited, small molecule drugs, natural products, antibodies (e.g., antibodies against CD20, CD3, CD4), biologics-based drugs, carbohydrate-based drugs, nanoparticles, liposomes, RNAi, antisense nucleic acids, aptamers, methotrexate, NSAIDs; fingolimod; natalizumab; alemtuzumab; anti-CD3; tacrolimus (FK506), etc. Further immunosuppressants, are known to those of skill in the art, and the invention is not limited in this respect.

"Inflammatory disease" means any disease, disorder or condition in which undesired inflammation occurs.

"Load" of the immunosuppressant or antigen is the amount of the immunosuppressant or antigen coupled to a synthetic nanocarrier based on the total weight of materials in an entire synthetic nanocarrier (weight/weight). Generally, the load is calculated as an average across a population of synthetic nanocarriers. In one embodiment, the load of the immunosuppressant on average across the first population of synthetic nanocarriers is between 0.0001% and 50%. In another embodiment, the load of the antigen on average across the first and/or second population of synthetic nanocarriers is between 0.0001% and 50%. In yet another embodiment, the load of the immunosuppressant and/or antigen is between 0.01% and 20%. In a further embodiment, the load of the immunosuppressant and/or antigen is between 0.1% and 10%. In still a further embodiment, the load of the immunosuppressant and/or antigen is between 1% and 10%. In yet another embodiment, the load of the immunosuppressant and/or the antigen is at least 0.1%, at least 0.2%, at least 0.3%, at least 0.4%, at least 0.5%, at least 0.6%, at least 0.7%, at least 0.8%, at least 0.9%, at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19% or at least 20% on average across a population of synthetic nanocarriers. In yet a further embodiment, the load of the immunosuppressant and/or the antigen is 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19% or 20% on average across a population of synthetic nanocarriers. In some embodiments of the above embodiments, the load of the immunosuppressant and/or the antigen is no more than 25% on average across a population of synthetic nanocarriers. In embodiments, the load is calculated as described in the Examples.

In embodiments of any of the compositions and methods provided, the load may be calculated as follows: Approximately 3 mg of synthetic nanocarriers are collected and centrifuged to separate supernatant from synthetic nanocarrier pellet. Acetonitrile is added to the pellet, and the sample is sonicated and centrifuged to remove any insoluble material. The supernatant and pellet are injected on RP-HPLC and absorbance is read at 278 nm. The μg found in the pellet is used to calculate % entrapped (load), μg in supernatant and pellet are used to calculate total μg recovered.

"Maintenance dose" refers to a dose that is administered to a subject, after an initial dose has resulted in an immunosuppressive (e.g., tolerogenic) response in a subject, to sustain a desired immunosuppressive (e.g., tolerogenic) response. A maintenance dose, for example, can be one that maintains the tolerogenic effect achieved after the initial dose, prevents an undesired immune response in the subject, or prevents the subject becoming a subject at risk of experiencing an undesired immune response, including an undesired level of an immune response. In some embodiments, the maintenance dose is one that is sufficient to sustain an appropriate level of a desired immune response. In some embodiments, the maintenance dose is one that is sufficient to sustain an appropriate antibody titre or level of regulatory B cell number and/or activity necessary to sustain a tolerogenic immune response or defend against a challenge with an agent that results in an undesired immune response.

"Maximum dimension of a synthetic nanocarrier" means the largest dimension of a nanocarrier measured along any axis of the synthetic nanocarrier. "Minimum dimension of a synthetic nanocarrier" means the smallest dimension of a synthetic nanocarrier measured along any axis of the synthetic nanocarrier. For example, for a spheroidal synthetic nanocarrier, the maximum and minimum dimension of a synthetic nanocarrier would be substantially identical, and would be the size of its diameter. Similarly, for a cuboidal synthetic nanocarrier, the minimum dimension of a synthetic nanocarrier would be the smallest of its height, width or length, while the maximum dimension of a synthetic nanocarrier would be the largest of its height, width or length. In an embodiment, a minimum dimension of at least 75%, preferably at least 80%, more preferably at least 90%, of the synthetic nanocarriers in a sample, based on the total number of synthetic nanocarriers in the sample, is equal to or greater than 100 nm. In an embodiment, a maximum dimension of at least 75%, preferably at least 80%, more preferably at least 90%, of the synthetic nanocarriers in a sample, based on the total number of synthetic nanocarriers in the sample, is equal to or less than 5 μm. Preferably, a minimum dimension of at least 75%, preferably at least 80%, more preferably at least 90%, of the synthetic nanocarriers in a sample, based on the total number of synthetic nanocarriers in the sample, is greater than 110 nm, more preferably greater than 120 nm, more preferably greater than 130 nm, and more preferably still greater than 150 nm. Aspects ratios of the maximum and minimum dimensions of inventive synthetic nanocarriers may vary depending on the embodiment. For instance, aspect ratios of the maximum to minimum dimensions of the synthetic nanocarriers may vary from 1:1 to 1,000,000:1, preferably from 1:1 to 100,000:1, more preferably from 1:1 to 10,000:1, more preferably from 1:1 to 1000:1, still more preferably from 1:1 to 100:1, and yet more preferably from 1:1 to 10:1. Preferably, a maximum dimension of at least 75%, preferably at least 80%, more preferably at least 90%, of the synthetic nanocarriers in a sample, based on the total number of synthetic nanocarriers in the sample is equal to or less than 3 μm, more preferably equal to or less than 2 μm, more preferably equal to or less than 1 μm, more preferably equal to or less than 800 nm, more preferably equal to or less than 600 nm, and more preferably still equal to or less than 500 nm. In preferred embodiments, a minimum dimension of at least 75%, preferably at least 80%, more preferably at least 90%, of the synthetic nanocarriers in a sample, based on the total number of synthetic nanocarriers in the sample, is equal to or greater than 100 nm, more preferably equal to or greater than 120 nm, more preferably equal to or greater than 130 nm, more preferably equal to or greater than 140 nm, and more preferably still equal to or greater than 150 nm. Measurement of synthetic nanocarrier dimensions (e.g., diameter) is obtained by suspending the synthetic nanocarriers in a liquid (usually aqueous) media and using dynamic light scattering (DLS) (e.g. using a Brookhaven ZetaPALS instrument). For example, a suspension of synthetic nanocarriers can be diluted from an aqueous buffer into purified water to achieve a final synthetic nanocarrier suspension concentration of approximately 0.01 to 0.1 mg/mL. The diluted suspension may be prepared directly inside, or transferred to, a suitable cuvette for DLS analysis. The cuvette may then be placed in the DLS, allowed to equilibrate to the controlled temperature, and then scanned for sufficient time to acquire a stable and reproducible distribution based on appropriate inputs for viscosity of the medium and refractive indicies of the sample. The effective diameter, or mean of the distribution, is then reported. "Dimension" or "size" or "diameter" of synthetic nanocarriers means the mean of a particle size distribution obtained using dynamic light scattering.

"MHC" refers to major histocompatibility complex, a large genomic region or gene family found in most vertebrates that encodes MHC molecules that display fragments or epitopes of processed proteins on the cell surface. The presentation of MHC:peptide on cell surfaces allows for surveillance by immune cells, usually a T cell. There are two general classes of MHC molecules: Class I and Class II. Generally, Class I MHC molecules are found on nucleated cells and present peptides to cytotoxic T cells. Class II MHC molecules are found on certain immune cells, chiefly macrophages, B cells and dendritic cells, collectively known as professional APCs. The best-known genes in the MHC region are the subset that encodes antigen-presenting proteins on the cell surface. In humans, these genes are referred to as human leukocyte antigen (HLA) genes.

"Non-methoxy-terminated polymer" means a polymer that has at least one terminus that ends with a moiety other than methoxy. In some embodiments, the polymer has at least two termini that ends with a moiety other than methoxy. In other embodiments, the polymer has no termini that ends with methoxy. "Non-methoxy-terminated, pluronic polymer" means a polymer other than a linear pluronic polymer with methoxy at both termini. Polymeric nanoparticles as provided herein can comprise non-methoxy-terminated polymers or non-methoxy-terminated, pluronic polymers.

"Obtained" means taken directly from a material and used with substantially no modification and/or processing.

"Pharmaceutically acceptable excipient" means a pharmacologically inactive material used together with the recited synthetic nanocarriers to formulate the inventive compositions. Pharmaceutically acceptable excipients comprise a variety of materials known in the art, including but not limited to saccharides (such as glucose, lactose, and the like), preservatives such as antimicrobial agents, reconstitution aids, colorants, saline (such as phosphate buffered saline), and buffers.

"Protocol" refers to any dosing regimen of one or more substances to a subject. A dosing regimen may include the amount, frequency and/or mode of administration. In some embodiments, such a protocol may be used to administer one or more compositions of the invention to one or more test subjects. Immune responses in these test subject can then be assessed to determine whether or not the protocol was effective in reducing an undesired immune response or generating a desired immune response (e.g., the promotion of a tolerogenic effect). Any other therapeutic and/or prophylactic effect may also be assessed instead of or in addition to the aforementioned immune responses. Whether or not a protocol had a desired effect can be determined using any of the methods provided herein or otherwise known in the art. For example, a population of cells may be obtained from a subject to which a composition provided herein has been administered according to a specific protocol in order to determine whether or not specific immune cells, cytokines, antibodies, etc. were reduced, generated, activated, etc. Useful methods for detecting the presence and/or number of immune cells include, but are not limited to, flow cytometric methods (e.g., FACS) and immunohistochemistry methods. Antibodies and other binding agents for specific staining of immune cell markers, are commercially available. Such kits typically include staining reagents for multiple antigens that allow for FACS-based detection, separation and/or quantitation of a desired cell population from a heterogeneous population of cells.

"Providing a subject" is any action or set of actions that causes a clinician to come in contact with a subject and administer a composition provided herein thereto or to perform a method provided herein thereupon. Preferably, the subject is one who is in need of a tolerogenic immune response as provided herein. The action or set of actions may be either directly oneself or indirectly, such as, but not limited to, an unrelated third party that takes an action through reliance on one's words or deeds.

"Regulatory B cells" are art-recognized and refer to a type of tolerogenic B cells or that have suppressive regulatory function. Surface markers and chemokine profiles characteristic of regulatory B cells, as well as subsets of regulatory B cells (e.g., IL-10 producing Bregs) are known to those of skill in the art (e.g., as described in DiLillo et al., B10 cells and regulatory B cells balance immune response during inflammation, autoimmunity, and cancer, Ann N. Y. Acad. Sci. 1183 (2010) 38-57, ISSN 0077-8923; the entire contents of which are incorporated herein by reference). The presence of regulatory B cells can be determined by intracellular staining for IL-10 by flow cytometry. For example, after treatment B cells can be stained for surface markers, then fixed and permeabilized and stained for intracellular IL-10 and analyzed by flow cytometry.

"Subject" means animals, including warm blooded mammals such as humans and primates; avians; domestic household or farm animals such as cats, dogs, sheep, goats, cattle, horses and pigs; laboratory animals such as mice, rats and guinea pigs; fish; reptiles; zoo and wild animals; and the like.

"Substantially no MHC Class I-restricted epitopes" refers to the absence of MHC Class I-restricted epitopes in an amount that by itself, within the context of the antigen, in conjunction with a carrier or in conjunction with an inventive composition stimulates substantial activation of an immune response specific to the epitope presented in the Class I context. In embodiments, a composition with substantially no MHC I-restricted epitopes does not contain a measurable amount of MHC Class I-restricted epitopes of an antigen. In other embodiments, such a composition may comprise a measurable amount of MHC Class I-restricted epitopes of an antigen but said amount is not effective to generate a measurable cytotoxic T cell immune response (by itself, within the context of the antigen, in conjunction with a carrier or in conjunction with an inventive composition) or is not effective to generate a significant measurable cytotoxic T cell immune response (by itself, within the context of the antigen, in conjunction with a carrier or in conjunction with an inventive composition). In some embodiments, a significant measurable cytotoxic T cell immune response is one that produces or would be expected to produce an adverse clinical result in a subject. In other embodiments, a significant measurable cytotoxic T cell immune response is one that is greater than the level of the same type of immune response produced by a control antigen (e.g., one known not to comprise MHC Class I-restricted epitopes or to stimulate cytotoxic T cell immune responses).

In embodiments, the compositions do not comprise MHC Class I-restricted epitopes (by itself, within the context of the antigen, in conjunction with a carrier or in conjunction with an inventive composition) that generate antigen-specific cytotoxic T cell immune responses or an undesired level thereof. In some embodiments, to ensure that a composition does not comprise such epitopes, antigens are selected such that they do not comprise MHC Class I-restricted epitopes for coupling to the synthetic nanocarriers as provided herein. In other embodiments, to ensure that a composition does not comprise such epitopes, synthetic nanocarriers coupled to antigen are produced and tested for cytotoxic T cell immune responses. The appropriate synthetic nanocarriers may then be selected.

"Synthetic nanocarrier(s)" means a discrete object that is not found in nature, and that possesses at least one dimension that is less than or equal to 5 microns in size. Albumin nanoparticles are generally included as synthetic nanocarriers, however in certain embodiments the synthetic nanocarriers do not comprise albumin nanoparticles. In embodiments, inventive synthetic nanocarriers do not comprise chitosan. In other embodiments, inventive synthetic nanocarriers are not lipid-based nanoparticles. In further embodiments, inventive synthetic nanocarriers do not comprise a phospholipid.

A synthetic nanocarrier can be, but is not limited to, one or a plurality of lipid-based nanoparticles (also referred to herein as lipid nanoparticles, i.e., nanoparticles where the majority of the material that makes up their structure are lipids), polymeric nanoparticles, metallic nanoparticles, surfactant-based emulsions, dendrimers, buckyballs, nanowires, virus-like particles (i.e., particles that are primarily made up of viral structural proteins but that are not infectious or have low infectivity), peptide or protein-based particles (also referred to herein as protein particles, i.e., particles where the majority of the material that makes up their structure are peptides or proteins) (such as albumin nanoparticles) and/or nanoparticles that are developed using a combination of nanomaterials such as lipid-polymer nanoparticles. Synthetic nanocarriers may be a variety of different shapes, including but not limited to spheroidal, cuboidal, pyramidal, oblong, cylindrical, toroidal, and the like. Synthetic nanocarriers according to the invention comprise one or more surfaces. Exemplary synthetic nanocarriers that can be adapted for use in the practice of the present invention comprise: (1) the biodegradable nanoparticles disclosed in U.S. Pat. No. 5,543,158 to Gref et al., (2) the polymeric nanoparticles of Published US Patent Application 20060002852 to Saltzman et al., (3) the lithographically constructed nanoparticles of Published US Patent Application 20090028910 to DeSimone et al., (4) the disclosure of WO 2009/051837 to von Andrian et al., (5) the nanoparticles disclosed in Published US Patent Application 2008/0145441 to Penades et al., (6) the protein nanoparticles disclosed in Published US Patent Application 20090226525 to de los Rios et al., (7) the virus-like particles disclosed in published US Patent Application 20060222652 to Sebbel et al., (8) the nucleic acid coupled virus-like particles disclosed in published US Patent Application 20060251677 to Bachmann et al., (9) the virus-like particles disclosed in WO2010047839A1 or WO2009106999A2, (10) the nanoprecipitated nanoparticles disclosed in P. Paolicelli et al., "Surface-modified PLGA-based Nanoparticles that can Efficiently Associate and Deliver Virus-like Particles" Nanomedicine. 5(6):843-853 (2010), or (11) apoptotic cells, apoptotic bodies or the synthetic or semisynthetic mimics disclosed in U.S. Publication 2002/0086049. In embodiments, synthetic nanocarriers may possess an aspect ratio greater than 1:1, 1:1.2, 1:1.5, 1:2, 1:3, 1:5, 1:7, or greater than 1:10.

Synthetic nanocarriers according to the invention that have a minimum dimension of equal to or less than about 100 nm, preferably equal to or less than 100 nm, do not comprise a surface with hydroxyl groups that activate complement or alternatively comprise a surface that consists essentially of moieties that are not hydroxyl groups that activate complement. In a preferred embodiment, synthetic nanocarriers according to the invention that have a minimum dimension of equal to or less than about 100 nm, preferably equal to or less than 100 nm, do not comprise a surface that substantially activates complement or alternatively comprise a surface that consists essentially of moieties that do not substantially activate complement. In a more preferred embodiment, synthetic nanocarriers according to the invention that have a minimum dimension of equal to or less than about 100 nm, preferably equal to or less than 100 nm, do not comprise a surface that activates complement or alternatively comprise a surface that consists essentially of moieties that do not activate complement. In embodiments, synthetic nanocarriers exclude virus-like particles. In embodiments, synthetic nanocarriers may possess an aspect ratio greater than 1:1, 1:1.2, 1:1.5, 1:2, 1:3, 1:5, 1:7, or greater than 1:10.

"T cell antigen" means a CD4+ T-cell antigen or CD8+ cell antigen. "CD4+ T-cell antigen" means any antigen that is recognized by and triggers an immune response in a CD4+ T-cell e.g., an antigen that is specifically recognized by a T-cell receptor on a CD4+ T cell via presentation of the antigen or portion thereof bound to a Class II major histocompatability complex molecule (MHC). "CD8+ T cell antigen" means any antigen that is recognized by and triggers an immune response in a CD8+ T-cell e.g., an antigen that is specifically recognized by a T-cell receptor on a CD8+ T cell via presentation of the antigen or portion thereof bound to a Class I major histocompatability complex molecule (MHC). In some embodiments, an antigen that is a T cell antigen is also a B cell antigen. In other embodiments, the T cell antigen is not also a B cell antigen. T cell antigens generally are proteins or peptides.

A "therapeutic protein" refers to any protein or protein-based therapy that may be administered to a subject and have a therapeutic effect. Such therapies include protein replacement and protein supplementation therapies. Such therapies also include the administration of exogenous or foreign protein, antibody therapies, and cell or cell-based therapies. Therapeutic proteins include enzymes, enzyme cofactors, hormones, blood clotting factors, cytokines, growth factors, monoclonal antibodies and polyclonal antibodies. Examples of other therapeutic proteins are provided elsewhere herein. Therapeutic proteins may be produced in, on or by cells and may be obtained from such cells or administered in the form of such cells. In embodiments, the therapeutic protein is produced in, on or by mammalian cells, insect cells, yeast cells, bacteria cells, plant cells, transgenic animal cells, transgenic plant cells, etc. The therapeutic protein may be recombinantly produced in such cells. The therapeutic protein may be produced in, on or by a virally transformed cell. The therapeutic protein may also be produced in, on or by autologous cells that have been transfected, transduced or otherwise manipulated to express it. Alternatively, the therapeutic protein may be administered as a nucleic acid or by introducing a nucleic acid into a virus, VLP, liposome, etc. Alternatively, the therapeutic protein may be obtained from such forms and administered as the therapeutic protein itself. Subjects, therefore, include any subject that has received, is receiving or will receive any of the foregoing. Such subject includes subjects that have received, is receiving or will receive gene therapy, autologous cells that have been transfected, transduced or otherwise manipulated to express a therapeutic protein, polypeptide or peptide; or cells that express a therapeutic protein, polypeptide or peptide.

"Therapeutic protein antigen" means an antigen that is associated with a therapeutic protein that can be, or a portion of which can be, presented for recognition by cells of the immune system and can generate an undesired immune response (e.g., the production of therapeutic protein-specific antibodies) against the therapeutic protein. Therapeutic protein antigens generally include proteins, polypeptides, peptides, lipoproteins, or are contained or expressed in, on or by cells.

"Tolerogenic immune response" means any immune response that can lead to immune suppression specific to an antigen or a cell, tissue, organ, etc. that expresses such an antigen. Such immune responses include any reduction, delay or inhibition in an undesired immune response specific to the antigen or cell, tissue, organ, etc. that expresses such antigen. Such immune responses also include any stimulation, production, induction, promotion or recruitment in a desired immune response specific to the antigen or cell, tissue, organ, etc. that expresses such antigen. Tolerogenic immune responses, therefore, include the absence of or reduction in an undesired immune response to an antigen that can be mediated by antigen reactive cells as well as the presence or promotion of suppressive cells. Tolerogenic immune responses as provided herein include immunological tolerance. To "generate a tolerogenic immune response"

refers to the generation of any of the foregoing immune responses specific to an antigen or cell, tissue, organ, etc. that expresses such antigen. The tolerogenic immune response can be the result of MHC Class I-restricted presentation and/or MHC Class II-restricted presentation and/or B cell presentation and/or presentation by CD1d, etc. In embodiments, to ensure that a composition comprises desired epitopes, antigens are selected such that they comprise such epitopes for coupling to the synthetic nanocarriers as provided herein. In other embodiments, to ensure that a composition comprises such epitopes, synthetic nanocarriers coupled to an antigen are produced and tested for regulatory B cell immune responses, such as activation or generation. The appropriate synthetic nanocarriers may then be selected.

Tolerogenic immune responses include any reduction, delay or inhibition in CD4+ T cell, CD8+ T cell or B cell proliferation and/or activity. Tolerogenic immune responses also include a reduction in antigen-specific antibody production. Tolerogenic immune responses can also include any response that leads to the stimulation, induction, production or recruitment of regulatory cells, such as CD4+ Treg cells, CD8+ Treg cells, Breg cells, etc. In some embodiments, the tolerogenic immune response, is one that results in the conversion to a regulatory phenotype characterized by the production, induction, stimulation or recruitment of regulatory cells.

Tolerogenic immune responses also include any response that leads to the stimulation, production or recruitment of CD4+ Treg cells and/or CD8+ Treg cells. CD4+ Treg cells can express the transcription factor FoxP3 and inhibit inflammatory responses and auto-immune inflammatory diseases (Human regulatory T cells in autoimmune diseases. Cvetanovich G L, Hafler D A. Curr Opin Immunol. 2010 December; 22(6):753-60. Regulatory T cells and autoimmunity. Vila J, Isaacs J D, Anderson A E. Curr Opin Hematol. 2009 July; 16(4):274-9). Such cells also suppress T-cell help to B-cells and induce tolerance to both self and foreign antigens (Therapeutic approaches to allergy and autoimmunity based on FoxP3+ regulatory T-cell activation and expansion. Miyara M, Wing K, Sakaguchi S. J Allergy Clin Immunol. 2009 April; 123(4):749-55). CD4+ Treg cells recognize antigen when presented by Class II proteins on APCs. CD8+ Treg cells, which recognize antigen presented by Class I (and Qa-1), can also suppress T-cell help to B-cells and result in activation of antigen-specific suppression inducing tolerance to both self and foreign antigens. Disruption of the interaction of Qa-1 with CD8+ Treg cells has been shown to dysregulate immune responses and results in the development of auto-antibody formation and an auto-immune lethal systemic-lupus-erythematosus (Kim et al., Nature. 2010 Sep. 16, 467 (7313): 328-32). CD8+ Treg cells have also been shown to inhibit models of autoimmune inflammatory diseases including rheumatoid arthritis and colitis (CD4+CD25+ regulatory T cells in autoimmune arthritis. Oh S, Rankin A L, Caton A J. Immunol Rev. 2010 January; 233(1):97-111. Regulatory T cells in inflammatory bowel disease. Boden E K, Snapper S B. Curr Opin Gastroenterol. 2008 November; 24(6):733-41). In some embodiments, the compositions provided can effectively result in both types of responses (CD4+ Treg and CD8+ Treg). In other embodiments, FoxP3 can be induced in other immune cells, such as macrophages, iNKT cells, etc., and the compositions provided herein can result in one or more of these responses as well.

Tolerogenic immune responses also include, but are not limited to, the induction of regulatory cytokines, such as Treg cytokines; induction of inhibitory cytokines; the inhibition of inflammatory cytokines (e.g., IL-4, IL-1b, IL-5, TNF-α, IL-6, GM-CSF, IFN-γ, IL-2, IL-9, IL-12, IL-17, IL-18, IL-21, IL-22, IL-23, M-CSF, C reactive protein, acute phase protein, chemokines (e.g., MCP-1, RANTES, MIP-1α, MIP-1β, MIG, ITAC or IP-10), the production of anti-inflammatory cytokines (e.g., IL-4, IL-13, IL-10, etc.), chemokines (e.g., CCL-2, CXCL8), proteases (e.g., MMP-3, MMP-9), leukotrienes (e.g., CysLT-1, CysLT-2), prostaglandins (e.g., PGE2) or histamines; the inhibition of polarization to a Th17, Th1 or Th2 immune response; the inhibition of effector cell-specific cytokines: Th17 (e.g., IL-17, IL-25), Th1 (IFN-γ), Th2 (e.g., IL-4, IL-13); the inhibition of Th1-, Th2- or TH17-specific transcription factors; the inhibition of proliferation of effector T cells; the induction of apoptosis of effector T cells; the induction of tolerogenic dendritic cell-specific genes, the induction of FoxP3 expression, the inhibition of IgE induction or IgE-mediated immune responses; the inhibition of antibody responses (e.g., antigen-specific antibody production); the inhibition of T helper cell response; the production of TGF-β and/or IL-10; the inhibition of effector function of autoantibodies (e.g., inhibition in the depletion of cells, cell or tissue damage or complement activation); etc.

Any of the foregoing may be measured in vivo in one or more animal models or may be measured in vitro. One of ordinary skill in the art is familiar with such in vivo or in vitro measurements. Undesired immune responses or tolerogenic immune responses can be monitored using, for example, methods of assessing immune cell number and/or function, tetramer analysis, ELISPOT, flow cytometry-based analysis of cytokine expression, cytokine secretion, cytokine expression profiling, gene expression profiling, protein expression profiling, analysis of cell surface markers, PCR-based detection of immune cell receptor gene usage (see T. Clay et al., "Assays for Monitoring Cellular Immune Response to Active Immunotherapy of Cancer" Clinical Cancer Research 7:1127-1135 (2001)), etc. Undesired immune responses or tolerogenic immune responses may also be monitored using, for example, methods of assessing protein levels in plasma or serum, immune cell proliferation and/or functional assays, etc. In some embodiments, tolerogenic immune responses can be monitored by assessing the induction of FoxP3. In addition, specific methods are described in more detail in the Examples.

Preferably, tolerogenic immune responses lead to the inhibition of the development, progression or pathology of the diseases, disorders or conditions described herein. Whether or not the inventive compositions can lead to the inhibition of the development, progression or pathology of the diseases, disorders or conditions described herein can be measured with animal models of such diseases, disorders or conditions. In some embodiments, the reduction of an undesired immune response or generation of a tolerogenic immune response may be assessed by determining clinical endpoints, clinical efficacy, clinical symptoms, disease biomarkers and/or clinical scores. Undesired immune responses or tolerogenic immune responses can also be assessed with diagnostic tests to assess the presence or absence of a disease, disorder or condition as provided herein. Undesired or desired immune responses can further be assessed by methods of measuring therapeutic proteins levels and/or function in a subject. In embodiments, methods for monitoring or assessing undesired allergic responses include assessing an allergic response in a subject by skin reactivity and/or allergen-specific antibody production.

In some embodiments, monitoring or assessing the generation of an undesired immune response or a tolerogenic immune response in a subject can be prior to the administration of a composition of synthetic nanocarriers provided herein and/or prior to administration of a transplantable graft or therapeutic protein or exposure to an allergen. In other embodiments, assessing the generation of an undesired immune response or tolerogenic immune response can be after administration of a composition of synthetic nanocarriers provided herein and/or after administration of a transplantable graft or therapeutic protein or exposure to an allergen. In some embodiments, the assessment is done after administration of the composition of synthetic nanocarriers, but prior to administration of a transplantable graft or therapeutic protein or exposure to an allergen. In other embodiments, the assessment is done after administration of a transplantable graft or therapeutic protein or exposure to an allergen, but prior to administration of the composition. In still other embodiments, the assessment is performed prior to both the administration of the synthetic nanocarriers and administration of a transplantable graft or therapeutic protein or exposure to an allergen, while in yet other embodiments the assessment is performed after both the administration of synthetic nanocarriers and the administration of a transplantable graft or therapeutic protein or exposure to an allergen. In further embodiments, the assessment is performed both prior to and after the administration of the synthetic nanocarriers and/or administration of a transplantable graft or therapeutic protein or exposure to an allergen. In still other embodiments, the assessment is performed more than once on the subject to determine that a desirable immune state is maintained in the subject, such as a subject that has or is at risk of having an inflammatory disease, an autoimmune disease, an allergy, organ or tissue rejection or graft versus host disease. Other subjects include those that have undergone or will undergo transplantation as well as those that have received, are receiving or will receive a therapeutic protein against which they have experienced, are experiencing or are expected to experience an undesired immune response.

An antibody response can be assessed by determining one or more antibody titers. "Antibody titer" means a measurable level of antibody production. Methods for measuring antibody titers are known in the art and include Enzyme-linked Immunosorbent Assay (ELISA). In embodiments, the antibody response can be quantitated, for example, as the number of antibodies, concentration of antibodies or titer. The values can be absolute or they can be relative. Assays for quantifying an antibody response include antibody capture assays, enzyme-linked immunosorbent assays (ELISAs), inhibition liquid phase absorption assays (ILPAAs), rocket immunoelectrophoresis (RIE) assays and line immunoelectrophoresis (LIE) assays. When an antibody response is compared to another antibody response the same type of quantitative value (e.g., titer) and method of measurement (e.g., ELISA) is preferably used to make the comparison.

An ELISA method for measuring an antibody titer, for example, a typical sandwich ELISA, may consist of the following steps (i) preparing an ELISA-plate coating material such that the antibody target of interest is coupled to a substrate polymer or other suitable material (ii) preparing the coating material in an aqueous solution (such as PBS) and delivering the coating material solution to the wells of a multiwell plate for overnight deposition of the coating onto the multiwell plate (iii) thoroughly washing the multiwell plate with wash buffer (such as 0.05% Tween-20 in PBS) to remove excess coating material (iv) blocking the plate for nonspecific binding by applying a diluent solution (such as 10% fetal bovine serum in PBS), (v) washing the blocking/diluent solution from the plate with wash buffer (vi) diluting the serum sample(s) containing antibodies and appropriate standards (positive controls) with diluent as required to obtain a concentration that suitably saturates the ELISA response (vii) serially diluting the plasma samples on the multiwell plate such to cover a range of concentrations suitable for generating an ELISA response curve (viii) incubating the plate to provide for antibody-target binding (ix) washing the plate with wash buffer to remove antibodies not bound to antigen (x) adding an appropriate concentration of a secondary detection antibody in same diluent such as a biotin-coupled detection antibody capable of binding the primary antibody (xi) incubating the plate with the applied detection antibody, followed by washing with wash buffer (xii) adding an enzyme such as streptavidin-HRP (horse radish peroxidase) that will bind to biotin found on biotinylated antibodies and incubating (xiii) washing the multiwell plate (xiv) adding substrate(s) (such as TMB solution) to the plate (xv) applying a stop solution (such as 2N sulfuric acid) when color development is complete (xvi) reading optical density of the plate wells at a specific wavelength for the substrate (450 nm with subtraction of readings at 570 nm) (xvi) applying a suitable multiparameter curve fit to the data and defining half-maximal effective concentration (EC50) as the concentration on the curve at which half the maximum OD value for the plate standards is achieved.

A "transplantable graft" refers to a biological material, such as cells, tissues and organs (in whole or in part) that can be administered to a subject. Transplantable grafts may be autografts, allografts, or xenografts of, for example, a biological material such as an organ, tissue, skin, bone, nerves, tendon, neurons, blood vessels, fat, cornea, pluripotent cells, differentiated cells (obtained or derived in vivo or in vitro), etc. In some embodiments, a transplantable graft is formed, for example, from cartilage, bone, extracellular matrix, or collagen matrices. Transplantable grafts may also be single cells, suspensions of cells and cells in tissues and organs that can be transplanted. Transplantable cells typically have a therapeutic function, for example, a function that is lacking or diminished in a recipient subject. Some non-limiting examples of transplantable cells are β-cells, hepatocytes, hematopoietic stem cells, neuronal stem cells, neurons, glial cells, or myelinating cells. Transplantable cells can be cells that are unmodified, for example, cells obtained from a donor subject and usable in transplantation without any genetic or epigenetic modifications. In other embodiments, transplantable cells can be modified cells, for example, cells obtained from a subject having a genetic defect, in which the genetic defect has been corrected, or cells that are derived from reprogrammed cells, for example, differentiated cells derived from cells obtained from a subject.

"Transplantation" refers to the process of transferring (moving) a transplantable graft into a recipient subject (e.g., from a donor subject, from an in vitro source (e.g., differentiated autologous or heterologous native or induced pluripotent cells)) and/or from one bodily location to another bodily location in the same subject.

"Undesired immune response" refers to any undesired immune response that results from exposure to an antigen, promotes or exacerbates a disease, disorder or condition provided herein (or a symptom thereof), or is symptomatic of a disease, disorder or condition provided herein. Such immune responses generally have a negative impact on a subject's health or is symptomatic of a negative impact on a subject's health.

C. Inventive Compositions

Provided herein are methods and compositions for generating regulatory B cells. Regulatory B cells are believed to modulate immune responses, for example, in that IL-10 release from regulatory B cells exerts anti-inflammatory and immunosuppressive effects on most hematopoietic cells. IL-10 also suppresses pro-inflammatory cytokine production by monocytes and macrophages and the proliferation of antigen-specific CD4+ T cells. Without wishing to be bound by any particular theory, it is believed that the compositions provided herein can affect the number and/or activity of regulatory B cells in vitro and/or in vivo by, for example, interacting with naïve B cells or regulatory B cell precursors, resulting in an induction of regulatory B cell maturation or an increase in regulatory B cell proliferation and/or activity. The effect on regulatory B cell number and/or activity may also be a result of the generation of other regulatory cell or tolerogenic immune responses, such as through regulatory T cell production and/or activation.

Provided herein are tolerogenic methods that include the administration of synthetic nanocarrier compositions comprising immunosuppressants and B cell and/or MHC Class II-restricted epitopes of an antigen and related compositions. Such methods and compositions are useful for generating, stimulating or recruiting regulatory B cells and promoting the generation of tolerogenic immune responses. The methods provided may also include the administration therapeutic proteins and/or transplantable grafts. The compositions provided, therefore, may also include the therapeutic proteins and/or transplantable grafts. The compositions may be administered to subjects in which a tolerogenic immune response is desired. Such subjects include those that have or are at risk of having an inflammatory disease, an autoimmune disease, an allergy, organ or tissue rejection or graft versus host disease. Such subjects also include those that have been, are being or will be administered a therapeutic protein against which the subject has experienced or is expected to experience an undesired immune response. Such subjects also include those that have undergone or will undergo transplantation.

Preferably, the compositions of the invention result in the generation, recruitment or activation of regulatory B cells. One hallmark of regulatory B cells is the ability to produce and secrete IL-10. Some regulatory B cells are CD1d+ or CD1dhigh. Some regulatory B cells are CD5+ and/or CD19+. For example, some regulatory B cells are CD1dhighCD5+CD19+. Some regulatory B cells are CD24+ or CD24high; and/or CD38+ or CD38high. For example, some regulatory B cells are CD19+ CD24highCD38high. Some regulatory B cells produce and secrete IL-10. Additional surface markers and chemokine secretion profiles that can be used to identify regulatory B cells are known to those of skill in the art. Based on the knowledge of surface markers useful for the identification of various regulatory B cell populations, those of skill in the art are able to identify and enumerate regulatory B cells in a heterogeneous population of cells, for example, in a population of cells in culture or in a population of cells obtained from a subject.

As mentioned above, the synthetic nanocarriers are designed to comprise B cell epitopes and/or MHC Class II-restricted epitopes and/or immunosuppressants. A wide variety of synthetic nanocarriers can be used according to the invention. In some embodiments, synthetic nanocarriers are spheres or spheroids. In some embodiments, synthetic nanocarriers are flat or plate-shaped. In some embodiments, synthetic nanocarriers are cubes or cubic. In some embodiments, synthetic nanocarriers are ovals or ellipses. In some embodiments, synthetic nanocarriers are cylinders, cones, or pyramids.

In some embodiments, it is desirable to use a population of synthetic nanocarriers that is relatively uniform in terms of size, shape, and/or composition so that each synthetic nanocarrier has similar properties. For example, at least 80%, at least 90%, or at least 95% of the synthetic nanocarriers, based on the total number of synthetic nanocarriers, may have a minimum dimension or maximum dimension that falls within 5%, 10%, or 20% of the average diameter or average dimension of the synthetic nanocarriers. In some embodiments, a population of synthetic nanocarriers may be heterogeneous with respect to size, shape, and/or composition.

Synthetic nanocarriers can be solid or hollow and can comprise one or more layers. In some embodiments, each layer has a unique composition and unique properties relative to the other layer(s). To give but one example, synthetic nanocarriers may have a core/shell structure, wherein the core is one layer (e.g. a polymeric core) and the shell is a second layer (e.g. a lipid bilayer or monolayer). Synthetic nanocarriers may comprise a plurality of different layers.

In some embodiments, synthetic nanocarriers may optionally comprise one or more lipids. In some embodiments, a synthetic nanocarrier may comprise a liposome. In some embodiments, a synthetic nanocarrier may comprise a lipid bilayer. In some embodiments, a synthetic nanocarrier may comprise a lipid monolayer. In some embodiments, a synthetic nanocarrier may comprise a micelle. In some embodiments, a synthetic nanocarrier may comprise a core comprising a polymeric matrix surrounded by a lipid layer (e.g., lipid bilayer, lipid monolayer, etc.). In some embodiments, a synthetic nanocarrier may comprise a non-polymeric core (e.g., metal particle, quantum dot, ceramic particle, bone particle, viral particle, proteins, nucleic acids, carbohydrates, etc.) surrounded by a lipid layer (e.g., lipid bilayer, lipid monolayer, etc.).

In other embodiments, synthetic nanocarriers may comprise metal particles, quantum dots, ceramic particles, etc. In some embodiments, a non-polymeric synthetic nanocarrier is an aggregate of non-polymeric components, such as an aggregate of metal atoms (e.g., gold atoms).

In some embodiments, synthetic nanocarriers may optionally comprise one or more amphiphilic entities. In some embodiments, an amphiphilic entity can promote the production of synthetic nanocarriers with increased stability, improved uniformity, or increased viscosity. In some embodiments, amphiphilic entities can be associated with the interior surface of a lipid membrane (e.g., lipid bilayer, lipid monolayer, etc.). Many amphiphilic entities known in the art are suitable for use in making synthetic nanocarriers in accordance with the present invention. Such amphiphilic entities include, but are not limited to, phosphoglycerides; phosphatidylcholines; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohols such as polyethylene glycol (PEG); polyoxyethylene-9-lauryl ether; a surface active fatty acid, such as palmitic acid or oleic acid; fatty acids; fatty acid monoglycerides; fatty acid diglycerides; fatty acid amides; sorbitan trioleate (Span®85) glycocholate; sorbitan monolaurate (Span®20); polysorbate 20 (Tween®20); polysorbate 60 (Tween®60); polysorbate 65 (Tween®65); polysorbate 80 (Tween®80); polysorbate 85 (Tween®85); polyoxyethylene monostearate; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebrosides; dicetylphosphate; dipalmitoylphosphatidylglycerol; stearylamine; dodecylamine; hexadecyl-amine; acetyl palmitate; glycerol ricinoleate; hexadecyl sterate; isopropyl myristate; tyloxapol; poly(ethylene glycol)5000-phosphatidylethanolamine; poly(ethylene glycol)400-monostearate; phospholipids; synthetic and/or natural detergents having high surfactant properties; deoxycholates; cyclodextrins; chaotropic salts; ion pairing agents; and combinations thereof. An amphiphilic entity component may be a mixture of different amphiphilic entities. Those skilled in the art will recognize that this is an exemplary, not comprehensive, list of substances with surfactant activity. Any amphiphilic entity may be used in the production of synthetic nanocarriers to be used in accordance with the present invention.

In some embodiments, synthetic nanocarriers may optionally comprise one or more carbohydrates. Carbohydrates may be natural or synthetic. A carbohydrate may be a derivatized natural carbohydrate. In certain embodiments, a carbohydrate comprises monosaccharide or disaccharide, including but not limited to glucose, fructose, galactose, ribose, lactose, sucrose, maltose, trehalose, cellbiose, mannose, xylose, arabinose, glucoronic acid, galactoronic acid, mannuronic acid, glucosamine, galatosamine, and neuramic acid. In certain embodiments, a carbohydrate is a polysaccharide, including but not limited to pullulan, cellulose, microcrystalline cellulose, hydroxypropyl methylcellulose (HPMC), hydroxycellulose (HC), methylcellulose (MC), dextran, cyclodextran, glycogen, hydroxyethylstarch, caragenan, glycon, amylose, chitosan, N,O-carboxylmethylchitosan, algin and alginic acid, starch, chitin, inulin, konjac, glucommannan, pustulan, heparin, hyaluronic acid, curdlan, and xanthan. In embodiments, the inventive synthetic nanocarriers do not comprise (or specifically exclude) carbohydrates, such as a polysaccharide. In certain embodiments, the carbohydrate may comprise a carbohydrate derivative such as a sugar alcohol, including but not limited to mannitol, sorbitol, xylitol, erythritol, maltitol, and lactitol.

In some embodiments, synthetic nanocarriers can comprise one or more polymers. In some embodiments, the synthetic nanocarriers comprise one or more polymers that is a nonmethoxy-terminated, pluronic polymer. In some embodiments, at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 97%, or 99% (weight/weight) of the polymers that make up the synthetic nanocarriers are non-methoxy-terminated, pluronic polymers. In some embodiments, all of the polymers that make up the synthetic nanocarriers are non-methoxy-terminated, pluronic polymers. In some embodiments, the synthetic nanocarriers can comprise one or more polymers that is a non-methoxy-terminated polymer. In some embodiments, at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 97%, or 99% (weight/weight) of the polymers that make up the synthetic nanocarriers are non-methoxy-terminated polymers. In some embodiments, all of the polymers that make up the synthetic nanocarriers are non-methoxy-terminated polymers. In some embodiments, the synthetic nanocarriers comprise one or more polymers that do not comprise pluronic polymer. In some embodiments, at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 97%, or 99% (weight/weight) of the polymers that make up the synthetic nanocarriers do not comprise pluronic polymer. In some embodiments, all of the polymers that make up the synthetic nanocarriers do not comprise pluronic polymer. In some embodiments, such a polymer can be surrounded by a coating layer (e.g., liposome, lipid monolayer, micelle, etc.). In some embodiments, various elements of the synthetic nanocarriers can be coupled with the polymer.

The immunosuppressants and/or antigens can be coupled to the synthetic nanocarriers by any of a number of methods. Generally, the coupling can be a result of bonding between the immunosuppressants and/or antigens and the synthetic nanocarriers. This bonding can result in the immunosuppressants and/or antigens being attached to the surface of the synthetic nanocarriers and/or contained within (encapsulated) the synthetic nanocarriers. In some embodiments, however, the immunosuppressants and/or antigens are encapsulated by the synthetic nanocarriers as a result of the structure of the synthetic nanocarriers rather than bonding to the synthetic nanocarriers. In preferable embodiments, the synthetic nanocarriers comprise a polymer as provided herein, and the immunosuppressants and/or antigens are coupled to the polymer.

When coupling occurs as a result of bonding between the immunosuppressants and/or antigens and synthetic nanocarriers, the coupling may occur via a coupling moiety. A coupling moiety can be any moiety through which an immunosuppressant and/or antigen is bonded to a synthetic nanocarrier. Such moieties include covalent bonds, such as an amide bond or ester bond, as well as separate molecules that bond (covalently or non-covalently) the immunosuppressant and/or antigen to the synthetic nanocarrier. Such molecules include linkers or polymers or a unit thereof. For example, the coupling moiety can comprise a charged polymer to which an immunosuppressant and/or antigen electrostatically binds. As another example, the coupling moiety can comprise a polymer or unit thereof to which it is covalently bonded.

In preferred embodiments, the synthetic nanocarriers comprise a polymer as provided herein. These synthetic nanocarriers can be completely polymeric or they can be a mix of polymers and other materials.

In some embodiments, the polymers of a synthetic nanocarrier associate to form a polymeric matrix. In some of these embodiments, a component, such as an immunosuppressant or antigen, can be covalently associated with one or more polymers of the polymeric matrix. In some embodiments, covalent association is mediated by a linker. In some embodiments, a component can be noncovalently associated with one or more polymers of the polymeric matrix. For example, in some embodiments a component can be encapsulated within, surrounded by, and/or dispersed throughout a polymeric matrix. Alternatively or additionally, a component can be associated with one or more polymers of a polymeric matrix by hydrophobic interactions, charge interactions, van der Waals forces, etc. A wide variety of polymers and methods for forming polymeric matrices therefrom are known conventionally.

Polymers may be natural or unnatural (synthetic) polymers. Polymers may be homopolymers or copolymers comprising two or more monomers. In terms of sequence, copolymers may be random, block, or comprise a combination of random and block sequences. Typically, polymers in accordance with the present invention are organic polymers.

In some embodiments, the polymer comprises a polyester, polycarbonate, polyamide, or polyether, or unit thereof. In other embodiments, the polymer comprises poly(ethylene glycol) (PEG), polypropylene glycol, poly(lactic acid), poly (glycolic acid), poly(lactic-co-glycolic acid), or a polycaprolactone, or unit thereof. In some embodiments, it is preferred that the polymer is biodegradable. Therefore, in these embodiments, it is preferred that if the polymer comprises a polyether, such as poly(ethylene glycol) or polypropylene glycol or unit thereof, the polymer comprises a block-copolymer of a polyether and a biodegradable polymer such that the polymer is biodegradable. In other embodiments, the polymer does not solely comprise a polyether or unit thereof, such as poly(ethylene glycol) or polypropylene glycol or unit thereof.

Other examples of polymers suitable for use in the present invention include, but are not limited to polyethylenes, polycarbonates (e.g. poly(1,3-dioxan-2one)), polyanhydrides (e.g. poly(sebacic anhydride)), polypropylfumerates, polyamides (e.g. polycaprolactam), polyacetals, polyethers, polyesters (e.g., polylactide, polyglycolide, polylactide-coglycolide, polycaprolactone, polyhydroxyacid (e.g. poly(β-hydroxyalkanoate))), poly(orthoesters), polycyanoacrylates, polyvinyl alcohols, polyurethanes, polyphosphazenes, polyacrylates, polymethacrylates, polyureas, polystyrenes, and polyamines, polylysine, polylysine-PEG copolymers, and poly(ethyleneimine), poly(ethylene imine)-PEG copolymers.

In some embodiments, polymers in accordance with the present invention include polymers which have been approved for use in humans by the U.S. Food and Drug Administration (FDA) under 21 C.F.R. §177.2600, including but not limited to polyesters (e.g., polylactic acid, poly(lactic-co-glycolic acid), polycaprolactone, polyvalerolactone, poly(1,3-dioxan-2one)); polyanhydrides (e.g., poly(sebacic anhydride)); polyethers (e.g., polyethylene glycol); polyurethanes; polymethacrylates; polyacrylates; and polycyanoacrylates.

In some embodiments, polymers can be hydrophilic. For example, polymers may comprise anionic groups (e.g., phosphate group, sulphate group, carboxylate group); cationic groups (e.g., quaternary amine group); or polar groups (e.g., hydroxyl group, thiol group, amine group). In some embodiments, a synthetic nanocarrier comprising a hydrophilic polymeric matrix generates a hydrophilic environment within the synthetic nanocarrier. In some embodiments, polymers can be hydrophobic. In some embodiments, a synthetic nanocarrier comprising a hydrophobic polymeric matrix generates a hydrophobic environment within the synthetic nanocarrier. Selection of the hydrophilicity or hydrophobicity of the polymer may have an impact on the nature of materials that are incorporated (e.g. coupled) within the synthetic nanocarrier.

In some embodiments, polymers may be modified with one or more moieties and/or functional groups. A variety of moieties or functional groups can be used in accordance with the present invention. In some embodiments, polymers may be modified with polyethylene glycol (PEG), with a carbohydrate, and/or with acyclic polyacetals derived from polysaccharides (Papisov, 2001, ACS Symposium Series, 786:301). Certain embodiments may be made using the general teachings of U.S. Pat. No. 5,543,158 to Gref et al., or WO publication WO2009/051837 by Von Andrian et al.

In some embodiments, polymers may be modified with a lipid or fatty acid group. In some embodiments, a fatty acid group may be one or more of butyric, caproic, caprylic, capric, lauric, myristic, palmitic, stearic, arachidic, behenic, or lignoceric acid. In some embodiments, a fatty acid group may be one or more of palmitoleic, oleic, vaccenic, linoleic, alpha-linoleic, gamma-linoleic, arachidonic, gadoleic, arachidonic, eicosapentaenoic, docosahexaenoic, or erucic acid.

In some embodiments, polymers may be polyesters, including copolymers comprising lactic acid and glycolic acid units, such as poly(lactic acid-co-glycolic acid) and poly(lactide-co-glycolide), collectively referred to herein as "PLGA"; and homopolymers comprising glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some embodiments, exemplary polyesters include, for example, polyhydroxyacids; PEG copolymers and copolymers of lactide and glycolide (e.g., PLA-PEG copolymers, PGA-PEG copolymers, PLGA-PEG copolymers, and derivatives thereof. In some embodiments, polyesters include, for example, poly(caprolactone), poly(caprolactone)-PEG copolymers, poly(L-lactide-co-L-lysine), poly(serine ester), poly(4-hydroxy-L-proline ester), poly[α-(4-aminobutyl)-L-glycolic acid], and derivatives thereof.

In some embodiments, a polymer may be PLGA. PLGA is a biocompatible and biodegradable co-polymer of lactic acid and glycolic acid, and various forms of PLGA are characterized by the ratio of lactic acid:glycolic acid. Lactic acid can be L-lactic acid, D-lactic acid, or D,L-lactic acid. The degradation rate of PLGA can be adjusted by altering the lactic acid:glycolic acid ratio. In some embodiments, PLGA to be used in accordance with the present invention is characterized by a lactic acid:glycolic acid ratio of approximately 85:15, approximately 75:25, approximately 60:40, approximately 50:50, approximately 40:60, approximately 25:75, or approximately 15:85.

In some embodiments, polymers may be one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid anhydride), methyl methacrylate, polymethacrylate, poly(methyl methacrylate) copolymer, polyacrylamide, aminoalkyl methacrylate copolymer, glycidyl methacrylate copolymers, polycyanoacrylates, and combinations comprising one or more of the foregoing polymers. The acrylic polymer may comprise fully-polymerized copolymers of acrylic and methacrylic acid esters with a low content of quaternary ammonium groups.

In some embodiments, polymers can be cationic polymers. In general, cationic polymers are able to condense and/or protect negatively charged strands of nucleic acids (e.g. DNA, or derivatives thereof). Amine-containing polymers such as poly(lysine) (Zauner et al., 1998, Adv. Drug Del. Rev., 30:97; and Kabanov et al., 1995, Bioconjugate Chem., 6:7), poly(ethylene imine) (PEI; Boussif et al., 1995, Proc. Natl. Acad. Sci., USA, 1995, 92:7297), and poly (amidoamine) dendrimers (Kukowska-Latallo et al., 1996, Proc. Natl. Acad. Sci., USA, 93:4897; Tang et al., 1996, Bioconjugate Chem., 7:703; and Haensler et al., 1993, Bioconjugate Chem., 4:372) are positively-charged at physiological pH, form ion pairs with nucleic acids, and mediate transfection in a variety of cell lines. In embodiments, the inventive synthetic nanocarriers may not comprise (or may exclude) cationic polymers.

In some embodiments, polymers can be degradable polyesters bearing cationic side chains (Putnam et al., 1999, Macromolecules, 32:3658; Barrera et al., 1993, J. Am. Chem. Soc., 115:11010; Kwon et al., 1989, Macromolecules, 22:3250; Lim et al., 1999, J. Am. Chem. Soc., 121:5633; and Zhou et al., 1990, Macromolecules, 23:3399). Examples of these polyesters include poly(L-lactide-co-L-lysine) (Barrera et al., 1993, J. Am. Chem. Soc., 115:11010), poly(serine ester) (Zhou et al., 1990, Macromolecules, 23:3399), poly(4-hydroxy-L-proline ester) (Putnam et al., 1999, Macromolecules, 32:3658; and Lim et al., 1999, J. Am. Chem. Soc., 121:5633), and poly(4-hydroxy-L-proline ester) (Putnam et al., 1999, Macromolecules, 32:3658; and Lim et al., 1999, J. Am. Chem. Soc., 121:5633).

The properties of these and other polymers and methods for preparing them are well known in the art (see, for example, U.S. Pat. Nos. 6,123,727; 5,804,178; 5,770,417; 5,736,372; 5,716,404; 6,095,148; 5,837,752; 5,902,599; 5,696,175; 5,514,378; 5,512,600; 5,399,665; 5,019,379; 5,010,167; 4,806,621; 4,638,045; and 4,946,929; Wang et al., 2001, J. Am. Chem. Soc., 123:9480; Lim et al., 2001, J. Am. Chem. Soc., 123:2460; Langer, 2000, Acc. Chem. Res., 33:94; Langer, 1999, J. Control. Release, 62:7; and Uhrich et al., 1999, Chem. Rev., 99:3181). More generally, a variety of methods for synthesizing certain suitable polymers are described in Concise Encyclopedia of Polymer Science and Polymeric Amines and Ammonium Salts, Ed. by Goethals, Pergamon Press, 1980; Principles of Polymerization by Odian, John Wiley & Sons, Fourth Edition, 2004; Contemporary Polymer Chemistry by Allcock et al., Prentice-Hall, 1981; Deming et al., 1997, Nature, 390:386; and in U.S. Pat. Nos. 6,506,577, 6,632,922, 6,686,446, and 6,818,732.

In some embodiments, polymers can be linear or branched polymers. In some embodiments, polymers can be dendrimers. In some embodiments, polymers can be substantially cross-linked to one another. In some embodiments, polymers can be substantially free of cross-links. In some embodiments, polymers can be used in accordance with the present invention without undergoing a cross-linking step. It is further to be understood that inventive synthetic nanocarriers may comprise block copolymers, graft copolymers, blends, mixtures, and/or adducts of any of the foregoing and other polymers. Those skilled in the art will recognize that the polymers listed herein represent an exemplary, not comprehensive, list of polymers that can be of use in accordance with the present invention.

Compositions according to the invention comprise synthetic nanocarriers in combination with pharmaceutically acceptable excipients, such as preservatives, buffers, saline, or phosphate buffered saline. The compositions may be made using conventional pharmaceutical manufacturing and compounding techniques to arrive at useful dosage forms. In an embodiment, inventive synthetic nanocarriers are suspended in sterile saline solution for injection together with a preservative.

In embodiments, when preparing synthetic nanocarriers as carriers, methods for coupling components to the synthetic nanocarriers may be useful. If the component is a small molecule it may be of advantage to attach the component to a polymer prior to the assembly of the synthetic nanocarriers. In embodiments, it may also be an advantage to prepare the synthetic nanocarriers with surface groups that are used to couple the component to the synthetic nanocarrier through the use of these surface groups rather than attaching the component to a polymer and then using this polymer conjugate in the construction of synthetic nanocarriers.

In certain embodiments, the coupling can be a covalent linker. In embodiments, peptides according to the invention can be covalently coupled to the external surface via a 1,2,3-triazole linker formed by the 1,3-dipolar cycloaddition reaction of azido groups on the surface of the nanocarrier with antigen or immunosuppressant containing an alkyne group or by the 1,3-dipolar cycloaddition reaction of alkynes on the surface of the nanocarrier with components containing an azido group. Such cycloaddition reactions are preferably performed in the presence of a Cu(I) catalyst along with a suitable Cu(I)-ligand and a reducing agent to reduce Cu(II) compound to catalytic active Cu(I) compound. This Cu(I)-catalyzed azide-alkyne cycloaddition (CuAAC) can also be referred as the click reaction.

Additionally, the covalent coupling may comprise a covalent linker that comprises an amide linker, a disulfide linker, a thioether linker, a hydrazone linker, a hydrazide linker, an imine or oxime linker, an urea or thiourea linker, an amidine linker, an amine linker, and a sulfonamide linker.

An amide linker is formed via an amide bond between an amine on one component with the carboxylic acid group of a second component such as the nanocarrier. The amide bond in the linker can be made using any of the conventional amide bond forming reactions with suitably protected amino acids or components and activated carboxylic acid such N-hydroxysuccinimide-activated ester.

A disulfide linker is made via the formation of a disulfide (S—S) bond between two sulfur atoms of the form, for instance, of R1-S—S—R2. A disulfide bond can be formed by thiol exchange of a component containing thiol/mercaptan group (—SH) with another activated thiol group on a polymer or nanocarrier or a nanocarrier containing thiol/mercaptan groups with a component containing activated thiol group.

A triazole linker, specifically a 1,2,3-triazole of the form

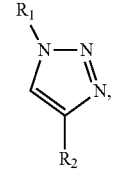

wherein R1 and R2 may be any chemical entities, is made by the 1,3-dipolar cycloaddition reaction of an azide attached to a first component such as the nanocarrier with a terminal alkyne attached to a second component such as the immunosuppressant or antigen. The 1,3-dipolar cycloaddition reaction is performed with or without a catalyst, preferably with Cu(I)-catalyst, which links the two components through a 1,2,3-triazole function. This chemistry is described in detail by Sharpless et al., Angew. Chem. Int. Ed. 41(14), 2596, (2002) and Meldal, et al, Chem. Rev., 2008, 108(8), 2952-3015 and is often referred to as a "click" reaction or CuAAC.

In embodiments, a polymer containing an azide or alkyne group, terminal to the polymer chain is prepared. This polymer is then used to prepare a synthetic nanocarrier in such a manner that a plurality of the alkyne or azide groups are positioned on the surface of that nanocarrier. Alternatively, the synthetic nanocarrier can be prepared by another route, and subsequently functionalized with alkyne or azide groups. The component is prepared with the presence of either an alkyne (if the polymer contains an azide) or an azide (if the polymer contains an alkyne) group. The component is then allowed to react with the nanocarrier via the 1,3-dipolar cycloaddition reaction with or without a catalyst which covalently couples the component to the particle through the 1,4-disubstituted 1,2,3-triazole linker.

A thioether linker is made by the formation of a sulfur-carbon (thioether) bond in the form, for instance, of R1-S—R2. Thioether can be made by either alkylation of a thiol/mercaptan (—SH) group on one component such as the component with an alkylating group such as halide or epoxide on a second component such as the nanocarrier. Thioether linkers can also be formed by Michael addition of a thiol/mercaptan group on one component to an electron-deficient alkene group on a second component such as a polymer containing a maleimide group or vinyl sulfone group as the Michael acceptor. In another way, thioether linkers can be prepared by the radical thiol-ene reaction of a thiol/mercaptan group on one component with an alkene group on a second component such as a polymer or nanocarrier.

A hydrazone linker is made by the reaction of a hydrazide group on one component with an aldehyde/ketone group on the second component such as the nanocarrier.

A hydrazide linker is formed by the reaction of a hydrazine group on one component with a carboxylic acid group on the second component such as the nanocarrier. Such reaction is generally performed using chemistry similar to the formation of amide bond where the carboxylic acid is activated with an activating reagent.

An imine or oxime linker is formed by the reaction of an amine or N-alkoxyamine (or aminooxy) group on one component with an aldehyde or ketone group on the second component such as the nanocarrier.

An urea or thiourea linker is prepared by the reaction of an amine group on one component with an isocyanate or thioisocyanate group on the second component such as the nanocarrier.

An amidine linker is prepared by the reaction of an amine group on one component with an imidoester group on the second component such as the nanocarrier.

An amine linker is made by the alkylation reaction of an amine group on one component with an alkylating group such as halide, epoxide, or sulfonate ester group on the second component such as the nanocarrier. Alternatively, an amine linker can also be made by reductive amination of an amine group on one component with an aldehyde or ketone group on the second component such as the nanocarrier with a suitable reducing reagent such as sodium cyanoborohydride or sodium triacetoxyborohydride.

A sulfonamide linker is made by the reaction of an amine group on one component with a sulfonyl halide (such as sulfonyl chloride) group on the second component such as the nanocarrier.

A sulfone linker is made by Michael addition of a nucleophile to a vinyl sulfone. Either the vinyl sulfone or the nucleophile may be on the surface of the nanocarrier or attached to a component.

The component can also be conjugated to the nanocarrier via non-covalent conjugation methods. For example, a negative charged antigen or immunosuppressant can be conjugated to a positive charged nanocarrier through electrostatic adsorption. A component containing a metal ligand can also be conjugated to a nanocarrier containing a metal complex via a metal-ligand complex.

In embodiments, the component can be attached to a polymer, for example polylactic acid-block-polyethylene glycol, prior to the assembly of the synthetic nanocarrier or the synthetic nanocarrier can be formed with reactive or activatable groups on its surface. In the latter case, the component may be prepared with a group which is compatible with the attachment chemistry that is presented by the synthetic nanocarriers' surface. In other embodiments, a peptide component can be attached to VLPs or liposomes using a suitable linker. A linker is a compound or reagent that capable of coupling two molecules together. In an embodiment, the linker can be a homobifuntional or heterobifunctional reagent as described in Hermanson 2008. For example, an VLP or liposome synthetic nanocarrier containing a carboxylic group on the surface can be treated with a homobifunctional linker, adipic dihydrazide (ADH), in the presence of EDC to form the corresponding synthetic nanocarrier with the ADH linker. The resulting ADH linked synthetic nanocarrier is then conjugated with a peptide component containing an acid group via the other end of the ADH linker on NC to produce the corresponding VLP or liposome peptide conjugate.

For detailed descriptions of available conjugation methods, see Hermanson G T "Bioconjugate Techniques", 2nd Edition Published by Academic Press, Inc., 2008. In addition to covalent attachment the component can be coupled by adsorption to a pre-formed synthetic nanocarrier or it can be coupled by encapsulation during the formation of the synthetic nanocarrier.

Any immunosuppressant as provided herein can be coupled to the synthetic nanocarrier. Immunosuppressants include, but are not limited to, statins; mTOR inhibitors, such as rapamycin or a rapamycin analog; TGF-β signaling agents; TGF-β receptor agonists; histone deacetylase (HDAC) inhibitors; corticosteroids; inhibitors of mitochondrial function, such as rotenone; P38 inhibitors; NF-κβ inhibitors; adenosine receptor agonists; prostaglandin E2 agonists; phosphodiesterase inhibitors, such as phosphodiesterase 4 inhibitor; proteasome inhibitors; kinase inhibitors; G-protein coupled receptor agonists; G-protein coupled receptor antagonists; glucocorticoids; retinoids; cytokine inhibitors; cytokine receptor inhibitors; cytokine receptor activators; peroxisome proliferator-activated receptor antagonists; peroxisome proliferator-activated receptor agonists; histone deacetylase inhibitors; calcineurin inhibitors; phosphatase inhibitors and oxidized ATPs. Immunosuppressants also include IDO, vitamin D3, cyclosporine A, aryl hydrocarbon receptor inhibitors, resveratrol, azathiopurine, 6-mercaptopurine, aspirin, niflumic acid, estriol, tripolide, interleukins (e.g., IL-1, IL-10), cyclosporine A, siRNAs targeting cytokines or cytokine receptors and the like.

Examples of statins include atorvastatin (LIPITOR®, TORVAST®), cerivastatin, fluvastatin (LESCOL®, LESCOL® XL), lovastatin (MEVACOR®, ALTOCOR®, ALTOPREV®), mevastatin (COMPACTIN®), pitavastatin (LIVALO®, PIAVA®), rosuvastatin (PRAVACHOL®, SELEKTINE®, LIPOSTAT®), rosuvastatin (CRESTOR®), and simvastatin (ZOCOR®, LIPEX®).

Examples of mTOR inhibitors include rapamycin and analogs thereof (e.g., CCL-779, RAD001, AP23573, C20-methallylrapamycin (C20-Marap), C16-(S)-butylsulfonamidorapamycin (C16-BSrap), C16-(S)-3-methylindolerapamycin (C16-iRap) (Bayle et al. Chemistry & Biology 2006, 13:99-107)), AZD8055, BEZ235 (NVP-BEZ235), chrysophanic acid (chrysophanol), deforolimus (MK-8669), everolimus (RAD0001), KU-0063794, PI-103, PP242, temsirolimus, and WYE-354 (available from Selleck, Houston, Tex., USA).

Examples of TGF-β signaling agents include TGF-β ligands (e.g., activin A, GDF1, GDF11, bone morphogenic proteins, nodal, TGF-βs) and their receptors (e.g., ACVR1B, ACVR1C, ACVR2A, ACVR2B, BMPR2, BMPR1A, BMPR1B, TGFβRI, TGFβRII), R-SMADS/co-SMADS (e.g., SMAD1, SMAD2, SMAD3, SMAD4, SMAD5, SMAD8), and ligand inhibitors (e.g, follistatin, noggin, chordin, DAN, lefty, LTBP1, THBS1, Decorin).

Examples of inhibitors of mitochondrial function include atractyloside (dipotassium salt), bongkrekic acid (triammonium salt), carbonyl cyanide m-chlorophenylhydrazone, carboxyatractyloside (e.g., from *Atractylis gummifera*), CGP-37157, (−)-Deguelin (e.g., from *Mundulea sericea*), F16, hexokinase II VDAC binding domain peptide, oligomycin, rotenone, Ru360, SFK1, and valinomycin (e.g., from *Streptomyces fulvissimus*) (EMD4Biosciences, USA).

Examples of P38 inhibitors include SB-203580 (4-(4-Fluorophenyl)-2-(4-methylsulfinylphenyl)-5-(4-pyridyl) 1H-imidazole), SB-239063 (trans-1-(4hydroxycyclohexyl)-4-(fluorophenyl)-5-(2-methoxy-pyrimidin-4-yl) imidazole), SB-220025 (5-(2amino-4-pyrimidinyl)-4-(4-fluorophenyl)-1-(4-piperidinyl)imidazole)), and ARRY-797.

Examples of NF (e.g., NK-κβ) inhibitors include IFRD1, 2-(1,8-naphthyridin-2-yl)-Phenol, 5-aminosalicylic acid, BAY 11-7082, BAY 11-7085, CAPE (Caffeic Acid Phenethylester), diethylmaleate, IKK-2 Inhibitor IV, IMD 0354, lactacystin, MG-132 [Z-Leu-Leu-Leu-CHO], NFκB Activation Inhibitor III, NF-κB Activation Inhibitor II, JSH-23, parthenolide, Phenylarsine Oxide (PAO), PPM-18, pyrrolidinedithiocarbamic acid ammonium salt, QNZ, RO 106-9920, rocaglamide, rocaglamide AL, rocaglamide C, rocaglamide I, rocaglamide J, rocaglaol, (R)-MG-132, sodium salicylate, triptolide (PG490), wedelolactone.

Examples of adenosine receptor agonists include CGS-21680 and ATL-146e.

Examples of prostaglandin E2 agonists include E-Prostanoid 2 and E-Prostanoid 4.

Examples of phosphodiesterase inhibitors (non-selective and selective inhibitors) include caffeine, aminophylline, IBMX (3-isobutyl-1-methylxanthine), paraxanthine, pentoxifylline, theobromine, theophylline, methylated xanthines, vinpocetine, EHNA (erythro-9-(2-hydroxy-3-nonyl) adenine), anagrelide, enoximone (PERFAN™), milrinone, levosimendon, mesembrine, ibudilast, piclamilast, luteolin, drotaverine, roflumilast (DAXAS™, DALIRESP™), sildenafil (REVATION®, VIAGRA®), tadalafil (ADCIRCA®, CIALIS®), vardenafil (LEVITRA®, STAXYN®), udenafil, avanafil, icariin, 4-methylpiperazine, and pyrazolo pyrimidin-7-1.

Examples of proteasome inhibitors include bortezomib, disulfiram, epigallocatechin-3-gallate, and salinosporamide A.

Examples of kinase inhibitors include bevacizumab, BIBW 2992, cetuximab (ERBITUX®), imatinib (GLEEVEC®), trastuzumab (HERCEPTIN®), gefitinib (IRESSA®), ranibizumab (LUCENTIS®), pegaptanib, sorafenib, dasatinib, sunitinib, erlotinib, nilotinib, lapatinib, panitumumab, vandetanib, E7080, pazopanib, mubritinib.

Examples of glucocorticoids include hydrocortisone (cortisol), cortisone acetate, prednisone, prednisolone, methylprednisolone, dexamethasone, betamethasone, triamcinolone, beclometasone, fludrocortisone acetate, deoxycorticosterone acetate (DOCA), and aldosterone.

Examples of retinoids include retinol, retinal, tretinoin (retinoic acid, RETIN-A®), isotretinoin (ACCUTANE®, AMNESTEEM®, CLARAVIS®, SOTRET®), alitretinoin (PANRETIN®), etretinate (TEGISON™) and its metabolite acitretin (SORIATANE®), tazarotene (TAZORAC®, AVAGE®, ZORAC®), bexarotene (TARGRETIN®), and adapalene (DIFFERIN®).

Examples of cytokine inhibitors include IL1ra, IL1 receptor antagonist, IGFBP, TNF-BF, uromodulin, Alpha-2-Macroglobulin, Cyclosporin A, Pentamidine, and Pentoxifylline (PENTOPAK®, PENTOXIL®, TRENTAL®).

Examples of peroxisome proliferator-activated receptor antagonists include GW9662, PPARγ antagonist III, G335, T0070907 (EMD4Biosciences, USA).

Examples of peroxisome proliferator-activated receptor agonists include pioglitazone, ciglitazone, clofibrate, GW1929, GW7647, L-165,041, LY 171883, PPARγ activator, Fmoc-Leu, troglitazone, and WY-14643 (EMD4Biosciences, USA).

Examples of histone deacetylase inhibitors include hydroxamic acids (or hydroxamates) such as trichostatin A, cyclic tetrapeptides (such as trapoxin B) and depsipeptides, benzamides, electrophilic ketones, aliphatic acid compounds such as phenylbutyrate and valproic acid, hydroxamic acids such as vorinostat (SAHA), belinostat (PXD101), LAQ824, and panobinostat (LBH589), benzamides such as entinostat (MS-275), CI994, and mocetinostat (MGCD0103), nicotinamide, derivatives of NAD, dihydrocoumarin, naphthopyranone, and 2-hydroxynaphaldehydes.

Examples of calcineurin inhibitors include cyclosporine, pimecrolimus, voclosporin, and tacrolimus.

Examples of phosphatase inhibitors include BN82002 hydrochloride, CP-91149, calyculin A, cantharidic acid, cantharidin, cypermethrin, ethyl-3,4-dephostatin, fostriecin sodium salt, MAZ51, methyl-3,4-dephostatin, NSC 95397, norcantharidin, okadaic acid ammonium salt from prorocentrum concavum, okadaic acid, okadaic acid potassium salt, okadaic acid sodium salt, phenylarsine oxide, various phosphatase inhibitor cocktails, protein phosphatase 1C, protein phosphatase 2A inhibitor protein, protein phosphatase 2A1, protein phosphatase 2A2, sodium orthovanadate.

In some embodiments, antigens as described herein are also coupled to synthetic nanocarriers. In some embodiments, the antigens are coupled to the same or different synthetic nanocarriers as to which the immunosuppressants are coupled. In other embodiments, the antigens are not coupled to any synthetic nanocarriers. Antigens include any of the antigens provided herein, or fragments or derivatives thereof, such antigens are associated with inflammatory, autoimmune diseases, allergy, organ or tissue rejection, graft versus host disease, transplant antigens and therapeutic protein antigens. The epitopes, or proteins, polypeptides or peptides that comprise the epitopes, can be obtained or derived from any of the antigens provided or otherwise known in the art.

Therapeutic proteins include, but are not limited to, infusible therapeutic proteins, enzymes, enzyme cofactors, hormones, blood clotting factors, cytokines and interferons, growth factors, monoclonal antibodies, and polyclonal antibodies (e.g., that are administered to a subject as a replacement therapy), and proteins associated with Pompe's disease (e.g., alglucosidase alfa, rhGAA (e.g., Myozyme and Lumizyme (Genzyme)). Therapeutic proteins also include proteins involved in the blood coagulation cascade. Therapeutic proteins include, but are not limited to, Factor VIII, Factor VII, Factor IX, Factor V, von Willebrand Factor, von Heldebrant Factor, tissue plasminogen activator, insulin, growth hormone, erythropoietin alfa, VEGF, thrombopoietin, lysozyme, antithrombin and the like. Therapeutic proteins also include adipokines, such as leptin and adiponectin. Other examples of therapeutic proteins are as described below and elsewhere herein. Also included are fragments or derivatives of any of the therapeutic proteins provided as the antigen.

Examples of therapeutic proteins used in enzyme replacement therapy of subjects having a lysosomal storage disorder include, but are not limited to, imiglucerase for the treatment of Gaucher's disease (e.g., CEREZYME™), a-galactosidase A (a-gal A) for the treatment of Fabry disease (e.g., agalsidase beta, FABRYZYME™), acid a-glucosidase (GAA) for the treatment of Pompe disease (e.g., alglucosidase alfa, LUMIZYME™, MYOZYME™), arylsulfatase B for the treatment of Mucopolysaccharidoses (e.g., laronidase, ALDURAZYME™, idursulfase, ELAPRASE™, arylsulfatase B, NAGLAZYME™).

Examples of enzymes include oxidoreductases, transferases, hydrolases, lyases, isomerases, and ligases.

Examples of hormones include Melatonin (N-acetyl-5-methoxytryptamine), Serotonin, Thyroxine (or tetraiodothyronine) (a thyroid hormone), Triiodothyronine (a thyroid hormone), Epinephrine (or adrenaline), Norepinephrine (or noradrenaline), Dopamine (or prolactin inhibiting hormone), Antimullerian hormone (or mullerian inhibiting factor or hormone), Adiponectin, Adrenocorticotropic hormone (or corticotropin), Angiotensinogen and angiotensin, Antidiuretic hormone (or vasopressin, arginine vasopressin), Atrial-natriuretic peptide (or atriopeptin), Calcitonin, Cholecystokinin, Corticotropin-releasing hormone, Erythropoietin, Follicle-stimulating hormone, Gastrin, Ghrelin, Glucagon, Glucagon-like peptide (GLP-1), GIP, Gonadotropin-releasing hormone, Growth hormone-releasing hormone, Human chorionic gonadotropin, Human placental lactogen, Growth hormone, Inhibin, Insulin, Insulin-like growth factor (or somatomedin), Leptin, Luteinizing hormone, Melanocyte stimulating hormone, Orexin, Oxytocin, Parathyroid hormone, Prolactin, Relaxin, Secretin, Somatostatin, Thrombopoietin, Thyroid-stimulating hormone (or thyrotropin), Thyrotropin-releasing hormone, Cortisol, Aldosterone, Testosterone, Dehydroepiandrosterone, Androstenedione, Dihydrotestosterone, Estradiol, Estrone, Estriol, Progesterone, Calcitriol (1,25-dihydroxyvitamin D3), Calcidiol (25-hydroxyvitamin D3), Prostaglandins, Leukotrienes, Prostacyclin, Thromboxane, Prolactin releasing hormone, Lipotropin, Brain natriuretic peptide, Neuropeptide Y, Histamine, Endothelin, Pancreatic polypeptide, Renin, and Enkephalin.

Examples of blood and blood coagulation factors include Factor I (fibrinogen), Factor II (prothrombin), tissue factor, Factor V (proaccelerin, labile factor), Factor VII (stable factor, proconvertin), Factor VIII (antihemophilic globulin), Factor IX (Christmas factor or plasma thromboplastin component), Factor X (Stuart-Prower factor), Factor Xa, Factor XI, Factor XII (Hageman factor), Factor XIII (fibrin-stabilizing factor), von Willebrand factor, prekallikrein (Fletcher factor), high-molecular weight kininogen (HMWK) (Fitzgerald factor), fibronectin, fibrin, thrombin, antithrombin III, heparin cofactor II, protein C, protein S, protein Z, protein Z-related protease inhibitot (ZPI), plasminogen, alpha 2-antiplasmin, tissue plasminogen activator (tPA), urokinase, plasminogen activator inhibitor-1 (PAI1), plasminogen activator inhibitor-2 (PAI2), cancer procoagulant, and epoetin alfa (Epogen, Procrit).

Examples of cytokines include lymphokines, interleukins, and chemokines, type 1 cytokines, such as IFN-γ, TGF-β, and type 2 cytokines, such as IL-4, IL-10, and IL-13.

Examples of growth factors include Adrenomedullin (AM), Angiopoietin (Ang), Autocrine motility factor, Bone morphogenetic proteins (BMPs), Brain-derived neurotrophic factor (BDNF), Epidermal growth factor (EGF), Erythropoietin (EPO), Fibroblast growth factor (FGF), Glial cell line-derived neurotrophic factor (GDNF), Granulocyte colony-stimulating factor (G-CSF), Granulocyte macrophage colony-stimulating factor (GM-CSF), Growth differentiation factor-9 (GDF9), Hepatocyte growth factor (HGF), Hepatoma-derived growth factor (HDGF), Insulin-like growth factor (IGF), Migration-stimulating factor, Myostatin (GDF-8), Nerve growth factor (NGF) and other neurotrophins, Platelet-derived growth factor (PDGF), Thrombopoietin (TPO), Transforming growth factor alpha (TGF-α), Transforming growth factor beta (TGF-β), Tumour_necrosis_factor-alpha (TNF-α), Vascular endothelial growth factor (VEGF), Wnt Signaling Pathway, placental growth factor (PlGF), [(Foetal Bovine Somatotrophin)] (FBS), IL-1, IL-2, IL-3, IL-4, IL-5, IL-6, and IL-7.

Examples of monoclonal antibodies include Abagovomab, Abciximab, Adalimumab, Adecatumumab, Afelimomab, Afutuzumab, Alacizumab pegol, ALD, Alemtuzumab, Altumomab pentetate, Anatumomab mafenatox, Anrukinzumab, Anti-thymocyte globin, Apolizumab, Arcitumomab, Aselizumab, Atlizumab (tocilizumab), Atorolimumab, Bapineuzumab, Basiliximab, Bavituximab, Bectumomab, Belimumab, Benralizumab, Bertilimumab, Besilesomab, Bevacizumab, Biciromab, Bivatuzumab mertansine, Blinatumomab, Brentuximab vedotin, Briakinumab, Canakinumab, Cantuzumab mertansine, Capromab pendetide, Catumaxomab, Cedelizumab, Certolizumab pegol, Cetuximab, Citatuzumab bogatox, Cixutumumab, Clenoliximab, Clivatuzumab tetraxetan, Conatumumab, Dacetuzumab, Daclizumab, Daratumumab, Denosumab, Detumomab, Dorlimomab aritox, Dorlixizumab, Ecromeximab, Eculizumab, Edobacomab, Edrecolomab, Efalizumab, Efungumab, Elotuzumab, Elsilimomab, Enlimomab pegol, Epitumomab cituxetan, Epratuzumab, Erlizumab, Ertumaxomab, Etaracizumab, Exbivirumab, Fanolesomab, Faralimomab, Farletuzumab, Felvizumab, Fezakinumab, Figitumumab, Fontolizumab, Foravirumab, Fresolimumab, Galiximab, Gantenerumab, Gavilimomab, Gemtuzumab ozogamicin, GC1008, Girentuximab, Glembatumumab vedotin, Golimumab, Gomiliximab, Ibalizumab, Ibritumomab tiuxetan, Igovomab, Imciromab, Infliximab, Intetumumab, Inolimomab, Inotuzumab ozogamicin, Ipilimumab, Iratumumab, Keliximab, Labetuzumab, Lebrikizumab, Lemalesomab, Lerdelimumab, Lexatumumab, Libivirumab, Lintuzumab, Lorvotuzumab mertansine, Lucatumumab, Lumiliximab, Mapatumumab, Maslimomab, Matuzumab, Mepolizumab, Metelimumab, Milatuzumab, Minretumomab, Mitumomab, Morolimumab, Motavizumab, Muromonab-CD3, Nacolomab tafenatox, Naptumomab estafenatox, Natalizumab, Nebacumab, Necitumumab, Nerelimomab, Nimotuzumab, Nofetumomab merpentan, Ocrelizumab, Odulimomab, Ofatumumab, Olaratumab, Omalizumab, Oportuzumab monatox, Oregovomab, Otelixizumab, Pagibaximab, Palivizumab, Panitumumab, Panobacumab, Pascolizumab, Pemtumomab, Pertuzumab, Pexelizumab, Pintumomab, Priliximab, Pritumumab, Rafivirumab, Ramucirumab, Ranibizumab, Raxibacumab, Regavirumab Reslizumab, Rilotumumab, Rituximab, Robatumumab, Rontalizumab, Rovelizumab, Rupluzumab, Satumomab pendetide, Sevirumab, Sibrotuzumab, Sifalimumab, Siltuximab, Siplizumab, Solanezumab, Sonepcizumab, Sontuzumab, Stamulumab, Sulesomab, Tacatuzumab tetraxetan, Tadocizumab, Talizumab, Tanezumab, Taplitumomab paptox, Tefibazumab, Telimomab aritox, Tenatumomab, Teneliximab, Teplizumab, Ticilimumab (tremelimumab), Tigatuzumab, Tocilizumab (atlizumab), Toralizumab, Tositumomab, Trastuzumab, Tremelimumab, Tucotuzumab celmoleukin, Tuvirumab, Urtoxazumab, Ustekinumab, Vapaliximab, Vedolizumab, Veltuzumab, Vepalimomab, Visilizumab, Volociximab, Votumumab, Zalutumumab, Zanolimumab, Ziralimumab, and Zolimomab aritox.

Examples of infusion therapy or injectable therapeutic proteins include, for example, Tocilizumab (Roche/Actemra®), alpha-1 antitrypsin (Kamada/AAT), Hematide® (Affymax and Takeda, synthetic peptide), albinterferon alfa-2b (Novartis/Zalbin™), Rhucin® (Pharming Group, C1 inhibitor replacement therapy), tesamorelin (Theratechnologies/Egrifta, synthetic growth hormone-releasing factor), ocrelizumab (Genentech, Roche and Biogen), belimumab (GlaxoSmithKline/Benlysta®), pegloticase (Savient Pharmaceuticals/Krystexxa™), taliglucerase alfa (Protalix/Uplyso), agalsidase alfa (Shire/Replagal®), velaglucerase alfa (Shire).

Additional therapeutic proteins useful in accordance to aspects of this invention will be apparent to those of skill in the art, and the invention is not limited in this respect.

In some embodiments, a component, such as an antigen or immunosuppressant, may be isolated. Isolated refers to the element being separated from its native environment and present in sufficient quantities to permit its identification or use. This means, for example, the element may be (i) selectively produced by expression cloning or (ii) purified as by chromatography or electrophoresis. Isolated elements may be, but need not be, substantially pure. Because an isolated element may be admixed with a pharmaceutically acceptable excipient in a pharmaceutical preparation, the element may comprise only a small percentage by weight of the preparation. The element is nonetheless isolated in that it has been separated from the substances with which it may be associated in living systems, i.e., isolated from other lipids or proteins. Any of the elements provided herein can be included in the compositions in isolated form.

D. Methods of Making and Using the Inventive Compositions and Related Methods Synthetic nanocarriers may be prepared using a wide variety of methods known in the art. For example, synthetic nanocarriers can be formed by methods as nanoprecipitation, flow focusing using fluidic channels, spray drying, single and double emulsion solvent evaporation, solvent extraction, phase separation, milling, microemulsion procedures, microfabrication, nanofabrication, sacrificial layers, simple and complex coacervation, and other methods well known to those of ordinary skill in the art. Alternatively or additionally, aqueous and organic solvent syntheses for monodisperse semiconductor, conductive, magnetic, organic, and other nanomaterials have been described (Pellegrino et al., 2005, Small, 1:48; Murray et al., 2000, Ann. Rev. Mat. Sci., 30:545; and Trindade et al., 2001, Chem. Mat., 13:3843). Additional methods have been described in the literature (see, e.g., Doubrow, Ed., "Microcapsules and Nanoparticles in Medicine and Pharmacy," CRC Press, Boca Raton, 1992; Mathiowitz et al., 1987, J. Control. Release, 5:13; Mathiowitz et al., 1987, Reactive Polymers, 6:275; and Mathiowitz et al., 1988, J. Appl. Polymer Sci., 35:755; U.S. Pat. Nos. 5,578,325 and 6,007,845; P. Paolicelli et al., "Surface-modified PLGA-based Nanoparticles that can Efficiently Associate and Deliver Virus-like Particles" Nanomedicine. 5(6):843-853 (2010)).

Various materials may be encapsulated into synthetic nanocarriers as desirable using a variety of methods including but not limited to C. Astete et al., "Synthesis and characterization of PLGA nanoparticles" J. Biomater. Sci. Polymer Edn, Vol. 17, No. 3, pp. 247-289 (2006); K. Avgoustakis "Pegylated Poly(Lactide) and Poly(Lactide-Co-Glycolide) Nanoparticles: Preparation, Properties and Possible Applications in Drug Delivery" Current Drug Delivery 1:321-333 (2004); C. Reis et al., "Nanoencapsulation I. Methods for preparation of drug-loaded polymeric nanoparticles" Nanomedicine 2:8-21 (2006); P. Paolicelli et al., "Surface-modified PLGA-based Nanoparticles that can Efficiently Associate and Deliver Virus-like Particles" Nanomedicine. 5(6):843-853 (2010). Other methods suitable for encapsulating materials into synthetic nanocarriers may be used, including without limitation methods disclosed in U.S. Pat. No. 6,632,671 to Unger Oct. 14, 2003.

In certain embodiments, synthetic nanocarriers are prepared by a nanoprecipitation process or spray drying. Conditions used in preparing synthetic nanocarriers may be altered to yield particles of a desired size or property (e.g., hydrophobicity, hydrophilicity, external morphology, "stickiness," shape, etc.). The method of preparing the synthetic nanocarriers and the conditions (e.g., solvent, temperature, concentration, air flow rate, etc.) used may depend on the materials to be coupled to the synthetic nanocarriers and/or the composition of the polymer matrix.

If particles prepared by any of the above methods have a size range outside of the desired range, particles can be sized, for example, using a sieve.

Elements (i.e., components) of the inventive synthetic nanocarriers (such as moieties of which an immunofeature surface is comprised, targeting moieties, polymeric matrices, antigens, immunosuppressants and the like) may be coupled to the overall synthetic nanocarrier, e.g., by one or more covalent bonds, or may be coupled by means of one or more linkers. Additional methods of functionalizing synthetic nanocarriers may be adapted from Published US Patent Application 2006/0002852 to Saltzman et al., Published US Patent Application 2009/0028910 to DeSimone et al., or Published International Patent Application WO/2008/127532 A1 to Murthy et al.

Alternatively or additionally, synthetic nanocarriers can be coupled to components directly or indirectly via non-covalent interactions. In non-covalent embodiments, the non-covalent coupling is mediated by non-covalent interactions including but not limited to charge interactions, affinity interactions, metal coordination, physical adsorption, host-guest interactions, hydrophobic interactions, TT stacking interactions, hydrogen bonding interactions, van der Waals interactions, magnetic interactions, electrostatic interactions, dipole-dipole interactions, and/or combinations thereof. Such couplings may be arranged to be on an external surface or an internal surface of an inventive synthetic nanocarrier. In embodiments, encapsulation and/or absorption is a form of coupling. In embodiments, the inventive synthetic nanocarriers can be combined with an antigen by admixing in the same vehicle or delivery system.

Populations of synthetic nanocarriers may be combined to form pharmaceutical dosage forms according to the present invention using traditional pharmaceutical mixing methods. These include liquid-liquid mixing in which two or more suspensions, each containing one or more subsets of nanocarriers, are directly combined or are brought together via one or more vessels containing diluent. As synthetic nanocarriers may also be produced or stored in a powder form, dry powder-powder mixing could be performed as could the re-suspension of two or more powders in a common media. Depending on the properties of the nanocarriers and their interaction potentials, there may be advantages conferred to one or another route of mixing.

Typical inventive compositions that comprise synthetic nanocarriers may comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), antifoaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and co-solvents (e.g., glycerol, polyethylene glycol, ethanol).

Compositions according to the invention comprise inventive synthetic nanocarriers in combination with pharmaceutically acceptable excipients. The compositions may be made using conventional pharmaceutical manufacturing and compounding techniques to arrive at useful dosage forms. Techniques suitable for use in practicing the present invention may be found in Handbook of Industrial Mixing: Science and Practice, Edited by Edward L. Paul, Victor A. Atiemo-Obeng, and Suzanne M. Kresta, 2004 John Wiley & Sons, Inc.; and Pharmaceutics: The Science of Dosage Form Design, 2nd Ed. Edited by M. E. Auten, 2001, Churchill Livingstone. In an embodiment, inventive synthetic nanocarriers are suspended in sterile saline solution for injection together with a preservative.

It is to be understood that the compositions of the invention can be made in any suitable manner, and the invention is in no way limited to compositions that can be produced using the methods described herein. Selection of an appropriate method may require attention to the properties of the particular moieties being associated.

In some embodiments, inventive synthetic nanocarriers are manufactured under sterile conditions or are terminally sterilized. This can ensure that resulting compositions are sterile and non-infectious, thus improving safety when compared to non-sterile compositions. This provides a valuable safety measure, especially when subjects receiving synthetic nanocarriers have immune defects, are suffering from infection, and/or are susceptible to infection. In some embodiments, inventive synthetic nanocarriers may be lyophilized and stored in suspension or as lyophilized powder depending on the formulation strategy for extended periods without losing activity.

The compositions of the invention can be administered by a variety of routes, including but not limited to subcutaneous, intranasal, oral, intravenous, intraperitoneal, intramuscular, transmucosal, transmucosal, sublingual, rectal, ophthalmic, pulmonary, intradermal, transdermal, transcutaneous or intradermal or by a combination of these routes. Routes of administration also include administration by inhalation or pulmonary aerosol. Techniques for preparing aerosol delivery systems are well known to those of skill in the art (see, for example, Sciarra and Cutie, "Aerosols," in Remington's Pharmaceutical Sciences, 18th edition, 1990, pp. 1694-1712; incorporated by reference).

The transplantable grafts or therapeutic proteins provided as a cell-based therapy of the invention may be administered by parenteral, intraarterial, intranasal or intravenous administration or by injection to lymph nodes or anterior chamber of the eye or by local administration to an organ or tissue of interest. The administration may be by subcutaneous, intrathecal, intraventricular, intramuscular, intraperitoneal, intracoronary, intrapancreatic, intrahepatic or bronchial injection.

The compositions of the invention can be administered in effective amounts, such as the effective amounts described elsewhere herein. Doses of dosage forms contain varying amounts of populations of synthetic nanocarriers and/or varying amounts of immunosuppressants and/or antigens, according to the invention. The amount of synthetic nanocarriers and/or immunosuppressants and/or antigens present in the inventive dosage forms can be varied according to the nature of the antigens, the therapeutic benefit to be accomplished, and other such parameters. In embodiments, dose ranging studies can be conducted to establish optimal therapeutic amount of the population of synthetic nanocarriers and the amount of immunosuppressants and/or antigens to be present in the dosage form. In embodiments, the synthetic nanocarriers and/or the immunosuppressants and/or antigens are present in the dosage form in an amount effective to generate a tolerogenic immune response to the antigens upon administration to a subject. It may be possible to determine amounts of the immunosuppressants and/or antigens effective to generate a tolerogenic immune response using conventional dose ranging studies and techniques in subjects. Inventive dosage forms may be administered at a variety of frequencies. In a preferred embodiment, at least one administration of the dosage form is sufficient to generate a pharmacologically relevant response. In more preferred embodiments, at least two administrations, at least three administrations, or at least four administrations, of the dosage form are utilized to ensure a pharmacologically relevant response.

Prophylactic administration of the inventive compositions can be initiated prior to the onset of disease, disorder or condition or therapeutic administration can be initiated after a disorder, disorder or condition is established.

In some embodiments, administration of synthetic nanocarriers is undertaken e.g., prior to administration of a therapeutic protein or transplantable graft or exposure to an allergen. In exemplary embodiments, synthetic nanocarriers are administered at one or more times including, but not limited to, 30, 25, 20, 15, 14, 13, 12, 11, 10, 9, 8, 7, 6, 5, 4, 3, 2, 1, or 0 days prior to administration of a therapeutic protein or transplantable graft or exposure to an allergen. In addition or alternatively, synthetic nanocarriers can be administered to a subject following administration of a therapeutic protein or transplantable graft or exposure to an allergen. In exemplary embodiments, synthetic nanocarriers are administered at one or more times including, but not limited to, 1, 2, 3, 4, 5, 6, 7, 8, 9, 10, 11, 12, 13, 14, 15, 20, 25, 30, etc. days following administration of a therapeutic protein or transplantable graft or exposure to an allergen.

In some embodiments, a maintenance dose (e.g., of a synthetic nanocarrier composition provided herein) is administered to a subject after an initial administration has resulted in a tolerogenic response in the subject, for example to maintain the tolerogenic effect achieved after the initial dose, to prevent an undesired immune reaction in the subject, or to prevent the subject becoming a subject at risk of experiencing an undesired immune response or an undesired level of an immune response. In some embodiments, the maintenance dose is the same dose as the initial dose the subject received. In some embodiments, the maintenance dose is a lower dose than the initial dose. For example, in some embodiments, the maintenance dose is about $3/4$, about $2/3$, about $1/2$, about $1/3$, about $1/4$, about $1/8$, about $1/10$, about $1/20$, about $1/25$, about $1/50$, about $1/100$, about $1/1,000$, about $1/10,000$, about $1/100,000$, or about $1/1,000,000$ (weight/weight) of the initial dose.

The compositions and methods described herein can be used to induce or enhance a tolerogenic immune response and/or to suppress, modulate, direct or redirect an undesired immune response for the purpose of immune suppression. The compositions and methods described herein can be used in the diagnosis, prophylaxis and/or treatment of diseases, disorders or conditions in which immune suppression (e.g., tolerogenic immune response) would confer a treatment benefit. Such diseases, disorders or conditions include inflammatory diseases, autoimmune diseases, allergies, organ or tissue rejection and graft versus host disease. The compositions and methods described herein can also be used in subjects who have undergone or will undergo transplantation. The compositions and methods described herein can also be used in subjects who have received, are receiving or will receive a therapeutic protein against which they have generated or are expected to generate an undesired immune response.

Autoimmune diseases include, but are not limited to, rheumatoid arthritis, multiple sclerosis, immune-mediated or Type I diabetes mellitus, inflammatory bowel disease (e.g., Crohn's disease or ulcerative colitis), systemic *lupus* erythematosus, psoriasis, scleroderma, autoimmune thyroid disease, alopecia areata, Grave's disease, Guillain-Barré syndrome, celiac disease, Sjögren's syndrome, rheumatic fever, gastritis, autoimmune atrophic gastritis, autoimmune hepatitis, insulitis, oophoritis, orchitis, uveitis, phacogenic uveitis, myasthenia gravis, primary myxoedema, pernicious anemia, autoimmune haemolytic anemia, Addison's disease, scleroderma, Goodpasture's syndrome, nephritis, for example, glomerulonephritis, psoriasis, pemphigus vulgaris, pemphigoid, sympathetic opthalmia, idiopathic thrombocylopenic purpura, idiopathic feucopenia, Wegener's granulomatosis and poly/dermatomyositis.

Some additional exemplary autoimmune diseases, associated autoantigens, and autoantibodies, which are contemplated for use in the invention, are described in Table 1 below:

| Autoantibody Type | Autoantibody | Autoantigen | Autoimmune disease or disorder |
|---|---|---|---|
| Antinuclear antibodies | Anti-SSA/Ro autoantibodies | ribonucleoproteins | Systemic lupus erythematosus, neonatal heart block, primary Sjögren's syndrome |
| | Anti-La/SS-B autoantibodies | ribonucleoproteins | Primary Sjögren's syndrome |
| | Anti-centromere antibodies | centromere | CREST syndrome |
| | Anti-neuronal nuclear antibody-2 | Ri[disambiguation needed] | Opsoclonus |
| | Anti-dsDNA | double-stranded DNA | SLE |
| | Anti-Jo1 | histidine-tRNA ligase | Inflammatory myopathy |
| | Anti-Smith | snRNP core proteins | SLE |
| | Anti-topoisomerase antibodies | Type I topoisomerase | Systemic sclerosis (anti-Scl-70 antibodies) |
| | Anti-histone antibodies | histones | SLE and Drug-induced LE[2] |
| | Anti-p62 antibodies [3] | nucleoporin 62 | Primary biliary cirrhosis[3][4][5] |
| | Anti-sp100 antibodies [4] | Sp100 nuclear antigen | |
| | Anti-glycoprotein-210 antibodies[5] | nucleoporin 210 kDa | |
| Anti-transglutaminase antibodies | Anti-tTG | | Coeliac disease |
| | Anti-eTG | | Dermatitis herpetiformis |
| Anti-ganglioside antibodies | | ganglioside GQ1B | Miller-Fisher Syndrome |
| | | ganglioside GD3 | Acute motor axonal neuropathy (AMAN) |
| | | ganglioside GM1 | Multifocal motor neuropathy with conduction block (MMN) |
| Anti-actin antibodies | | actin | Coeliac disease anti-actin antibodies correlated with the level of intestinal damage [6][7] |
| Liver kidney microsomal type 1 antibody | | | Autoimmune hepatitis. [8] |
| Lupus anticoagulant | Anti-thrombin antibodies | thrombin | Systemic lupus erythematosus |
| Anti-neutrophil cytoplasmic antibody | c-ANCA | phospholipid proteins in neutrophil cytoplasm | Antiphospholipid syndrome Wegener's granulomatosis |
| | p-ANCA | neutrophil perinuclear | Microscopic polyangiitis, Churg-Strauss syndrome, systemic vasculitides (non-specific) |

-continued

| Autoantibody Type | Autoantibody | Autoantigen | Autoimmune disease or disorder |
|---|---|---|---|
| Rheumatoid factor | | IgG | Rheumatoid arthritis |
| Anti-smooth muscle antibody | | smooth muscle | Chronic autoimmune hepatitis |
| Anti-mitochondrial antibody | | mitochondria | Primary biliary cirrhosis[9] |
| Anti-SRP | | signal recognition particle | Polymyositis[10] |
| | | exosome complex | Scleromyositis |
| | | nicotinic acetylcholine receptor | Myasthenia gravis |
| | | muscle-specific kinase (MUSK) | Myasthenia gravis |
| Anti-VGCC | | voltage-gated calcium channel (P/Q-type) | Lambert-Eaton myasthenic syndrome |
| | | thyroid peroxidase (microsomal) | Hashimoto's thyroiditis |
| | | TSH receptor | Graves' disease |
| | | Hu | Paraneoplastic cerebellar syndrome |
| | | Yo (cerebellar Purkinje Cells) | Paraneoplastic cerebellar syndrome |
| | | amphiphysin | Stiff person syndrome, paraneoplastic cerebellar syndrome |
| Anti-VGKC | | voltage-gated potassium channel (VGKC) | Limbic encephalitis, Isaac's Syndrome (autoimmune neuromyotonia) |
| | | basal ganglia neurons | Sydenham's chorea, paediatric autoimmune neuropsychiatric disease associated with *Streptococcus* (PANDAS) |
| | | N-methyl-D-aspartate receptor (NMDA) | Encephalitis |
| | | glutamic acid decarboxylase (GAD) | Diabetes mellitus type 1, stiff person syndrome |
| | | aquaporin-4 | Neuromyelitis optica (Devic's syndrome) |

Inflammatory diseases include, but are not limited to, Alzheimer's, Ankylosing spondylitis, arthritis, asthma, atherosclerosis, Behçet's disease, chronic inflammatory demyelinating polyradiculoneuropathy, Crohn's disease, colitis, cystic fibrosis, dermatitis, diverticulitis, hepatitis, irritable bowel syndrome (IBS), lupus erythematous, muscular dystrophy, nephritis, Parkinson's, shingles and ulcerative colitis. Inflammatory diseases also include, for example, cardiovascular disease, chronic obstructive pulmonary disease (COPD), bronchiectasis, chronic cholecystitis, tuberculosis, Hashimoto's thyroiditis, sepsis, sarcoidosis, silicosis and other pneumoconioses, and an implanted foreign body in a wound, but are not so limited. As used herein, the term "sepsis" refers to a well-recognized clinical syndrome associated with a host's systemic inflammatory response to microbial invasion. The term "sepsis" as used herein refers to a condition that is typically signaled by fever or hypothermia, tachycardia, and tachypnea, and in severe instances can progress to hypotension, organ dysfunction, and even death.

In some embodiments, the inflammatory disease is non-autoimmune inflammatory bowel disease, post-surgical adhesions, coronary artery disease, hepatic fibrosis, acute respiratory distress syndrome, acute inflammatory pancreatitis, endoscopic retrograde cholangiopancreatography-induced pancreatitis, burns, atherogenesis of coronary, cerebral and peripheral arteries, appendicitis, cholecystitis, diverticulitis, visceral fibrotic disorders, wound healing, skin scarring disorders (keloids, hidradenitis suppurativa), granulomatous disorders (sarcoidosis, primary biliary cirrhosis), asthma, pyoderma gandrenosum, Sweet's syndrome, Behçet's disease, primary sclerosing cholangitis or an abscess. In some preferred embodiment the inflammatory disease is inflammatory bowel disease (e.g., Crohn's disease or ulcerative colitis).

In other embodiments, the inflammatory disease is an autoimmune disease. The autoimmune disease in some embodiments is rheumatoid arthritis, rheumatic fever, ulcerative colitis, Crohn's disease, autoimmune inflammatory bowel disease, insulin-dependent diabetes mellitus, diabetes mellitus, juvenile diabetes, spontaneous autoimmune diabetes, gastritis, autoimmune atrophic gastritis, autoimmune hepatitis, thyroiditis, Hashimoto's thyroiditis, insulitis, oophoritis, orchitis, uveitis, phacogenic uveitis, multiple sclerosis, myasthenia gravis, primary myxoedema, thyrotoxicosis, pernicious anemia, autoimmune haemolytic anemia, Addison's disease, Anklosing spondylitis, sarcoidosis, scleroderma, Goodpasture's syndrome, Guillain-Barre syndrome, Graves' disease, glomerulonephritis, psoriasis, pemphigus vulgaris, pemphigoid, excema, bulous pemiphigous, sympathetic opthalmia, idiopathic thrombocylopenic purpura, idiopathic feucopenia, Sjogren's syndrome, systemic sclerosis, Wegener's granulomatosis, poly/dermatomyositis, primary biliary cirrhosis, primary sclerosing cholangitis, lupus or systemic lupus erythematosus.

Graft versus host disease (GVHD) is a complication that can occur after a pluripotent cell (e.g., stem cell) or bone marrow transplant in which the newly transplanted material results in an attack on the transplant recipient's body. In some instances, GVHD takes place after a blood transfusion. Graft-versus-host-disease can be divided into acute and chronic forms. The acute or fulminant form of the disease (aGVHD) is normally observed within the first 100 days post-transplant, and is a major challenge to transplants owing to associated morbidity and mortality. The chronic form of graft-versus-host-disease (cGVHD) normally occurs after 100 days. The appearance of moderate to severe cases of cGVHD adversely influences long-term survival.

EXAMPLES

Example 1: Immune Response of Synthetic Nanocarriers with Coupled Rapamycin with and without Ovalbumin Peptide (323-339)

Materials

Ovalbumin peptide 323-339, a 17 amino acid peptide known to be a T and B cell epitope of Ovalbumin protein, was purchased from Bachem Americas Inc. (3132 Kashiwa Street, Torrance Calif. 90505; Part #4065609). Rapamycin was purchased from TSZ CHEM (185 Wilson Street, Framingham, Mass. 01702; Product Catalogue # R1017). PLGA with a lactide:glycolide ratio of 3:1 and an inherent viscosity of 0.75 dL/g was purchased from SurModics Pharmaceuticals (756 Tom Martin Drive, Birmingham, Ala. 35211; Product Code 7525 DLG 7A). Polyvinyl alcohol (85-89% hydrolyzed) was purchased from EMD Chemicals (Product Number 1.41350.1001).

Solution 1: Ovalbumin peptide 323-339 @ 20 mg/mL in dilute hydrochloric acid aqueous solution. The solution was prepared by dissolving ovalbumin peptide in 0.13 M hydrochloric acid solution at room temperature.

Solution 2: Rapamycin @ 50 mg/mL in methylene chloride. The solution was prepared by dissolving rapamycin in pure methylene chloride.

Solution 3: PLGA @ 100 mg/mL in methylene chloride. The solution was prepared by dissolving PLGA in pure methylene chloride.

Solution 4: Polyvinyl alcohol @ 50 mg/mL in 100 mM pH 8 phosphate buffer.

Method for Preparing Synthetic Nanocarrier Containing Rapamycin and Ovalbumin (323-339)

A primary water-in-oil emulsion was prepared first. W1/O1 was prepared by combining solution 1 (0.2 mL), solution 2 (0.2 mL), and solution 3 (1.0 mL) in a small pressure tube and sonicating at 50% amplitude for 40 seconds using a Branson Digital Sonifier 250. A secondary emulsion (W1/O1/W2) was then prepared by combining solution 4 (3.0 mL) with the primary W1/O1 emulsion, vortexing for 10 s, and sonicating at 30% amplitude for 60 seconds using the Branson Digital Sonifier 250.

The W1/O1/W2 emulsion was added to a beaker containing 70 mM pH 8 phosphate buffer solution (30 mL) and stirred at room temperature for 2 hours to allow the methylene chloride to evaporate and for the synthetic nanocarriers to form. A portion of the synthetic nanocarriers were washed by transferring the synthetic nanocarrier suspension to a centrifuge tube and centrifuging at 21,000×g and 4° C. for one hour, removing the supernatant, and re-suspending the pellet in phosphate buffered saline. The washing procedure was repeated, and the pellet was re-suspended in phosphate buffered saline for a final synthetic nanocarrier dispersion of about 10 mg/mL.

The amounts of peptide and rapamycin in the synthetic nanocarriers were determined by HPLC analysis. The total dry-synthetic nanocarrier mass per mL of suspension was determined by a gravimetric method.

Method for Synthetic Nanocarrier Containing Rapamycin

A primary water-in-oil emulsion was prepared first. W1/O1 was prepared by combining 0.13 M hydrochloric acid solution (0.2 mL), solution 2 (0.2 mL), and solution 3 (1.0 mL) in a small pressure tube and sonicating at 50% amplitude for 40 seconds using a Branson Digital Sonifier 250. A secondary emulsion (W1/O1/W2) was then prepared by combining solution 4 (3.0 mL) with the primary W1/O1 emulsion, vortexing for 10 s, and sonicating at 30% amplitude for 60 seconds using the Branson Digital Sonifier 250.

The W1/O1/W2 emulsion was added to a beaker containing 70 mM pH 8 phosphate buffer solution (30 mL) and stirred at room temperature for 2 hours to allow the methylene chloride to evaporate and for the synthetic nanocarriers to form. A portion of the synthetic nanocarriers were washed by transferring the synthetic nanocarrier suspension to a centrifuge tube and centrifuging at 21,000×g and 4° C. for one hour, removing the supernatant, and re-suspending the pellet in phosphate buffered saline. The washing procedure was repeated, and the pellet was re-suspended in phosphate buffered saline for a final synthetic nanocarrier dispersion of about 10 mg/mL.

The amount of rapamycin in the synthetic nanocarrier was determined by HPLC analysis. The total dry-synthetic nanocarrier mass per mL of suspension was determined by a gravimetric method.

Method for Measuring Rapamycin Load

Approximately 3 mg of synthetic nanocarriers were collected and centrifuged to separate supernatant from synthetic nanocarrier pellet. Acetonitrile was added to the pellet, and the sample was sonicated and centrifuged to remove any insoluble material. The supernatant and pellet were injected on RP-HPLC and absorbance was read at 278 nm. The μg found in the pellet were used to calculate % entrapped (load), μg in supernatant and pellet were used to calculate total μg recovered.

Method for Measuring Ovalbumin (323-339) Load

Approximately 3 mg of synthetic nanocarriers were collected and centrifuged to separate supernatant from synthetic nanocarrier pellet. Trifluoroethanol was added to the pellet and the sample was sonicated to dissolve the polymer, 0.2% trifluoroacetic acid was added and sample was sonicated and then centrifuged to remove any insoluble material. The supernatant and pellet were injected on RP-HPLC and absorbance was read at 215 nm. The μg found in the pellet were used to calculate % entrapped (load), μg in supernatant and pellet were used to calculate total μg recovered.

Antigen-specific Tolerogenic Dendritic Cells (Tdc) Activity on Treg Cell Development The assay included the use of OTII mice which have a transgenic T-cell receptor specific for an immune-dominant ovalbumin (323-339). In order to create antigen-specific tDCs, CD11c+ splenocytes were isolated, and the ovalbumin (323-339) peptide added in vitro at 1 μg/ml or no antigen. Soluble or nanocarrier-encapsulated rapamycin was then added to the DCs for 2 hours which were then washed extensively to remove free rapamycin from the culture. Purified responder CD4+CD25− cells were isolated from OTII mice and added to tDC at a 10:1 T to DC ratio. The mixture of tDC and OTII T-cells were then cultured for 4-5 days, and the frequency of Treg cells (CD4+ CD25highFoxP3+) were analyzed by flow cytometry as shown in FIG. 1. Regions were selected based on isotype controls.

Example 2: Mesoporous Silica Nanoparticles with Coupled Ibuprofen (Prophetic)

Mesoporous $SiO_2$ nanoparticle cores are created through a sol-gel process. Hexadecyltrimethyl-ammonium bromide (CTAB) (0.5 g) is dissolved in deionized water (500 mL), and then 2 M aqueous NaOH solution (3.5 mL) is added to the CTAB solution. The solution is stirred for 30 min, and then Tetraethoxysilane (TEOS) (2.5 mL) is added to the solution. The resulting gel is stirred for 3 h at a temperature of 80° C. The white precipitate which forms is captured by filtration, followed by washing with deionized water and drying at room temperature. The remaining surfactant is then extracted from the particles by suspension in an ethanolic solution of HCl overnight. The particles are washed with ethanol, centrifuged, and redispersed under ultrasonication. This wash procedure is repeated two additional times.

The $SiO_2$ nanoparticles are then functionalized with amino groups using (3-aminopropyl)-triethoxysilane (APTMS). To do this, the particles are suspended in ethanol (30 mL), and APTMS (50 µL) is added to the suspension. The suspension is allowed to stand at room temperature for 2 h and then is boiled for 4 h, keeping the volume constant by periodically adding ethanol. Remaining reactants are removed by five cycles of washing by centrifugation and redispersing in pure ethanol.

In a separate reaction, 1-4 nm diameter gold seeds are created. All water used in this reaction is first deionized and then distilled from glass. Water (45.5 mL) is added to a 100 mL round-bottom flask. While stirring, 0.2 M aqueous NaOH (1.5 mL) is added, followed by a 1% aqueous solution of tetrakis(hydroxymethyl)phosphonium chloride (THPC) (1.0 mL). Two minutes after the addition of THPC solution, a 10 mg/mL aqueous solution of chloroauric acid (2 mL), which has been aged at least 15 min, is added. The gold seeds are purified through dialysis against water.

To form the core-shell nanocarriers, the amino-functionalized $SiO_2$ nanoparticles formed above are first mixed with the gold seeds for 2 h at room temperature. The gold-decorated $SiO_2$ particles are collected through centrifugation and mixed with an aqueous solution of chloroauric acid and potassium bicarbonate to form the gold shell. The particles are then washed by centrifugation and redispersed in water. Ibuprofen is loaded by suspending the particles in a solution of sodium ibuprofen (1 mg/L) for 72 h. Free ibuprofen is then washed from the particles by centrifugation and redispersing in water.

Example 3: Liposomes Containing Cyclosporine A (Prophetic)

The liposomes are formed using thin film hydration. 1,2-Dipalmitoyl-sn-glycero-3-phosphocholine (DPPC) (32 µmol), cholesterol (32 µmol), and cyclosporin A (6.4 µmol) are dissolved in pure chloroform (3 mL). This lipid solution is added to a 50 mL round-bottom flask, and the solvent is evaporated on a rotary evaporator at a temperature of 60° C. The flask is then flushed with nitrogen gas to remove remaining solvent. Phosphate buffered saline (2 mL) and five glass beads are added to the flask, and the lipid film is hydrated by shaking at 60° C. for 1 h to form a suspension. The suspension is transferred to a small pressure tube and sonicated at 60° C. for four cycles of 30 s pulses with a 30 s delay between each pulse. The suspension is then left undisturbed at room temperature for 2 h to allow for complete hydration. The liposomes are washed by centrifugation followed by resuspension in fresh phosphate buffered saline.

Example 4: Polymeric Nanocarrier Containing Polymer-Rapamycin Conjugate (Prophetic)

Preparation of PLGA-Rapamycin Conjugate:
PLGA polymer with acid end group (7525 DLG1A, acid number 0.46 mmol/g, Lakeshore Biomaterials; 5 g, 2.3 mmol, 1.0 eq) is dissolved in 30 mL of dichloromethane (DCM). N,N-Dicyclohexylcarbodiimide (1.2 eq, 2.8 mmol, 0.57 g) is added followed by rapamycin (1.0 eq, 2.3 mmol, 2.1 g) and 4-dimethylaminopyridine (DMAP) (2.0 eq, 4.6 mmol, 0.56 g). The mixture is stirred at rt for 2 days. The mixture is then filtered to remove insoluble dicyclohexylurea. The filtrate is concentrated to ca. 10 mL in volume and added to 100 mL of isopropyl alcohol (IPA) to precipitate out the PLGA-rapamycin conjugate. The IPA layer is removed and the polymer is then washed with 50 mL of IPA and 50 mL of methyl t-butyl ether (MTBE). The polymer is then dried under vacuum at 35 C for 2 days to give PLGA-rapamycin as a white solid (ca. 6.5 g).

Preparation of Nanocarrier Containing PLGA-Rapamycin Conjugate and Ovalbumin Peptide (323-339):
Nanocarrier containing PLGA-rapamycin is prepared according to the procedure described in Example 1 as follows:

Solutions for nanocarrier formation are prepared as follows:

Solution 1: Ovalbumin peptide 323-339 @ 20 mg/mL in dilute hydrochloric acid aqueous solution. The solution is prepared by dissolving ovalbumin peptide in 0.13 M hydrochloric acid solution at room temperature. Solution 2: PLGA-rapamycin @ 100 mg/mL in methylene chloride. The solution is prepared by dissolving PLGA-rapamycin in pure methylene chloride. Solution 3: PLA-PEG @ 100 mg/mL in methylene chloride. The solution is prepared by dissolving PLA-PEG in pure methylene chloride. Solution 4: Polyvinyl alcohol @ 50 mg/mL in 100 mM pH 8 phosphate buffer.

A primary water-in-oil emulsion is prepared first. W1/O1 is prepared by combining solution 1 (0.2 mL), solution 2 (0.75 mL), and solution 3 (0.25 mL) in a small pressure tube and sonicating at 50% amplitude for 40 seconds using a Branson Digital Sonifier 250. A secondary emulsion (W1/O1/W2) is then prepared by combining solution 4 (3.0 mL) with the primary W1/O1 emulsion, vortexing for 10 s, and sonicating at 30% amplitude for 60 seconds using the Branson Digital Sonifier 250. The W1/O1/W2 emulsion is added to a beaker containing 70 mM pH 8 phosphate buffer solution (30 mL) and stirred at room temperature for 2 hours to allow the methylene chloride to evaporate and for the nanocarriers to form. A portion of the nanocarriers is washed by transferring the nanocarrier suspension to a centrifuge tube and centrifuging at 75,600×g and 4° C. for 35 min, removing the supernatant, and re-suspending the pellet in phosphate buffered saline. The washing procedure is repeated, and the pellet is re-suspended in phosphate buffered saline for a final nanocarrier dispersion of about 10 mg/mL.

Example 5: Preparation of Gold Nanocarriers (AuNCs) Containing Rapamycin (Prophetic)

Preparation of HS-PEG-Rapamycin:
A solution of PEG acid disulfide (1.0 eq), rapamycin (2.0-2.5 eq), DCC (2.5 eq) and DMAP (3.0 eq) in dry DMF is stirred at rt overnight. The insoluble dicyclohexylurea is removed by filtration and the filtrate is added to isopropyl alcohol (IPA) to precipitate out the PEG-disulfide-di-rapamycin ester and washed with IPA and dried. The polymer is then treated with tris(2-carboxyethyl)phosphine hydrochloride in DMF to reduce the PEG disulfide to thiol PEG rapamycin ester (HS-PEG-rapamycin). The resulting polymer is recovered by precipitation from IPA and dried as previously described and analyzed by H NMR and GPC.

Formation of Gold NCs (AuNCs):

An aq. solution of 500 mL of 1 mM HAuCl4 is heated to reflux for 10 min with vigorous stirring in a 1 L round-bottom flask equipped with a condenser. A solution of 50 mL of 40 mM of trisodium citrate is then rapidly added to the stirring solution. The resulting deep wine red solution is kept at reflux for 25-30 min and the heat is withdrawn and the solution is cooled to room temperature. The solution is then filtered through a 0.8 µm membrane filter to give the AuNCs solution. The AuNCs are characterized using visible spectroscopy and transmission electron microscopy. The AuNCs are ca. 20 nm diameter capped by citrate with peak absorption at 520 nm.

AuNCs Conjugate with HS-PEG-Rapamycin:

A solution of 150 µl of HS-PEG-rapamycin (10 µM in 10 mM pH 9.0 carbonate buffer) is added to 1 mL of 20 nm diameter citrate-capped gold nanocarriers (1.16 nM) to produce a molar ratio of thiol to gold of 2500:1. The mixture is stirred at room temperature under argon for 1 hour to allow complete exchange of thiol with citrate on the gold nanocarriers. The AuNCs with PEG-rapamycin on the surface is then purified by centrifuge at 12,000 g for 30 minutes. The supernatant is decanted and the pellet containing AuNC-S-PEG-rapamycin is then pellet washed with 1×PBS buffer. The purified Gold-PEG-rapamycin nanocarriers are then resuspend in suitable buffer for further analysis and bioassays.

Example 6: Mesoporous Silica-Gold Core-Shell Nanocarriers Containing Ovalbumin (Prophetic)

Mesoporous SiO2 nanoparticle cores are created through a sol-gel process. Hexadecyltrimethyl-ammonium bromide (CTAB) (0.5 g) is dissolved in deionized water (500 mL), and then 2 M aqueous NaOH solution (3.5 mL) is added to the CTAB solution. The solution is stirred for 30 min, and then Tetraethoxysilane (TEOS) (2.5 mL) is added to the solution. The resulting gel is stirred for 3 h at a temperature of 80° C. The white precipitate which forms is captured by filtration, followed by washing with deionized water and drying at room temperature. The remaining surfactant is then extracted from the particles by suspension in an ethanolic solution of HCl overnight. The particles are washed with ethanol, centrifuged, and redispersed under ultrasonication. This wash procedure is repeated two additional times.

The SiO2 nanoparticles are then functionalized with amino groups using (3-aminopropyl)-triethoxysilane (APTMS). To do this, the particles are suspended in ethanol (30 mL), and APTMS (50 µL) is added to the suspension. The suspension is allowed to stand at room temperature for 2 h and then is boiled for 4 h, keeping the volume constant by periodically adding ethanol. Remaining reactants are removed by five cycles of washing by centrifugation and redispersing in pure ethanol.

In a separate reaction, 1-4 nm diameter gold seeds are created. All water used in this reaction is first deionized and then distilled from glass. Water (45.5 mL) is added to a 100 mL round-bottom flask. While stirring, 0.2 M aqueous NaOH (1.5 mL) is added, followed by a 1% aqueous solution of tetrakis(hydroxymethyl)phosphonium chloride (THPC) (1.0 mL). Two minutes after the addition of THPC solution, a 10 mg/mL aqueous solution of chloroauric acid (2 mL), which has been aged at least 15 min, is added. The gold seeds are purified through dialysis against water.

To form the core-shell nanocarriers, the amino-functionalized SiO2 nanoparticles formed above are first mixed with the gold seeds for 2 h at room temperature. The gold-decorated SiO2 particles are collected through centrifugation and mixed with an aqueous solution of chloroauric acid and potassium bicarbonate to form the gold shell. The particles are then washed by centrifugation and redispersed in water. Thiolated Ovalbumin (made by treating Ovalbumin with 2-iminothiolane hydrochloride) is loaded by suspending the particles in a solution of thiolated Ovalbumin (1 mg/L) for 72 h. The particles is then pellet washed with 1×PBS (pH 7.4) to remove free protein. The resulting silica-gold core-shell nanocarriers containing Ovalbumin are then re-suspended in 1×PBS for further analysis and assays.

Example 7: Liposomes Containing Rapamycin and Ovalbumin (Prophetic)

The liposomes are formed by thin film hydration. 1,2-Dipalmitoyl-sn-glycero-3-phosphocholine (DPPC) (32 µmol), cholesterol (32 µmol), and rapamycin (6.4 µmol) are dissolved in pure chloroform (3 mL). This lipid solution is added to a 10 mL glass tube and the solvent is removed under nitrogen gas stream and desiccated for 6 hr. under vacuum. Multilamellar vesicles are obtained by hydration of the film with 2.0 ml of 25 mM MOPS buffer pH 8.5, containing excess amount of Ovalbumin. The tube is vortexed until the lipid film is peeled of from the tube surface. To break the multilamellar vesicles into monolamellar, ten cycles of freezing (liquid nitrogen) and thawing (30° C. water bath) are applied. The sample is then diluted to 1 ml in 25 mM MOPS buffer pH 8.5. Size of the resulting liposome is homogenized by extrusion by passing the sample 10 fold through a 200 nm pore polycarbonate filters. The resulting liposomes are then used for further analysis and bioassays.

Example 8: Polymeric Nanocarriers Composed of Modified Polyamino Acid with Surface Conjugated Ovalbumin (Prophetic)

Step-1. Preparation of Poly(γ-glutamic acid) (γ-PGA) modified with L-phenylalanine ethyl ester (L-PAE): 4.7 unit mmol of 7-PGA (Mn=300 kD) is dissolved in 0.3 N—NaHCO3 aqueous solution (50 mL). L-PAE (4.7 mmol) and EDC.HCl (4.7 mmol) are added to the solution and stirred for 30 min at 4 C. The solution is then maintained at room temperature with stirring for 24 h. Low-molecular-weight chemicals are removed by dialysis using dialysis membrane with MWCO 50 kD. The resulting γ-PGA-graft-L-PAE is obtained by freeze-drying.

Step-2. Preparation of nanoparticles from γ-PGA-graft-L-PAE polymer: Nanoparticles composed of γ-PGA-graft-L-PAE are prepared by a precipitation and dialysis method. γ-PGA-graft-L-PAE (20 mg) was dissolved in 2 ml of DMSO followed by addition of 2 mL of water to form a translucent solution. The solution is then dialyzed against distilled water using cellulose membrane tubing (50,000 MWCO) to form the nanoparticles and to remove the organic solvents for 72 h at room temperature. The distilled water is exchanged at intervals of 12 h. The resulting nanoparticle solution (10 mg/mL in water) is then used for antigen conjugation.

Step-3. Ovalbumin conjugation to γ-PGA nanoparticles: Surface carboxylic acid groups of the γ-PGA nanoparticles (10 mg/ml) are first activated by EDC and NHS (10 mg/mL each in phosphate buffer, pH 5.8) for 2 h at ambient temperature. After pellet washing to remove excess EDC/NHS, the activated nanoparticles are mixed with 1 mL of Ovalbumin (10 mg/ml) in phosphate-buffered saline (PBS, pH 7.4) and the mixture is incubated at 4-8 C for 24 h. The resulting Ovalbumin conjugated γ-PGA nanoparticles are washed twice with PBS and resuspended at 5 mg/mL in PBS for further analysis and bioassays.

Example 9: Erythropoietin (EPO)-Encapsulated γ-PGA Nanoparticles (Prophetic)

To prepare the EPO-encapsulated γ-PGA nanoparticles, 0.25-4 mg of EPO is dissolved in 1 mL of PBS (pH 7.4) and 1 mL of the γ-PGA-graft-L-PAE (10 mg/mL in DMSO) is added to the EPO solution. The resulting solution is centrifuged at 14,000×g for 15 min and repeatedly rinsed with PBS. The resulting EPO-encapsulated γ-PGA nanoparticles are then resuspended in PBS (5 mg/mL) for further analysis and bioassay.

Example 10: Preparation of Gold Nanocarriers (AuNCs) Containing Ovalbumin (Prophetic)

Step-1. Formation of Gold NCs (AuNCs): An aq. solution of 500 mL of 1 mM HAuCl4 is heated to reflux for 10 min with vigorous stirring in a 1 L round-bottom flask equipped with a condenser. A solution of 50 mL of 40 mM of trisodium citrate is then rapidly added to the stirring solution. The resulting deep wine red solution is kept at reflux for 25-30 min and the heat is withdrawn and the solution is cooled to room temperature. The solution is then filtered through a 0.8 μm membrane filter to give the AuNCs solution. The AuNCs are characterized using visible spectroscopy and transmission electron microscopy. The AuNCs are ca. 20 nm diameter capped by citrate with peak absorption at 520 nm.

Step-2. Conjugation of Ovalbumin to AuNCs: A solution of 150 μl of thiolated Ovalbumin (10 μM in 10 mM pH 9.0 carbonate buffer) is added to 1 mL of 20 nm diameter citrate-capped gold nanocarriers (1.16 nM) to produce a molar ratio of thiol to gold of 2500:1. The mixture is stirred at room temperature under argon for 1 hour to allow complete exchange of thiol with citrate on the gold nanocarriers. The AuNCs with Ovalbumin on the surface is then purified by centrifuge at 12,000 g for 30 minutes. The supernatant is decanted and the pellet containing AuNC-Ovalbumin is then pellet washed with 1×PBS buffer. The purified Gold-Ovalbumin nanocarriers are then resuspend in suitable buffer for further analysis and bioassays.

Example 11: Evaluating Tolerogenic Immune Response to Antigen In Vivo (Prophetic)

Balb/c mice are immunized with an antigen in incomplete Freund's adjuvant, and the level of regulatory B cell proliferation is assessed. Subsequently, a composition of the invention is administered in a dose-dependent manner. The same mice are then again exposed to the antigen, and the level of regulatory B cell proliferation is again assessed. Changes in regulatory B cell proliferation are then monitored with an increase upon subsequent challenge with the antigen indicating a tolerogenic immune response.

Example 12: Evaluating In Vitro Induction of Regulatory B Cells (Prophetic)

A cell population comprising regulatory B cells or regulatory B cell precursors is contacted in vitro with a composition provided herein. After a time sufficient for the composition to interact with the regulatory B cells or regulatory B cell precursors in the cell population, an increase in the number of regulatory B cells is expected. A time sufficient for the increase in the number of regulatory B cells in the population of cells is, in some embodiment, a period of about 1 day, about 2 days, about 3 days, about 4 days, about 5 days, about 6 days, about 1 week, about 2 weeks, about 3 weeks, or about 4 weeks. In some embodiments, the number of regulatory B cells is increased after that time, for example, to at least about 5 times, at least about 10 times, at least about 20 times, at least about 50 times, at least about 100 times, at least about 1.000 times, at least about 10.000 times, at least about 100.000 times, or at least about 1.000.000 times as compared to the original total or relative number of regulatory B cells in the population. In some embodiments, the number of regulatory B cells is increased after that time, for example, to about 1%, about 5%, about 10%, about 15%, about 20%, about 25%, about 30%, about 40%, about 50%, about 75%, about 90%, or about 95% of the total cells in the population or of the lymphocytes in the cell population. In some embodiments, regulatory B cells are absent from the cell population before the contacting, but are present after the contacting.

In some embodiments, the total and/or relative number of regulatory B cells in the population is determined before the population of cells is contacted with a composition provided herein to establish a baseline number of regulatory B cells in the population. In some embodiments, the population of cells is contacted once with a composition provided herein. In some embodiments, the population of cells is contacted repeatedly with a composition provided herein.

The number and/or presence of regulatory B cells in the population of cells is also determined after the contacting. In some embodiments, the number and/or presence of regulatory B cells is monitored over a period of time, for example, by performing a plurality of subsequent regulatory B cell detection assays. In some embodiments, the number and/or presence of regulatory B cells in the population of cells is determined by taking a sample from the cell population that is representative of the cell population, staining cells contained in that sample with antibodies or staining agents that specifically detect regulatory B cell markers, and detecting cells that express regulatory B cell markers in the sample, for example, by FACS or by immunohistochemistry. In some embodiments, the regulatory B cells are quantified. In some embodiments, the quantity of regulatory B cells determined after the contacting is compared to the quantity of regulatory B cells before the contacting, for example, to the baseline number of regulatory B cells, wherein, if the number of regulatory B cells in the population of cells is higher after the contacting than the baseline number, then it is determined that a tolerogenic response to the composition has occurred.

Example 13: Evaluating In Vivo Induction of Regulatory B Cells (Prophetic)

A cell population comprising regulatory B cells or regulatory B cell precursors is contacted in vivo with a composition provided herein. In some embodiments, the composition is administered to a subject harboring the cell population comprising regulatory B cells or regulatory B cell precursors. After a time sufficient for the composition to interact with the regulatory B cells or regulatory B cell precursors in the subject, an increase in the number of regulatory B cells is expected. A time sufficient for the increase in the number of regulatory B cells in the population is, in some embodiment, a period of about 1 day, about 2 days, about 3 days, about 4 days, about 5 days, about 6 days, about 1 week, about 2 weeks, about 3 weeks, or about 4 weeks. In some embodiments, the period of time sufficient to effect an increase in the number of regulatory B cells is longer than 4 weeks. In some embodiments, the number of regulatory B cells is increased after that time to at least about 5 times, at least about 10 times, at least about 20 times, at least about 50 times, at least about 100 times, at least about 1,000 times, at least about 10,000 times, at least about 100,000 times, or at least about 1,000,000 times as compared to the original total or relative number of regulatory B cells in the subject. In some embodiments, the number of regulatory B cells is increased after that time, for example, to about 1%, about 5%, about 10%, about 15%, about 20%, about 25%, about 30%, about 40%, about 50%, about 75%, about 90%, or about 95% of the total cells in the subject, or of a lymphocyte population in the subject. In some embodiments, regulatory B cells are absent from the subject before the administration, but are present after the administration.

In some embodiments, the total and/or relative number of regulatory B cells in the subject is determined before the subject is administered a composition provided herein to establish a baseline number of regulatory B cells in the subject. In some embodiments, the composition provided herein is administered to a subject once. In some embodiments, a composition provided herein is administered to a subject multiple times, for example, until a desired increase or abundance of regulatory B cells is observed in the subject.

The number and/or presence of regulatory B cells in the subject is determined after the administration. In some embodiments, the number and/or presence of regulatory B cells is monitored over a period of time, for example, by performing a plurality of subsequent regulatory B cell detection assays. In some embodiments, the number and/or presence of regulatory B cells in the subject is determined by taking a sample from the subject, for example, a peripheral blood sample, or a lymph sample, that is representative of a lymphocyte population in the subject, staining cells contained in that sample with antibodies or staining agents that specifically detect regulatory B cell markers, and detecting cells that express regulatory B cell markers in the sample, for example, by FACS or by immunohistochemistry. In some embodiments, the regulatory B cells are quantified. In some embodiments, the quantity of regulatory B cells determined after administration is compared to the quantity of regulatory B cells before administration, for example, to the baseline number of regulatory B cells, wherein, if the number of regulatory B cells in the subject is higher after the administration than the baseline number, then it is determined that a tolerogenic response to the composition has occurred.

Example 14: In Vivo Induction of a Desired Immune Response Against Transplantable Bone Marrow Cells (Prophetic)

A population of at least $10^6$ synthetic nanocarriers comprising immunosuppressant and antigens obtained or derived from bone marrow cells are administered subcutaneously to a subject four weeks prior to the subject receiving a bone marrow transplant. After the transplant is received by the subject, the generation of a desired immune response in the subject is assessed once daily during the first week after receiving the transplant, and then weekly for the next three weeks, and then monthly for the next 11 months. As part of the assessment, regulatory B cell counts are taken and compared to regulatory B cell counts taken prior to administering the bone marrow transplant or the synthetic nanocarriers to the subject. During the first year, maintenance doses of the synthetic nanocarriers are administered bi-monthly to the subject. The subject is expected to exhibit higher or desired levels of regulatory B cells specific to the bone marrow transplant.

Example 15: Assessing the Effects of Nanocarriers with Antigens and Immunosuppressants Nanocarriers Ovalbumin peptide 323-339, a 17 amino acid peptide known to be a T and B cell epitope of Ovalbumin protein, was purchased from Bachem Americas Inc. (3132 Kashiwa Street, Torrance Calif. 90505; Part #4065609). PLGA with a lactide:glycolide ratio of 3:1 and an inherent viscosity of 0.75 dL/g was purchased from SurModics Pharmaceuticals (756 Tom Martin Drive, Birmingham, Ala. 35211; Product Code 7525 DLG 7A). PLA-PEG block co-polymer with a PEG block of approximately 5,000 Da and PLA block of approximately 20,000 Da was synthesized. Polyvinyl alcohol (85-89% hydrolyzed) was purchased from EMD Chemicals (Product Number 1.41350.1001).

Solutions were prepared as follows: Solution 1: Ovalbumin peptide 323-339 @ 20 mg/mL in dilute hydrochloric acid aqueous solution. The solution was prepared by dissolving ovalbumin peptide in 0.13 M hydrochloric acid solution at room temperature. Solution 2: PLGA @ 100 mg/mL in methylene chloride. The solution was prepared by dissolving PLGA in pure methylene chloride. Solution 3: PLA-PEG @ 100 mg/mL in methylene chloride. The solution was prepared by dissolving PLA-PEG in pure methylene chloride. Solution 4: Polyvinyl alcohol @ 50 mg/mL in 100 mM pH 8 phosphate buffer. A primary water-in-oil emulsion was prepared first. W1/O1 was prepared by combining solution 1 (0.2 mL), solution 2 (0.75 mL), and solution 3 (0.25 mL) in a small pressure tube and sonicating at 50% amplitude for 40 seconds using a Branson Digital Sonifier 250. A secondary emulsion (W1/O1/W2) was then prepared by combining solution 4 (3.0 mL) with the primary W1/O1 emulsion, vortexing for 10 s, and sonicating at 30% amplitude for 60 seconds using the Branson Digital Sonifier 250.

The W1/O1/W2 emulsion was added to a beaker containing 70 mM pH 8 phosphate buffer solution (30 mL) and stirred at room temperature for 2 hours to allow the methylene chloride to evaporate and for the nanocarriers to form. A portion of the nanocarriers were washed by transferring the nanocarrier suspension to a centrifuge tube and centrifuging at 75,600×g and 4° C. for 35 min, removing the supernatant, and re-suspending the pellet in phosphate buffered saline. The washing procedure was repeated, and the pellet was re-suspended in phosphate buffered saline for a final nanocarrier dispersion of about 10 mg/mL.

Nanocarrier size was determined by dynamic light scattering. The amount of peptide in the nanocarrier was determined by HPLC analysis. The total dry-nanocarrier mass per mL of suspension was determined by a gravimetric method.

| Nanocarrier | Effective Diameter (nm) | Peptide Content (% w/w) |
|---|---|---|
| 1 | 234 | 2.1 |

Ovalbumin peptide 323-339, a 17 amino acid peptide known to be a T and B cell epitope of Ovalbumin protein, was purchased from Bachem Americas Inc. (3132 Kashiwa Street, Torrance Calif. 90505; Part #4065609). Rapamycin was purchased from TSZ CHEM (185 Wilson Street, Framingham, Mass. 01702; Product Catalogue # R1017). PLGA with a lactide:glycolide ratio of 3:1 and an inherent viscosity of 0.75 dL/g was purchased from SurModics Pharmaceuticals (756 Tom Martin Drive, Birmingham, Ala. 35211; Product Code 7525 DLG 7A). PLA-PEG block co-polymer with a PEG block of approximately 5,000 Da and PLA block of approximately 20,000 Da was synthesized. Polyvinyl alcohol (85-89% hydrolyzed) was purchased from EMD Chemicals (Product Number 1.41350.1001).

Solutions were prepared as follows: Solution 1: Ovalbumin peptide 323-339 @ 20 mg/mL in dilute hydrochloric acid aqueous solution. The solution was prepared by dissolving ovalbumin peptide in 0.13 M hydrochloric acid solution at room temperature. Solution 2: Rapamycin @ 50 mg/mL in methylene chloride. The solution was prepared by dissolving rapamycin in pure methylene chloride. Solution 3: PLGA @ 100 mg/mL in methylene chloride. The solution was prepared by dissolving PLGA in pure methylene chloride. Solution 4: PLA-PEG @ 100 mg/mL in methylene chloride. The solution was prepared by dissolving PLA-PEG in pure methylene chloride. Solution 5: Polyvinyl alcohol @ 50 mg/mL in 100 mM pH 8 phosphate buffer.

A primary water-in-oil emulsion was prepared first. W1/O1 was prepared by combining solution 1 (0.2 mL), solution 2 (0.2 mL), solution 3 (0.75 mL), and solution 4 (0.25 mL) in a small pressure tube and sonicating at 50% amplitude for 40 seconds using a Branson Digital Sonifier 250. A secondary emulsion (W1/O1/W2) was then prepared by combining solution 5 (3.0 mL) with the primary W1/O1 emulsion, vortexing for 10 s, and sonicating at 30% amplitude for 60 seconds using the Branson Digital Sonifier 250.

The W1/O1/W2 emulsion was added to a beaker containing 70 mM pH 8 phosphate buffer solution (30 mL) and stirred at room temperature for 2 hours to allow the methylene chloride to evaporate and for the nanocarriers to form. A portion of the nanocarriers were washed by transferring the nanocarrier suspension to a centrifuge tube and centrifuging at 21,000×g and 4° C. for 45 min, removing the supernatant, and re-suspending the pellet in phosphate buffered saline. The washing procedure was repeated, and the pellet was re-suspended in phosphate buffered saline for a final nanocarrier dispersion of about 10 mg/mL.

Nanocarrier size was determined by dynamic light scattering. The amounts of peptide and rapamycin in the nanocarrier were determined by HPLC analysis. The total dry-nanocarrier mass per mL of suspension was determined by a gravimetric method.

| Nanocarrier ID | Effective Diameter (nm) | Rapamycin Content (% w/w) | Peptide Content (% w/w) |
|---|---|---|---|
| 2 | 227 | 9.0 | 2.5 |

Measurement of synthetic nanocarrier dimensions was obtained by dynamic light scattering (DLS). A suspension of the synthetic nanocarriers was diluted with purified water to achieve a final synthetic nanocarrier suspension concentration of approximately 0.01 to 0.1 mg/mL. The diluted suspension was prepared directly inside a suitable cuvette for DLS analysis. The cuvette was then placed in a Brookhaven Instruments Corp. ZetaPALS, allowed to equilibrate to 25° C., and then scanned for sufficient time to acquire a stable and reproducible distribution based on appropriate inputs for viscosity of the medium and refractive indicies of the sample. The effective diameter, or mean of the distribution, was then reported.

Immunization

The nanocarriers were thawed and equilibrated. Initial dilutions constituted a 10× stock solution, and were further diluted to a concentration of 100 m/ml in $OVA_{323-339}$, or a 1× solution. This 1× solution was used for injections at 200 μl per i.v. injection. Animals were immunized with OVA protein (OVA) and treated with $OVA_{323-339}$ peptide. Immunization routes were as follows: 10 μg of OVA+ 4 mg Alum i.p. in 400 μl per each Balb/C immunologically naïve female mouse. Experimental groups consisted of 5 animals each. Spleen cells were restimulated with antigen using CFSE or CTO to determine the amount of Ag-specific proliferation.

Measuring Regulatory B Cells

The frequency of Ovalbumin reactive IL-10 secreting B cells was calculated by way of flow cytometry. Splenocytes from experimental animals were stained with CFSE, a thiol-reactive Fluorescent Probe suitable for long-term cell labeling, and cultured in complete media at 37 C, 5% CO2 with Ovalbumin protein for 3 days. On day 3 the cells were assayed for their potential to secrete different cytokines by intracellular staining using standard methods and kits. Briefly, cells were restimulated with phorbol myristate acetate (PMA) and lonomycin for 2 hours and protein transport was blocked for another 4 hours. Unspecific binding of antibodies was blocked with anti-CD16/32 antibody and then cells were stained with conjugated antibodies specific recognizing specifically B cells (CD45R (B220) and CD19). After fixation with paraformaldehyde cells were permeabilized to allow monoclonal antibodies into the cells and label intracellular epitopes (cytokines). Splenocytes that were B220+CD19+ were assessed for proliferation by comparing the differential CFSE staining and the proportion of IL-10-secreting cells determined.

Measurement of IgE Antibodies

IgE antibodies were measured using a Mouse OVA-IgE ELISA kit provided by MDBioproducts (Cat# M036005) consistent with the manufacturer's instructions.

Results

Figure 2:
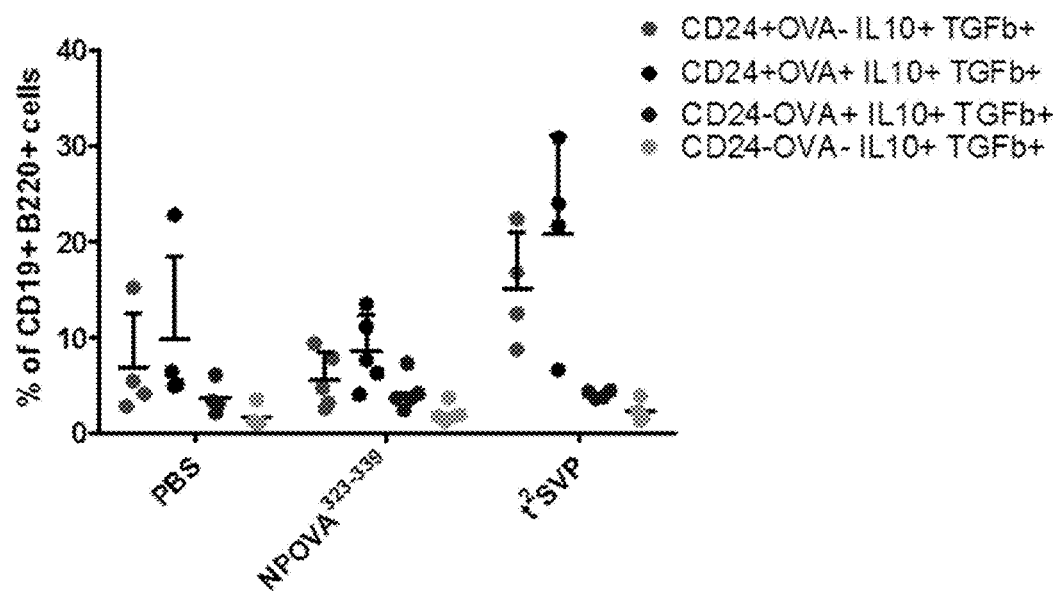
FIG. 2 demonstrates that synthetic nanocarriers of the invention resulted in higher proportions of antigen-specific Bregs.
Figure 3:
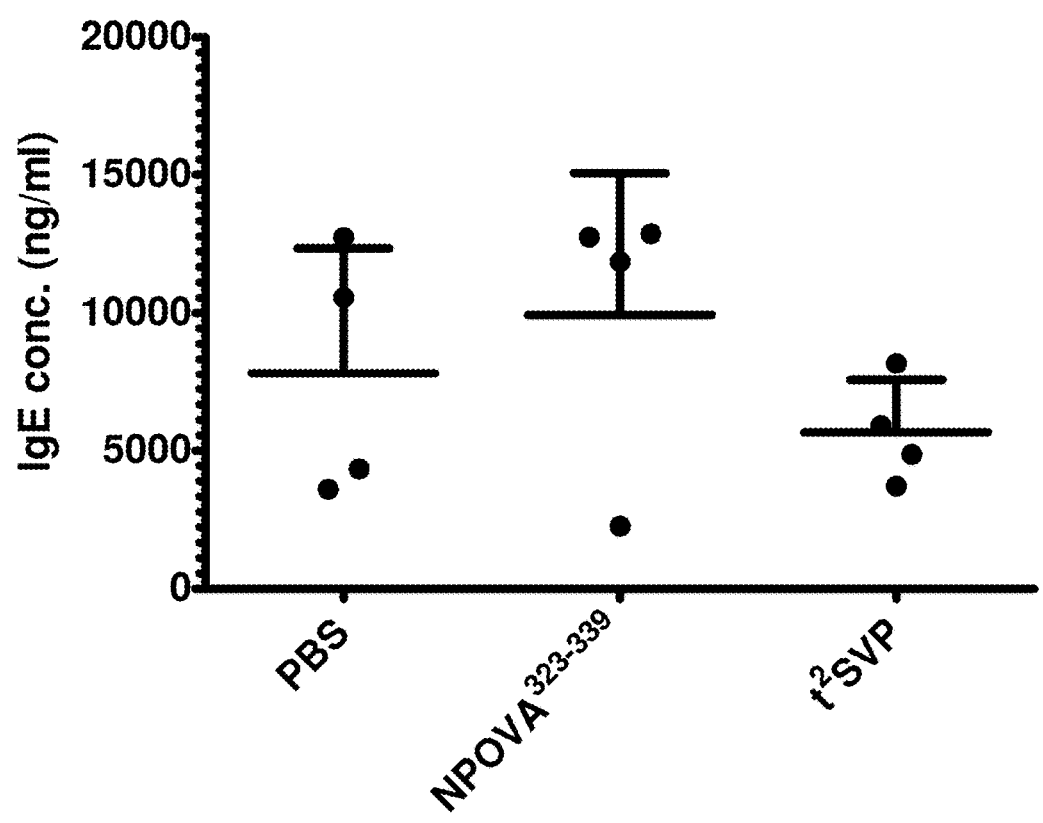
FIG. 3 shows a decrease in IgE production with synthetic nanocarriers of the invention.

FIG. 2 demonstrate the effectiveness of the nanocarriers in the generation of regulatory B cells in lavage samples from animal subjects treated with synthetic nanocarriers comprising $OVA_{323-339}$ and immunosuppressant. The figure demonstrates that synthetic nanocarriers of the invention resulted in the production of IL-10 and TGF-β by antigen-specific CD24+ B cells. FIG. 3 shows a decrease in IgE production with synthetic nanocarriers of the invention.

Example 16: Isolation of Regulatory B Cell (Bregs) Cells from a Subject after Administration of Inventive Synthetic Nanocarriers (Prophetic)

Bregs are isolated from biological samples, for example, from peripheral blood, obtained from a subject after the subject is administered a synthetic nanocarrier composition as described herein. Typically, the biological sample is obtained from the subject after a time period sufficient for the administered itDCs to induce Bregs. Bregs are isolated from the biological sample, for example, from whole blood, by negative and/or positive selection.

For example, the cellular fraction of whole blood is obtained by centrifugation, and erythrocytes are lysed using erythrocyte lysis buffer. After lysis, peripheral blood mononuclear cells are depleted for CD4+ cells and CD8+ T cells. Subsequently, Bregs are enriched for by positive selection for the markers provided elsewhere herein or otherwise known in the art. In some embodiments, the isolation of regulatory B cells is performed with a cocktail of biotinylated antibodies and anti-biotin magnetic beads for the recognition of one or more of these markers.

What is claimed is:

1. A method for generating antigen-specific regulatory B cells that produce IL-10 in a mammalian subject, comprising:

administering to the mammalian subject a composition that comprises:

(i) a first population of polymeric synthetic nanocarriers coupled to rapamycin, and (ii) a second population of polymeric synthetic nanocarriers coupled to B cell and/or MHC Class II-restricted epitopes of an antigen, wherein at least 75% of the polymeric synthetic nanocarriers of the first and/or second population of polymeric synthetic nanocarriers have a minimum dimension, obtained using dynamic light scattering, that is greater than 110 nm and a maximum dimension, obtained using dynamic light scattering, that is equal to or less than 500 nm, wherein the load of the rapamycin on average across the first population of polymeric synthetic nanocarriers is at least 2% but no more than 25% (weight/weight), wherein the load of the epitopes on average across the second population of polymeric synthetic nanocarriers is between 1% and 10% (weight/weight), and wherein the composition is in an amount effective to generate antigen-specific regulatory B cells that produce IL-10 in the mammalian subject.

2. A method for generating antigen-specific regulatory B cells that produce IL-10 in a mammalian subject comprising:
generating antigen-specific regulatory B cells that produce IL-10 in the mammalian subject by administering a composition that comprises:
(i) a first population of polymeric synthetic nanocarriers coupled to rapamycin, and
(ii) a second population of polymeric synthetic nanocarriers coupled to B cell and/or MHC Class II-restricted epitopes of an antigen,
wherein at least 75% of the polymeric synthetic nanocarriers of the first and/or second population of polymeric synthetic nanocarriers have a minimum dimension, obtained using dynamic light scattering, that is greater than 110 nm and a maximum dimension, obtained using dynamic light scattering, that is equal to or less than 500 nm,
wherein the load of the rapamycin on average across the first population of polymeric synthetic nanocarriers is at least 2% but no more than 25% (weight/weight), and
wherein the load of the epitopes on average across the second population of polymeric synthetic nanocarriers is between 1% and 10% (weight/weight).

3. A method for generating antigen-specific regulatory B cells that produce IL-10 in a mammalian subject comprising:
administering to the mammalian subject a composition according to a protocol that was previously shown to generate antigen-specific regulatory B cells that produce IL-10 in one or more test subjects;
wherein the composition comprises:
(i) a first population of polymeric synthetic nanocarriers coupled to rapamycin, and
(ii) a second population of polymeric synthetic nanocarriers coupled to B cell and/or MHC Class II-restricted epitopes of an antigen,
wherein at least 75% of the polymeric synthetic nanocarriers of the first and/or second population of polymeric synthetic nanocarriers have a minimum dimension, obtained using dynamic light scattering, that is greater than 110 nm and a maximum dimension, obtained using dynamic light scattering, that is equal to or less than 500 nm,
wherein the load of the rapamycin on average across the first population of polymeric synthetic nanocarriers is at least 2% but no more than 25% (weight/weight), and
wherein the load of the epitopes on average across the second population of polymeric synthetic nanocarriers is between 1% and 10% (weight/weight).

4. The method of claim 1, wherein the antigens are coupled to the same synthetic nanocarriers as to which the rapamycin is coupled population are the same population.

5. The method of claim 1, wherein the antigen is a therapeutic protein, an autoantigen or an allergen, or is associated with an inflammatory disease, an autoimmune disease, organ or tissue rejection or graft versus host disease.

6. The method of claim 1, wherein the method further comprises assessing the generation of antigen-specific regulatory B cells in the subject prior to and/or after the administration of the composition.

7. The method of claim 1, wherein the subject has or is at risk of having an inflammatory disease, an autoimmune disease, an allergy, organ or tissue rejection or graft versus host disease.

8. The method of claim 1, wherein the subject has undergone transplantation.

9. The method of claim 1, wherein the subject has or is at risk of having an undesired immune response against a therapeutic protein.

10. The method of claim 1, wherein the aspect ratio of the maximum to minimum dimensions of the synthetic nanocarriers of the first population and/or second population is greater than 1:1, 1:1.2, 1:1.5, 1:2, 1:3, 1:5, 1:7 or 1:10.

11. The method of claim 1, wherein the polymeric synthetic nanocarriers of the first population and/or second population comprise a polymer that is a non-methoxy-terminated, polymer.

12. The method of claim 1, wherein the polymeric synthetic nanocarriers of the first population and/or second population comprise a polyester, a polyester coupled to a polyether, polyamino acid, polycarbonate, polyacetal, polyketal, polysaccharide, polyethyloxazoline or polyethyleneimine.

13. The method of claim 1, wherein at least 80% of the polymeric synthetic nanocarriers, based on the total number of polymeric synthetic nanocarriers, have a minimum dimension or maximum dimension that falls within 20% of the average minimum dimension or the average maximum dimension, respectively, of the polymeric synthetic nanocarriers.

14. The method of claim 13, wherein at least 90% of the polymeric synthetic nanocarriers have the minimum dimension or maximum dimension.

15. The method of claim 14, wherein at least 95% of the polymeric synthetic nanocarriers have the minimum dimension or maximum dimension.

16. The method of claim 13 or 14, wherein the minimum dimension or maximum dimension falls within 10%.

17. The method of claim 16, wherein the minimum dimension or maximum dimension falls within 5%.

* * * * *